US009644014B2

(12) United States Patent
Tian et al.

(10) Patent No.: US 9,644,014 B2
(45) Date of Patent: May 9, 2017

(54) MODIFIED ANIMAL ERYTHROPOIETIN POLYPEPTIDES AND THEIR USES

(71) Applicants: Ambrx, Inc., La Jolla, CA (US); Eli Lilly and Company, Indianapolis, IN (US)

(72) Inventors: Feng Tian, San Diego, CA (US); Anna-Maria A. Hays Putnam, San Diego, CA (US); Frank Song, San Diego, CA (US); Stephanie Chu, Simi Valley, CA (US); Joseph Sheffer, Cardiff, CA (US); Richard S. Barnett, San Marcos, CA (US); Marc Siladi, San Diego, CA (US); Kyle Atkinson, Golden, CO (US); Darin Lee, San Diego, CA (US); Peter C. Canning, Indianapolis, IN (US)

(73) Assignees: Ambrx, Inc., La Jolla, CA (US); Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/854,819

(22) Filed: Sep. 15, 2015

(65) Prior Publication Data
US 2016/0024166 A1 Jan. 28, 2016

Related U.S. Application Data

(60) Division of application No. 14/032,963, filed on Sep. 20, 2013, now Pat. No. 9,156,899, which is a continuation of application No. 13/556,754, filed on Jul. 24, 2012, now Pat. No. 8,569,233, which is a division of application No. 12/567,627, filed on Sep. 25, 2009, now Pat. No. 8,278,418.

(60) Provisional application No. 61/100,692, filed on Sep. 26, 2008, provisional application No. 61/100,679, filed on Sep. 26, 2008.

(51) Int. Cl.
*A61K 38/00* (2006.01)
*A61K 38/18* (2006.01)
*C07K 14/505* (2006.01)
*C12N 15/10* (2006.01)
*A61K 47/48* (2006.01)

(52) U.S. Cl.
CPC .......... *C07K 14/505* (2013.01); *A61K 38/00* (2013.01); *A61K 38/1816* (2013.01); *A61K 47/48215* (2013.01); *C12N 15/102* (2013.01)

(58) Field of Classification Search
None
See application file for complete search history.

(56) References Cited

U.S. PATENT DOCUMENTS

| 3,773,919 A | 11/1973 | Boswell et al. |
|---|---|---|
| 4,289,872 A | 9/1981 | Denkewalter et al. |
| 4,412,989 A | 11/1983 | Iwashita et al. |
| 4,414,148 A | 11/1983 | Jansen et al. |
| 4,485,045 A | 11/1984 | Regen |
| 4,511,502 A | 4/1985 | Builder et al. |
| 4,511,503 A | 4/1985 | Olson et al. |
| 4,512,922 A | 4/1985 | Jones et al. |
| 4,544,545 A | 10/1985 | Ryan et al. |
| 4,551,433 A | 11/1985 | DeBoer |
| 4,569,789 A | 2/1986 | Blattler et al. |
| 4,589,071 A | 5/1986 | Yamamuro et al. |
| 4,619,794 A | 10/1986 | Hauser |
| 4,659,839 A | 4/1987 | Nicolotti et al. |
| 4,667,016 A | 5/1987 | Lai et al. |
| 4,670,417 A | 6/1987 | Iwasaki et al. |
| 4,671,958 A | 6/1987 | Rodwell et al. |
| 4,680,338 A | 7/1987 | Sundoro |
| 4,689,406 A | 8/1987 | Banks et al. |
| 4,699,784 A | 10/1987 | Shih et al. |
| 4,703,008 A | 10/1987 | Lin |
| 4,738,921 A | 4/1988 | Belagaje et al. |
| 4,755,465 A | 7/1988 | Gray et al. |
| 4,812,405 A | 3/1989 | Lair et al. |
| 4,818,700 A | 4/1989 | Cregg et al. |
| 4,837,148 A | 6/1989 | Cregg |
| 4,859,600 A | 8/1989 | Gray et al. |
| 4,876,197 A | 10/1989 | Burke et al. |
| 4,880,734 A | 11/1989 | Burke et al. |
| 4,902,502 A | 2/1990 | Nitecki et al. |
| 4,904,584 A | 2/1990 | Shaw |
| 4,929,555 A | 5/1990 | Cregg et al. |
| 5,021,234 A | 6/1991 | Ehrenfeld |
| 5,089,398 A | 2/1992 | Rosenberg et al. |
| 5,106,954 A | 4/1992 | Fibi et al. |
| 5,122,614 A | 6/1992 | Zalipsky |
| 5,162,601 A | 11/1992 | Slightom |

(Continued)

FOREIGN PATENT DOCUMENTS

| CA | 2680236 A1 | 9/2008 |
|---|---|---|
| DE | 3218121 A1 | 11/1983 |

(Continued)

OTHER PUBLICATIONS

Macleod., Clinical Trials of Recombinant Feline EPO Underway. (2011), p. 1-2.*
Bernstein, F. C. et al. "The Protein Data Bank: A Computer-based Archival File for Macromolecular Structures," J. Mol. Biol. 1977 112:535-542.
Gillam, S. et al. "Site-Specific Mutagenesis Using Synthetic Oligodeoxyribonucleotide Primers: I. Optimum Conditions and Minimum Oligodeoxyribo-Nucleotide Length," Gene 1979; 8:81-97.

(Continued)

*Primary Examiner* — Christine J Saoud
*Assistant Examiner* — Jegatheesan Seharaseyon
(74) *Attorney, Agent, or Firm* — Drinker Biddle & Reath LLP

(57) ABSTRACT

Modified animal erythropoietin polypeptides and uses thereof are provided.

12 Claims, 37 Drawing Sheets

(56) References Cited

U.S. PATENT DOCUMENTS

| | | |
|---|---|---|
| 5,219,564 A | 6/1993 | Zalipsky et al. |
| 5,229,490 A | 7/1993 | Tam |
| 5,231,178 A | 7/1993 | Holtz et al. |
| 5,252,714 A | 10/1993 | Harris et al. |
| 5,278,065 A | 1/1994 | D'Andrea et al. |
| 5,281,698 A | 1/1994 | Nitecki |
| 5,290,686 A | 3/1994 | Kendal et al. |
| 5,292,654 A | 3/1994 | Yoshimura et al. |
| 5,324,639 A | 6/1994 | Brierley et al. |
| 5,324,844 A | 6/1994 | Zalipsky |
| 5,382,657 A | 1/1995 | Karasiewicz et al. |
| 5,387,808 A | 2/1995 | Nozu |
| 5,441,868 A | 8/1995 | Lin |
| 5,446,090 A | 8/1995 | Harris |
| 5,457,089 A | 10/1995 | Fibi et al. |
| 5,468,478 A | 11/1995 | Saifer et al. |
| 5,473,034 A | 12/1995 | Yasui et al. |
| 5,476,653 A | 12/1995 | Pitt et al. |
| 5,516,657 A | 5/1996 | Murphy et al. |
| 5,516,673 A | 5/1996 | Margel et al. |
| 5,532,142 A | 7/1996 | Johnston et al. |
| 5,547,933 A | 8/1996 | Lin |
| 5,559,213 A | 9/1996 | Hakimi et al. |
| 5,571,709 A | 11/1996 | Devauchelle et al. |
| 5,580,723 A | 12/1996 | Wells et al. |
| 5,583,023 A | 12/1996 | Cerutti et al. |
| 5,583,272 A | 12/1996 | Sprecker et al. |
| 5,602,034 A | 2/1997 | Tekamp-Olson |
| 5,605,827 A | 2/1997 | Jackwood et al. |
| 5,612,460 A | 3/1997 | Zalipsky |
| 5,614,184 A | 3/1997 | Sytkowski et al. |
| 5,618,698 A | 4/1997 | Lin |
| 5,621,080 A | 4/1997 | Lin |
| 5,629,203 A | 5/1997 | Shuster |
| 5,629,384 A | 5/1997 | Veronese et al. |
| 5,643,575 A | 7/1997 | Martinez et al. |
| 5,650,234 A | 7/1997 | Dolence et al. |
| 5,672,662 A | 9/1997 | Harris et al. |
| 5,674,706 A | 10/1997 | Shuster |
| 5,688,679 A | 11/1997 | Powell |
| 5,712,370 A | 1/1998 | Fibi et al. |
| RE35,749 E | 3/1998 | Rosenberg et al. |
| 5,736,383 A | 4/1998 | Raymond |
| 5,736,625 A | 4/1998 | Callstrom et al. |
| 5,739,208 A | 4/1998 | Harris |
| 5,747,646 A | 5/1998 | Hakimi et al. |
| 5,750,373 A | 5/1998 | Garrard et al. |
| 5,753,220 A | 5/1998 | Suzuki et al. |
| 5,756,349 A | 5/1998 | Lin |
| 5,762,939 A | 6/1998 | Smith et al. |
| 5,766,885 A | 6/1998 | Carrington et al. |
| 5,767,078 A | 6/1998 | Johnson et al. |
| 5,773,569 A | 6/1998 | Wrighton et al. |
| 5,808,096 A | 9/1998 | Zalipsky |
| 5,824,778 A | 10/1998 | Ishikawa et al. |
| 5,824,784 A | 10/1998 | Kinstler et al. |
| 5,830,851 A | 11/1998 | Wrighton et al. |
| 5,834,250 A | 11/1998 | Wells et al. |
| 5,834,594 A | 11/1998 | Hakimi et al. |
| 5,843,733 A | 12/1998 | Estes |
| 5,849,860 A | 12/1998 | Hakimi et al. |
| 5,856,298 A | 1/1999 | Strickland |
| 5,858,368 A | 1/1999 | Smith et al. |
| 5,861,279 A | 1/1999 | Zhang et al. |
| 5,871,986 A | 2/1999 | Boyce |
| 5,888,768 A | 3/1999 | Raymond |
| 5,888,772 A | 3/1999 | Okasinski et al. |
| 5,891,676 A | 4/1999 | Estes |
| 5,900,461 A | 5/1999 | Harris |
| 5,932,462 A | 8/1999 | Harris et al. |
| 5,939,285 A | 8/1999 | Devauchelle et al. |
| 5,955,349 A | 9/1999 | Raymond |
| 5,955,422 A | 9/1999 | Lin |
| 5,965,393 A | 10/1999 | Hasnain et al. |
| 5,980,948 A | 11/1999 | Goedemoed et al. |
| 5,986,047 A | 11/1999 | Wrighton et al. |
| 5,989,868 A | 11/1999 | Harrison et al. |
| 5,990,237 A | 11/1999 | Bentley et al. |
| 6,004,573 A | 12/1999 | Rathi et al. |
| 6,013,433 A | 1/2000 | Pellett et al. |
| 6,013,478 A | 1/2000 | Wells et al. |
| 6,017,731 A | 1/2000 | Tekamp-Olson et al. |
| 6,048,971 A | 4/2000 | Sytkowski et al. |
| 6,083,723 A | 7/2000 | Tekamp-Olson |
| 6,096,304 A | 8/2000 | McCutchen |
| 6,099,830 A | 8/2000 | Kaushansky |
| 6,126,944 A | 10/2000 | Pellett et al. |
| 6,129,912 A | 10/2000 | Hortin et al. |
| 6,153,407 A | 11/2000 | Sytkowski et al. |
| 6,165,283 A | 12/2000 | Dahlin et al. |
| 6,168,932 B1 | 1/2001 | Uckun et al. |
| 6,171,821 B1 | 1/2001 | Korneluk et al. |
| 6,180,401 B1 | 1/2001 | Chen et al. |
| 6,183,985 B1 | 2/2001 | Shuster |
| 6,183,987 B1 | 2/2001 | van de Wiel et al. |
| 6,187,564 B1 | 2/2001 | Sytkowski |
| 6,201,072 B1 | 3/2001 | Rathi et al. |
| 6,214,966 B1 | 4/2001 | Harris |
| 6,221,608 B1 | 4/2001 | Middleton et al. |
| 6,225,060 B1 | 5/2001 | Clark et al. |
| 6,239,109 B1 | 5/2001 | Rodgers et al. |
| 6,245,528 B1 | 6/2001 | Chao |
| 6,258,559 B1 | 7/2001 | Zamost |
| 6,261,805 B1 | 7/2001 | Wood |
| 6,268,336 B1 | 7/2001 | Niitsu et al. |
| RE37,343 E | 8/2001 | Tekamp-Olson |
| 6,281,211 B1 | 8/2001 | Cai et al. |
| 6,306,821 B1 | 10/2001 | Mikos et al. |
| 6,310,078 B1 | 10/2001 | Connolly et al. |
| 6,312,923 B1 | 11/2001 | Tekamp-Olson |
| 6,316,254 B1 | 11/2001 | Kaushansky |
| 6,337,191 B1 | 1/2002 | Swartz et al. |
| 6,338,846 B1 | 1/2002 | Kang et al. |
| 6,340,742 B1 | 1/2002 | Burg et al. |
| 6,342,216 B1 | 1/2002 | Fidler et al. |
| 6,361,969 B1 | 3/2002 | Galeotti |
| 6,368,825 B1 | 4/2002 | Chao |
| 6,368,854 B2 | 4/2002 | Weiss et al. |
| 6,376,218 B1 | 4/2002 | Hsu et al. |
| 6,420,339 B1 | 7/2002 | Gegg et al. |
| 6,423,685 B1 | 7/2002 | Drummond et al. |
| 6,428,954 B1 | 8/2002 | Wells et al. |
| 6,436,386 B1 | 8/2002 | Roberts et al. |
| 6,451,346 B1 | 9/2002 | Shah et al. |
| 6,451,561 B1 | 9/2002 | Wells et al. |
| 6,461,603 B2 | 10/2002 | Bentley et al. |
| 6,489,293 B1 | 12/2002 | Sytkowski et al. |
| 6,515,100 B2 | 2/2003 | Harris |
| 6,521,245 B1 | 2/2003 | Zaharia |
| 6,521,427 B1 | 2/2003 | Evans |
| 6,531,121 B2 | 3/2003 | Brines et al. |
| 6,544,748 B2 | 4/2003 | Stern et al. |
| 6,548,653 B1 | 4/2003 | Young et al. |
| 6,552,167 B1 | 4/2003 | Rose |
| 6,579,525 B1 | 6/2003 | Haran-Ghera et al. |
| 6,583,272 B1 | 6/2003 | Bailon |
| 6,586,207 B2 | 7/2003 | Tirrell et al. |
| 6,586,398 B1 | 7/2003 | Kinstler et al. |
| 6,602,498 B2 | 8/2003 | Shen |
| 6,608,183 B1 | 8/2003 | Cox, III |
| 6,610,281 B2 | 8/2003 | Harris |
| 6,642,353 B1 | 11/2003 | McConnell et al. |
| 6,646,110 B2 | 11/2003 | Nissen et al. |
| 6,676,947 B1 | 1/2004 | Gottschalk et al. |
| 6,682,910 B2 | 1/2004 | Powell |
| 6,696,056 B1 | 2/2004 | Cheung et al. |
| 6,703,480 B1 | 3/2004 | Balu |
| 6,800,740 B1 * | 10/2004 | Cunningham ....... C07K 14/505 |
| | | 530/399 |
| 6,927,042 B2 | 8/2005 | Schultz et al. |
| 7,045,337 B2 * | 5/2006 | Schultz ................. C07K 14/00 |
| | | 435/15 |
| 7,083,970 B2 | 8/2006 | Schultz et al. |
| 8,278,418 B2 | 10/2012 | Tian et al. |

(56) References Cited

U.S. PATENT DOCUMENTS

| | | | |
|---|---|---|---|
| 8,569,233 B2 * | 10/2013 | Tian | C07K 14/505 424/198.1 |
| 2001/0021763 A1 | 9/2001 | Harris | |
| 2001/0027217 A1 | 10/2001 | Jaetsch et al. | |
| 2001/0044526 A1 | 11/2001 | Shen | |
| 2001/0056171 A1 | 12/2001 | Kozlowski | |
| 2002/0002250 A1 | 1/2002 | Bentley et al. | |
| 2002/0037949 A1 | 3/2002 | Harris et al. | |
| 2002/0040076 A1 | 4/2002 | Harris et al. | |
| 2002/0042097 A1 | 4/2002 | Tirrell et al. | |
| 2002/0052009 A1 | 5/2002 | Hornauer et al. | |
| 2002/0052430 A1 | 5/2002 | Harris et al. | |
| 2002/0055169 A1 | 5/2002 | Tekamp-Olson | |
| 2002/0072573 A1 | 6/2002 | Bentley et al. | |
| 2002/0081660 A1 | 6/2002 | Swartz et al. | |
| 2002/0082345 A1 | 6/2002 | Kozlowski et al. | |
| 2002/0086939 A1 | 7/2002 | Kozlowski | |
| 2002/0099133 A1 | 7/2002 | Kozlowski | |
| 2002/0156047 A1 | 10/2002 | Zhao | |
| 2003/0023023 A1 | 1/2003 | Harris et al. | |
| 2003/0082575 A1 | 5/2003 | Schultz et al. | |
| 2003/0105224 A1 | 6/2003 | Roberts et al. | |
| 2003/0105275 A1 | 6/2003 | Bentley et al. | |
| 2003/0108885 A1 | 6/2003 | Schultz et al. | |
| 2003/0114647 A1 | 6/2003 | Harris et al. | |
| 2003/0143596 A1 | 7/2003 | Bentley et al. | |
| 2003/0158333 A1 | 8/2003 | Roberts et al. | |
| 2003/0162949 A1 | 8/2003 | Cox | |
| 2003/0220447 A1 | 11/2003 | Harris | |
| 2003/0228274 A1 | 12/2003 | Rose | |
| 2004/0001838 A1 | 1/2004 | Zhao et al. | |
| 2004/0013637 A1 | 1/2004 | Bentley et al. | |
| 2004/0115774 A1 | 6/2004 | Kochendoerfer et al. | |
| 2004/0198637 A1 | 10/2004 | Schultz et al. | |
| 2005/0009049 A1 | 1/2005 | Chin et al. | |
| 2005/0085619 A1 | 4/2005 | Wilson | |
| 2005/0170404 A1 | 8/2005 | Cho et al. | |
| 2005/0220762 A1 | 10/2005 | Cho et al. | |
| 2006/0189529 A1 | 8/2006 | Cho et al. | |
| 2008/0097083 A1 | 4/2008 | Cho et al. | |
| 2008/0146781 A1 | 6/2008 | Cho et al. | |
| 2008/0300163 A1 * | 12/2008 | Cho | C07H 21/04 514/1.1 |

FOREIGN PATENT DOCUMENTS

| | | |
|---|---|---|
| EP | 036676 A1 | 9/1981 |
| EP | 036776 A2 | 9/1981 |
| EP | 052322 A2 | 5/1982 |
| EP | 058481 A1 | 8/1982 |
| EP | 073657 A1 | 3/1983 |
| EP | 0088046 A2 | 9/1983 |
| EP | 102324 A2 | 3/1984 |
| EP | 121775 A1 | 10/1984 |
| EP | 127839 A2 | 12/1984 |
| EP | 133988 A2 | 3/1985 |
| EP | 0142641 A2 | 5/1985 |
| EP | 143949 A1 | 6/1985 |
| EP | 154316 A2 | 9/1985 |
| EP | 155476 A1 | 9/1985 |
| EP | 164556 A2 | 12/1985 |
| EP | 183503 A2 | 6/1986 |
| EP | 188256 A2 | 7/1986 |
| EP | 229108 A1 | 7/1987 |
| EP | 244234 A2 | 11/1987 |
| EP | 267851 A2 | 5/1988 |
| EP | 284044 A1 | 9/1988 |
| EP | 324274 A1 | 7/1989 |
| EP | 329203 A1 | 8/1989 |
| EP | 340986 A2 | 11/1989 |
| EP | 400472 A2 | 12/1990 |
| EP | 402378 A1 | 12/1990 |
| EP | 439508 A1 | 8/1991 |
| EP | 0460071 A1 | 12/1991 |
| EP | 480480 A2 | 4/1992 |
| EP | 510356 A1 | 10/1992 |
| EP | 605963 A2 | 7/1994 |
| EP | 0640619 A1 | 3/1995 |
| EP | 732403 A1 | 9/1996 |
| EP | 809996 A2 | 12/1997 |
| EP | 921131 A1 | 6/1999 |
| EP | 946736 A1 | 10/1999 |
| EP | 1064951 A2 | 1/2001 |
| EP | 1929860 A1 | 6/2008 |
| JP | 83-118008 A | 1/1985 |
| WO | WO-8807082 A1 | 9/1988 |
| WO | WO-8901037 A1 | 2/1989 |
| WO | WO-8901038 A1 | 2/1989 |
| WO | WO-9002186 A1 | 3/1990 |
| WO | WO-9002566 A1 | 3/1990 |
| WO | WO-9005785 A1 | 5/1990 |
| WO | WO-9010078 A1 | 9/1990 |
| WO | WO-9010277 A1 | 9/1990 |
| WO | WO-9013540 A1 | 11/1990 |
| WO | WO-9014428 A1 | 11/1990 |
| WO | WO-9100357 A1 | 1/1991 |
| WO | WO-9201801 A1 | 2/1992 |
| WO | WO-9202628 A1 | 2/1992 |
| WO | WO-9216555 A1 | 10/1992 |
| WO | WO-9216619 A1 | 10/1992 |
| WO | WO-9303173 A1 | 2/1993 |
| WO | WO-9315189 A1 | 8/1993 |
| WO | WO-9321259 A1 | 10/1993 |
| WO | WO-9404193 A1 | 3/1994 |
| WO | WO-9409027 A1 | 4/1994 |
| WO | WO-9414758 A1 | 7/1994 |
| WO | WO-9415625 A1 | 7/1994 |
| WO | WO-9417039 A1 | 8/1994 |
| WO | WO-9418247 A1 | 8/1994 |
| WO | WO 9424160 A2 * | 10/1994 ........... C07K 14/505 |
| WO | WO-9428024 A1 | 12/1994 |
| WO | WO-9500162 A1 | 1/1995 |
| WO | WO-9506058 A1 | 3/1995 |
| WO | WO-9511924 A1 | 5/1995 |
| WO | WO-9513090 A1 | 5/1995 |
| WO | WO-9513312 A1 | 5/1995 |
| WO | WO-9520672 A1 | 8/1995 |
| WO | WO-9533490 A1 | 12/1995 |
| WO | WO-9600080 A1 | 1/1996 |
| WO | WO-9601556 A1 | 1/1996 |
| WO | WO-9606161 A1 | 2/1996 |
| WO | WO-9607670 A1 | 3/1996 |
| WO | WO-9621469 A1 | 7/1996 |
| WO | WO-9625496 A1 | 8/1996 |
| WO | WO-9629400 A1 | 9/1996 |
| WO | WO-9635718 A1 | 11/1996 |
| WO | WO-9640791 A1 | 12/1996 |
| WO | WO-9641813 A2 | 12/1996 |
| WO | WO-9703106 A1 | 1/1997 |
| WO | WO-9718832 A1 | 5/1997 |
| WO | WO-9726332 A1 | 7/1997 |
| WO | WO-9732607 A2 | 9/1997 |
| WO | WO-9805363 A2 | 2/1998 |
| WO | WO-9826080 A1 | 6/1998 |
| WO | WO-9832466 A1 | 7/1998 |
| WO | WO-9837208 A1 | 8/1998 |
| WO | WO-9841562 A1 | 9/1998 |
| WO | WO-9848837 A1 | 11/1998 |
| WO | WO-9903887 A1 | 1/1999 |
| WO | WO-9905268 A1 | 2/1999 |
| WO | WO-9905297 A1 | 2/1999 |
| WO | WO-9907862 A1 | 2/1999 |
| WO | WO-9909193 A1 | 2/1999 |
| WO | WO-9910515 A1 | 3/1999 |
| WO | WO-9911781 A1 | 3/1999 |
| WO | WO-9931257 A2 | 6/1999 |
| WO | WO-9932134 A1 | 7/1999 |
| WO | WO-9932139 A1 | 7/1999 |
| WO | WO-9932140 A1 | 7/1999 |
| WO | WO-9938890 A1 | 8/1999 |
| WO | WO-9945130 A1 | 9/1999 |
| WO | WO-9951721 A1 | 10/1999 |
| WO | WO-9966054 A2 | 12/1999 |

(56) References Cited

FOREIGN PATENT DOCUMENTS

| | | |
|---|---|---|
| WO | WO-9967291 A2 | 12/1999 |
| WO | WO-0020032 A1 | 4/2000 |
| WO | WO-0026354 A1 | 5/2000 |
| WO | WO-0032772 A1 | 6/2000 |
| WO | WO-0055345 A2 | 9/2000 |
| WO | WO-0055353 A1 | 9/2000 |
| WO | WO-0105956 A2 | 1/2001 |
| WO | WO-0127301 A2 | 4/2001 |
| WO | WO-01/76640 A2 | 10/2001 |
| WO | WO-0190390 A1 | 11/2001 |
| WO | WO-02/053580 A2 | 7/2002 |
| WO | WO-02085923 A2 | 10/2002 |
| WO | WO-02086075 A2 | 10/2002 |
| WO | WO-03101972 A1 | 12/2003 |
| WO | WO-2004/003176 A2 | 1/2004 |
| WO | WO-2004/004656 A2 | 1/2004 |
| WO | WO-2004035605 A2 | 4/2004 |
| WO | WO-2004035743 A2 | 4/2004 |
| WO | WO-2004058946 A2 | 7/2004 |
| WO | WO-2004094593 A2 | 11/2004 |
| WO | WO-2005007624 A2 | 1/2005 |
| WO | WO-2005007870 A2 | 1/2005 |
| WO | WO-2005019415 A2 | 3/2005 |
| WO | WO-2005035727 A2 | 4/2005 |
| WO | WO-2005074524 A2 | 8/2005 |
| WO | WO-2005074546 A2 | 8/2005 |
| WO | WO-2005074650 A2 | 8/2005 |
| WO | WO-2006/002646 A2 | 1/2006 |
| WO | WO-2008065372 A2 | 6/2008 |
| WO | WO-2010/011735 A2 | 1/2010 |

OTHER PUBLICATIONS

Narhi, L. O. et al. "Asn to Lys mutations at three sites which are N-glycosylated in the mammalian protein decrease the aggregation of *Escherichia coli*-derived erythropoietin," Protein Engineering 2001 14(2):135-140.
Roberts, S. et al. "Generation of an antibody with enhanced affinity and specificity for its antigen by protein engineering," Nature Aug. 20, 1987;328:731-734.
Schneider, E. et al. "Functional Purification of a Bacterial ATP-Binding Cassette Transporter Protein (Malk) from the Cytoplasmic Fraction of an Overproducing Strain," Protein Expression and Purification 1995 6:10-14.
Polyethylene glycol and derivatives for advanced PEGylation, Nektar molecular engineering catalog, 2003, pp. 1-17.
Polyethylene glycol and derivatives for biomedical applications, Shearwater Corporation catalog, 2001.
Tondelli, L. et al. "Poly(ethylene Glycol) Imidazolyl Formates as Oligomeric Drug-Binding Matrices," J. Controlled Release 1985;1(4):251-7.
Tornoe, CW et al., "Peptidotriazoles on solid phase: [1,2,3]-triazoles by regiospecific copper(i)-catalyzed 1,3-dipolar cycloadditions of terminal alkynes to azides," J Org Chem. May 3, 2002;67(9):3057-64.
Trotter, KM and HA Wood, "Transfection techniques for producing recombinant baculoviruses," in Methods in Molecular Biology—Baculovirus Expression Protocols, vol. 39 (1995); Ed. C.D. Richardson, 97-107.
Tschumper, G. et al., "Sequence of a yeast DNA fragment containing a chromosomal replicator and the TRP1 gene," Gene 1980; 10(2):157-66.
Turcatti, G et al. "Probing the structure and function of the tachykinin neurokinin-2 receptor through biosynthetic incorporation of fluorescent amino acids at specific sites," J Biol Chem. Aug. 16, 1996;271(33):19991-8.
Van Den Berg, JA et al., "Kluyveromyces as a host for heterologous gene expression: expression and secretion of prochymosin," Biotechnology (N Y). Feb. 1990;8(2):135-9.
Van Hest, JC and DA Tirrell, "Efficient introduction of alkene functionality into proteins in vivo," FEBS Lett. May 22, 1998;428(1-2):68-70.

Van Hest, J. C. et al., "Efficient Incorporation of Unsaturated Methionine Analogues into Proteins in Vivo," J. Am. Chem. Soc. 2000 ;122 (7); 1282-1288.
Van Solingen, P. et JB van der Pleat. "Fusion of yeast spheroplasts," J Bacteriol. May 1977;130(2):946-7.
Veronese, FM et al., "Surface modification of proteins. Activation of monomethoxy-polyethylene glycols by phenylchloroformates and modification of ribonuclease and superoxide dismutase," Appl Biochem Biotechnol. Apr. 1985;11(2):141-52.
Vlak, JM et al., "Functional studies on the p10 gene of Autographa californica nuclear polyhedrosis virus using a recombinant expressing a p10-beta-galactosidase fusion gene," J Gen Virol. Apr. 1988;69 ( Pt 4):765-76.
Wang, Q., et al., "Bioconjugation by Copper(I)-Catalyzed Azide-Alkyne [3 + 2] Cycloaddition," J. Am. Chem. Soc. 2003; 125(11):3192-3193.
Wang, L. et al., "Addition of the keto functional group to the genetic code of *Escherichia coli*," Proc. Natl. Acad. Sci. (2003); 100(1):56-61.
Wang, L et al., "Expanding the genetic code of *Escherichia coli*," Science. Apr. 20, 2001;292(5516):498-500.
Holland, MJ et JP Holland., "Isolation and identification of yeast messenger ribonucleic acids coding for enolase, glyceraldehyde-3-phosphate dehydrogenase, and phosphoglycerate kinase," Biochemistry. Nov. 14, 1978;17(23):4900-7.
Holland, MJ et al., "The primary structures of two yeast enolase genes. Homology between the 5' noncoding flanking regions of yeast enolase and glyceraldehyde-3-phosphate dehydrogenase genes," J Biol Chem. Feb. 10, 1981;256(3)1385-95.
Hsiao, CL et J Carbon, "High-frequency transformation of yeast by plasmids containing the cloned yeast ARG4 gene," Proc Natl Acad Sci U S A. Aug. 1979;76(8):3829-33.
Huisgen, R. in 1,3-Dipolar Cycloaddition Chemistry, vol. 1, 1984; Ed. Padwa A.; John Wiley and Sons, New York, p. 1-176.
Hwang, KJ et al., "Hepatic uptake and degradation of unilamellar sphingomyelin/cholesterol liposomes: a kinetic study," Proc Natl Acad Sci U S A. Jul. 1980;77(7):4030-4.
Ibba, M et al., "Substrate specificity is determined by amino acid binding pocket size in *Escherichia coli* phenylalanyl-tRNA synthetase," Biochemistry. Jun. 14, 1994;33(23):7107-12.
Ibba, M and H Hennecke, "Relaxing the substrate specificity of an aminoacyl-tRNA synthetase allows in vitro and in vivo synthesis of proteins containing unnatural amino acids," FEBS Lett. May 15, 1995;364(3):272-5.
Ito, H. et al., "Transformation of intact yeast cells treated with alkali cations," J. Bacteriol. 1983; 153(1):163-8.
Jackson, DY et al. "A designed peptide ligase for total synthesis of ribonuclease A with unnatural catalytic residues," Science. Oct. 14, 1994;266(5183):243-7.
Jakobsson, PJ et al., "Identification and characterization of a novel human microsomal glutathione S-transferase with leukotriene C4 synthase activity and significant sequence identity to 5-lipoxygenase-activating protein and leukotriene C4 synthase," J Biol Chem. Sep. 6, 1996;271(36):22203-10.
Jencks, W.P., "Studies on the Mechanism of Oxime and Semicarbazone Formation," J. Am. Chem. Soc.; 1959; 81(2):475-481.
Joppich, M. et al. "Peptides Flanked by Two Polymer Chains, 1; Synthesis of Glycyl-L-tryptophylglycine Substituted by Poly(ethylene oxide) at both the Carboxy and the Amino End Groups," Makromol. Chem. 1979;180:1381-4.
Kaiser, ET. "Synthetic approaches to biologically active peptides and proteins including enzymes," Acc Chem Res, (1989); 22(2):47-54.
Kaiser, ET et al. "The chemical modification of enzymatic specificity," Annu Rev Biochem. 1985;54:565-95.
Kaiser, ET and DS Lawrence. "Chemical mutation of enzyme active sites," Science. Nov. 2, 1984;226(4674):505-11.
Karlin, S and SF Altschul "Applications and statistics for multiple high-scoring segments in molecular sequences," Proc Natl Acad Sci U S A. Jun. 15, 1993;90(12):5873-7.

(56) References Cited

OTHER PUBLICATIONS

Kayser, B., et al., "Alkyne bridged alpha-amino acids by palladium mediated coupling of alkynes with N-t-Boc-4-iodo-phenylalanine methyl ester," Tetrahedron (1997); 53(7): 2475-2484.
Kelly, JM and MJ Hynes, "Transformation of Aspergillus niger by the amdS gene of Aspergillus nidulans," EMBO J. 1985; 4(2):475-479.
Kiick, K. L. and D. A. Tirrell, "Protein Engineering by In Vivo Incorporation of Non-Natural Amino Acids: Control of Incorporation of Methionine Analogues by Methionyl-tRNA Synthetase," Tetrahedron (2000), 56:9487-9493.
Kiick, KL et al., "Incorporation of azides into recombinant proteins for chemoselective modification by the Staudinger ligation," Proc Natl Acad Sci U S A. Jan. 8, 2002;99(1):19-24. Epub Dec. 18, 2001.
Kim, DM and JR Swartz, "Regeneration of adenosine triphosphate from glycolytic intermediates for cell-free protein synthesis," Biotechnol Bioeng. Aug. 20, 2001;74(4):309-16.
Kim, DM and JR Swartz, "Oxalate improves protein synthesis by enhancing ATP supply in a cell-free free system derived from *Escherichia coli*," Biotechnology Letters, 2000; 22:1537-1542.
Kim, DM, and JR Swartz, "Prolonging cell-free protein synthesis by selective reagent additions," Biotechnol Prog. May-Jun. 2000;16(3):385-90.
Kim, DM and JR Swartz, "Prolonging cell-free protein synthesis with a novel ATP regeneration system," Biotechnol Bioeng. 1999;66(3):180-8.
King, F.E. & Kidd, D.A.A. "A New Synthesis of Glutamine and of gamma-Dipeptides of Glutamic Acid from Phthylated Intermediates," J. Chem. Soc. 1949; 3315-3319.
Kingsman, AJ et al., "Replication in *Saccharomyces cerevisiae* of plasmid pBR313 carrying DNA from the yeast trpl region," Gene. Oct. 1979;7(2):141-52.
Kitts, PA et al. "Linearization of baculovirus DNA enhances the recovery of recombinant virus expression vectors," Nucleic Acids Res. Oct. 11, 1990;18(19):5667-72.
Klein, TM et al., "High-velocity microprojectiles for delivering nucleic acids into living cells," Nature 1987; 327(6117):70-73.
Kobayashi, T. et al., "Structural basis for orthogonal tRNA specificities of tyrosyl-tRNA synthetases for genetic code expansion," Nature Structural Biology (2003); 10(6):425-432.
Kogan, TP. "The synthesis of substituted methoxy-poly(ethyleneglycol) derivatives suitable for selective protein modification," Synthetic Comm. 1992; 22(16):2417-24.
Kool, ET. "Synthetically modified DNAs as substrates for polymerases," Curr Opin Chem Biol. Dec. 2000;4(6):602-8.
Koskinen, A.M.P. & Rapoport, H. "Synthesis of 4-Substituted Prolines as Conformationally Constrained Amino Acid Analogues," J. Org. Chem. (1989) 54(8):1859-1866.
Kost, TA et al., "Production of a urokinase plasminogen activator-IgG fusion protein (uPA-IgG) in the baculovirus expression system," Gene. Apr. 29, 1997;190(1):139-44.
Kramer, W et al., "The gapped duplex DNA approach to oligo-nucleotide-directed mutation construction," Nucleic Acids Res. Dec. 21, 1984;12(24):9441-56.
Kramer, W & Fritz HJ. "Oligonucleotide-directed construction of mutations via gapped duplex DNA" Methods Enzymol. 1987;154:350-67.
Kramer, W. et al., "Improved enzymatic in vitro reactions in the gapped duplex DNA approach to oligonucleotide-directed construction of mutations," Nucleic Acids Res. Jul. 25, 1988;16(14B):7207.
Abuchowski, A. et al. "Cancer therapy with chemically modified enzymes. I. Antitumor properties of polyethylene glycol-asparaginase conjugates," Cancer Biochem Biophys. Jun. 1984;7(2):175-86.
Altschul, SF et al. "Gapped BLAST and PSI-BLAST: a new generation of protein database search programs," Nucleic Acids Res. Sep. 1, 1997;25(17):3389-402.
Altschul, SF et al. "Basic local alignment search tool," J Mol Biol. Oct. 5, 1990;215(3):403-10.

Amann, E et al., "Vectors bearing a hybrid trp-lac promoter useful for regulated expression of cloned genes in *Escherichia coli*," Gene. Nov. 1983;25(2-3):167-78.
Anderson, JC et al., "Exploring the limits of codon and anticodon size," Chem Biol. Feb. 2002;9(2):237-44.
Andresz, H et al. Abstract of "Chemische Synthese verzweigter Polysaccharide, 5; Kopplung von Oligosacchariden and Amylose an verschiedene Träger durch Hydrazonbindung," Makromol. Chem. 1978;179:301 Abstract.
Arnold, FH. "Protein engineering for unusual environments," Curr Opin Biotechnol. Aug. 1993;4(4):450-5.
Azoulay, M., et al. "Glutamine analogues as Potential Antimalarials," Eur. J. Med. Chem. (1991); 26(2):201-5.
Bain, JD, et al. "Biosynthetic site-specific incorporation of a non-natural amino acid into a polypeptide," J. Am Chem Soc 1989;111(20):8013-8014.
Ballance, DJ et al., "Transformation of Aspergillus nidulans by the orotidine-5'-phosphate decarboxylase gene of Neurospora crassa," Biochem Biophys Res Commun. Apr. 15, 1983;112(1):284-9.
Barany, F. et al., "Genetic disease detection and DNA amplification using cloned thermostable ligase," Proc Natl Acad Sci U S A. Jan. 1, 1991;88(1):189-93.
Barton, DHR et al., "Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives," Tetrahedron (1987) 43:4297-4308.
Bass, S et al., "Mutant Trp repressors with new DNA-binding specificities," Science (1988) 242:240-245.
Batzer, MA et al., "Enhanced evolutionary PCR using oligonucleotides with inosine at the 3'-terminus," Nucleic Acids Res. 1991 Step 25;19(18):5081.
Beach, D et al., "Functionally homologous cell cycle control genes in budding and fission yeast," Nature Dec. 1982; 300:706-709.
Beauchamp, CO et al., "A new procedure for the synthesis of polyethylene glycol-protein adducts; effects on function, receptor recognition, and clearance of superoxide dismutase, lactoferrin, and alpha 2-macroglobulin," Anal Biochem. May 1983;131(1):25-33.
Bernstein, FC, et al. "The protein data bank: a computer-based archival file for macromolecular structures," J. Mol. Biol. 1977; 112:535-542.
Boissel, JP et al., "Erythropoietin structure-function relationships. Mutant proteins that test a model of tertiary structure," J Biol Chem. Jul. 25, 1993;268(21):15983-93.
Boles, JO et al. "Bio-incorporation of telluromethionine into buried residues of dihydrofolate reductase," Nat Struct Biol. May 1994;1(5):283-4.
Botstein, D et D Shortle, "Strategies and applications of in vitro mutagenesis," Science. Sep. 20, 1985;229(4719):1193-201.
Brunner, J. "New photolabeling and crosslinking methods," Annu Rev Biochem. 1993;62:483-514.
Buchner, J. et al., "A method for increasing the yield of properly folded recombinant fusion proteins: Single-chain immunotoxins from renaturation of bacterial inclusion bodies," Anal. Biochem. 1992; 205(2): 263-270.
Bückmann et al. "Functionalization of Poly(ethylene glycol) and Monomethoxy-Poly(ethylene glycol)," Makromol. Chem. 1981;182:1379-84.
Budisa, N et al. "High-level biosynthetic substitution of methionine in proteins by its analogs 2-aminohexanoic acid, selenomethionine, telluromethionine and ethionine in *Escherichia coli*," Eur J Biochem. Jun. 1, 1995;230(2):788-96.
Budisa, N et al., "Bioincorporation of telluromethionine into proteins: a promising new approach for X-ray structure analysis of proteins," J Mol Biol. Jul. 25, 1997;270(4):616-23.
Budisa, N et al., "Toward the experimental codon reassignment in vivo: protein building with an expanded amino acid repertoire," FASEB J. Jan. 1999;13(1):41-51.
Cai, X-Y et al., "Expression, Purification, and Characterization of an Activated Cytokine-Suppressive Anti-inflammatory Drug-Binding Protein 2 (CSBP2) Kinase from Baculovirus-Infected Insect Cells," Protein Expression and Purification 1997; 10(2):263-74.

(56) References Cited

OTHER PUBLICATIONS

Carbonell, LF et al., "Baculovirus-mediated expression of bacterial genes in dipteran and mammalian cells," J Virol. Oct. 1985;56(1):153-60.
Carrasco, M. and R. Brown, "A Versatile Set of Aminooxy Amino Acids for the Synthesis of Neoglycopeptides," J. Org. Chem. (2003); 68(23): 8853-8858.
Carter, P. "Site-directed mutagenesis," Biochem J. Jul. 1, 1986; 237(1):1-7.
Carter, P et al. "Improved oligonucleotide site-directed mutagenesis using M13 vectors" Nucleic Acids Res. Jun. 25, 1985;13(12):4431-43.
Carter, P. "Improved oligonucleotide-directed mutagenesis using M13 vectors" Methods Enzymol. 1987;154:382-403.
Chaiken, IM. "Semisynthetic peptides and proteins," CRC Crit Rev Biochem. 1981;11(3):255-301.
Chin, JW et al., "Addition of p-azido-L-phenylalanine to the genetic code of E. coli," J Am Chem Soc. Aug. 7, 2002;124(31):9026-7.
Chin, JW et al., "Addition of a photocrosslinking amino acid to the genetic code of Escherichia coli," Proc Natl Acad Sci U S A. Aug. 20, 2002;99(17):11020-4. Epub Aug. 1, 2002.
Chin, JW et al., "An expanded eukaryotic genetic code," Science. Aug. 15, 2003;301(5635):964-7.
Chin, JW & P. G. Schultz, "In vivo photocrosslinking with unnatural amino acid mutagenesis," Chembiochem. Nov. 4, 2002; 3(11): 1135-7.
Christie, B.D. & Rapoport, H. "Synthesis of Optically Pure Pipecolates from L-Asparagine. Application to the Total Synthesis of (+)-Apovincamine through Amino Acid Decarbonylation and Iminium Ion Cyclization," J. Org. Chem. 1985;50(8):1239-1246.
Clark, R et al., "Long-acting growth hormones produced by conjugation with polyethylene glycol," J Biol Chem. Sep. 6, 1996;271(36):21969-77.
Corey, D.R., Schultz, P.G. "Generation of a hybrid sequence-specific single-stranded deoxyribonuclease," Science 1987; 238(4832):1401-1403.
Cornish, VW, et al., "Site-Specific Protein Modification Using a Ketone Handle," J. Am. Chem. Soc. 1996; 118(34):8150-8151.
Cornish, VW et al., "Probing Protein Structure and Function with an Expanded Genetic Code," Angew Chem Int Ed Engl,1995;34(6):621-33.
Craig, J.C. et al. "Absolute Configuration of the Enantiomers of 7-Chloro-4 [[4-(diethylamino)-1-methylbutyl]amino]quinoline (Chloroquine)," J. Org. Chem. 1988; 53(6):1167-1170.
Cregg, JM et al., "Pichia pastoris as a host system for transformations," Mol Cell Biol. Dec. 1985;5(12):3376-85.
Crick, FHC, et al. "General nature of the genetic code for proteins," Nature. Dec. 30, 1961;192:1227-32.
Dale et al., Oligonucleotide-directed random mutagenesis using the phosphorothioate method, Methods Mol. Biol.1996;57:369-374.
Das, S et al., "Transformation of Kluyveromyces fragilis," J Bacteriol. Jun. 1984;158(3):1165-7.
Dawson, P. E. and S. B. H. Kent, "Synthesis of native proteins by chemical ligation," Annu. Rev. Biochem. 2000; 69:923-60.
De Boer, HA et al., "The tac promoter: a functional hybrid derived from the trp and lac promoters," Proc Natl Acad Sci U S A. Jan. 1983;80(1):21-5.
De Louvencourt, L et al., "Transformation of Kluyveromyces lactis by killer plasmid DNA," J Bacteriol. May 1983;154(2):737-42.
Kramer, B. et al., "Different base/base mismatches are corrected with different efficiencies by the methyl-directed DNA mismatch-repair system of E. coli," Cell. Oct. 1984;38(3):879-87.
Kreitman, RJ and I. Pastan "Purification and characterization of IL6-PE4E, a recombinant fusion of interleukin 6 with Pseudomonas exotoxin," Bioconjug Chem. Nov.-Dec. 1993;4(6):581-5.
Krieg, UC, et al. "Photocrosslinking of the signal sequence of nascent preprolactin to the 54-kilodalton polypeptide of the signal recognition particle," Proc Natl Acad Sci U S A. Nov. 1986;83(22):8604-8.
Kunitani, M. et al., "Reversed-phase chromatography of interleukin-2 muteins," J Chromatogr. May 30, 1986;359:391-402.
Kunkel, "The efficiency of oligonucleotide directed mutagenesis," in Nucleic Acids & Molecular Biology 1987; Eckstein, F. and Lilley, D.M.J. eds.; Springer Verlag, Berlin; 124-135.
Kunkel, TA "Rapid and efficient site-specific mutagenesis without phenotypic selection," Proc Natl Acad Sci U S A. Jan. 1985;82(2):488-92.
Kunkel, TA et al., "Rapid and efficient site-specific mutagenesis without phenotypic selection," Methods Enzymol. 1987;154:367-82.
Kunze, G et al., "Transformation of the industrially important yeasts Candida maltosa and Pichia guilliermondii," J. Basic Microbiol. 1985; 25:141-4.
Kurtz et al., "Integrative transformation of Candida albicans, using a cloned Candida ADE2 gene," Mol Cell Biol. Jan. 1986;6(1):142-9.
Kurtzhals, P et al., "Albumin binding of insulins acylated with fatty acids: characterization of the ligand-protein interaction and correlation between binding affinity and timing of the insulin effect in vivo," Biochem J. Dec. 15, 1995;312 ( Pt 3):725-31.
Langer, R et al., "Biocompatibility of polymeric delivery systems for macromolecules," J Biomed Mater Res. Mar. 1981;15(2):267-77.
Langer, R. "Controlled release of macromolecules," Chem. Tech. 1982; 12: 98-105.
Liebman, JM et al., "When less is more: enhanced baculovirus production of recombinant proteins at very low multiplicities of infection," Biotechniques. Jan. 1999;26(1):36-8, 40, 42.
Ling, MM et BH Robinson, "Approaches to DNA mutagenesis: an overview" Anal Biochem. Dec. 15, 1997;254(2):157-78.
Wang, L & PG Schultz, "Expanding the genetic code," Chem Commun (Camb). Jan. 7, 2002;1:1-11.
Weissmann, C. "The cloning of interferon and other mistakes." in Interferon 3 1981; ed. I. Gresser; Academic Press, London, 101-134.
Wells, JA et al., "Importance of hydrogen-bond formation in stabilizing the transition state of subtilisin," Phil. Trans. R. Soc. Lond. A 1986; 317: 415-423.
Wells, JA et al., "Cassette mutagenesis: an efficient method for generation of multiple mutations at defined sites," Gene. 1985;34(2-3):315-23.
Woghiren, C et al. "Protected thiol-polyethylene glycol: a new activated polymer for reversible protein modification," Bioconjug Chem. Sep.-Oct. 1993;4(5):314-8.
Wong, SS et LJ Wong, "Chemical crosslinking and the stabilization of proteins and enzymes," Enzyme Microb Technol. Nov. 1992;14(11):866-74.
Wright, K. "Biotechnology: Insect virus as super-vector?," Nature (1986) 321(6072):718.
Duncan, R. "The dawning era of polymer therapeutics," Nat Rev Drug Discov May 2003;2(5):347-60.
Gaertner, HF et RE Offord. "Site-specific attachment of functionalized poly(ethylene glycol) to the amino terminus of proteins," Bioconjug Chem Jan.-Feb. 1996;7(1):38-44.
Gu, Z et al. "Chromatographic methods for the isolation of, and refolding of proteins from, Escherichia coli inclusion bodies," Protein Expr Purif. Jun. 2002;25(1):174-9.
Hohsaka, T et M Sisido. "Incorporation of non-natural amino acids into proteins," Curr Opin Chem Biol. Dec. 2002;6(6):809-15.
Lilie, H et al. "Advances in refolding of proteins produced in E. coli," Curr Opin Biotechnol. Oct. 1998;9(5):497-501.
Tsumoto, K et al. "Practical considerations in refolding proteins from inclusion bodies," Protein Expr Purif. Mar. 2003;28(1):1-8.
Wang, W. "Instability, stabilization, and formulation of liquid protein pharmaceuticals," Int J Pharm. Aug. 20, 1999;185(2):129-88.
Debinski, W et al. "A wide range of human cancers express interleukin 4 (IL4) receptors that can be targeted with chimeric toxin composed of IL4 and Pseudomonas exotoxin," J Biol Chem. Jul. 5, 1993;268(19):14065-70.
Deiters, A., et al., "Adding Amino Acids with Novel Reactivity to the Genetic Code of Saccharomyces cerevisiae," J. Am. Chem. Soc. 2003; 125(39):11782-11783.

(56) References Cited

OTHER PUBLICATIONS

Delgado, C et al., "The uses and properties of PEG-linked proteins," Crit Rev Ther Drug Carrier Syst. 1992;9(3-4):249-304.
Dennis, MS et al., "Albumin binding as a general strategy for improving the pharmacokinetics of proteins," J Biol Chem. Sep. 20, 2002;277(38):35035-43. Epub Jul. 15, 2002.
Dolphin, CT et al., "Missense mutation in flavin-containing monooxygenase 3 gene, FMO3, underlies fish-odour syndrome," Nat Genet. Dec. 1997;17(4):491-4.
Doring, V et al., "Enlarging the amino acid set of *Escherichia coli* by infiltration of the valine coding pathway," Science. Apr. 20, 2001;292(5516):501-4.
Dougherty, DA. "Unnatural amino acids as probes of protein structure and function," Curr Opin Chem Biol. Dec. 2000;4(6):645-52.
Duewel, H et al., "Incorporation of trifluoromethionine into a phage lysozyme: implications and a new marker for use in protein 19F NMR," Biochemistry. Mar. 18, 1997;36(11):3404-16.
Eghtedarzadeh MK & S Henikoff "Use of oligonucleotides to generate large deletions" Nucleic Acids Res. Jun. 25, 1986;14(12):5115.
Elling L et MR Kula., "Immunoaffinity partitioning: synthesis and use of polyethylene glycol-oxirane for coupling to bovine serum albumin and monoclonal antibodies," Biotechnol Appl Biochem. Jun. 1991;13(3):354-62.
Elliott, S et al., "Yeast-derived recombinant human insulin-like growth factor I: production, purification, and structural characterization," J Protein Chem. Feb. 1990;9(1):95-104.
Ellman, J.A., Mendel, D., Anthony-Cahill, S., Noren, C.J., Schultz, P.G. "Biosynthetic method for introducing unnatural amino acids site-specifically into proteins," Methods in Enz., 1992; 202:301-336.
Ellman, JA, et al. "Site-specific incorporation of novel backbone structures into proteins," Science. Jan. 10, 1992;255(5041):197-200.
England, P. M., et al., "Backbone mutations in transmembrane domains of a ligand-gated ion channel: implications for the mechanism of gating," Cell. Jan. 8, 1999;96(1):89-98.
Eppstein et al., "Biological Activity of Liposome-Encapsulated Murine Interferon is Mediated by a Cell Membrane Receptor," Proc. Natl. Acad. Sci. U.S.A.(1985); 82: 3688-3692.
Fieschko, JC et al., "Controlled expression and purification of human immune interferon from high-cell-density fermentations of *Saccharomyces cerevisiae*," Biotech. Bioeng. (1987) 29(9):1113-21.
Forster, AC et al., "Programming peptidomimetic syntheses by translating genetic codes designed de novo," Proc Natl Acad Sci U S A. May 27, 2003;100(11):6353-7. Epub May 16, 2003.
Frankel, A et al., "Encodamers: unnatural peptide oligomers encoded in RNA," Chem Biol. Nov. 2003;10(11):1043-50.
Fraser, MJ et al., "Expression of eucaryotic genes in insect cell cultures," In Vitro Cell. Dev. Biol. 1989; 25:225-235.
Friedman, O.M. & R. Chatterrji. "Synthesis of Derivatives of Glutamine as Model Substrates for Anti-Tumor Agents," J. Am. Chem. Soc. 1959; 81(14):3750-3752.
Fritz HJ et al., "Oligonucleotide-directed construction of mutations: a gapped duplex DNA procedure without enzymatic reactions in vitro," Nucleic Acids Res. Jul. 25, 1988;16(14B):6987-99.
Fromm, M. et al., "Expression of Genes Transferred into Monocot and Dicot Plant Cells by Electroporation," Proc. Natl. Acad. Sci. USA (1985) 82:5824-8.
Furter, R. "Expansion of the genetic code: site-directed p-fluorophenylalanine incorporation in *Escherichia coli*," Protein Sci. Feb. 1998;7(2):419-26.
Gaertner, HF et al., "Construction of protein analogues by site-specific condensation of unprotected fragments," Bioconjug Chem. May-Jun. 1992;3(3):262-8.
Gaertner, HF et al., "Chemo-enzymic backbone engineering of proteins. Site-specific incorporation of synthetic peptides that mimic the 64-74 disulfide loop of granulocyte colony-stimulating factor," J Biol Chem. Mar. 11, 1994;269(10):7224-30.
Gallivan, JP et al., "Site-specific incorporation of biotinylated amino acids to identify surface-exposed residues in integral membrane proteins," Chem Biol. Oct. 1997;4(10):739-49.
Gellissen, G et al., "Heterologous protein production in yeast," Antonie Van Leeuwenhoek. Aug. 1992;62(1-2):79-93.
Geoghegan, KF and JG Stroh, "Site-directed conjugation of nonpeptide groups to peptides and proteins via periodate oxidation of a 2-amino alcohol. Application to modification at N-terminal serine," Bioconjug Chem. Mar.-Apr. 1992;3(2):138-46.
Gillam, S. & M Smith, "Site-specific mutagenesis using synthetic oligodeoxyribonucleotide primers: I. Optimum conditions and minimum oligodeoxyribonucleotide length," Gene 1979; 8(1):81-97.
Gleeson, MA et al., "Transformation of the methylotrophic yeast hansenula polymorphica," J. Gen. Microbiol. (1986) 132:3459-3465.
Goeddel, DV, "Systems for heterologous gene expression," Methods Enzymol. 1990;185:3-7.
Goeddel, DV et al., "Synthesis of human fibroblast interferon by *E. coli*," Nucleic Acids Res. Sep. 25, 1980;8(18):4057-74.
Goodson RJ et NV Katre. "Site-directed pegylation of recombinant interleukin-2 at its glycosylation site," Biotechnology (N Y). Apr. 1990;8(4):343-6.
Graves, SW et al., "Expression, purification, and initial kinetic characterization of the large subunit of the human mitochondrial DNA polymerase," Biochemistry. Apr. 28, 1998;37(17):6050-8.
Griffin, BA et al., "Specific Covalent Labeling of Recombinant Protein Molecules Inside Live Cells," Science (1998) 281:269-272.
Grundström T et al., "Oligonucleotide-directed mutagenesis by microscale 'shot-gun' gene synthesis," Nucleic Acids Res. May 10, 1985;13(9):3305-16.
Guckian, KM and ET Kool, "Highly Precise Shape Mimicry by a Difluorotoluene Deoxynucleoside, a Replication-Competent Substitute for Thymidine," Angew. Chem. Int. Ed. Engl (1998) 36(24):2825-8.
Hamano-Takaku, F et al., "A mutant *Escherichia coli* tyrosyl-tRNA synthetase utilizes the unnatural amino acid azatyrosine more efficiently than tyrosine," J Biol Chem. Dec. 22, 2000;275(51):40324-8.
Hang, HC and CR Bertozzi, "Chemoselective approaches to glycoprotein assembly," Acc Chem Res. Sep. 2001;34(9):727-36.
Harris, JM et al. "Synthesis and Characterization of Poly(ethylene Glycol) Derivatives," J. Polym. Sci. Chem. Ed. 1984; 22:341-352.
Harris, JM. "Laboratory Synthesis of Polyethylene Glycol Derivatives," JMS-Rev. Macromol. Chem. Phys. 1985;C25(3): 325-373.
Hendrickson, WA et al., "Selenomethionyl proteins produced for analysis by multiwavelength anomalous diffraction (MAD): a vehicle for direct determination of three-dimensional structure," EMBO J. May 1990;9(5):1665-72.
Henikoff, S and JG Henikoff "Amino Acid Substitution Matrices from Protein Blocks," Proc. Natl. Acad. Sci. USA 1992; 89:10915-9.
Hess, B. et al., "Cooperation of glycolytic enzymes," J. Adv. Enzyme Reg. (1969) 7:149-67.
Hinnen, A et al., "Transformation of yeast," Proc Natl Acad Sci U S A. Apr. 1978;75(4):1929-33.
Hirao, I et al., "An unnatural base pair for incorporating amino acid analogues into proteins," Nat Biotechnol. Feb. 2002;20(2):177-82.
Hitzeman, RA et al., "Isolation and characterization of the yeast 3-phosphoglycerokinase gene (PGK) by an immunological screening technique," J. Biol Chem. Dec. 25, 1980;255(24):12073-80.
Hofmann, K., et H. Bohn. "Studies on polypeptides. XXXVI. The effect of pyrazole-imidazole replacements on the S-protein activating potency of an S-peptide fragment," J. Am Chem, (1966); 88(24):5914-5919.
Hohsaka, T et al., "Efficient Incorporation of Nonnatural Amino Acids with Large Aromatic Groups into Streptavidin in In Vitro Protein Synthesizing Systems," J. Am. Chem. Soc. 1999; 121(1); 34-40.

(56) References Cited

OTHER PUBLICATIONS

Hohsaka, T et al., "Incorporation of Two Different Nonnatural Amino Acids Independently into a Single Protein through Extension of the Genetic Code," J. Am. Chem. Soc. 1999; 121(51):12194-12195.

Liu, H. et al. "A Method for the Generation of Glycoprotein Mimetics," J. Am. Chem. Soc. 2003 125(7): 1702-1703.

Liu, D.R. & Schultz, P.G. "Progress toward the evolution of an organism with an expanded genetic code," Proc Natl Acad Sci U S A. Apr. 27, 1999;96(9):4780-5.

Lorimer, I. A. et I. Pastan, "Random recombination of antibody single chain Fv sequences after fragmentation with DNaseI in the presence of Mn2+," Nucleic Acids Res. Aug. 11, 1995;23(15):3067-8.

Lu, T. et al. "Probing ion permeation and gating in a K +channel with backbone mutations in the selectivity filter," Nature Neurosci. Mar. 2001;4(3):239-246.

Luckow, VA and MD Summers, "High level expression of nonfused foreign genes with Autographa californica nuclear polyhedrosis virus expression vectors," Virology. May 1989;170(1):31-9.

Ma, C et al., "In vitro protein engineering using synthetic tRNA(Ala) with different anticodons," Biochemistry. Aug. 10, 1993;32(31):7939-45.

Magliery, TJ et al. "Expanding the Genetic Code: Selection of Efficient Suppressors of Four-base Codons and Identification of "Shifty" Four-base Codons with a Library Approach in *Escherichia coli*," J Mol Biol. Mar. 30, 2001;307(3):755-69.

Mahal, L. K., et al., "Engineering chemical reactivity on cell surfaces through oligosaccharide biosynthesis," Science. May 16, 1997;276(5315):1125-8.

Makrides, SC et al., "Extended in vivo half-life of human soluble complement receptor type 1 fused to a serum albumin-binding receptor," J Pharmacol Exp Ther. Apr. 1996;277(1):534-42.

Mamot, C, et al., "Epidermal growth factor receptor (EGFR)-targeted immunoliposomes mediate specific and efficient drug delivery to EGFR- and EGFRvIII-overexpressing tumor cells," Cancer Res. Jun. 15, 2003;63(12):3154-61.

Mandecki, W. Oligonucleotide-directed double-strand break repair in plasmids of *Escherichia coli*: a method for site-specific mutagenesis, Proc Natl Acad Sci U S A. Oct. 1986;83(19):7177-81.

Mann, SG and LA King, "Efficient transfection of insect cells with baculovirus DNA using electroporation," J Gen Virol. Dec. 1989;70 (Pt 12):3501-5.

Matsoukas, JM et al., "Differences in backbone structure between angiotensin II agonists and type I antagonists," J Med Chem. Nov. 10, 1995;38(23):4660-9.

McMinn, DL et al., "Efforts toward Expansion of the Genetic Alphabet: DNA Polymerase Recognition of a Highly Stable, Self-Pairing Hydrophobic Base," J. Am. Chem. Soc. 1999; 121(49):11585-6.

Meggers, E et al., "A Novel Copper-Mediated DNA Base Pair," J. Am. Chem. Soc. 2000; 122(43):10714-10715.

Mehvar, R.,"Modulation of the pharmacokinetics and pharmacodynamics of proteins by polyethylene glycol conjugation" J Pharm Pharm Sci. Jan.-Apr. 2000;3(1):125-36.

Mendel, D, et al. "Site-directed mutagenesis with an expanded genetic code," Annu Rev Biophys Biomol Struct. 1995;24:435-62.

Miller, LK, "Baculoviruses as gene expression vectors," Ann. Rev. Microbiol. 1988; 42:177-99.

Miller, LK. "Insect baculoviruses: powerful gene expression vectors," Bioessays. Oct. 1989;11(4):91-5.

Miller, JC et al. "Flash decaging of tyrosine sidechains in an ion channel," Neuron. Apr. 1998;20(4):619-24.

Minks, C. et al., Noninvasive tracing of recombinant proteins with "fluorophenylalanine-fingers," Anal Biochem. Aug. 15, 2000;284(1):29-34.

Miyanohara, A et al., "Expression of hepatitis B surface antigen gene in yeast," Proc Natl Acad Sci U S A. Jan. 1983;80(1):1-5.

Moore, B. et al., "Quadruplet codons: implications for code expansion and the specification of translation step size," J. Mol. Biol. 2000; 298(2):195-209.

Mosbach, K. et al., "Formation of proinsulin by immobilized Bacillus subtilis," Nature Apr. 1983; 302:543-545.

Nakamaye, KL & Eckstein F, "Inhibition of restriction endonuclease Nci I cleavage by phosphorothioate groups and its application to oligonucleotide-directed mutagenesis" Nucleic Acids Res. Dec. 22, 1986;14(24):9679-98.

Nakatsuka, T., et al. "Peptide segment coupling catalyzed by the semisynthetic enzyme thiosubtilisin," J Am Chem Soc, 1987; 109(12): 3808-3810.

Nambiar, KP et al., "Total synthesis and cloning of a gene coding for the ribonuclease S protein," Science (1984) 223: 1299-1301.

Needleman, SB and Wunsch CD, "A general method applicable to the search for similarities in the amino acid sequence of two proteins," J Mol Biol. Mar. 1970;48(3):443-53.

Neet, KE et al. "Properties of thiol-subtilisin. The consequences of converting the active serine residue to cysteine in a serine protease," J Biol Chem. Dec. 25, 1968;243(24):6392-401.

Nielsen, UB, et al., "Therapeutic efficacy of anti-ErbB2 immunoliposomes targeted by a phage antibody selected for cellular endocytosis," Biochim Biophys Acta. Aug. 19, 2002;1591(1-3):109-118.

Nomura, T. et al., "Purification, cDNA Cloning, and Expression of UDP-Gal: Glucosylceramide-1,4-Galactosyltransferase from Rat Brain," J. Biol. Chem. 1998; 273(22):13570-7.

Noren, CJ et al. "A general method for site-specific incorporation of unnatural amino acids into proteins," Science. Apr. 14, 1989;244(4901):182-8.

Nowak, MW et al., "Nicotinic receptor binding site probed with unnatural amino acid incorporation in intact cells," Science. Apr. 21, 1995;268(5209):439-42.

Ogawa, AK et al., "Efforts toward the Expansion of the Genetic Alphabet: Information Storage and Replication with Unnatural Hydrophobic Base Pairs," J. Am. Chem. Soc. 2000; 122(14):3274-3287.

Ogawa, AK et al., "Rational Design of an Unnatural Base Pair with Increased Kinetic Selectivity," J. Am. Chem. Soc. 2000; 122(36); 8803-8804.

Ohtsuka, E et al., "An alternative approach to deoxyoligonucleotides as hybridization probes by insertion of deoxyinosine at ambiguous codon positions," J Biol Chem. Mar. 10, 1985;260(5):2605-8.

Olson et al. "Preparation and Characterization of Poly(ethylene glycol)yated Human Growth Hormone Antagonist," in Poly(ethylene glycol) Chemistry & Biological Applications, 1997; Eds. JM Harris & S. Zalipsky; ACS, Washington, D.C., 170-181.

Padwa, A. "Intermolecular 1,3-Dipolar Cycloadditions," in Comprehensive Organic Synthesis, vol. 4, (1991) Ed. Trost, B. M.; Pergamon, Oxford, 1069-1109.

Palva, I et al., "Secretion of interferon by Bacillus subtilis," Gene. May-Jun. 1983;22(2-3):229-35.

Park, JW, et al., "Development of anti-p185HER2 immunoliposomes for cancer therapy," Proc Natl Acad Sci U S A. Feb. 28, 1995;92(5):1327-31.

Park, JW, et al., "Anti-HER2 immunoliposomes: enhanced efficacy attributable to targeted delivery," Clin Cancer Res. Apr. 2002;8(4):1172-81.

Patnaik, R. and JR Swartz, "*E. coli*-based in vitro transcription/translation: in vivo-specific synthesis rates and high yields in a batch system," Biotechniques. May 1998;24(5):862-8.

Pearson, WR and DJ Lipman, "Improved tools for biological sequence comparison," Proc Natl Acad Sci U S A. Apr. 1988;85(8):2444-8.

Pepinsky, RB., et al., "Improved pharmacokinetic properties of a polyethylene glycol-modified form of interferon-beta-1a with preserved in vitro bioactivity," J Pharmacol Exp Ther. Jun. 2001;297(3):1059-66.

Piccirilli, JA et al., "Enzymatic incorporation of a new base pair into DNA and RNA extends the genetic alphabet," Nature 1990; 343:33-37.

(56) References Cited

OTHER PUBLICATIONS

Pintar, A et al. "CX, an algorithm that identifies protruding atoms in proteins," Bioinformatics. Jul. 2002;18(7):980-4.
Pitha, J et al. "Detergents linked to polysaccharides: preparation and effects on membranes and cells," Eur J Biochem. Feb. 15, 1979;94(1):11-8.
Polgar, L. and ML Bender. "A new enzyme containing a synthetically formed active site. Thiol-subtilisin." J. Am Chem Soc., 1966; 88(13): 3153-3154.
Pollack, SJ et al. "Introduction of nucleophiles and spectroscopic probes into antibody combining sites," Science. Nov. 18, 1988;242(4881):1038-40.
Preneta, AZ. "Separation on the basis of size: gel permeation chromatography," in Protein Purification Methods, a practical approach, 1989; Eds. Harris & Angal; IRL Press, Oxford; 293-306.
Yelton, MM et al., "Transformation of Aspergillus nidulans by using a trpC plasmid," Proc Natl Acad Sci U S A. Mar. 1984;81(5):1470-4.
Yelverton, E et al., "Bacterial synthesis of a novel human leukocyte interferon," Nucleic Acids Res. Feb. 11, 1981;9(3):731-41.
Zalipsky, S et al. "Attachment of drugs to polyethylene glycols," Eur. Polymer Journal. 1983 19(12):1177-83.
Zalipsky, S. "Functionalized poly(ethylene glycol) for preparation of biologically relevant conjugates," Bioconjug Chem. Mar.-Apr. 1995;6(2):150-65.
Zhang, Z., et al. "A new strategy for the site-specific modification of proteins in vivo," Biochemistry. Jun. 10, 2003;42(22):6735-46.
Zoller, MJ & M Smith, "Oligonucleotide-directed mutagenesis using M13-derived vectors: an efficient and general procedure for the production of point mutations in any fragment of DNA" Nucleic Acids Res. Oct. 25, 1982;10(20):6487-500.
Zoller, MJ & M. Smith, "Oligonucleotide-directed mutagenesis of DNA fragments cloned into M13 vectors" Methods Enzymol. 1983;100:468-500.
Raibaud, O et M Schwartz. "Positive control of transcription initiation in bacteria," Annu Rev Genet. 1984;18:173-206.
Reverey, H. et al., "Differential Fatty Acid Selection during Biosynthetic S-Acylation of a Transmembrane Protein (HEF) and Other Proteins in Insect Cells (Sf9) and in Mammalian Cells (CV1)," J. Biol. Chem. 1996; 271(39):23607-10.
Rivier, J et R McClintock, "Reversed-phase high-performance liquid chromatography of insulins from different species," J Chromatogr. Sep. 23, 1983;268(1):112-9.
Roberts, et al., "Generation of an antibody with enhanced affinity and specificity for its antigen by protein engineering," Nature 1987;328:731-734.
Roberts, RW and JW Szostak, "RNA-peptide fusions for the in vitro selection of peptides and proteins," Proc Natl Acad Sci U S A. Nov. 11, 1997;94(23):12297-302.
Roggenkamp, R. et al., "Transformation of the methylotrophic yeast Hansenula polymorpha by autonomous replication and integration vectors," MOL. Genetics and Genomics 1986;202(2):302-8.
Romani et al. "Synthesis of unsymmetrical cystine peptides: directed disulfide pairing with the sulfenohydrazide method," in Chemistry of Peptides and Proteins 1984; eds. Voelter, W. et al.; Walter de Gruyter et al., Berlin; vol. 2:29-33.
Romanos, MA et al., "Foreign gene expression in yeast: a review," Yeast. Jun. 1992;8(6):423-88.
Tae, EL et al., "Efforts toward Expansion of the Genetic Alphabet: Replication of DNA with Three Base Pairs," J. Am. Chem. Soc. 2001; 123(30):7439-7440.
Tang, Y et al., "Fluorinated Coiled-Coil Proteins Prepared In Vivo Display Enhanced Thermal and Chemical Stability," Angew Chem Int Ed Engl. Apr. 17, 2001;40(8):1494-1496.
Taylor, JW et al., "The use of phosphorothioate-modified DNA in restriction enzyme reactions to prepare nicked DNA," Nucleic Acids Res. Dec. 20, 1985;13(24):8749-64.
Taylor, JW et al., "The rapid generation of oligonucleotide-directed mutations at high frequency using phosphorothioate-modified DNA," Nucleic Acids Res. Dec. 20, 1985;13(24):8765-85.

Tijssen, P. "Overview of principles of hybridization and the strategy of nucleic acid assays," in Laboratory Techniques in Biochemistry and Molecular Biology—Hybridization with Nucleic Probes, Part I, 1993; Elsevier Science Publishers, Amsterdam, 19-78.
Tilburn, J. et al., "Transformation by integration in Aspergillus nidulans," Gene. Dec. 1983;26(2-3):205-21.
Mehl, RA et al. "Generation of a bacterium with a 21 amino acid genetic code," J Am Chem Soc. Jan. 29, 2003;125(4):935-9.
Santoro, SW et al. "An efficient system for the evolution of aminoacyl-tRNA synthetase specificity," Nat Biotechnol. Oct. 2002;20(10):1044-8. Epub Sep. 16, 2002.
Caliceti, P et FM Veronese. "Pharmacokinetic and biodistribution properties of poly(ethylene glycol)-protein conjugates," Adv Drug Deliv Rev. Sep. 26, 2003;55(10):1261-77.
Clark, EDB, "Refolding of recombinant proteins," Curr Opin Biotechnol Apr. 1, 1998;9(2):157-63.
Clark, EDB, "Protein refolding for industrial processes," Curr Opin Biotechnol Apr. 2001;12(2):202-7.
Davis, GD et al., "New fusion protein systems designed to give soluble expression in *Escherichia coli*," Biotechnol Bioeng Nov. 20, 1999;65(4):382-8.
English Translation of the Opposition Brief filed in the Colombian Application No. 11-049.164.
International Search Report dated May 21, 2010 in PCT/JP2005/013489 filed Sep. 25, 2009.
Written Opinion of the International Searching Authority dated May 21, 2010 in PCT/US2009/058482 filed Sep. 25, 2009.
International Preliminary Report on Patentability dated Mar. 29, 2011 in PCT/US2009/058482 filed Sep. 25, 2009.
Zoller, MJ & Smith M, "Oligonucleotide-directed mutagenesis: a simple method using two oligonucleotide primers and a single-stranded DNA template," Methods Enzymol. 1987;154:329-50.
Balint et al., "Antibody engineering by parsimonious mutagenesis", Gene (1993) 137(1):109-18.
Barbas III et al. "In vitro evolution of a neutralizing human antibody to human immunodeficiency virus type 1 to enhance affinity and broaden strain cross-reactivity", P.N.A.S. USA (1994) 91(9):3809-3813.
Bazan, "Haemopoietic receptors and helical cytokines", Immunology Today (1990) 11(10): 350-354.
Bazan, "Unraveling the Structure of IL-2", Science (1992) 257: 410-411.
Bazan, "Structural Design and Molecular Evolution of a Cytokine Receptor Superfamily", P.N.A.S. USA (1990) 87:6934-6938.
Bittorf et al., "Structural and functional characterisation of recombinant human erythropoietin analogues", FEBS Letters, (1993) 336(1):133-6.
Bondurant et al., "Control of globin gene transcription by erythropoietin in erythroblasts from friend virus-infected mice", Mol. Cell Biol. (1985) 5(4):675-83.
Cheetham et al. "NMR structure of human erythropoietin and a comparison with its receptor bound conformation" Nat Struct Biol. (1998) 5(10):861-866.
Chiba et al. "Tryptophan residue of Trp-Ser-X-Trp-Ser motif in extracellular domains of erythropoietin receptor is essential for signal transduction," Biochim. Biophys. Res. Comm. (1992) 184: 485-490.
Chiswell et al., "Phage antibodies: will new 'colicional' antibodies replace monoclonal antibodies?", Trends in Biotechnology (1992) 10(3):80-84.
Cotes et al., "Bio-assay of erythropoietin in mice made polycythaemic by exposure to air at a reduced pressure", Nature (1961) 191:1065-1067.
Cowgill, et al., "Use of recombinant human erythropoietin for management of anemia in dogs and cats with renal failure", J. Am. Vet. Med. Assoc. (1998) 212(4):521-8.
Darling et al., "Glycosylation of erythropoietin affects receptor binding kinetics: role of electrostatic interactions", Biochemistry (2002) 41(49):14524-14531.
Davidow et al., "Integrative Transformation of the Yeast Yarrowia Lipolytica" Curr. Genet. (1985) 10:39-48.

(56) References Cited

OTHER PUBLICATIONS

Davis et al., "LIFR-beta and gp130 as Heterodimerizing Signal Transducers of the Tripartite CNTF Receptor", Science (1993) 260:1805-1808.
Diederichs et al. "Novel fold and putative receptor binding site of granulocyte-macrophage colony-stimulating factor," Science (1991) 154:1779-1782.
Elliot et al., "Mapping of the active site of recombinant human erythropoietin", Blood, (1997) 89(2):493-502.
Funakoshi et al., "Gene expression of mutant erythropoietin in hepatocellular carcinoma", Biochem. Biophys. Res. Comm. (1993) 195(2):717-22.
Gaillardin et al., "Integrative Transformation of the Yeast Yarrowia Lipolytica" Curr. Genet. (1985) 10:49-58.
Gan et al., "Functional characterization of the internal ribosome entry site of eIF4G mRNA", J. Biol. Chem. (1998) 273(9):5006-12.
Hawkins et al., "Selection of phage antibodies by binding affinity: Mimicking affinity maturation", J. Mol. Biol. (1992) 226(3):889-896.
Hill et al. "The Structure of Granulocyte-Colony-Stimulating Factor and its Relationship to Other Growth Factors," Proc. Natl. Acad. Sci. USA (1993) 90:5167-71.
Hudson, "Recombinant antibody fragments", Curr. Opin. Biotechnol. (1998) 9(4):395-402.
Jacobs et al., Isolation and characterization of genomic and cDNA clones of human erythropoietin, Nature (1985) 313(6005):806-810.
Koury et al., "The role of erythropoietin in the production of principal erythrocyte proteins other than hemoglobin during terminal erythroid differentiation", J. Cell. Physiol. (1986) 126(2):259-65.
Macejak et al., "Internal initiation of translation mediated by the 5' leader of a cellular mRNA", Nature (1991) 353(6339):90-94.
Matthews et al., "A sequential dimerization mechanism for erythropoietin receptor activation", Proc. Natl. Acad. Sci. USA (1996) 93(18):9471-6.
Maynard et al., "Antibody engineering", Annu. Rev. Biomed. Eng. (2000) 2:339-76.
McKay, "Response", Science (1992) 257:412-413.
Milburn et al., "A Novel Dimer Configuration Revealed by the Crystal Structure at 2.4 A Resolution of Human Interleukin-5", Nature (1993) 363:172-176.
Miyanohara et al., "Expression of Hepatitis B Surface Antigen Gene in Yeast", Proc. Natl. Acad. Sci. USA (1983) 80:1-5.
Mordenti et al., "Interspecies scaling of clearance and volume of distribution data for five therapeutic proteins", Pharm Res. (1991) 8(11):1351-9.
Rosenthal, GA. "L-canaline: a potent antimetabolite and anti-cancer agent from leguminous plants," Life Sci.1997;60(19):1635-41.
Rossolini, GM et al., "Use of deoxyinosine-containing primers vs degenerate primers for polymerase chain reaction based on ambiguous sequence information," Mol. Cell. Probes 1994; 8:91-98.
Rostovtsev, VV et al., "A stepwise huisgen cycloaddition process: copper(I)-catalyzed regioselective "ligation" of azides and terminal alkynes," Angew Chem Int Ed Engl Jul. 15, 2002;41(14):2596-9.
Rowles, J et al., "Cloning and characterization of PDK4 on 7q21.3 encoding a fourth pyruvate dehydrogenase kinase isoenzyme in human," J Biol Chem. Sep. 13, 1996;271(37):22376-82.
Sakmar, TP and Khorana HG, "Total synthesis and expression of a gene for the alpha-subunit of bovine rod outer segment guanine nucleotide-binding protein (transducin)" Nucleic Acids Res. Jul. 25, 1988;16(14A):6361-72.
Sandler and Karo, "Polyoxyalkylation of hydroxyl compounds," in Polymer Synthesis, vol. 3, 1980; Academic Press, New York, 138-161.
Sartore, L et al., "Enzyme modification by MPEG with an amino acid or peptide as spacer arms," Appl Biochem Biotechnol. Jan. 1991;27(1):45-54.
Sawhney, AS et al., "Bioerodible Hydrogels Based on Photopolymerized Poly(ethylene glycol)-co-poly(alpha-hydroxy acid) Diacrylate Macromers," Macromolecules 1993; 26(4):581-7.

Saxon, E and C. Bertozzi, "Cell Surface Engineering by a Modified Staudinger Reaction," Science (2000); 287(5460):2007-2010.
Sayers, JR et al., "Strand specific cleavage of phosphorothioate-containing DNA by reaction with restriction endonucleases in the presence of ethidium bromide" Nucleic Acids Res. Feb. 11, 1988;16(3):803-14.
Sayers, JR, et al. "5'-3' exonucleases in phosphorothioate-based oligonucleotide-directed mutagenesis," Nucleic Acids Res. Feb. 11, 1988;16(3):791-802.
Schanbacher, FL et al. "Galactosyltransferase Acceptor Specificity of the Lactose Synthetase A Protein," J. Biol. Chem. 1970; 245(19):5057-5061.
Schmidt, M et al., "Baculovirus-mediated large-scale expression and purification of a polyhistidine-tagged rubella virus capsid protein," Protein Expr Purif. Apr. 1998;12(3):323-30.
Schneider, E., et al., "Functional Purification of a Bacterial ATP-Binding Cassette Transporter Protein (MalK) from the Cytoplasmic Fraction of an Overproducing Strain," Protein Expr. Purif. 1995; 6(1):10-14.
Schnolzer, M. and SBH Kent. "Constructing proteins by dovetailing unprotected synthetic peptides: backbone-engineered HIV protease," Science. Apr. 10, 1992;256(5054):221-5.
Scouten, WH. "A survey of enzyme coupling techniques," Methods Enzymol. 1987;135:30-65.
Shao, J and JP Tam, "Unprotected Peptides as Building Blocks for the Synthesis of Peptide Dendrimers with Oxime, Hydrazone, and Thiazolidine Linkages," J. Am. Chem. Soc. 1995; 117(14):3893-3899.
Sharma, N et al., "Efficient introduction of aryl bromide functionality into proteins in vivo," FEBS Lett. Feb. 4, 2000;467(1):37-40.
Mott et al., "Four-Helix Bundle Growth Factors and their receptors: protein-protein interactions", Current Opinion in Structural Biology (1995) 5:114-121.
Nahri et al., "The Effect of Carbohydrate on the Structure and Stability of Erythropoietin", J. Biol. Chem, (1991) 266(34):23022-23026.
Nambru et al., "Alternative Translation of the Proto-oncogene c-myc by an Internal Ribosome Entry Site", J. Biol. Chem. (1997) 272(51): 32061-32066.
Narhi et al., "Asn to Lys mutations at three sites which are N-glycosylated in the mammalian protein decrease the aggregation of *Escherichia coli*-derived erythropoietin", Protein Engineering, (2001) 14(2):135-40.
Offord, "Protein engineering by chemical means?", Protein Eng., (1987) 1(3):151-157.
Oh et al., "Homeotic gene Antennapedia mRNA contains 5'-noncoding sequences that confer translational initiation by internal ribosome binding", Genes Dev. (1992) 6(9):1643-53.
Paonessa et al., "Two distinct and independent sites on IL-6 trigger gp 130 dimer formation and signaling", EMBO J. (1995) 14(9):1942-51.
Pearson et al., "The Importance of Silica Type for Reverse-Phase Protein Separations", Anal Biochem. (1982) 124:217-230.
Peng et al., Rapid purification of recombinant baculovirus using fluorescence-activated cell sorting, BioTechniques (1993) 14(2):274-7.
Powers et al., "Three-dimensional solution structure of human interleukin-4 by multidimensional heteronuclear magnetic resonance spectroscopy", Science (1992) 256(5064):1673-1677.
Rader et al., "Phage display of combinatorial antibody libraries", Current Opinion Biotech. (1997) 8(4):503-8.
Randolph et al., "Expression, bioactivity, and clinical assessment of recombinant feline erythropoietin", Am J Vet Res. (2004) 65(10):1355-1366.
Redfield et al., "Secondary structure and topology of human interleukin 4 in solution", Biochemistry (1991) 30(46):11029-11035.
Ridgway, "Mammalian Expression Vectors", Vectors, Rodriguez and Denhardt, Eds. (1988, Butterworths, Boston, Mass); Chapter 24; p. 467-92).
Saski et al. "Site-Specific Glycosylation of Human Recombinant Erythropietin: Analysis of Glcyopeptides or Peptides at Each

(56) References Cited

OTHER PUBLICATIONS

Glycosylation Site by Fast Atom Bombardment Mass Spectrometry", Biochemistry (1988) 27:8618-8626.
Schier et al., "Isolation of picomolar affinity anti-c-erbB-2 single-chain Fv by molecular evolution of the complementarity determining regions in the center of the antibody binding site", J. Mol. Biol. (1996) 263(4):551-567.
Spencer et al., "Rabbit Liver Growth Hormone Receptor and Serum Binding Protein", J. Biol. Chem., (1988) 263(16):7862-7867.
Stein et al., "Translation of vascular endothelial growth factor mRNA by internal ribosome entry: implications for translation under hypoxia", Mol. Cell. Biol. (1998) 18(6):3112-9.
Stoneley et al., "C-Myc 5' untranslated region contains an internal ribosome entry segment", Oncogene (1998) 16(3):423-428.
Syed et al., "Efficiency of Signalling Through Cytokine Receptors Depends Critically on Receptor Orientation", Nature, (1998) 395:511-516.
Sytkowski et al. "An erythropoietin fusion protein comprised of identical repeating domains exhibits enhanced biological properties", J Biol Chem. (1999) 274(35):24773-24778.
Sytkowski et al., "Human erythropoietin dimers with markedly enhanced in vivo activity", Proc Natl Acad Sci U S A. (1998) 95(3):1184-1188.
Takeuchi et al. "Comparative study of the asparagine-linked sugar chains of human erythropoietins purified from urine and the culture medium of recombinant Chinese hamster ovary cells", J Biol Chem. (1988) 263(8):3657-3663.
Thompson et al., "Affinity maturation of a high-affinity human monoclonal antibody against the third hypervariable loop of human immunodeficiency virus: use of phage display to improve affinity and broaden strain reactivity", J. Mol. Biol. (1996) 256(1):77-88.
Vagner et al., "Alternative translation of human fibroblast growth factor 2 mRNA occurs by internal entry of ribosomes", Mol. Cell. Biol. (1995) 15(1):35-44.
Walker, et al., "Expression of erythropoietin in cats treated with a recombinant adeno-associated viral vector", Am J Vet Res. 2005 66(3):450-456.
Walter et al. "Three-dimensional structure of recombinant human granulocyte-macrophage colony-stimulating factor," J Mol Biol. (1992) 224(4):1075-1085.
Wen et al., "Erythropoietin structure-function relationships. Identification of functionally important domains", J. Biol. Chem. (1994) 269(36):22839-22846.
Wrighton et al., "Increased potency of an erythropoietin peptide mimetic through covalent dimerization", Nature Biotechnology (1997) 15(12):1261-1265.
Wu et al. "Stepwise in vitro affinity maturation of Vitaxin, an alphav beta3-specific humanized mAb", Proc Natl Acad Sci U S A. (1998) 95(11):6037-6042.
Yang et al. "CDR walking mutagenesis for the affinity maturation of a potent human anti-HIV-1 antibody into the picomolar range", J. Mol. Biol. (1995) 254(3):392-403.
Ye et al., "Ultrabithorax and Antennapedia 5' untranslated regions promote developmentally regulated internal translation initiation", Mol. Cell. Biol. (1997) 17(3):1714-1721.

Shimatake, H et M Rosenberg, "Purified gamma regulatory protein cll positively activates promoters for lysogenic development," Nature Jul. 1981; 292:128-132.
Shine, J and L Dalgarno, "Determinant of cistron specificity in bacterial ribosomes," Nature. Mar. 6, 1975;254(5495):34-8.
Sidman, KR et al., "Controlled release of macromolecules and pharmaceuticals from synthetic polypeptides based on glutamic acid," Biopolymers. Jan. 1983;22(1):547-56.
Sieber, V. et al., "Libraries of hybrid proteins from distantly related sequences," Nature Biotechnology, May 2001;19:456-460.
Siffert, W et al., "Association of a human G-protein beta3 subunit variant with hypertension," Nat Genet. Jan. 1998;18(1):45-8.
Sikorski, RS et al., "A System of Shuttle Vectors and Yeast Host Strains Designed for Efficient Manipulation of DNA in *Saccharomyces cerevisiae*," Genetics (1989) 122:19-27.
Sisk, WP et al., "High-level expression and purification of secreted forms of herpes simplex virus type 1 glycoprotein gD synthesized by baculovirus-infected insect cells," J Virol. Feb. 1994;68(2):766-75.
Sjolander, A et al., "The serum albumin-binding region of streptococcal protein G: a bacterial fusion partner with carrier-related properties," J Immunol Methods. Feb. 14, 1997;201(1):115-23.
Smith, M. "In vitro mutagenesis" Ann. Rev. Genet. 1985; 19:423-462.
Smith, GE et al., "Production of human beta interferon in insect cells infected with a baculovirus expression vector," Mol Cell Biol. Dec. 1983;3(12):2156-65.
Stanley, SL et al., "The serine-rich Entamoeba histolytica protein is a phosphorylated membrane protein containing O-linked terminal N-acetylglucosamine residues," J Biol Chem. Feb. 24, 1995;270(8):4121-6.
Steitz, JA et al. "Genetic signals and nucleotide sequences in messenger RNA," in Biological Regulation and Development: Gene Expression 1979; ed. R. F. Goldberger; Plenum Press, New York; 349-399.
Stemmer, WPC, "Rapid evolution of a protein in vitro by DNA shuffling," Nature 1994;370(4):389-391.
Stemmer, WP "DNA shuffling by random fragmentation and reassembly: In vitro recombination for molecular evolution," Proc Natl Acad Sci U S A. Oct. 25, 1994;91(22):10747-51.
Studier, FW et BA Moffatt, "Use of bacteriophage T7 RNA polymerase to direct selective high-level expression of cloned genes," J. Mol Biol. May 5, 1986;189(1):113-30.
Subasinghe, N. et al., "Quisqualic acid analogues: synthesis of beta-heterocyclic 2-aminopropanoic acid derivatives and their activity at a novel quisqualate-sensitized site," J Med Chem. Nov. 27, 1992;35(24):4602-7.
Switzer, C et al., "Enzymatic incorporation of a new base pair into DNA and RNA," J. Am. Chem. Soc. 1989; 111(21):8322-8323.
Wen, D. et al., (1993) "Erythropoietin structure-function relationships: high degree of sequence homology among mammals," Blood 82(5):1507-1516.
Lei Wang (2004) "Expansion of Codon," Science & Culture Review, vol. 1, No. 2, pp. 75-82.
"New Formulations and New Technology of Drugs, 2nd Edition," ed. L. Bin, People's Medical Publishing House, 2005, pp. 769-773.

* cited by examiner

Figure 1

Sequence Alignment of Human and Feline EPO

```
T-COFFEE, Version_1.41Fri June 28 14:24:48 MDT 2002
 Notredame, Higgins, Heringa, JMB302pp205-217,2000
CPU TIME:0 sec.
SCORE=100

*
BAD AVG_GOOD
*
1EER_A|PDBID|CH              :100
felineEPO          :100

1EER_A|PDBID|CH    ----------------------APPRLICDSRVLERYLLEA
felineEPO          MGSCECPALLLLLSLLLLPLGLPVLGAPPRLICDSRVLERYILGA Cons                                       ************:* *

1EER_A|PDBID|CH    KEAEKITTGCAEHCSLNEKITVPDTKVNFYAWKRMEVGQQAVEVW
felineEPO          REAENVTMGCAEGCSfsenitvpdtkvnfytwkrmdvgqqavevw Cons               :***:;* ** :.*:***********:;******

1EER_A|PDBID|CH    QGLALLSEAVLRGQALLVKSSQPWEPLQLHVDKAVSGLRSLTTLL
felineEPO          qglallseailrgqallanssqpsetlqlhvdkavsslrsltsll

CONS               ********:******..**** *.**********.*****:**

1EER_A|PDBID|CH    RALGAQKEAISNSDAASAAPLRTITADTFRKLFRVYSNFLRGKLK
felineEPO          ralgaqkeatslpeatsaaplrtftvdtlcklfriysnflrgklt

CONS               ********* *.:*:*******:*.**: ****;**********.

1EER_A|PDBID|CH    LYTGEACRTGDR
felineEPO          lytgeacrrgdr

Cons               ******** ***
```

Figure 2

Feline EPO sequence

- Two fEPO sequences were deposited in Gene bank
    - --Genbank accession No U00685 (18th codon GGG)
    - --Genbank accession No L10606 (18th codong GAG)

```
              1        10        20        30        40        50        60        70        80
_Fepo1_10606  ..................................APPRLICDSRVLERYILEAREAEVTGCAEGCSFSEMITVPDTKVNFYTWKRMS
_feline epo   MGSCERPALLLLLSLLSLPLGLSVLGAPPRLICDSRVLERYILEAREAEVTGCAEGCSFSEMITVPDTKVNFYTWKRMS
Consensus                                       APPRLICDSRVLERYIL AREAEVTGCAEGCSFSEMITVPDTKVNFYTWKRMS
```

- 12 cats used in one study (24 fEPO alleles) were sequenced
    - --They are all GAG at the 18th codon

- E18 is conserved across species

|  | 1 |  |  |  |  |  |  | 10 |  |  |  |  |  | ↓ |  | A |  |  | 20 |  |  |
|---|---|---|---|---|---|---|---|---|---|---|---|---|---|---|---|---|---|---|---|---|---|
| Human | A | P | P | R | L | I | C | D | S | R | V | L | E | R | Y | L | L | E | A | K | E | A | E | N |
| Cynomolgus monkey | A | P | P | R | L | I | C | D | S | R | V | L | E | R | Y | L | L | E | A | K | E | A | E | N |
| Rhesus monkey | A | P | P | R | L | V | C | D | S | R | V | L | E | R | Y | L | L | E | A | K | E | A | E | N |
| Mouse | A | P | P | R | L | I | C | D | S | R | V | L | E | R | Y | I | L | E | A | K | E | A | E | N |
| Rat | A | P | P | R | L | I | C | D | S | R | V | L | E | R | Y | I | L | E | A | K | E | A | E | N |
| Sheep | A | P | P | R | L | I | C | D | S | R | V | L | E | R | Y | I | L | E | A | R | E | A | E | N |
| Pib | A | P | P | R | L | I | C | D | S | R | V | L | E | R | Y | I | L | E | A | K | E | G | E | N |
| Cat | A | P | P | R | L | I | C | D | S | R | V | L | E | R | Y | I | L | E | A | R | E | A | E | N |
| Dog | A | P | P | R | L | I | C | D | S | R | V | L | E | R | Y | I | L | E | A | R | E | A | E | N |

Model of fEPO Showing High and Low Affinity Receptors for EPO

Model of fEPO

Model of Top pAF Sites In Feline EPO

Top View of pAF Sites

Side View of pAF Sites

Figure 8

Sites For Non-natural Amino Acid Incorporation
(no specific order)

| Residue | Position Feline | Average Cx |
|---------|-----------------|------------|
| ARG     | 53              | 1.92       |
| ASP     | 55              | 1.4        |
| LYS     | 116             | 1.32       |
| GLU     | 89              | 2.29       |
| GLU     | 72              | 0.93       |
| GLN     | 86              | 1.46       |
| loop    | 128-133         |            |
| GLU     | 31              | 3.24       |
| THR     | 132             | 1.41       |
| ARG     | 163             | 1.13       |
| SER     | 120             | 1.34       |

Figure 9

Sites For Non-natural Amino Acid Incorporation Into fEPO

→ N-linked Glycosylation site in human EPO

| Residue | Position | Average Cx |
|---------|----------|------------|
| ARG | 53 | 1.92 |
| ASP | 55 | 1.4 |
| ARG | 76 | 0.79 |
| → ASN | 24 | 1.1 |
| LYS | 116 | 1.32 |
| → ASN | 38 | 1.1 |
| GLU | 89 | 2.29 |
| GLU | 37 | 1.04 |
| GLU | 72 | 0.93 |
| GLN | 86 | 1.46 |
| TYR | 49 | 2.16 |
| → ASN | 83 | 2.03 |
| GLU | 21 | 0.85 |
| SER | 36 | 1.21 |
| loop | 128-133 | N/A |

Figure 10a

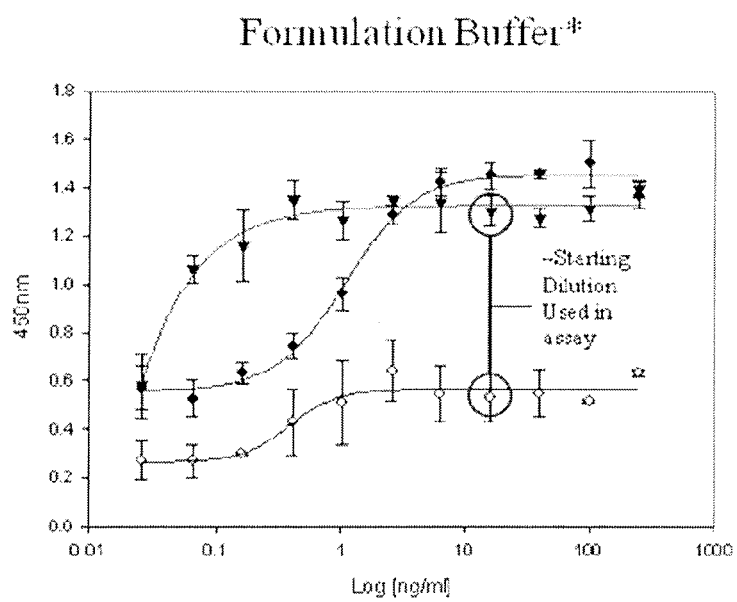

The starting concentration for formulation buffer is 25%. 2.5X dilutions were made and added to cells (black) or cells + an EC75 dose of fEPO (red). Blue = reference curve. Conclusion: Formulation buffer has no measurable effect at the dilution used in the assay

* 2.5 mg/mL Albumin (human), 1.3 mg/mL sodium citrate, 0.11mg/mL citric acid, 8.2 mg/mL sodium chloride, 1% benzyl alcohol (ie. 10 mg/mL), pH 6.1
** Endotoxin purchased from USP. CAT # 1235503 10,000 units/vial

Figure 10b

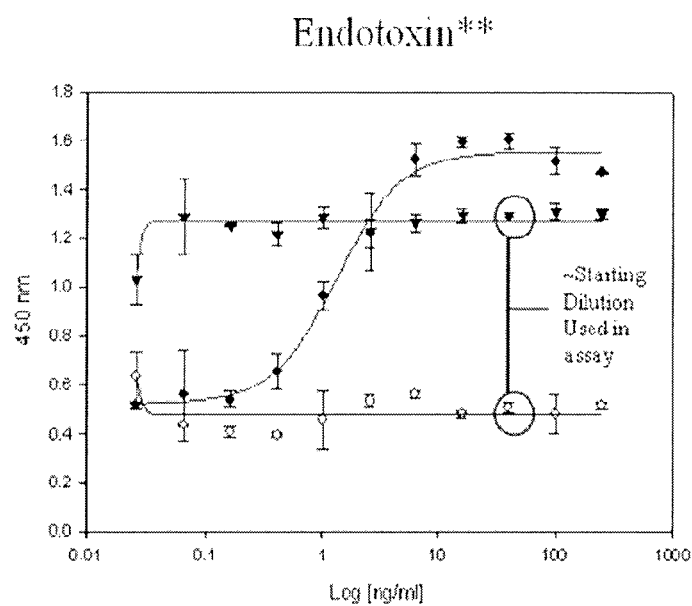

The starting concentration for endotoxin is
100 EU/well or 1000EU/ml. 2.5X dilutions were
made and added to cells (black) or cells + an EC75
dose of fEPO (red). Blue = reference curve.
Conclusion: Endotoxin has no measurable effect
at the concentration used in the assay \* 2.5 mg/mL Albumin (human), 1.3 mg/mL sodium citrate, 0.11mg/mL citric acid, 8.2 mg/mL sodium chloride, 1% benzyl alcohol (ie. 10 mg/mL), pH 6.1
\*\*Endotoxin purchased from USP, CAT # 1235503 10,000 units/vial

TF-1 Proliferation Assay fEPO Receptors Homodimerize upon Ligand Binding: fEPO(FEPOR)2

Bell Shaped Dose Response Curve

1. Seeding Density     40,000/30,000/20,000/10,000
2. Incubation Time     48 Hours vs. 72 Hours
3. fEPO Starting Concentration     2500ng/ml → 500ng/ml
4. Dilution Scheme     3x → 2.5X
5. Cell Starvation     0 Hr Vs. 24 Hr Cell Seeding Density

Effects of Cell Starvation

Figure 17

Assay Performance wt fEPO (Formulation Buffer)

| Date | Passage # | EC50 | R2 | Top OD | Bottom OD | Dynamic Range |
|---|---|---|---|---|---|---|
| 15-Feb-08 | 5 | 2.4 | 0.989 | 0.950 | 0.2127 | 4.5 |
| 18-Feb-08 | 6 | 2.9 | 0.994 | 0.925 | 0.235 | 3.9 |
| 18-Feb-08 | 6 | 2.8 | 0.994 | 0.842 | 0.205 | 4.1 |
| 22-Feb-08 | 7 | 3.2 | 0.998 | 1.085 | 0.222 | 4.9 |
| 22-Feb-08 | 7 | 3.2 | 0.998 | 1.102 | 0.235 | 4.7 |
| 25-Feb-08 | 8 | 3.5 | 0.999 | 1.008 | 0.224 | 4.5 |
| 29-Feb-08 | 9 | 2.5 | 0.990 | 0.789 | 0.220 | 3.6 |
| 29-Feb-08 | 9 | 2.2 | 0.984 | 0.772 | 0.220 | 3.5 |
| 3-Mar-08 | 10 | 3.2 | 0.997 | 0.999 | 0.2281 | 4.4 |
| 3Mar-08 | 10 | 2.4 | 0.996 | 0.990 | 0.223 | 4.4 |

| ES50 Ave | STD | %CV |
|---|---|---|
| 2.8 | 0.439 | 15.5 |

Assay Performance wt fEPO (Formulation Buffer)

| Starting [fEPO] | EC50 | Theoretical Activity | Actual Activity |
|---|---|---|---|
| 1000ng/ml | 1.4ng/ml | 2x | 2x |
| 500ng/ml | 2.8ng/ml | 1x | 1x |
| 250ng/ml | 4.7ng/ml | 0.5x | 0.6x |

Assay Performance wt hEPO vs. wt fEPO

Variants from 1st run standardized to equal amount of
Conditioned CHO Supernatant/PEI ~15%

Amber Variants

| +pAF Variant | Relative activity compared to wt fEPO |
|---|---|
| T132 | 3.2X |
| E21 | 3.1X |
| Y49 | 2.6X |
| L130 | 2.6X |
| F133 | 2.2X |
| R53 | 1.6X |
| S120 | 1.6X |
| A128 | 1.4X |
| D55 | 1.4X |
| E31 | 1.4X |
| E37 | 1.2X |
| E72 | 1.2X |
| R163 | 1.1X |
| A1 | 1.1X |
| S36 | 0.9X |
| P129 | 0.9X |
| R131 | 0.8X |
| K116 | 0.7X |
| R76 | 0.6X |

Analysis of Amber Variants

R76  1.6x < active than WT
A128 1.4x > active than WT

Figure 25

Lucy F vector

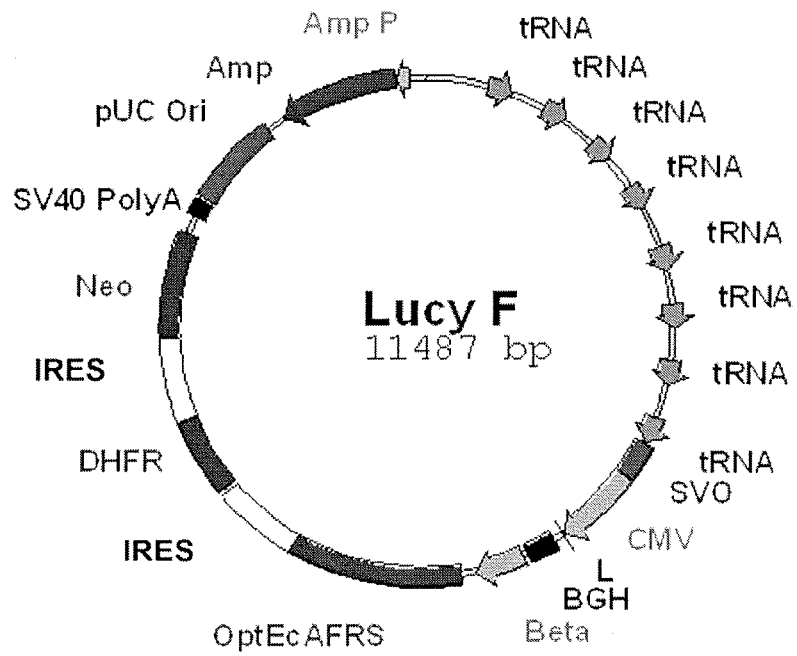

| | |
|---|---|
| tRNA = | tRNA gene |
| SVO = | SV40 Origin of Replication |
| CVM = | Human Cytomegaloviurs Promoter |
| L = | Secretory Signal Peptide |
| BGH = | Bovine Growth Hormone Polydenylation Signal |
| OptECAFRS = | Specific tRNA Synthetase |
| IRES = | Internal Ribosome Entry Site |
| DHFR = | Murine Dihydrofolate Reductase |
| Neo = | Neomycin Phosphotransferase |
| SV40 PolyA = | SV40 Polydenylation Signal |
| pUC Ori = | pUC Bacterial Origin of Replication |
| Amp = | Betalactamase |
| Amp P = | Betalactamase Promoter |

Figure 26

Irwin vector

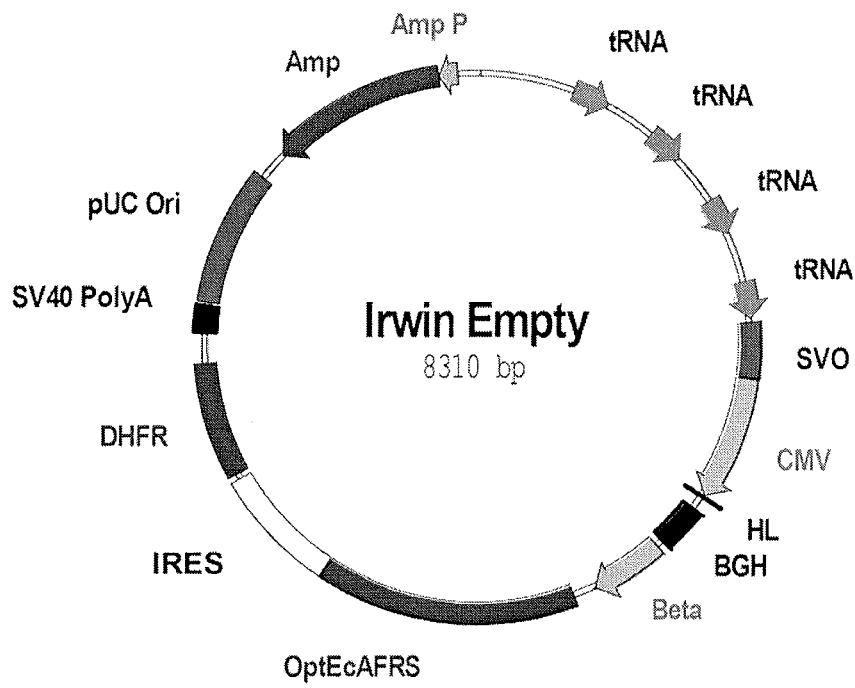

| | |
|---|---|
| tRNA = | tRNA gene |
| SVO = | SV40 Origin of Replication |
| CVM = | Human Cytomegaloviurs Promoter |
| HL = | Secretory Signal Peptide |
| BGH = | Bovine Growth Hormone Polydenylation Signal |
| OptECAFRS = | Specific tRNA Synthetase |
| IRES = | Internal Ribosome Entry Site |
| DHFR = | Murine Dihydrofolate Reductase |
| SV40 PolyA = | SV40 Polydenylation Signal |
| pUC Ori = | pUC Bacterial Origin of Replication |
| Amp = | Betalactamase |
| Amp P = | Betalactamase Promoter |

Figure 27

Suppression Expression Construct Nat L BB-Opti FEPO in Lucy F
For Feline Erythropoietin

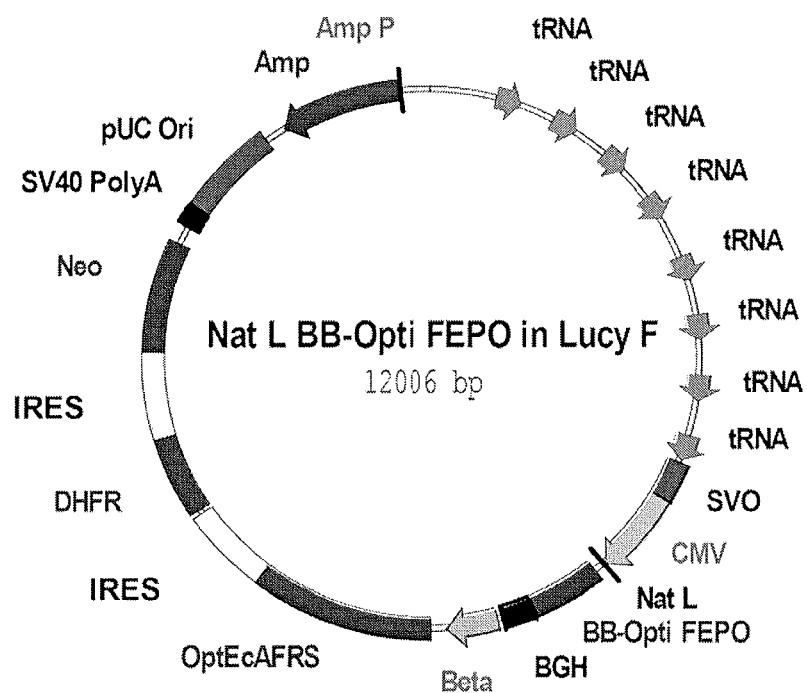

| | |
|---|---|
| tRNA = | tRNA gene |
| SVO = | SV40 Origin of Replication |
| CVM = | Human Cytomegaloviurs Promoter |
| Nat L = | Natural fEPO Secretory Signal Peptide |
| BB-Opti FEPO = | Codon Modified fEPO |
| BGH = | Bovine Growth Hormone Polydenylation Signal |
| OptECAFRS = | Specific tRNA Synthetase |
| IRES = | Internal Ribosome Entry Site |
| DHFR = | Murine Dihydrofolate Reductase |
| Neo = | Neomycin Phosphotransferase |
| SV40 PolyA = | SV40 Polydenylation Signal |
| pUC Ori = | pUC Bacterial Origin of Replication |
| Amp = | Betalactamase |
| Amp P = | Betalactamase Promoter |

Suppression Expression Construct Nat L BB-Opti FEPO in Irwin for Feline erythropoietin

| | |
|---|---|
| tRNA = | tRNA gene |
| SVO = | SV40 Origin of Replication |
| CVM = | Human Cytomegaloviurs Promoter |
| Nat L = | Natural fEPO Secretory Signal Peptide |
| BB-Opti FEPO = | Codon Modified fEPO |
| BGH = | Bovine Growth Hormone Polydenylation Signal |
| OptECA

Figure 29

Suppression Expression Construct Encoding a Generic Antibody
With Light and Heavy Chain Genes

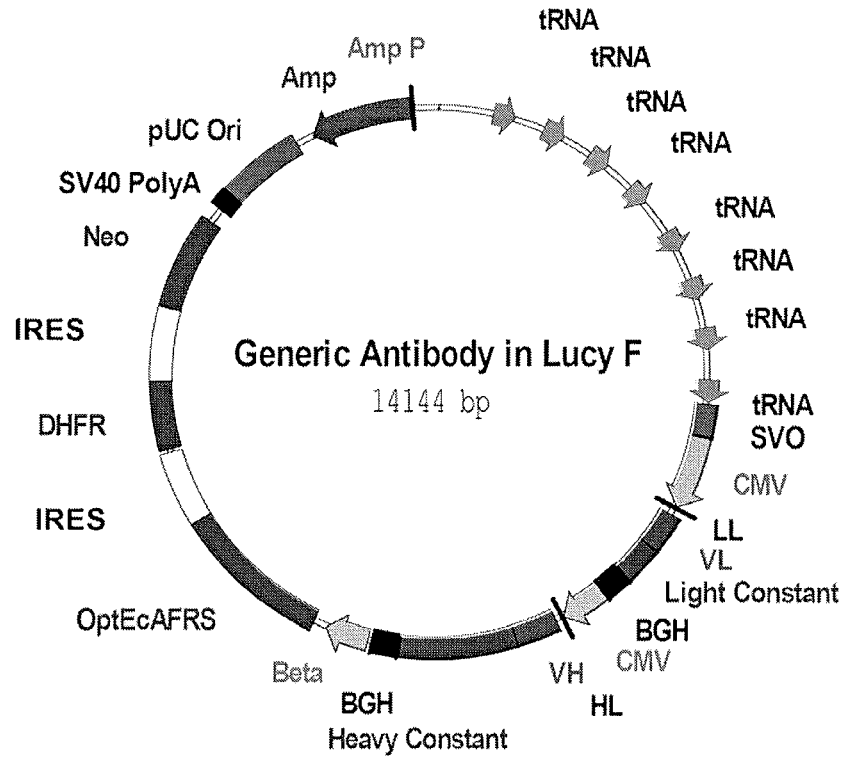

tRNA =         tRNA gene
SVO =          SV40 Origin of Replication
CVM =          Human Cytomegaloviurs Promoter
LL =           Light Chain Signal Peptide
VL =           Light Chain Variable Domain
Light Constant = Light Chain Constant Domain
BGH =          Bovine Growth Hormone Polydenylation Signal
HL =           Heavy Chain Signal Peptide
VL =           Heavy Chain Variable Domain
Heavy Constant = Heavy Chain Constant Domain
OptECAFRS =    Specific tRNA Synthetase
IRES =         Internal Ribosome Entry Site
DHFR =         Murine Dihydrofolate Reductase
Neo =          Neomycin Phosphotransferase
SV40 PolyA =   SV40 Polydenylation Signal
pUC Ori =      pUC Bacterial Origin of Replication
Amp =          Betalactamase
Amp P =        Betalactamase Promoter Suppression of fEPO variants in the presence of pAF Purified wild-type fEPO
A1 PEGylation

Figure 34

```
CLUSTAL 2.0.8 multiple sequence alignment seq1          APPRLICDSRVLERYILEAREAENVTMGCAQGCSFSENITVPDTKVNFYTWKRMDVGQQA
60
seq2          APPRLICDSRVLERYILGAREAENVTMGCAEGCSFSENITVPDTKVNFYTWKRMDVGQQA
60
              ***************:******:***:********************* seq1          LEVWQGLALLSEAILRGQALLANASQFSETPQLHVDKAVSSLRSLTSLLRALGAQKEAMS
120
seq2          VEVWQGLALLSEAILRGQALLANSSQPSETLQLHVDKAVSSLRSLTSLLRALGAQKEATS
120
              :********************: *:***************************  * seq1          LPEEASPAPLRTFTVDTLCKLFRIYSNFLRGKLTLYTGEACRRGDR 166
seq2          LPEATSAAPLRTFTVDTLCKLFRIYSNFLRGKLTLYTGEACRRGDR 166
              ***::*:*********************************** ***
```

Seq1 = Canine erythropoietin
Seq2 = Feline erythropoietin

94% Homology

Figure 35

```
CLUSTAL 2.0.8 multiple sequence alignment seq1            APPRLICDSRVLERYILEAREAENVTMGCAEGCSFGENVTVPDTKVNFYSWKRMEVEQQA
60
seq2            APPRLICDSRVLERYILGAREAENVTMGCAEGCSFSENITVPDTKVNFYTWKRMDVGQQA
60
                ************* *************..:********.**:* *** seq1            VEVWQGLALLSEAILQGQALLANSSQPSETLRLHVDKAVSSLRSLTSLLRALGAQKEAIS
120
seq2            VEVWQGLALLSEAILRGQALLANSSQPSETLQLHVDKAVSSLRSLTSLLRALGAQKEATS
120
                *************:***********:**************************  * seq1            PPDAASAAPLRTFAVDTLCKLFRIYSNFLRGKLKLYTGEACRRGDR 166
seq2            LPEATSAAPLRTFTVDTLCKLFRIYSNFLRGKLTLYTGEACRRGDR 166
                *:*:*******:************************.************
```

Seq1 = Equus caballus erythropoietin
Seq2 = Feline erythropoietin

91% Homology

SEQUENCE LISTING

```
<160> NUMBER OF SEQ ID NOS: 34

<210> SEQ ID NO 1
<211> LENGTH: 192
<212> TYPE: PRT
<213> ORGANISM: Felis catus

<400> SEQUENCE: 1

Met Gly Ser Cys Glu Cys Pro Ala Leu Leu Leu Leu Ser Leu Leu
1               5                   10                  15

Leu Leu Pro Leu Gly Leu Pro Val Leu Gly Ala Pro Pro Arg Leu Ile
                20                  25                  30

Cys Asp Ser Arg Val Leu Glu Arg Tyr Ile Leu Glu Ala Arg Glu Ala
            35                  40                  45

Glu Asn Val Thr Met Gly Cys Ala Glu Gly Cys Ser Phe Ser Glu Asn
    50                  55                  60

Ile Thr Val Pro Asp Thr Lys Val Asn Phe Tyr Thr Trp Lys Arg Met
65                  70                  75                  80

Asp Val Gly Gln Gln Ala Val Glu Val Trp Gln Gly Leu Ala Leu Leu
                85                  90                  95

Ser Glu Ala Ile Leu Arg Gly Gln Ala Leu Leu Ala Asn Ser Ser Gln
                100                 105                 110

Pro Ser Glu Thr Leu Gln Leu His Val Asp Lys Ala Val Ser Ser Leu
            115                 120                 125

Arg Ser Leu Thr Ser Leu Leu Arg Ala Leu Gly Ala Gln Lys Glu Ala
        130                 135                 140

Thr Ser Leu Pro Glu Ala Thr Ser Ala Ala Pro Leu Arg Thr Phe Thr
145                 150                 155                 160

Val Asp Thr Leu Cys Lys Leu Phe Arg Ile Tyr Ser Asn Phe Leu Arg
                165                 170                 175

Gly Lys Leu Thr Leu Tyr Thr Gly Glu Ala Cys Arg Arg Gly Asp Arg
                180                 185                 190
```

```
<210> SEQ ID NO 2
<211> LENGTH: 166
<212> TYPE: PRT
<213> ORGANISM: Felis catus

<400> SEQUENCE: 2

Ala Pro Pro Arg Leu Ile Cys Asp Ser Arg Val Leu Glu Arg Tyr Ile
1               5                   10                  15

Leu Glu Ala Arg Glu Ala Glu Asn Val Thr Met Gly Cys Ala Glu Gly
            20                  25                  30

Cys Ser Phe Ser Glu Asn Ile Thr Val Pro Asp Thr Lys Val Asn Phe
        35                  40                  45

Tyr Thr Trp Lys Arg Met Asp Val Gly Gln Gln Ala Val Glu Val Trp
    50                  55                  60

Gln Gly Leu Ala Leu Leu Ser Glu Ala Ile Leu Arg Gly Gln Ala Leu
65                  70                  75                  80

Leu Ala Asn Ser Ser Gln Pro Ser Glu Thr Leu Gln Leu His Val Asp
                85                  90                  95

Lys Ala Val Ser Ser Leu Arg Ser Leu Thr Ser Leu Leu Arg Ala Leu
            100                 105                 110

Gly Ala Gln Lys Glu Ala Thr Ser Leu Pro Glu Ala Thr Ser Ala Ala
        115                 120                 125

Pro Leu Arg Thr Phe Thr Val Asp Thr Leu Cys Lys Leu Phe Arg Ile
    130                 135                 140

Tyr Ser Asn Phe Leu Arg Gly Lys Leu Thr Leu Tyr Thr Gly Glu Ala
145                 150                 155                 160

Cys Arg Arg Gly Asp Arg
                165

<210> SEQ ID NO 3
<211> LENGTH: 192
<212> TYPE: PRT
<213> ORGANISM: Felis catus

<400> SEQUENCE: 3

Met Gly Ser Cys Glu Cys Pro Ala Leu Leu Leu Leu Leu Ser Leu Leu
1               5                   10                  15

Leu Leu Pro Leu Gly Leu Pro Val Leu Gly Ala Pro Pro Arg Leu Ile
            20                  25                  30

Cys Asp Ser Arg Val Leu Glu Arg Tyr Ile Leu Gly Ala Arg Glu Ala
        35                  40                  45

Glu Asn Val Thr Met Gly Cys Ala Glu Gly Cys Ser Phe Ser Glu Asn
    50                  55                  60

Ile Thr Val Pro Asp Thr Lys Val Asn Phe Tyr Thr Trp Lys Arg Met
65                  70                  75                  80

Asp Val Gly Gln Gln Ala Val Glu Val Trp Gln Gly Leu Ala Leu Leu
                85                  90                  95

Ser Glu Ala Ile Leu Arg Gly Gln Ala Leu Leu Ala Asn Ser Ser Gln
            100                 105                 110

Pro Ser Glu Thr Leu Gln Leu His Val Asp Lys Ala Val Ser Ser Leu
        115                 120                 125

Arg Ser Leu Thr Ser Leu Leu Arg Ala Leu Gly Ala Gln Lys Glu Ala
    130                 135                 140

Thr Ser Leu Pro Glu Ala Thr Ser Ala Ala Pro Leu Arg Thr Phe Thr
145                 150                 155                 160

Val Asp Thr Leu Cys Lys Leu Phe Arg Ile Tyr Ser Asn Phe Leu Arg
```

```
                    165                 170                 175
Gly Lys Leu Thr Leu Tyr Thr Gly Glu Ala Cys Arg Arg Gly Asp Arg
            180                 185                 190

<210> SEQ ID NO 4
<211> LENGTH: 166
<212> TYPE: PRT
<213> ORGANISM: Felis catus

<400> SEQUENCE: 4

Ala Pro Pro Arg Leu Ile Cys Asp Ser Arg Val Leu Glu Arg Tyr Ile
1               5                   10                  15

Leu Gly Ala Arg Glu Ala Glu Asn Val Thr Met Gly Cys Ala Glu Gly
            20                  25                  30

Cys Ser Phe Ser Glu Asn Ile Thr Val Pro Asp Thr Lys Val Asn Phe
        35                  40                  45

Tyr Thr Trp Lys Arg Met Asp Val Gly Gln Gln Ala Val Glu Val Trp
    50                  55                  60

Gln Gly Leu Ala Leu Leu Ser Glu Ala Ile Leu Arg Gly Gln Ala Leu
65                  70                  75                  80

Leu Ala Asn Ser Ser Gln Pro Ser Glu Thr Leu Gln Leu His Val Asp
                85                  90                  95

Lys Ala Val Ser Ser Leu Arg Ser Leu Thr Ser Leu Leu Arg Ala Leu
            100                 105                 110

Gly Ala Gln Lys Glu Ala Thr Ser Leu Pro Glu Ala Thr Ser Ala Ala
        115                 120                 125

Pro Leu Arg Thr Phe Thr Val Asp Thr Leu Cys Lys Leu Phe Arg Ile
    130                 135                 140

Tyr Ser Asn Phe Leu Arg Gly Lys Leu Thr Leu Tyr Thr Gly Glu Ala
145                 150                 155                 160

Cys Arg Arg Gly Asp Arg
                165

<210> SEQ ID NO 5
<211> LENGTH: 88
<212> TYPE: DNA
<213> ORGANISM: Artificial
<220> FEATURE:
<223> OTHER INFORMATION: An optimized amber supressor tRNA

<400> SEQUENCE: 5
cccagggtag ccaagctcgg ccaacggcga cggactctaa atccgttctc gtaggagttc    60
gagggttcga atcccttccc tgggacca                                      88

<210> SEQ ID NO 6
<211> LENGTH: 89
<212> TYPE: DNA
<213> ORGANISM: Artificial
<220> FEATURE:
<223> OTHER INFORMATION: An optimized AGGA frameshift supressor tRNA

<400> SEQUENCE: 6
gcgagggtag ccaagctcgg ccaacggcga cggacttcct aatccgttct cgtaggagtt    60
cgagggttcg aatccctccc ctcgcacca                                     89

<210> SEQ ID NO 7
<211> LENGTH: 307
<212> TYPE: PRT
<213> ORGANISM: Artificial
```

<220> FEATURE:
<223> OTHER INFORMATION: Aminoacyl tRNA synthetase for the incorporation of p-azido-L-phenylalanine

<400> SEQUENCE: 7

| Gly | Met | Asp | Glu | Phe | Glu | Met | Ile | Lys | Arg | Asn | Thr | Ser | Glu | Ile | Ile |
|---|---|---|---|---|---|---|---|---|---|---|---|---|---|---|---|
| 1 | | | | 5 | | | | | 10 | | | | | 15 | |

| Ser | Glu | Glu | Glu | Leu | Arg | Glu | Val | Leu | Lys | Lys | Asp | Glu | Lys | Ser | Ala |
|---|---|---|---|---|---|---|---|---|---|---|---|---|---|---|---|
| | | 20 | | | | | 25 | | | | | 30 | | | |

| Gly | Ile | Gly | Phe | Glu | Pro | Ser | Gly | Lys | Ile | His | Leu | Gly | His | Tyr | Leu |
|---|---|---|---|---|---|---|---|---|---|---|---|---|---|---|---|
| | | 35 | | | | | 40 | | | | | 45 | | | |

| Gln | Ile | Lys | Lys | Met | Ile | Asp | Leu | Gln | Asn | Ala | Gly | Phe | Asp | Ile | Ile |
|---|---|---|---|---|---|---|---|---|---|---|---|---|---|---|---|
| 50 | | | | | 55 | | | | | 60 | | | | | |

| Ile | Leu | Leu | Ala | Asp | Leu | His | Ala | Tyr | Leu | Asn | Gln | Lys | Gly | Glu | Leu |
|---|---|---|---|---|---|---|---|---|---|---|---|---|---|---|---|
| 65 | | | | | 70 | | | | | 75 | | | | | 80 |

| Asp | Glu | Ile | Arg | Lys | Ile | Gly | Asp | Tyr | Asn | Lys | Lys | Val | Phe | Glu | Ala |
|---|---|---|---|---|---|---|---|---|---|---|---|---|---|---|---|
| | | | | 85 | | | | | 90 | | | | | 95 | |

| Met | Gly | Leu | Lys | Ala | Lys | Tyr | Val | Tyr | Gly | Ser | Thr | Phe | Gln | Leu | Asp |
|---|---|---|---|---|---|---|---|---|---|---|---|---|---|---|---|
| | | | 100 | | | | | 105 | | | | | 110 | | |

| Lys | Asp | Tyr | Thr | Leu | Asn | Val | Tyr | Arg | Leu | Ala | Leu | Lys | Thr | Thr | Leu |
|---|---|---|---|---|---|---|---|---|---|---|---|---|---|---|---|
| | | | 115 | | | | | 120 | | | | | 125 | | |

| Lys | Arg | Ala | Arg | Arg | Ser | Met | Glu | Leu | Ile | Ala | Arg | Glu | Asp | Glu | Asn |
|---|---|---|---|---|---|---|---|---|---|---|---|---|---|---|---|
| 130 | | | | | 135 | | | | | 140 | | | | | |

| Pro | Lys | Val | Ala | Glu | Val | Ile | Tyr | Pro | Ile | Met | Gln | Val | Asn | Thr | Tyr |
|---|---|---|---|---|---|---|---|---|---|---|---|---|---|---|---|
| 145 | | | | | 150 | | | | | 155 | | | | | 160 |

| Tyr | Tyr | Leu | Gly | Val | Asp | Val | Ala | Val | Gly | Gly | Met | Glu | Gln | Arg | Lys |
|---|---|---|---|---|---|---|---|---|---|---|---|---|---|---|---|
| | | | | 165 | | | | | 170 | | | | | 175 | |

| Ile | His | Met | Leu | Ala | Arg | Glu | Leu | Leu | Pro | Lys | Lys | Val | Val | Cys | Ile |
|---|---|---|---|---|---|---|---|---|---|---|---|---|---|---|---|
| | | | 180 | | | | | 185 | | | | | 190 | | |

| His | Asn | Pro | Val | Leu | Thr | Gly | Leu | Asp | Gly | Glu | Gly | Lys | Met | Ser | Ser |
|---|---|---|---|---|---|---|---|---|---|---|---|---|---|---|---|
| | | 195 | | | | | 200 | | | | | 205 | | | |

| Ser | Lys | Gly | Asn | Phe | Ile | Ala | Val | Asp | Asp | Ser | Pro | Glu | Glu | Ile | Arg |
|---|---|---|---|---|---|---|---|---|---|---|---|---|---|---|---|
| | | 210 | | | | | 215 | | | | | 220 | | | |

| Ala | Lys | Ile | Lys | Lys | Ala | Tyr | Cys | Pro | Ala | Gly | Val | Val | Glu | Gly | Asn |
|---|---|---|---|---|---|---|---|---|---|---|---|---|---|---|---|
| 225 | | | | | 230 | | | | | 235 | | | | | 240 |

| Pro | Ile | Met | Glu | Ile | Ala | Lys | Tyr | Phe | Leu | Glu | Tyr | Pro | Leu | Thr | Ile |
|---|---|---|---|---|---|---|---|---|---|---|---|---|---|---|---|
| | | | 245 | | | | | 250 | | | | | 255 | | |

| Lys | Arg | Pro | Glu | Lys | Phe | Gly | Gly | Asp | Leu | Thr | Val | Asn | Ser | Tyr | Glu |
|---|---|---|---|---|---|---|---|---|---|---|---|---|---|---|---|
| | | | 260 | | | | | 265 | | | | | 270 | | |

| Glu | Leu | Glu | Ser | Leu | Phe | Lys | Asn | Lys | Glu | Leu | His | Pro | Met | Asp | Leu |
|---|---|---|---|---|---|---|---|---|---|---|---|---|---|---|---|
| | | 275 | | | | | 280 | | | | | 285 | | | |

| Lys | Asn | Ala | Val | Ala | Glu | Glu | Leu | Ile | Lys | Ile | Leu | Glu | Pro | Ile | Arg |
|---|---|---|---|---|---|---|---|---|---|---|---|---|---|---|---|
| | 290 | | | | | 295 | | | | | 300 | | | | |

| Lys | Arg | Leu |
|---|---|---|
| 305 | | |

<210> SEQ ID NO 8
<211> LENGTH: 306
<212> TYPE: PRT
<213> ORGANISM: Artificial
<220> FEATURE:
<223> OTHER INFORMATION: Aminoacyl tRNA synthetase for the incorporation of p-benzoyl-L-phenylalanine

<400> SEQUENCE: 8

| Met | Asp | Glu | Phe | Glu | Met | Ile | Lys | Arg | Asn | Thr | Ser | Glu | Ile | Ile | Ser |
|---|---|---|---|---|---|---|---|---|---|---|---|---|---|---|---|
| 1 | | | | 5 | | | | | 10 | | | | | 15 | |

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
 50                  55                  60

Leu Leu Ala Asp Leu His Ala Tyr Leu Asn Gln Lys Gly Glu Leu Asp
65                   70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
290                 295                 300

Arg Leu
305

<210> SEQ ID NO 9
<211> LENGTH: 305
<212> TYPE: PRT
<213> ORGANISM: Artificial
<220> FEATURE:
<223> OTHER INFORMATION: Aminoacyl tRNA synthetase for the incorporation
    of propargyl-phenylalanine

<400> SEQUENCE: 9

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
    210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
    290                 295                 300

Leu
305

<210> SEQ ID NO 10
<211> LENGTH: 305
<212> TYPE: PRT
<213> ORGANISM: Artificial
<220> FEATURE:
<223> OTHER INFORMATION: Aminoacyl tRNA synthetase for the incorporation
      of propargyl-phenylalanine

<400> SEQUENCE: 10

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Ile Pro Tyr
145                 150                 155                 160

Leu Pro Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
    210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
    290                 295                 300

Leu
305

<210> SEQ ID NO 11
<211> LENGTH: 305
<212> TYPE: PRT
<213> ORGANISM: Artificial
<220> FEATURE:
<223> OTHER INFORMATION: Aminoacyl tRNA synthetase for the incorporation
      of propargyl-phenylalanine

<400> SEQUENCE: 11

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
                100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

```
Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
                195                 200                 205

Gly Asn Phe Ile Ala Val Asp Asp Ser Pro Glu Glu Ile Arg Ala Lys
            210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
            245                 250                 255

Pro Glu Lys Phe Gly Gly Asp Leu Thr Val Asn Ser Tyr Glu Glu Leu
                260                 265                 270

Glu Ser Leu Phe Lys Asn Lys Glu Leu His Pro Met Asp Leu Lys Asn
            275                 280                 285

Ala Val Ala Glu Glu Leu Ile Lys Ile Leu Glu Pro Ile Arg Lys Arg
        290                 295                 300

Leu
305

<210> SEQ ID NO 12
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-phenylalanine

<400> SEQUENCE: 12

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Asn Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190
```

```
                180                 185                 190
Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
        260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
        290                 295                 300

Arg Leu
305

<210> SEQ ID NO 13
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-phenylalanine

<400> SEQUENCE: 13

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
        210                 215                 220
```

```
Lys Ile Lys Lys Ala Tyr Cys Pro Ala Gly Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Leu Ile Lys Ile Leu Glu Pro Ile Arg Lys
290                 295                 300

Arg Leu
305

<210> SEQ ID NO 14
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-phenylalanine

<400> SEQUENCE: 14

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270
```

```
Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
            290                 295                 300

Arg Leu
305

<210> SEQ ID NO 15
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-phenylalanine

<400> SEQUENCE: 15

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Ser His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
            290                 295                 300

Arg Leu
```

<210> SEQ ID NO 16
<211> LENGTH: 306
<212> TYPE: PRT
<213> ORGANISM: Artificial
<220> FEATURE:
<223> OTHER INFORMATION: Aminoacyl tRNA synthetase for the incorporation of p-acetyl-phenylalanine

<400> SEQUENCE: 16

```
Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Leu
            20                  25                  30
Ile Gly Phe Glu Pro Ser Gly Lys Ile His Leu Gly His Tyr Leu Gln
        35                  40                  45
Ile Lys Lys Met Ile Asp Leu Gln Asn Ala Gly Phe Asp Ile Ile Ile
    50                  55                  60
Leu Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Glu Phe Gln Leu Asp Lys
            100                 105                 110
Asp Tyr Thr Leu Asn Val Tyr Arg Leu Ala Leu Lys Thr Thr Leu Lys
        115                 120                 125
Arg Ala Arg Arg Ser Met Glu Leu Ile Ala Arg Glu Asp Glu Asn Pro
    130                 135                 140
Lys Val Ala Glu Val Ile Tyr Pro Ile Met Gln Val Asn Gly Cys His
145                 150                 155                 160
Tyr Arg Gly Val Asp Val Ala Val Gly Gly Met Glu Gln Arg Lys Ile
                165                 170                 175
His Met Leu Ala Arg Glu Leu Leu Pro Lys Lys Val Val Cys Ile His
            180                 185                 190
Asn Pro Val Leu Thr Gly Leu Asp Gly Glu Gly Lys Met Ser Ser Ser
        195                 200                 205
Lys Gly Asn Phe Ile Ala Val Asp Asp Ser Pro Glu Glu Ile Arg Ala
    210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
            260                 265                 270
Leu Glu Ser Leu Phe Lys Asn Lys Glu Leu His Pro Met Asp Leu Lys
        275                 280                 285
Asn Ala Val Ala Glu Glu Leu Ile Lys Ile Leu Glu Pro Ile Arg Lys
    290                 295                 300
Arg Leu
305
```

<210> SEQ ID NO 17
<211> LENGTH: 306
<212> TYPE: PRT
<213> ORGANISM: Artificial
<220> FEATURE:

<223> OTHER INFORMATION: Aminoacyl tRNA synthetase for the incorporation of p-acetyl-phenylalanine

<400> SEQUENCE: 17

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Thr His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 18
<211> LENGTH: 306
<212> TYPE: PRT
<213> ORGANISM: Artificial
<220> FEATURE:
<223> OTHER INFORMATION: Aminoacyl tRNA synthetase for the incorporation of p-acetyl-phenylalanine

<400> SEQUENCE: 18

```
Met Asp Glu Phe Glu Met Ile Lys Arg Asn Thr Ser Glu Ile Ile Ser
1               5                   10                  15
```

```
Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Gly His
145                 150                 155                 160

Tyr Leu Gly Val Asp Val Ile Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 19
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-phenylalanine

<400> SEQUENCE: 19

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60
```

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Val Phe Glu Ala Met
            85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Ile His
145                 150                 155                 160

Tyr Asp Gly Val Asp Val Ala Val Gly Gly Met Glu Gln Arg Lys Ile
            165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
            245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
            290                 295                 300

Arg Leu
305

<210> SEQ ID NO 20
<211> LENGTH: 306
<212> TYPE: PRT
<213> ORGANISM: Artificial
<220> FEATURE:
<223> OTHER INFORMATION: Aminoacyl tRNA synthetase for the incorporation
      of p-azido-phenylalanine

<400> SEQUENCE: 20

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Val Phe Glu Ala Met
            85                  90                  95

Gly Leu Lys Ala Lys Tyr Val Tyr Gly Ser Thr Phe Gln Leu Asp Lys

|  | 100 |  |  |  | 105 |  |  |  | 110 |  |  |
|---|---|---|---|---|---|---|---|---|---|---|---|

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 21
<211> LENGTH: 36
<212> TYPE: DNA
<213> ORGANISM: Artificial
<220> FEATURE:
<223> OTHER INFORMATION: Primer for cloning full length hEPO cDNA

<400> SEQUENCE: 21
cagttacata tgggagttca cgaatgtcct gcctgg                                 36

<210> SEQ ID NO 22
<211> LENGTH: 33
<212> TYPE: DNA
<213> ORGANISM: Artificial
<220> FEATURE:
<223> OTHER INFORMATION: Primer for cloning mature hEPO cDNA

<400> SEQUENCE: 22
cagttacata tgctccacca agattaatct gtg                                    33

<210> SEQ ID NO 23
<211> LENGTH: 34
<212> TYPE: DNA
<213> ORGANISM: Artificial
<220> FEATURE:
<223> OTHER INFORMATION: 3'Primer for cloning full length and mature
      hEPO cDNA

<400> SEQUENCE: 23
ctgcaactcg agtcatctgt cccctgtcct gcag                                   34

<210> SEQ ID NO 24
<211> LENGTH: 582
<212> TYPE: DNA
<213> ORGANISM: Artificial
<220> FEATURE:
<223> OTHER INFORMATION: Nucleotide sequence of full length hEPO cDNA

<400> SEQUENCE: 24

```
atggggtgc acgaatgtcc tgcctggctg tggcttctcc tgtccctgct gtcgctccct      60
ctgggcctcc cagtcctggg cgccccacca cgcctcatct gtgacagccg agtcctggag    120
aggtacctct tggaggccaa ggaggccgag aatatcacga cgggctgtgc tgaacactgc    180
agcttgaatg agaatatcac tgtcccagac accaaagtta atttctatgc ctggaagagg    240
atggaggtcg ggcagcaggc cgtagaagtc tggcagggcc tggccctgct gtcggaagct    300
gtcctgcggg gccaggccct gttggtcaac tcttcccagc cgtgggagcc cctgcagctg    360
catgtggata aagccgtcag tggccttcgc agcctcacca ctctgcttcg ggctctgcga    420
gcccagaagg aagccatctc ccctccagat gcggcctcag ctgctccact ccgaacaatc    480
actgctgaca ctttccgcaa actcttccga gtctactcca atttcctccg gggaaagctg    540
aagctgtaca caggggaggc ctgcaggaca ggggacagat ga                       582
```

<210> SEQ ID NO 25
<211> LENGTH: 501
<212> TYPE: DNA
<213> ORGANISM: Artificial
<220> FEATURE:
<223> OTHER INFORMATION: Nucleotide sequence of mature hEPO cDNA

<400> SEQUENCE: 25

```
gccccaccac gcctcatctg tgacagccga gtcctggaga ggtacctctt ggaggccaag      60
gaggccgaga atatcacgac gggctgtgct gaacactgca gcttgaatga gaatatcact    120
gtcccagaca ccaaagttaa tttctatgcc tggaagagga tggaggtcgg gcagcaggcc    180
gtagaagtct ggcagggcct ggccctgctg tcggaagctg tcctgcgggg ccaggccctg    240
ttggtcaact cttcccagcc gtgggagccc ctgcagctgc atgtggataa agccgtcagt    300
ggccttcgca gcctcaccac tctgcttcgg gctctgcgag cccagaagga agccatctcc    360
cctccagatg cggcctcagc tgctccactc cgaacaatca ctgctgacac tttccgcaaa    420
ctcttccgag tctactccaa tttcctccgg ggaaagctga agctgtacac aggggaggcc    480
tgcaggacag gggacagatg a                                              501
```

<210> SEQ ID NO 26
<211> LENGTH: 501
<212> TYPE: DNA
<213> ORGANISM: Artificial
<220> FEATURE:
<223> OTHER INFORMATION: Nucleotide sequence of G113R hEPO cDNA

<400> SEQUENCE: 26

```
gccccaccac gcctcatctg tgacagccga gtcctggaga ggtacctctt ggaggccaag      60
gaggccgaga atatcacgac gggctgtgct gaacactgca gcttgaatga gaatatcact    120
gtcccagaca ccaaagttaa tttctatgcc tggaagagga tggaggtcgg gcagcaggcc    180
gtagaagtct ggcagggcct ggccctgctg tcggaagctg tcctgcgggg ccaggccctg    240
ttggtcaact cttcccagcc gtgggagccc ctgcagctgc atgtggataa agccgtcagt    300
ggccttcgca gcctcaccac tctgcttcgg gctctgggag cccagaagga agccatctcc    360
```
cctccagatg cggcctcagc tgctccactc cgaacaatca ctgctgacac tttccgcaaa    420
ctcttccgag tctactccaa tttcctccgg ggaaagctga agctgtacac aggggaggcc    480
tgcaggacag gggacagatg a    501

<210> SEQ ID NO 27
<211> LENGTH: 503
<212> TYPE: DNA
<213> ORGANISM: Artificial
<220> FEATURE:
<223> OTHER INFORMATION: Optimized for expression of mature hEPO cDNA
      in E. coli

<400> SEQUENCE: 27
atgctccacc aagattaatc tgtgacagcc gagtcctgga gaggtacctc ttggaggcca    60
aggaggccga gaatatcacg acgggctgtg ctgaacactg cagcttgaat gagaatatca    120
ctgtcccaga caccaaagtt aatttctatg cctggaagag gatggaggtc gggcagcagg    180
ccgtagaagt ctggcagggc ctggccctgc tgtcggaagc tgtcctgcgg ggccaggccc    240
tgttggtcaa ctcttcccag ccgtgggagc ccctgcagct gcatgtggat aaagccgtca    300
gtggccttcg cagcctcacc actctgcttc gggctctgcg agcccagaag gaagccatct    360
cccctccaga tgcggcctca gctgctccac tccgaacaat cactgctgac actttccgca    420
aactcttccg agtctactcc aatttcctcc ggggaaagct gaagctgtac acaggggagg    480
cctgcaggac aggggacaga tga    503

<210> SEQ ID NO 28
<211> LENGTH: 12006
<212> TYPE: DNA
<213> ORGANISM: Felis catus

<400> SEQUENCE: 28
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcc cgtccgcgta ccggcgcgcc ggatgccaat cgatgaattc cggtgtgaaa    240
taccgcacag atgcgtaagg agaaaatacc gcatcaggcg ccattcgcca ttcaggctgc    300
gcaactgttg ggaagggcga tcggtgcggg cctcttcgct attacgccag ctggcgaaag    360
ggggatgtgc tgcaaggcga ttaagttggg taacgccagg gttttcccag tcacgacgtt    420
gtaaaacgac ggccagtgaa ttgatgcatc atcaattca tatttgcatg tcgctatgtg    480
ttctgggaaa tcaccataaa cgtgaaatgt ctttggattt gggaatctta agttctgt    540 atgagaccac tcggatccgg tggggtagcg aagtggctaa acgcggcgga ctctaaatcc    600
gctccctttg ggttcggcgg ttcgaatccg tcccccacca ttttttggaa cctagggaat    660
tccggtgtga ataccgcac agatgcgtaa ggagaaaata ccgcatcagg cgccattcgc    720
cattcaggct gcgcaactgt tgggaagggc gatcggtgcg ggcctcttcg ctattacgcc    780
agctggcgaa aggggggatgt gctgcaaggc gattaagttg ggtaacgcca gggttttccc    840
agtcacgacg ttgtaaaacg acggccagtg aattgatgca tccatcaatt catatttgca    900
tgtcgctatg tgttctggga atcaccata acgtgaaat gtctttggat ttgggaatct    960
tataagttct gtatgagacc actcggatcc ggtggggtag cgaagtggct aaacgcggcg    1020
gactctaaat ccgctcccctt tgggttcggc ggttcgaatc cgtcccccac catttttggg    1080

-continued

```
aagacgtcga attccggtgt gaaataccgc acagatgcgt aaggagaaaa taccgcatca    1140
ggcgccattc gccattcagg ctgcgcaact gttgggaagg gcgatcggtg cgggcctctt    1200
cgctattacg ccagctggcg aaaggggat gtgctgcaag gcgattaagt tgggtaacgc     1260
cagggttttc ccagtcacga cgttgtaaaa cgacggccag tgaattgatg catccatcaa    1320
ttcatatttg catgtcgcta tgtgttctgg gaaatcacca taaacgtgaa atgtctttgg    1380
atttgggaat cttataagtt ctgtatgaga ccactcggat ccggtggggt agcgaagtgg    1440
ctaaacgcgg cggactctaa atccgctccc tttgggttcg gcggttcgaa tccgtcccc     1500
accattttt ggaacatatg gaattccggt gtgaaatacc gcacagatgc gtaaggagaa     1560
aataccgcat caggcgccat cgccattca ggctgcgcaa ctgttgggaa gggcgatcgg     1620
tgcgggcctc ttcgctatta cgccagctgg cgaaaggggg atgtgctgca aggcgattaa    1680
gttgggtaac gccagggttt tcccagtcac gacgttgtaa aacgacggcc agtgaattga    1740
tgcatccatc aattcatatt tgcatgtcgc tatgtgttct gggaaatcac cataaacgtg    1800
aaatgtcttt ggatttggga atcttataag ttctgtatga ccactcggat ccggtgggg    1860
gtagcgaagt ggctaaacgc ggcggactct aaatccgctc cctttgggtt cggcggttcg    1920
aatccgtccc ccaccatttt ttggaactta attaaggcgc gccggatgcc aatcggccat    1980
caccatccaa cgggaaggcg atgaattccg tgtgaaata ccgcacagat gcgtaaggag     2040
aaaataccgc atcaggcgcc attcgccatt caggctgcgc aactgttggg aagggcgatc    2100
ggtgcgggcc tcttcgctat tacgccagct ggcgaaaggg ggatgtgctg caaggcgatt    2160
aagttgggta acgccagggt tttcccagtc acgacgttgt aaaacgacgg ccagtgaatt    2220
gatgcatcca tcaattcata tttgcatgtc gctatgtgtt ctgggaaatc accataaacg    2280
tgaaatgtct ttggatttgg gaatcttata agttctgtat gagaccactc ggatccggtg    2340
gggtagcgaa gtggctaaac gcggcggact ctaaatccgc tcccttttggg ttcggcggtt    2400
cgaatccgtc ccccaccatt ttttggaacc tagggaattc cggtgtgaaa taccgcacag    2460
atgcgtaagg agaaaatacc gcatcaggcg ccattcgcca ttcaggctgc gcaactgttg    2520
ggaagggcga tcggtgcggg cctcttcgct attacgccag ctggcgaaag gggatgtgc    2580
tgcaaggcga ttaagttggg taacgccagg gttttcccag tcacgacgtt gtaaaacgac    2640
ggccagtgaa ttgatgcatc catcaattca tatttgcatg tcgctatgtg ttctgggaaa    2700
tcaccataaa cgtgaaatgt ctttggattt gggaatctta taagttctgt atgagaccac    2760
tcggatccgg tggggtagcg aagtggctaa acgcggcgga ctctaaatcc gctccctttg    2820
ggttcggcgg ttcgaatccg tcccccacca ttttttggaa gacgtcgaat ccggtgtga    2880
aataccgcac agatgcgtaa ggagaaaata ccgcatcagg cgccattcgc cattcaggct    2940
gcgcaactgt tgggaagggc gatcggtgcg ggcctcttcg ctattacgcc agctggcgaa    3000
aggggatgt gctgcaaggc gattaagttg gtaacgcca gggttttccc agtcacgacg     3060
ttgtaaaacg acgccagtg aattgatgca tccatcaatt catatttgca tgtcgctatg    3120
tgttctggga aatcaccata aacgtgaaat gtctttggat ttgggaatct tataagttct    3180
gtatgagacc actcggatcc ggtggggtag cgaagtggct aaacgcggcg gactctaaat    3240
ccgctccctt tgggttcggc ggttcgaatc cgtcccccac cattttttgg aacatatgga    3300
attccggtgt gaaataccgc acagatgcgt aaggagaaaa taccgcatca ggcgccattc    3360
gccattcagg ctgcgcaact gttgggaagg gcgatcggtg cgggcctctt cgctattacg    3420
ccagctggcg aaaggggat gtgctgcaag gcgattaagt tgggtaacgc cagggttttc     3480
```

```
ccagtcacga cgttgtaaaa cgacggccag tgaattgatg catccatcaa ttcatatttg   3540
catgtcgcta tgtgttctgg gaaatcacca taaacgtgaa atgtctttgg atttgggaat   3600
cttataagtt ctgtatgaga ccactcggat ccggtggggt agcgaagtgg ctaaacgcgg   3660
cggactctaa atccgctccc tttgggttcg gcggttcgaa tccgtccccc accatttttt   3720
ggaacttaat taagtacggg cctccaaaaa agcctcctca ctacttctgg aatagctcag   3780
aggcagaggc ggcctcggcc tctgcataaa taaaaaaaat tagtcagcca tggggcggag   3840
aatgggcgga actgggcgga gttaggggcg ggatgggcgg agttaggggc gggactatgg   3900
ttgctgacta attgagatgc atgctttgca tacttctgcc tgctggggag cctggggact   3960
ttccacacct ggttgctgac taattgagat gcatgctttg catacttctg cccgcggagt   4020
tattaatagt aatcaattac ggggtcatta gttcatagcc catatatgga gttccgcgtt   4080
acataactta cggtaaatgg cccgcctggc tgaccgccca cgacccccg cccattgacg   4140
tcaataatga cgtatgttcc catagtaacg ccaatagggA ctttccattg acgtcaatgg   4200
gtggagtatt tacggtaaac tgcccacttg gcagtacatc aagtgtatca tatgccaagt   4260
acgccccta ttgacgtcaa tgacggtaaa tggcccgcct ggcattatgc ccagtacatg   4320
accttatggg actttcctac ttggcagtac atctacgtat tagtcatcgc tattaccatg   4380
gtgatgcggt tttggcagta catcaatggg cgtggatagc ggtttgactc acggggattt   4440
ccaagcctcc accccattga cgtcaatggg agtttgtttt ggcaccaaaa tcaacgggac   4500
tttccaaaat gtcgtaacaa ctccgcccca ttgacgcaaa tgggcggtag gcgtgtacgg   4560
tgggaggtct atataagcag agctctctgg ctaactagag aacccactgc ttactggctt   4620
atcgaaatta ctagtccacc atggggtcgt gcgaatgtcc tgccctgctg cttctgctat   4680
cttttgctgct gcttcccctg ggcctcccag tcctgggcgc cccccctcgc ctcatctgtg   4740
acagccgagt cctggagagg tacattctgg aggccaggga ggccgaaaat gtgaccatgg   4800
gctgcgctga aggctgcagc ttcagtgaga atatcaccgt tccggacacc aaggtcaact   4860
tctatacctg gaagaggatg gacgtcgggc agcaggctgt ggaagtctgg caggggctcg   4920
ccctcctcag cgaagccatc ctgcggggcc aggccctgct ggccaactcc tcccagcccc   4980
ctgagaccct gcagctgcat gtcgacaagg ccgtcagcag cctgcgcagc ctcacctccc   5040
tgctgcgcgc actgggagcc cagaaggaag ccacctccct tccgaggca acctctgccg   5100
ccccccttaag aaccttcact gtggacactt tgtgcaagct tttccgaatc tactccaact   5160
tcctgcgggg caagctgacg ctgtacacag gggaggcctg ccgaagagga cacaggtgag   5220
cggccgcatc agcctcgact gtgccttcta gttgccagcc atctgttgtt tgcccctccc   5280
ccgtgccttc cttgaccctg gaaggtgcca ctcccactgt cctttcctaa taaaatgagg   5340
aaattgcatc gcattgtctg agtaggtgtc attctattct ggggggtggg gtggggcagg   5400
acagcaaggg ggaggattgg gaagacaata gcaggcatgc tggggatgcg gtgggctcta   5460
tggcttctga gcggaaaga accagtgtac agctttgctt ctcaatttct tatttgcata   5520
atgagaaaaa aaggaaaatt aattttaaca ccaattcagt agttgattga gcaaatgcgt   5580
tgccaaaaag gatgctttag agacagtgtt ctctgcacag ataaggacaa acattattca   5640
gagggagtac ccagagctga gactcctaag ccagtgagtg cacagcatc caggagaaa   5700
tatgcttgtc atcaccgaag cctgattccg tagagccaca ccctggtaag gccaatctg   5760
ctcacacagg atagagaggg caggagccag ggcagagcat ataaggtgag gtaggatcag   5820
```

```
ttgctcctca catttgcttc tgacatagtt gtgttgggag cttggatagc ttggggggg     5880
gacagctcag ggctgcgatt tcgcgccaac ttgacggcaa tcctagcgtg aaggctggta     5940
ggattttatc cctcgagcca ccatggcctc cagcaacctg atcaagcagc tccaggagag     6000
gggcctcgtg gctcaggtca ccgacgaaga agcactcgct gaaagactgg cccagggacc     6060
cattgcactg atctgcgggt tcgatcctac agccgactct ctccacctgg gtcatctcgt     6120
gccactgctg tgtctcaaac ggtttcagca ggctggccac aagcccgtcg cactggtggg     6180
aggtgctact gggctgattg gcgatcctag tttcaaagcc gcagagcgca agctcaatac     6240
cgaggagaca gtgcaggaat gggtcgacaa aatccgaaag caggtcgccc catttctgga     6300
tttcgactgc ggagagaact cagctattgc cgcaaataac tacgattggt ttgggaatat     6360
gaacgtcctc actttcctgc gtgacatcgg taaacatttt tccgtgaatc agatgattaa     6420
caaggaagct gtgaagcaga ggctgaatag agagggccag ggaatcagct tcaccgaatt     6480
ttcttataat ctcctgcagg ggtacggtat ggcctgtgca aacaaacagt atggcgtcgt     6540
gctgcagatt ggaggcagtg atcagtgggg gaacatcaca tcaggtattg acctcactcg     6600
gcgcctgcac cagaatcagg tctttggact caccgtgccc ctgatcacaa aggctgatgg     6660
cacaaaattt ggtaagaccg agggtggagc cgtgtggctg gaccctaaaa agacatcccc     6720
atacaaattc tatcagttttt ggatcaacac tgcagatgct gacgtctacc gattcctcaa     6780
gttttttcacc tttatgagca ttgaggaaat caatgccctg gaggaagagg ataagaactc     6840
tggcaaagct ccccgtgcac agtatgtgct cgccgaacag gtcacaaggc tggtgcatgg     6900
ggaggaaggt ctgcaggctg ccaagagaat tactgagtgc ctcttcagtg gctcactgtc     6960
cgcactgagc gaagctgact ttgagcagct cgcccaggat ggagtgccta tggtcgagat     7020
ggaaaaaggc gcagacctga tgcaggctct cgtggattct gagctgcagc caagtcgggg     7080
gcaggcccgc aagaccatcg catcaaatgc tattacaatc aacggtgaaa acagtccga     7140
ccccgagtac ttctttaagg aagaggatcg actgttcgga cgttttaccc tcctgaggag     7200
aggcaaaaag aattattgtc tgatttgctg gaagtgatct agaggccgcg cagttaacgc     7260
cgcccctctc cctcccccc cctaacgtta ctggccgaag ccgcttggaa taaggccggt     7320
gtgcgtttgt ctatatgtta tattccacca tattgccgtc tattggcaat gtgagggccc     7380
ggaaacctgg ccctgtcttc ttgacgagca ttcctagggg tctttcccct ctcgccaaag     7440
gaatgcaagg tctgttgaat gtcgtgaagg aagcagttcc tctggaagct tcttgaagac     7500
aaacaacgtc tgtagcgacc cttgcaggc agcggaaccc cccacctggc gacaggtgcc     7560
tctgcggcca aaagccacgt gtataaaata cacctgcaaa ggcggcacaa ccccagtgcg     7620
acgttgtgag ttggatagtt gtggaaagag tcaaatggct ctcctcaagc gtattcaaca     7680
aggggctgaa ggatgcccag aaggtacccc attgtatggg atctgatctg gggcctcggt     7740
acacatgctt tacatgtgtt tagtcgaggt taaaaaaacg tctaggcccc ccgaaccacg     7800
gggacgtggt attcctttga aaacacgat gataatatgg ccacacccgt ccgagatcac     7860
cctcgagcca ccatggttcg accattgaac tgcatcgtcg ccgtgtccca aaatatgggg     7920
attggcaaga acgagacct accctggcct ccgctcagga acgagttcaa gtacttccaa     7980
agaatgacca caacctcttc agtggaaggt aaacagaatc tggtgattat gggtaggaaa     8040
acctggttct ccattcctga gaagaatcga ccttttaagg acagaattaa tatagttctc     8100
agtagagaac tcaaagaacc accacgagga gctcattttc ttgccaaaag tttgatgat     8160
gccttaagac ttattgaaca accggaattg gcaagtaaag tagacatggt ttggatagtc     8220
```

```
ggaggcagtt ctgtttacca ggaagccatg aatcaaccag gccacctcag actctttgtg    8280
acaaggatca tgcaggaatt tgaaagtgac acgttttcc cagaaattga tttggggaaa    8340
tataaacttc tcccagaata cccaggcgtc ctctctgagg tccaggagga aaaaggcatc   8400
aagtataagt ttgaagtcta cgagaagaaa gactaatcta gaggccgcgc acttaacgcc   8460
gcccctctcc ctcccccccc cctaacgtta ctggccgaag ccgcttggaa taaggccggt   8520
gtgcgtttgt ctatatgtta ttttccacca tattgccgtc ttttggcaat gtgagggccc   8580
ggaaacctgg ccctgtcttc ttgacgagca ttcctagggg tctttcccct ctcgccaaag   8640
gaatgcaagg tctgttgaat gtcgtgaagg aagcagttcc tctggaagct tcttgaagac   8700
aaacaacgtc tgtagcgacc ctttgcaggc agcggaaccc cccacctggc gacaggtgcc   8760
tctgcggcca aaagccacgt gtataagata cacctgcaaa ggcggcacaa ccccagtgcc   8820
acgttgtgag ttggatagtt gtggaaagag tcaaatggct ctcctcaagc gtattcaaca   8880
aggggctgaa ggatgcccag aaggtacccc attgtatggg atctgatctg ggcctcggt    8940 acacatgctt tacatgtgtt tagtcgaggt taaaaaaacg tctaggcccc ccgaaccacg   9000
gggacgtggt tttcctttga aaaacacgat gataatatgg ccacaagatc tatgcttgaa   9060
caagatggat tgcacgcagg ttctccggcc gcttgggtgg agaggctatt cggctatgac   9120
tgggcacaac agacaatcgg ctgctctgat gccgccgtgt tccggctgtc agcgcagggg   9180
cgcccggttc tttttgtcaa gaccgacctg tccggtgccc tgaatgaact gcaggacgag   9240
gcagcgcggc tatcgtggct ggccacgacg ggcgttcctt gcgcagctgt gctcgacgtt   9300
gtcactgaag cggaaggga ctggctgcta ttgggcgaag tgccggggca ggatctcctg    9360
tcatctcacc ttgctcctgc cgagaaagta tccatcatgg ctgatgcaat gcggcggctg   9420
catacgcttg atccggctac ctgcccattc gaccaccaag cgaaacatcg catcgagcga   9480
gcacgtactc ggatggaagc cggtcttgtc gatcaggatg atctggacga agagcatcag   9540
gggctcgcgc cagccgaact gttcgccagg ctcaaggcgc gcatgcccga cggcgaggat   9600
ctcgtcgtga cccatggcga tgcctgcttg ccgaatatca tggtggaaaa tggccgcttt   9660
tctggattca tcgactgtgg ccggctgggt gtggcggacc gctatcagga catagcgttg   9720
gctacccgtg atattgctga agagcttggc ggcgaatggg ctgaccgctt cctcgtgctt   9780
tacggtatcg ccgctcccga ttcgcagcgc atcgccttct atcgccttct tgacgagttc   9840
ttctgacaat tgcacgggct acgagatttc gattccaccg ccgccttcta tgaaaggttg   9900
ggcttcggaa tcgttttccg ggacgccggc tggatgatcc tccagcgcgg ggatctcatg   9960
ctggagttct tcgcccaccc caacttgttt attgcagctt ataatggtta caaataaagc   10020
aatagcatca caaatttcac aaataaagca tttttttcac tgcattctag ttgtggtttg   10080
tccaaactca tcaatgtatc ttatcatgtc ggttacccc gtccgacatg tgagcaaaag    10140
gccagcaaaa ggccaggaac cgtaaaaagg ccgcgttgct ggcgtttttc cataggctcc   10200
gcccccctga cgagcatcac aaaaatcgac gctcaagtca gaggtggcga aacccgacag   10260
gactataaag ataccaggcg tttccccctg gaagctccct cgtgcgctct cctgttccga   10320
ccctgccgct taccggatac ctgtccgcct ttctcccttc gggaagcgtg gcgctttctc   10380
atagctcacg ctgtaggtat ctcagttcgg tgtaggtcgt tcgctccaag ctgggctgtg   10440
tgcacgaacc cccgttcag cccgaccgct gcgccttatc cggtaactat cgtcttgagt    10500
ccaacccggt aagacacgac ttatcgccac tggcagcagc cactggtaac aggattagca   10560
```

| | | | | |
|---|---|---|---|---|
| gagcgaggta | tgtaggcggt | gctacagagt | tcttgaagtg | gtggcctaac tacggctaca | 10620 |
| ctagaagaac | agtatttggt | atctgcgctc | tgctgaagcc | agttaccttc ggaaaaagag | 10680 |
| ttggtagctc | ttgatccggc | aaacaaacca | ccgctggtag | cggtggtttt tttgtttgca | 10740 |
| agcagcagat | tacgcgcaga | aaaaaaggat | ctcaagaaga | tcctttgatc ttttctacgg | 10800 |
| ggtctgacgc | tcagtggaac | gaaaactcac | gttaagggat | tttggtcatg agattatcaa | 10860 |
| aaaggatctt | cacctagatc | cttttaaatt | aaaaatgaag | ttttaaatca atctaaagta | 10920 |
| tatatgagta | aacttggtct | gacagttacc | aatgcttaat | cagtgaggca cctatctcag | 10980 |
| cgatctgtct | atttcgttca | tccatagttg | cctgactccc | cgtcgtgtag ataactacga | 11040 |
| tacgggaggg | cttaccatct | ggccccagtg | ctgcaatgat | accgcgagac ccacgctcac | 11100 |
| cggctccaga | tttatcagca | ataaaccagc | cagccggaag | ggccgagcgc agaagtggtc | 11160 |
| ctgcaacttt | atccgcctcc | atccagtcta | ttaattgttg | ccgggaagct agagtaagta | 11220 |
| gttcgccagt | taatagtttg | cgcaacgttg | ttgccattgc | tacaggcatc gtggtgtcac | 11280 |
| gctcgtcgtt | tggtatggct | tcattcagct | ccggttccca | acgatcaagg cgagttacat | 11340 |
| gatcccccat | gttgtgcaaa | aaagcggtta | gctccttcgg | tcctccgatc gttgtcagaa | 11400 |
| gtaagttggc | cgcagtgtta | tcactcatgg | ttatggcagc | actgcataat tctcttactg | 11460 |
| tcatgccatc | cgtaagatgc | ttttctgtga | ctggtgagta | ctcaaccaag tcattctgag | 11520 |
| aatagtgtat | gcggcgaccg | agttgctctt | gcccggcgtc | aatacgggat aataccgcgc | 11580 |
| cacatagcag | aactttaaaa | gtgctcatca | ttggaaaacg | ttcttcgggg cgaaaactct | 11640 |
| caaggatctt | accgctgttg | agatccagtt | cgatgtaacc | cactcgtgca cccaactgat | 11700 |
| cttcagcatc | ttttactttc | accagcgttt | ctgggtgagc | aaaaacagga aggcaaaatg | 11760 |
| ccgcaaaaaa | gggaataagg | gcgacacgga | aatgttgaat | actcatactc ttcctttttc | 11820 |
| aatattattg | aagcatttat | cagggttatt | gtctcatgag | cggatacata tttgaatgta | 11880 |
| tttagaaaaa | taaacaaata | ggggttccgc | gcacatttcc | ccgaaaagtg ccacctgacg | 11940 |
| tctaagaaac | cattattatc | atgacattaa | cctataaaaa | taggcgtatc acgaggccct | 12000 |
| ttcgtc | | | | | 12006 |

<210> SEQ ID NO 29
<211> LENGTH: 8834
<212> TYPE: DNA
<213> ORGANISM: Felis catus

<400> SEQUENCE: 29

| | | | | |
|---|---|---|---|---|
| tcgcgcgttt | cggtgatgac | ggtgaaaacc | tctgacacat | gcagctcccg gagacggtca | 60 |
| cagcttgtct | gtaagcggat | gccgggagca | gacaagcccg | tcaggcgcg tcagcgggtg | 120 |
| ttggcgggtg | tcgggctgg | cttaactatg | cggcatcaga | gcagattgta ctgagagtgc | 180 |
| accatatgcc | cgtccgcgta | ccggcgcgcc | ggatgccaat | cgatgaattc cggtgtgaaa | 240 |
| taccgcacag | atgcgtaagg | agaaaatacc | gcatcaggcg | ccattcgcca ttcaggctgc | 300 |
| gcaactgttg | ggaagggcga | tcggtgcggg | cctcttcgct | attacgccag ctggcgaaag | 360 |
| ggggatgtgc | tgcaaggcga | ttaagttggg | taacgccagg | gttttcccag tcacgacgtt | 420 |
| gtaaaacgac | ggccagtgaa | ttgatgcatc | catcaattca | tatttgcatg tcgctatgtg | 480 |
| ttctgggaaa | tcaccataaa | cgtgaaatgt | ctttggattt | gggaatctta taagttctgt | 540 |
| atgagaccac | tcggatccgg | tggggtagcg | aagtggctaa | acgcggcgga ctctaaatcc | 600 |
| gctcccttg | ggttcggcgg | ttcgaatccg | tcccccacca | ttttttggaa cctagggaat | 660 |

```
tccggtgtga ataccgcac agatgcgtaa ggagaaaata ccgcatcagg cgccattcgc    720
cattcaggct gcgcaactgt tgggaagggc gatcggtgcg ggcctcttcg ctattacgcc    780
agctggcgaa aggggatgt gctgcaaggc gattaagttg ggtaacgcca gggttttccc    840
agtcacgacg ttgtaaaacg acggccagtg aattgatgca tccatcaatt catatttgca    900
tgtcgctatg tgttctggga aatcaccata aacgtgaaat gtctttggat ttgggaatct    960
tataagttct gtatgagacc actcggatcc ggtggggtag cgaagtggct aaacgcggcg   1020
gactctaaat ccgctccctt tgggttcggc ggttcgaatc cgtccccac cattttttgg    1080 aagacgtcga attccggtgt gaataccgc acagatgcgt aaggagaaaa taccgcatca    1140
ggcgccattc gccattcagg ctgcgcaact gttgggaagg gcgatcggtg cgggcctctt   1200
cgctattacg ccagctggcg aaaggggat gtgctgcaag gcgattaagt tgggtaacgc    1260
cagggttttc ccagtcacga cgttgtaaaa cgacggccag tgaattgatg catccatcaa   1320
ttcatatttg catgtcgcta tgtgttctgg gaaatcacca taaacgtgaa atgtctttgg   1380
atttgggaat cttataagtt ctgtatgaga ccactcggat ccggtggggt agcgaagtgg   1440
ctaaacgcgg cggactctaa atccgctccc tttgggttcg gcggttcgaa tccgtccccc   1500 accattttt ggaacatatg gaattccggt gtgaaatacc gcacagatgc gtaaggagaa    1560
aataccgcat caggcgccat cgccattca ggctgcgcaa ctgttgggaa gggcgatcgg    1620
tgcgggcctc ttcgctatta cgccagctgg cgaaagggg atgtgctgca aggcgattaa    1680
gttgggtaac gccagggttt tcccagtcac gacgttgtaa aacgacggcc agtgaattga   1740
tgcatccatc aattcatatt tgcatgtcgc tatgtgttct gggaaatcac cataaacgtg   1800
aaatgtcttt ggatttggga atcttataag ttctgtatga ccactcggg atccggtggg    1860 gtagcgaagt ggctaaacgc ggcggactct aaatccgctc cctttgggtt cggcggttcg   1920
aatccgtccc ccaccatttt ttggaactta attaagtacg ggcctccaaa aaagcctcct   1980
cactacttct ggaatagctc agaggcagag gcggcctcgg cctctgcata aataaaaaaa   2040
attagtcagc catggggcgg agaatgggcg gaactgggcg gagttagggg cgggatgggc   2100
ggagttaggg gcgggactat ggttgctgac taattgagat gcatgctttg catacttctg   2160
cctgctgggg agcctgggga cttttccacac ctggttgctg actaattgag atgcatgctt   2220
tgcatacttc tgccccgcgga gttattaata gtaatcaatt acgggtcat tagttcatag    2280 cccatatatg gagttccgcg ttacataact acggtaaat ggcccgcctg gctgaccgcc     2340
caacgacccc cgcccattga cgtcaataat gacgtatgtt cccatagtaa cgccaatagg   2400
gactttccat tgacgtcaat gggtggagta tttacggtaa actgcccact tggcagtaca   2460
tcaagtgtat catatgccaa gtacgccccc tattgacgtc aatgacggta atggcccgc    2520 ctggcattat gcccagtaca tgaccttatg gactttcct acttggcagt acatctacgt    2580
attagtcatc gctattacca tggtgatgcg gttttggcag tacatcaatg ggcgtggata   2640
gcggtttgac tcacggggat ttccaagcct ccacccatt gacgtcaatg ggagtttgtt    2700
ttggcaccaa aatcaacggg actttccaaa atgtcgtaac aactccgccc cattgacgca   2760
aatgggcggt aggcgtgtac ggtgggaggt ctatataagc agagctctct ggctaactag   2820
agaacccact gcttactggc ttatcgaaat tactagtcca ccatggggtc gtgcgaatgt   2880
cctgccctgc tgcttctgct atctttgctg ctgcttcccc tgggcctccc agtcctgggc   2940
gccccccctc gcctcatctg tgacagccga gtcctggaga ggtacattct ggaggccagg   3000
```

```
gaggccgaaa atgtgaccat gggctgcgct gaaggctgca gcttcagtga gaatatcacc   3060
gttccggaca ccaaggtcaa cttctatacc tggaagagga tggacgtcgg gcagcaggct   3120
gtggaagtct ggcagggcct cgccctcctc agcgaagcca tcctgcgggg ccaggccctg   3180
ctggccaact cctcccagcc ctctgagacc ctgcagctgc atgtcgacaa ggccgtcagc   3240
agcctgcgca gcctcacctc cctgctgcgc gcactgggag cccagaagga agccacctcc   3300
cttcccgagg caacctctgc cgccccctta agaaccttca ctgtggacac tttgtgcaag   3360
cttttccgaa tctactccaa cttcctgcgg ggcaagctga cgctgtacac aggggaggcc   3420
tgccgaagag gagacaggtg agcggccgca tcagcctcga ctgtgccttc tagttgccag   3480
ccatctgttg tttgcccctc ccccgtgcct tccttgaccc tggaaggtgc cactcccact   3540
gtcctttcct aataaaatga ggaaattgca tcgcattgtc tgagtaggtg tcattctatt   3600 ctgggggtg gggtggggca ggacagcaag ggggaggatt gggaagacaa tagcaggcat   3660
gctggggatg cggtgggctc tatggcttct gaggcgaaaa gaaccagtgt acagctttgc   3720
ttctcaattt cttatttgca taatgagaaa aaaggaaaa ttaattttaa caccaattca   3780
gtagttgatt gagcaaatgc gttgccaaaa aggatgcttt agagacagtg ttctctgcac   3840
agataaggac aaacattatt cagagggagt acccagagct gagactccta agccagtgag   3900
tggcacagca tccagggaga aatatgcttg tcatcaccga agcctgattc cgtagagcca   3960
caccctggta agggccaatc tgctcacaca ggatagagag gcaggagcc agggcagagc   4020 atataaggtg aggtaggatc agttgctcct cacatttgct tctgacatag ttgtgttggg   4080
agcttggata gcttgggggg gggacagctc agggctgcga tttcgcgcca acttgacggc   4140
aatcctagcg tgaaggctgg taggattta tccctcgagc caccatggcc tccagcaacc   4200
tgatcaagca gctccaggag agggcctcg tggctcaggt caccgacgaa gaagcactcg   4260
ctgaaagact ggcccaggga cccattgcac tgatctgcgg gttcgatcct acagccgact   4320
ctctccacct gggtcatctc gtgccactgc tgtgtctcaa acggtttcag caggctggcc   4380
acaagcccgt cgcactggtg ggaggtgcta ctgggctgat tggcgatcct agtttcaaag   4440
ccgcagagcg caagctcaat accgaggaga cagtgcagga tgggtcgac aaaatccgaa   4500 agcaggtcgc cccatttctg gatttcgact gcggagagaa ctcagctatt gccgcaaata   4560
actacgattg gtttgggaat atgaacgtcc tcactttcct gcgtgacatc ggtaaacatt   4620
tttccgtgaa tcagatgatt aacaaggaag ctgtgaagca gaggctgaat agagagggcc   4680
agggaatcag cttcaccgaa ttttcttata atctcctgca ggggtacggt atggcctgtg   4740
caaacaaaca gtatggcgtc gtgctgcaga ttggaggcag tgatcagtgg gggaacatca   4800
catcaggtat tgacctcact cggcgcctgc accagaatca ggtctttgga ctcaccgtgc   4860
ccctgatcac aaaggctgat ggcacaaaat tggtaagac cgagggtgga gccgtgtggc   4920
tggaccctaa aaagacatcc ccatacaaat tctatcagtt ttggatcaac actgcagatg   4980
ctgacgtcta ccgattcctc aagttttttca cctttatgag cattgaggaa atcaatgccc   5040
tggaggaaga ggataagaac tctggcaaag ctccccgtgc acagtatgtg ctcgccgaac   5100
aggtcacaag gctggtgcat ggggaggaag gtctgcaggc tgccaagaga attactgagt   5160
gcctcttcag tggctcactg tccgcactga gcgaagctga ctttgagcag ctcgcccagg   5220
atggagtgcc tatggtcgag atggaaaaag gcgcagacct gatgcaggct ctcgtggatt   5280
ctgagctgca gccaagtcgg gggcaggccc gcaagaccat cgcatcaaat gctattacaa   5340
tcaacggtga aaaacagtcc gaccccgagt acttctttaa ggaagaggat cgactgttcg   5400
```

```
gacgttttac cctcctgagg agaggcaaaa agaattattg tctgatttgc tggaagtgat    5460
ctagaggccg cgcagttaac gccgcccctc tccctccccc cccctaacgt tactggccga    5520
agccgcttgg aataaggccg gtgtgcgttt gtctatatgt tatattccac catattgccg    5580
tctattggca atgtgaggcc ccggaaacct ggccctgtct tcttgacgag cattcctagg    5640
ggtctttccc ctctcgccaa aggaatgcaa ggtctgttga atgtcgtgaa ggaagcagtt    5700
cctctggaag cttcttgaag acaaacaacg tctgtagcga cccttttgcag gcagcggaac    5760
cccccacctg gcgacaggtg cctctgcggc caaaagccac gtgtataaaa tacacctgca    5820
aaggcggcac aaccccagtg cgacgttgtg agttggatag ttgtggaaag agtcaaatgg    5880
ctctcctcaa gcgtattcaa caaggggctg aaggatgccc agaaggtacc ccattgtatg    5940
ggatctgatc tggggcctcg gtacacatgc tttacatgtg tttagtcgag gttaaaaaaa    6000
cgtctaggcc ccccgaacca cggggacgtg gtattccttt gaaaaacacg atgataatat    6060
ggccacaccc gtccgagatc accctcgagc caccatggtt cgaccattga actgcatcgt    6120
cgccgtgtcc caaaatatgg ggattggcaa gaacggagac ctaccctggc ctccgctcag    6180
gaacgagttc aagtacttcc aaagaatgac cacaacctct tcagtggaag gtaaacagaa    6240
tctggtgatt atgggtagga aaacctggtt ctccattcct gagaagaatc gacctttaaa    6300
ggacagaatt aatatagttc tcagtagaga actcaaagaa ccaccacgag gagctcattt    6360
tcttgccaaa agtttggatg atgccttaag acttattgaa caaccggaat ggcaagtaa    6420
agtagacatg gtttggatag tcggaggcag ttctgtttac caggaagcca tgaatcaacc    6480
aggccacctc agactctttg tgacaaggat catgcaggaa tttgaaagtg acacgttttt    6540
cccagaaatt gatttgggga aatataaact tctcccagaa tacccaggcg tcctctctga    6600
ggtccaggag gaaaaaggca tcaagtataa gtttgaagtc tacgagaaga aagactaatc    6660
tagagccaga tctccaattg cacgggctac gagatttcga ttccaccgcc gccttctatg    6720
aaaggttggg cttcggaatc gttttccggg acgccggctg gatgatcctc cagcgcgggg    6780
atctcatgct ggagttcttc gcccaccca acttgtttat tgcagcttat aatggttaca    6840
aataaagcaa tagcatcaca aatttcacaa ataaagcatt tttttcactg cattctagtt    6900
gtggttttgtc caaactcatc aatgtatctt atcatgtcgg ttaccccgt ccgacatgtg    6960
agcaaaaggc cagcaaaagg ccaggaaccg taaaaaggcc gcgttgctgg cgttttcca    7020
taggctccgc cccctgacg agcatcacaa aaatcgacgc tcaagtcaga ggtggcgaaa    7080
cccgacagga ctataaagat accaggcgtt tccccctgga agctccctcg tgcgctctcc    7140
tgttccgacc ctgccgctta ccggataccct gtccgccttt ctcccttcgg gaagcgtggc    7200
gctttctcat agctcacgct gtaggtatct cagttcggtg taggtcgttc gctccaagct    7260
gggctgtgtg cacgaacccc ccgttcagcc cgaccgctgc gccttatccg gtaactatcg    7320
tcttgagtcc aacccggtaa gacacgactt atcgccactg gcagcagcca ctggtaacag    7380
gattagcaga gcgaggtatg taggcggtgc tacagagttc ttgaagtggt ggcctaacta    7440
cggctacact agaagaacag tatttggtat ctgcgctctg ctgaagccag ttaccttcgg    7500
aaaaagagtt ggtagctctt gatccggcaa acaaaccacc gctggtagcg gtggtttttt    7560
tgtttgcaag cagcagatta cgcgcagaaa aaaaggatct caagaagatc ctttgatctt    7620
ttctacgggg tctgacgctc agtggaacga aaactcacgt taagggattt tggtcatgag    7680
attatcaaaa aggatcttca cctagatcct ttaaattaa aaatgaagtt ttaaatcaat    7740
```

-continued

```
ctaaagtata tatgagtaaa cttggtctga cagttaccaa tgcttaatca gtgaggcacc    7800
tatctcagcg atctgtctat ttcgttcatc catagttgcc tgactcccg tcgtgtagat    7860 aactacgata cgggagggct taccatctgg ccccagtgct gcaatgatac cgcgagaccc    7920
acgctcaccg gctccagatt tatcagcaat aaaccagcca gccggaaggg ccgagcgcag    7980
aagtggtcct gcaactttat ccgcctccat ccagtctatt aattgttgcc gggaagctag    8040
agtaagtagt tcgccagtta atagtttgcg caacgttgtt gccattgcta caggcatcgt    8100
ggtgtcacgc tcgtcgtttg gtatggcttc attcagctcc ggttcccaac gatcaaggcg    8160
agttacatga tccccatgt tgtgcaaaaa agcggttagc tccttcggtc ctccgatcgt    8220
tgtcagaagt aagttggccg cagtgttatc actcatggtt atggcagcac tgcataattc    8280
tcttactgtc atgccatccg taagatgctt ttctgtgact ggtgagtact caaccaagtc    8340
attctgagaa tagtgtatgc ggcgaccgag ttgctcttgc ccggcgtcaa tacgggataa    8400
taccgcgcca catagcagaa ctttaaaagt gctcatcatt ggaaaacgtt cttcggggcg    8460
aaaactctca aggatcttac cgctgttgag atccagttcg atgtaaccca ctcgtgcacc    8520
caactgatct tcagcatctt ttactttcac cagcgtttct gggtgagcaa aaacaggaag    8580
gcaaaatgcc gcaaaaaagg gaataagggc gacacgaaa tgttgaatac tcatactctt    8640 ccttttcaa tattattgaa gcatttatca gggttattgt ctcatgagcg gatacatatt    8700
tgaatgtatt tagaaaaata aacaaatagg ggttccgcgc acatttcccc gaaaagtgcc    8760
acctgacgtc taagaaacca ttattatcat gacattaacc tataaaaata ggcgtatcac    8820
gaggcccttt cgtc                                                       8834
```

<210> SEQ ID NO 30
<211> LENGTH: 206
<212> TYPE: PRT
<213> ORGANISM: Artificial
<220> FEATURE:
<223> OTHER INFORMATION: Full-length amino acid sequence of cEPO

<400> SEQUENCE: 30

```
Met Cys Glu Pro Ala Pro Pro Lys Pro Thr Gln Ser Ala Trp His Ser
 1               5                  10                  15

Phe Pro Glu Cys Pro Ala Leu Leu Leu Leu Ser Leu Leu Leu Leu
            20                  25                  30

Pro Leu Gly Leu Pro Val Leu Gly Ala Pro Pro Arg Leu Ile Cys Asp
        35                  40                  45

Ser Arg Val Leu Glu Arg Tyr Ile Leu Glu Ala Arg Glu Ala Glu Asn
    50                  55                  60

Val Thr Met Gly Cys Ala Gln Gly Cys Ser Phe Ser Glu Asn Ile Thr
65                  70                  75                  80

Val Pro Asp Thr Lys Val Asn Phe Tyr Thr Trp Lys Arg Met Asp Val
                85                  90                  95

Gly Gln Gln Ala Leu Glu Val Trp Gln Gly Leu Ala Leu Leu Ser Glu
            100                 105                 110

Ala Ile Leu Arg Gly Gln Ala Leu Leu Ala Asn Ala Ser Gln Pro Ser
        115                 120                 125

Glu Thr Pro Gln Leu His Val Asp Lys Ala Val Ser Ser Leu Arg Ser
    130                 135                 140

Leu Thr Ser Leu Leu Arg Ala Leu Gly Ala Gln Lys Glu Ala Met Ser
145                 150                 155                 160

Leu Pro Glu Glu Ala Ser Pro Ala Pro Leu Arg Thr Phe Thr Val Asp
```

```
                     165                 170                 175

Thr Leu Cys Lys Leu Phe Arg Ile Tyr Ser Asn Phe Leu Arg Gly Lys
            180                 185                 190

Leu Thr Leu Tyr Thr Gly Glu Ala Cys Arg Arg Gly Asp Arg
        195                 200                 205

<210> SEQ ID NO 31
<211> LENGTH: 166
<212> TYPE: PRT
<213> ORGANISM: Artificial
<220> FEATURE:
<223> OTHER INFORMATION: The mature amino acid sequence of cEPO

<400> SEQUENCE: 31

Ala Pro Pro Arg Leu Ile Cys Asp Ser Arg Val Leu Glu Arg Tyr Ile
1               5                   10                  15

Leu Glu Ala Arg Glu Ala Glu Asn Val Thr Met Gly Cys Ala Gln Gly
            20                  25                  30

Cys Ser Phe Ser Glu Asn Ile Thr Val Pro Asp Thr Lys Val Asn Phe
        35                  40                  45

Tyr Thr Trp Lys Arg Met Asp Val Gly Gln Gln Ala Leu Glu Val Trp
    50                  55                  60

Gln Gly Leu Ala Leu Leu Ser Glu Ala Ile Leu Arg Gly Gln Ala Leu
65                  70                  75                  80

Leu Ala Asn Ala Ser Gln Pro Ser Glu Thr Pro Gln Leu His Val Asp
                85                  90                  95

Lys Ala Val Ser Ser Leu Arg Ser Leu Thr Ser Leu Leu Arg Ala Leu
            100                 105                 110

Gly Ala Gln Lys Glu Ala Met Ser Leu Pro Glu Glu Ala Ser Pro Ala
        115                 120                 125

Pro Leu Arg Thr Phe Thr Val Asp Thr Leu Cys Lys Leu Phe Arg Ile
    130                 135                 140

Tyr Ser Asn Phe Leu Arg Gly Lys Leu Thr Leu Tyr Thr Gly Glu Ala
145                 150                 155                 160

Cys Arg Arg Gly Asp Arg
                165

<210> SEQ ID NO 32
<211> LENGTH: 192
<212> TYPE: PRT
<213> ORGANISM: Artificial
<220> FEATURE:
<223> OTHER INFORMATION: Full-length amino acid sequence of eEPO

<400> SEQUENCE: 32

Met Gly Val Arg Glu Cys Pro Ala Leu Leu Leu Leu Ser Leu Leu
1               5                   10                  15

Leu Pro Pro Leu Gly Leu Pro Ala Leu Gly Ala Pro Pro Arg Leu Ile
            20                  25                  30

Cys Asp Ser Arg Val Leu Glu Arg Tyr Ile Leu Glu Ala Arg Glu Ala
        35                  40                  45

Glu Asn Val Thr Met Gly Cys Ala Glu Gly Cys Ser Phe Gly Glu Asn
    50                  55                  60

Val Thr Val Pro Asp Thr Lys Val Asn Phe Tyr Ser Trp Lys Arg Met
65                  70                  75                  80

Glu Val Glu Gln Gln Ala Val Glu Val Trp Gln Gly Leu Ala Leu Leu
                85                  90                  95
```

```
Ser Glu Ala Ile Leu Gln Gly Gln Ala Leu Leu Ala Asn Ser Ser Gln
            100                 105                 110

Pro Ser Glu Thr Leu Arg Leu His Val Asp Lys Ala Val Ser Ser Leu
        115                 120                 125

Arg Ser Leu Thr Ser Leu Leu Arg Ala Leu Gly Ala Gln Lys Glu Ala
    130                 135                 140

Ile Ser Pro Pro Asp Ala Ala Ser Ala Ala Pro Leu Arg Thr Phe Ala
145                 150                 155                 160

Val Asp Thr Leu Cys Lys Leu Phe Arg Ile Tyr Ser Asn Phe Leu Arg
                165                 170                 175

Gly Lys Leu Lys Leu Tyr Thr Gly Glu Ala Cys Arg Arg Gly Asp Arg
            180                 185                 190

<210> SEQ ID NO 33
<211> LENGTH: 166
<212> TYPE: PRT
<213> ORGANISM: Artificial
<220> FEATURE:
<223> OTHER INFORMATION: The mature amino acid sequence of eEPO

<400> SEQUENCE: 33

Ala Pro Pro Arg Leu Ile Cys Asp Ser Arg Val Leu Glu Arg Tyr Ile
1               5                   10                  15

Leu Glu Ala Arg Glu Ala Glu Asn Val Thr Met Gly Cys Ala Glu Gly
            20                  25                  30

Cys Ser Phe Gly Glu Asn Val Thr Val Pro Asp Thr Lys Val Asn Phe
        35                  40                  45

Tyr Ser Trp Lys Arg Met Glu Val Glu Gln Gln Ala Val Glu Val Trp
    50                  55                  60

Gln Gly Leu Ala Leu Leu Ser Glu Ala Ile Leu Gln Gly Gln Ala Leu
65                  70                  75                  80

Leu Ala Asn Ser Ser Gln Pro Ser Glu Thr Leu Arg Leu His Val Asp
                85                  90                  95

Lys Ala Val Ser Ser Leu Arg Ser Leu Thr Ser Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Phe Ala Val Asp Thr Leu Cys Lys Leu Phe Arg Ile
    130                 135                 140

Tyr Ser Asn Phe Leu Arg Gly Lys Leu Lys Leu Tyr Thr Gly Glu Ala
145                 150                 155                 160

Cys Arg Arg Gly Asp Arg
                165

<210> SEQ ID NO 34
<211> LENGTH: 77
<212> TYPE: DNA
<213> ORGANISM: Methanococcus jannaschii

<400> SEQUENCE: 34
ccggcggtag ttcagcaggg cagaacggcg gactctaaat ccgcatggcg ctggttcaaa      60
tccggcccgc cggacca                                                    77
```

MODIFIED ANIMAL ERYTHROPOIETIN POLYPEPTIDES AND THEIR USES

CROSS-REFERENCE TO RELATED APPLICATION

The application is a divisional of U.S. application Ser. No. 14/032,963, filed on Sep. 20, 2013, which is a continuation of U.S. application Ser. No. 13/556,754, filed on Jul. 24, 2012, now U.S. Pat. No. 8,569,233, which is a divisional of U.S. application Ser. No. 12/567,627, filed on Sep. 25, 2009, now U.S. Pat. No. 8,278,418, issued on Oct. 2, 2012, which claims the benefit of the filing dates of U.S. Provisional Patent Application No. 61/100,679, filed Sep. 26, 2008, and U.S. Provisional Patent Application No. 61/100,692, filed Sep. 26, 2008. The entire disclosures of the aforesaid applications are incorporated herein by reference.

SEQUENCE LISTING

The instant application contains a Sequence Listing which has been submitted in ASCII format via EFS-Web and is hereby incorporated by reference in its entirety. Said ASCII copy, created on Sep. 9, 2015, is named 204257_531668_SL_ST25.txt and is 84,832 bytes in size.

FIELD OF THE INVENTION

This invention relates to feline, canine, and equine erythropoietin polypeptides modified with at least one non-naturally-encoded amino acid.

BACKGROUND OF THE INVENTION

The growth hormone (GH) supergene family (Bazan, F. *Immunology Today* 11: 350-354 (1991); Mott, H. R. and Campbell, I. D. *Current Opinion in Structural Biology* 5: 114-121 (1995); Silvennoinen, O. and Ihle, J. N. (1996) SIGNALING BY THE HEMATOPOIETIC CYTOKINE RECEPTORS) represents a set of proteins with similar structural characteristics. While there are still more members of the family yet to be identified, some members of the family include the following: growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor, leukemia inhibitory factor, alpha interferon, beta interferon, gamma interferon, omega interferon, tau interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). Members of the GH supergene family have similar secondary and tertiary structures, despite the fact that they generally have limited amino acid or DNA sequence identity. The shared structural features allow new members of the gene family to be readily identified.

One member of the GH supergene family is feline erythropoietin (fEPO). Naturally-occurring erythropoietin (EPO) is a glycoprotein hormone of molecular weight 34 kilo Daltons (kDa) that is produced in the mammalian kidney and liver. EPO is a key component in erythropoiesis, inducing the proliferation and differentiation of red cell progenitors. EPO activity also is associated with the activation of a number of erythroid-specific genes, including globin and carbonic anhydrase. See, e.g., Bondurant et al., *Mol. Cell Biol.* 5:675-683 (1985); Koury et al., *J. Cell. Physiol.* 126: 259-265 (1986).

The erythropoietin receptor (EpoR) is a member of the hematopoietic/cytokine/growth factor receptor family, which includes several other growth factor receptors, such as the interleukin (IL)-3, -4 and -6 receptors, the granulocyte macrophage colony-stimulating factor (GM-CSF) receptor as well as the prolactin and growth hormone receptors. See, Bazan, *Proc. Natl. Acad. Sci USA* 87: 6934-6938 (1990). Members of the cytokine receptor family contain four conserved cysteine residues and a tryptophan-serine-X-tryptophan-serine motif positioned just outside the transmembrane region. The conserved sequences are thought to be involved in protein-protein interactions. See, e.g., Chiba et al., *Biochim. Biophys. Res. Comm.* 184: 485-490 (1992).

U.S. Pat. Nos. 5,441,868; 5,547,933; 5,618,698; and 5,621,080 describe DNA sequences encoding human EPO and the purified and isolated polypeptide having part or all of the primary structural conformation and the biological properties of naturally occurring EPO.

The biological effects of EPO derive from its interaction with specific cellular receptors. The interaction between EPO and extracellular domain of its receptor (EPObp) is well understood. High-resolution x-ray crystallographic data has shown that EPO has two receptor binding sites and binds two receptor molecules sequentially using distinct sites on the molecule. The two receptor binding sites are referred to as Site I and Site II. Site I includes the carboxy terminal end of helix D and parts of helix A and the A-B loop, whereas Site II encompasses the amino terminal region of helix A and a portion of helix C. Binding of EPO to its receptor occurs sequentially, with site I binding first. Site II then engages a second EPO receptor, resulting in receptor dimerization and activation of the intracellular signaling pathways that lead to cellular responses to the hormone.

Recombinant human EPO is used as a therapeutic and has been approved for the treatment of human subjects. EPO deficiency leads to anemia, for example, which has been successfully treated by exogenous administration of the hormone.

Anemias can be broadly divided into two categories: regenerative and non-regenerative. Regenerative anemias tend to be caused by blood loss, or as a result of red blood cell destruction by the immune system. Non-regenerative anemias, on the other hand, are those in which the bone marrow does not or cannot respond to the anemia. A common cause of anemia is chronic renal failure (CRF) with most of the remaining cases being due to infection with the feline leukemia virus (FeLV). These two disorders are the number 1 (FeLV) and number 2 (CRF) causes of death in pet cats. hEPO has been used in treatment of feline anemia. Unfortunately, there are concerns regarding immunogenicity when using hEPO to treat feline anemia and around 25% to 33% of hEPO treated cats developed red cell aplasia (RCA). Studies have been done, including a study of 11 cats and 6 dogs with CRF treated with recombinant hEPO, and although there was some demonstrated ability to increase red blood cell (RBC) and reticulocyte countes, 5/11 cats developed anti-r-hEPO antibody (L D Cowgill, et al., *J Am Vet Med Assoc.* 1998 Feb. 15; 212(4):521-8). A study of the safety and efficacy of recombinant feline erythropoietin (rfEPO) was done with 26 test subject cats and found that although again RBC and reticulocyte counts were raised, eight out of the 26 cats (i.e. more than 30%) developed anti-r-fEPO antibodies (J E Randolph, et al., *Am J Vet Res.* 2004 October; 65(10):1355-66). In another study, a recombinant adeno-associated virus serotype 2 (rAAV2) vector containing feline erythropoietin cDNA was administered in a study group of 10 cats and they found that rAAV2 antibodies were detected in all vector-treated cats, one cat suffered pure RBC aplasia, and cats treated with lesser amounts showed no effect (M C Walker, et al., *Am J Vet Res*. 2005 March; 66(3):450-6).

Covalent attachment of the hydrophilic polymer poly (ethylene glycol), abbreviated PEG, is a method of increasing water solubility, bio availability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where biocompatibility, lack of toxicity, and lack of immunogenicity are of importance. In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

PEG derivatives are frequently linked to biologically active molecules through reactive chemical functionalities, such as lysine, cysteine and histidine residues, the N-terminus and carbohydrate moieties. Proteins and other molecules often have a limited number of reactive sites available for polymer attachment. Often, the sites most suitable for modification via polymer attachment play a significant role in receptor binding, and are necessary for retention of the biological activity of the molecule. As a result, indiscriminate attachment of polymer chains to such reactive sites on a biologically active molecule often leads to a significant reduction or even total loss of biological activity of the polymer-modified molecule. R. Clark et al., (1996), *J. Biol. Chem.*, 271:21969-21977. To form conjugates having sufficient polymer molecular weight for imparting the desired advantages to a target molecule, prior art approaches have typically involved random attachment of numerous polymer arms to the molecule, thereby increasing the risk of a reduction or even total loss in bioactivity of the parent molecule.

Reactive sites that form the loci for attachment of PEG derivatives to proteins are dictated by the protein's structure. Proteins, including enzymes, are built of various sequences of alpha-amino acids, which have the general structure H$_2$N—CHR—COOH. The alpha amino moiety (H$_2$N—) of one amino acid joins to the carboxyl moiety (—COOH) of an adjacent amino acid to form amide linkages, which can be represented as —(NH—CHR—CO)$_n$—, where the subscript "n" can equal hundreds or thousands. The fragment represented by R can contain reactive sites for protein biological activity and for attachment of PEG derivatives.

For example, in the case of the amino acid lysine, there exists an —NH$_2$ moiety in the epsilon position as well as in the alpha position. The epsilon —NH$_2$ is free for reaction under conditions of basic pH. Much of the art in the field of protein derivatization with PEG has been directed to developing PEG derivatives for attachment to the epsilon —NH$_2$ moiety of lysine residues present in proteins. "Polyethylene Glycol and Derivatives for Advanced PEGylation", Nektar Molecular Engineering Catalog, 2003, pp. 1-17. These PEG derivatives all have the common limitation, however, that they cannot be installed selectively among the often numerous lysine residues present on the surfaces of proteins. This can be a significant limitation in instances where a lysine residue is important to protein activity, existing in an enzyme active site for example, or in cases where a lysine residue plays a role in mediating the interaction of the protein with other biological molecules, as in the case of receptor binding sites.

A second and equally important complication of existing methods for protein PEGylation is that the PEG derivatives can undergo undesired side reactions with residues other than those desired. Histidine contains a reactive imino moiety, represented structurally as —N(H)—, but many derivatives that react with epsilon —NH$_2$ can also react with —N(H)—. Similarly, the side chain of the amino acid cysteine bears a free sulfhydryl group, represented structurally as —SH. In some instances, the PEG derivatives directed at the epsilon —NH$_2$ group of lysine also react with cysteine, histidine or other residues. This can create complex, heterogeneous mixtures of PEG-derivatized bioactive molecules and risks destroying the activity of the bioactive molecule being targeted. It would be desirable to develop PEG derivatives that permit a chemical functional group to be introduced at a single site within the protein that would then enable the selective coupling of one or more PEG polymers to the bioactive molecule at specific sites on the protein surface that are both well-defined and predictable.

In addition to lysine residues, considerable effort in the art has been directed toward the development of activated PEG reagents that target other amino acid side chains, including cysteine, histidine and the N-terminus. U.S. Pat. No. 6,610,281. "Polyethylene Glycol and Derivatives for Advanced PEGylation", Nektar Molecular Engineering Catalog, 2003, pp. 1-17. Cysteine residue can be introduced site-selectively into the structure of proteins using site-directed mutagenesis and other techniques known in the art, and the resulting free sulfhydryl moiety can be reacted with PEG derivatives that bear thiol-reactive functional groups. This approach is complicated, however, in that the introduction of a free sulfhydryl group can complicate the expression, folding and stability of the resulting protein. Thus, it would be desirable to have a means to introduce a chemical functional group into bioactive molecules that enables the selective coupling of one or more PEG polymers to the protein while simultaneously being compatible with (i.e., not engaging in undesired side reactions with) sulfhydryls and other chemical functional groups typically found in proteins.

As can be seen from a sampling of the art, many of these derivatives that have been developed for attachment to the side chains of proteins, in particular, the —NH$_2$ moiety on the lysine amino acid side chain and the —SH moiety on the cysteine side chain, have proven problematic in their synthesis and use. Some form unstable linkages with the protein that are subject to hydrolysis and therefore decompose, degrade, or are otherwise unstable in aqueous environments, such as in the blood stream. Some form more stable linkages, but are subject to hydrolysis before the linkage is formed, which means that the reactive group on the PEG derivative may be inactivated before the protein can be attached. Some are somewhat toxic and are therefore less suitable for use in vivo. Some are too slow to react to be practically useful. Some result in a loss of protein activity by attaching to sites responsible for the protein's activity. Some are not specific in the sites to which they will attach, which can also result in a loss of desirable activity and in a lack of reproducibility of results. In order to overcome the challenges associated with modifying proteins with poly(ethylene glycol) moieties, PEG derivatives have been developed that are more stable (e.g., U.S. Pat. No. 6,602,498) or that react selectively with thiol moieties on molecules and surfaces (e.g., U.S. Pat. No. 6,610,281). There is clearly a need in the art for PEG derivatives that are chemically inert in physiological environments until called upon to react selectively to form stable chemical bonds.

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Saccharomyces cerevisiae* (*S. cerevisiae*) (e.g., J. Chin et al., *Science* 301: 964-7 (2003)), which has enabled the incorporation of non-genetically encoded amino acids to proteins in vivo. A number of new amino acids with novel chemical, physical or biological properties, including photoaffinity labels and photoisomerizable amino acids, keto amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027; J. W. Chin, & P. G. Schultz, (2002), *ChemBioChem* 11:1135-1137; J. W. Chin, et al., (2002), *PNAS United States of America* 99:11020-11024: and, L. Wang, & P. G. Schultz, (2002), *Chem. Comm.*, 1-10. These studies have demonstrated that it is possible to selectively and routinely introduce chemical functional groups, such as alkyne groups and azide moieties, that are not found in proteins, that are chemically inert to all of the functional groups found in the 20 common, genetically-encoded amino acids and that may be used to react efficiently and selectively to form stable covalent linkages.

The ability to incorporate non-genetically encoded amino acids into proteins permits the introduction of chemical functional groups that could provide valuable alternatives to the naturally-occurring functional groups, such as the epsilon —$NH_2$ of lysine, the sulfhydryl —SH of cysteine, the imino group of histidine, etc. Certain chemical functional groups are known to be inert to the functional groups found in the 20 common, genetically-encoded amino acids but react cleanly and efficiently to form stable linkages. Azide and acetylene groups, for example, are known in the art to undergo a Huisgen [3+2] cycloaddition reaction in aqueous conditions in the presence of a catalytic amount of copper. See, e.g., Tornoe, et al., (2002) *Org. Chem.* 67:3057-3064; and, Rostovtsev, et al., (2002) *Angew. Chem. Int. Ed.* 41:2596-2599. By introducing an azide moiety into a protein structure, for example, one is able to incorporate a functional group that is chemically inert to amines, sulfhydryls, carboxylic acids, hydroxyl groups found in proteins, but that also reacts smoothly and efficiently with an acetylene moiety to form a cycloaddition product. Importantly, in the absence of the acetylene moiety, the azide remains chemically inert and unreactive in the presence of other protein side chains and under physiological conditions.

The present invention addresses, among other things, problems associated with the activity and production of EPO, and also addresses the production of a hEPO polypeptide with improved biological or pharmacological properties, such as improved therapeutic half-life.

BRIEF SUMMARY OF THE INVENTION

This invention provides fEPO polypeptides comprising a non-naturally encoded amino acid.

In some embodiments, the fEPO polypeptide is linked to a second fEPO polypeptide.

In some embodiments, the non-naturally encoded amino acid is linked to a water soluble polymer. In some embodiments, the water soluble polymer comprises a poly(ethylene glycol) moiety. In some embodiments, the poly(ethylene glycol) molecule is a bifunctional polymer. In some embodiments, the bifunctional polymer is linked to a second polypeptide. In some embodiments, the second polypeptide is a fEPO polypeptide.

In some embodiments, the fEPO polypeptide comprises at least two amino acids linked to a water soluble polymer comprising a poly(ethylene glycol) moiety. In some embodiments, at least one amino acid is a non-naturally encoded amino acid.

In some embodiments, the one or more non-naturally encoded amino acids are incorporated at any position in one or more of the following regions corresponding to secondary structures in fEPO as follows: 1-7 (N-terminus), 8-26 (A helix), 27-54 (region between A helix and B helix) 55-83 (B helix), 84-89 (region between B helix and C helix), 90-112 (C helix), 113-137 (region between C helix and D helix), 138-161 (D helix), 162-166 (C-terminus), 39-41 (beta sheet 1), 133-135 (beta sheet 2), 47-52 (mini B loop), 114-121 (mini C loop), 34-38 (loop between A helix and the anti-parallel beta1 sheet), 51-57 (C-terminal end of the B' helix, loop between B' helix and B helix and N-terminal end of the B-helix), 82-92 (region between the B helix and the C helix), and 120-133 (region between the C' helix and anti-parallel beta sheet 2). In some embodiments, the one or more non-naturally encoded amino acids are incorporated in one of the following positions in fEPO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165 and 166. In some embodiments, the one or more non-naturally encoded amino acids are incorporated in one of the following positions in fEPO: 1, 2, 3, 4, 5, 6, 7, 8, 9, 10, 11, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165 and 166. In some embodiments, the one or more non-naturally encoded amino acids are incorporated in one of the following positions in fEPO: 1, 2, 3, 4, 5, 6, 17, 21, 24, 27, 28, 30, 31, 32, 34, 35, 36, 37, 38, 40, 50, 51, 52, 53, 54, 55, 56, 57, 58, 68, 72, 76, 80, 82, 83, 84, 85, 86, 87, 88, 89, 90, 91, 92, 113, 116, 119, 120, 121, 122, 123, 124, 125, 126, 127, 128, 129, 130, 131, 132, 133, 134, 136, 162, 163, 164, 165 and 166. In some embodiments, the one or more non-naturally encoded amino acids are incorporated in one of the following positions in fEPO: 1, 2, 3, 4, 5, 6, 17, 18, 21, 24, 27, 28, 30, 31, 32, 34, 35, 36, 37, 38, 40, 50, 51, 52, 53, 54, 55, 56, 57, 58, 68, 72, 76, 80, 82, 83, 84, 85, 86, 87, 88, 89, 90, 91, 92, 113, 116, 119, 120, 121, 122, 123, 124, 125, 126, 127, 128, 129, 130, 131, 132, 133, 134, 136, 162, 163, 164, 165 and 166. In some embodiments, the fEPO polypeptides of the invention comprise one or more non-naturally occurring amino acids at one or more of the following positions: 21, 24, 27, 28, 30, 31, 34, 36, 37, 38, 40, 55, 68, 72, 76, 83, 85, 86, 87, 89, 113, 116, 119, 120, 121, 123, 124, 125, 126, 127, 128, 129, 130, 136, and 162. In some embodiments, the non-naturally occurring amino acid at these or other positions is linked to a water soluble molecule, including but not limited to positions 21, 24, 38, 83, 85, 116, and 119. In some embodiments, the fEPO polypeptides of the invention comprise one or more non-naturally occurring amino acids at one or more of the following positions: 18, 53, 58, 116, 121, 89, 94, 72, 77, 86, 91, 31, 36, 132, 137, 163, 168, 120, 125, 55, and 60. In some embodiments, the fEPO polypeptides of the invention comprise one or more non-naturally occurring amino acids at one or more of the following positions: 53, 58, 116, 121, 89, 94, 72, 77, 86, 91, 31, 36, 132, 137, 163, 168, 120, 125, 55, and 60. In some embodiments, the fEPO polypeptides of the invention comprise one or more non-naturally occurring amino acids at one or more of the following positions: 18, 53, 58, 116, 121, 89, 94, 72, 77, 86, 91, 31, 36, 132, 137, 163, 168, 120, 125, 55, and 60. In some embodiments, the non-naturally occurring amino acid at these or other positions is linked to a water soluble molecule, including but not limited to positions 53, 58, 116, 121, 89, 94, 72, 77, 86, 91, 31, 36, 132, 137, 163, 168, 120, 125, 55, and 60. In some embodiments, the fEPO polypeptides of the invention comprise one or more non-naturally occurring amino acids at one or more of the following positions: 123, 124, 125, 126, 127, 128, 129, and 130. In some embodiments, the non-naturally occurring amino acid at these or other positions is linked to a water soluble molecule, including but not limited to positions 123, 124, 125, 126, 127, 128, 129, and 130.

In some embodiments, the fEPO polypeptide comprises a substitution, addition or deletion that increases affinity of the fEPO polypeptide for an erythropoietin receptor. In some embodiments, the fEPO polypeptide comprises a substitution, addition, or deletion that increases the stability of the fEPO polypeptide. In some embodiments, the fEPO polypeptide comprises a substitution, addition, or deletion that increases the aqueous solubility of the fEPO polypeptide. In some embodiments, the fEPO polypeptide comprises a substitution, addition, or deletion that increases the solubility of the fEPO polypeptide produced in a host cell. In some embodiments, the fEPO polypeptide comprises a substitution of an amino acid selected from the group consisting of, but not limited to, N24, N36, N38, Q58, Q65, N83, Q86, G113, Q115, and S126 and combination thereof in SEQ ID NO: 2. In some embodiments, the fEPO polypeptide comprises a substitution of an amino acid selected from the group consisting of, but not limited to, N24, N36, N38, Q58, Q65, N83, Q86, G113, Q115, and S126 and combination thereof in SEQ ID NO: 4.

In some embodiments the amino acid substitutions in the fEPO polypeptide may be with naturally occurring or non-naturally occurring amino acids, provided that at least one substitution is with a non-naturally encoded amino acid.

In some embodiments, the non-naturally encoded amino acid comprises a carbonyl group, an acetyl group, an aminooxy group, a hydrazine group, a hydrazide group, a semicarbazide group, an azide group, or an alkyne group.

In some embodiments, the non-naturally encoded amino acid comprises a carbonyl group. In some embodiments, the non-naturally encoded amino acid has the structure:

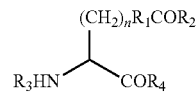

wherein n is 0-10; $R_1$ is an alkyl, aryl, substituted alkyl, or substituted aryl; $R_2$ is H, an alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group.

In some embodiments, the non-naturally encoded amino acid comprises an aminooxy group. In some embodiments, the non-naturally encoded amino acid comprises a hydrazide group. In some embodiments, the non-naturally encoded amino acid comprises a hydrazine group. In some embodiments, the non-naturally encoded amino acid residue comprises a semicarbazide group.

In some embodiments, the non-naturally encoded amino acid residue comprises an azide group. In some embodiments, the non-naturally encoded amino acid has the structure:

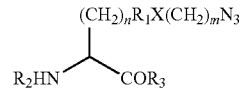

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group.

In some embodiments, the non-naturally encoded amino acid comprises an alkyne group. In some embodiments, the non-naturally encoded amino acid has the structure:

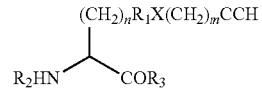

wherein n is 0-10; R1 is an alkyl, aryl, substituted alkyl, or substituted aryl; X is O, N, S or not present; m is 0-10, $R_2$ is H, an amino acid, a polypeptide, or an amino terminus modification group, and $R_3$ is H, an amino acid, a polypeptide, or a carboxy terminus modification group.

In some embodiments, the polypeptide is an erythropoietin agonist, partial agonist, antagonist, partial antagonist, or inverse agonist. In some embodiments, the erythropoietin agonist, partial agonist, antagonist, partial antagonist, or inverse agonist comprises a non-naturally encoded amino acid is linked to a water soluble polymer. In some embodiments, the water soluble polymer comprises a poly(ethylene glycol) moiety. In some embodiments, the non-naturally encoded amino acid linked to a water soluble polymer is present within the Site 2 region (the region of the protein encompassing the AC helical-bundle face) of fEPO. In some embodiments, the fEPO polypeptide comprising a non-naturally encoded amino acid linked to a water soluble polymer prevents dimerization of the fEPO receptor by preventing the fEPO antagonist from binding to a second fEPO receptor molecule. In some embodiments, an amino acid other than leucine is substituted for L108 in SEQ ID NO: 2. In some embodiments, arginine or lysine is substituted for L108 in SEQ ID NO: 2. In some embodiments, a non-naturally encoded amino acid is substituted for L108 in SEQ ID NO: 2.

The present invention also provides isolated nucleic acids comprising a polynucleotide that hybridizes under stringent conditions to SEQ ID NO: 24, 25, 26, or 27, wherein the polynucleotide comprises at least one selector codon. In some embodiments, the selector codon is selected from the group consisting of an amber codon, ochre codon, opal codon, a unique codon, a rare codon, and a four-base codon.

The present invention also provides methods of making a fEPO polypeptide linked to a water soluble polymer. In some embodiments, the method comprises contacting an isolated fEPO polypeptide comprising a non-naturally encoded amino acid with a water soluble polymer comprising a moiety that reacts with the non-naturally encoded amino acid. In some embodiments, the non-naturally encoded amino acid incorporated into fEPO is reactive toward a water soluble polymer that is otherwise unreactive toward any of the 20 common amino acids.

In some embodiments, the fEPO polypeptide linked to the water soluble polymer is made by reacting a fEPO polypeptide comprising a carbonyl-containing amino acid with a poly(ethylene glycol) molecule comprising an aminooxy, a hydroxylamine, hydrazine, hydrazide or semicarbazide group. In some embodiments, the aminooxy, hydroxylamine, hydrazine, hydrazide or semicarbazide group is linked to the poly(ethylene glycol) molecule through an amide linkage.

In some embodiments, the fEPO polypeptide linked to the water soluble polymer is made by reacting a poly(ethylene glycol) molecule comprising a carbonyl group with a polypeptide comprising a non-naturally encoded amino acid that comprises a hydroxylamine, hydrazide or semicarbazide group.

In some embodiments, the fEPO polypeptide linked to the water soluble polymer is made by reacting a fEPO polypeptide comprising an alkyne-containing amino acid with a poly(ethylene glycol) molecule comprising an azide moiety. In some embodiments, the azide or alkyne group is linked to the poly(ethylene glycol) molecule through an amide linkage.

In some embodiments, the fEPO polypeptide linked to the water soluble polymer is made by reacting a fEPO polypeptide comprising an azide-containing amino acid with a poly(ethylene glycol) molecule comprising an alkyne moiety. In some embodiments, the azide or alkyne group is linked to the poly(ethylene glycol) molecule through an amide linkage.

In some embodiments, the poly(ethylene glycol) molecule has a molecular weight of between about 1 and about 100 kDa. In some embodiments, the poly(ethylene glycol) molecule has a molecular weight of between 1 kDa and 50 kDa.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa.

In some embodiments, the water soluble polymer linked to fEPO comprises a polyalkylene glycol moiety. In some embodiments, the non-naturally encoded amino acid residue incorporated into fEPO comprises a carbonyl group, an acetyl group, an aminooxy group, a hydrazide group, a semicarbazide group, an azide group, or an alkyne group. In some embodiments, the non-naturally encoded amino acid residue incorporated into fEPO comprises a carbonyl moiety and the water soluble polymer comprises an aminooxy, a hydroxylamine, hydrazide or semicarbazide moiety. In some embodiments, the non-naturally encoded amino acid residue incorporated into fEPO comprises an alkyne moiety and the water soluble polymer comprises an azide moiety. In some embodiments, the non-naturally encoded amino acid residue incorporated into fEPO comprises an azide moiety and the water soluble polymer comprises an alkyne moiety.

The present invention also provides compositions comprising a fEPO polypeptide comprising a non-naturally-encoded amino acid and a pharmaceutically acceptable carrier. In some embodiments, the non-naturally encoded amino acid is linked to a water soluble polymer.

The present invention also provides cells comprising a polynucleotide encoding the fEPO polypeptide comprising a selector codon. In some embodiments, the cells comprise an orthogonal RNA synthetase and/or an orthogonal tRNA for substituting a non-naturally encoded amino acid into the fEPO polypeptide.

The present invention also provides methods of making a fEPO polypeptide comprising a non-naturally encoded amino acid. In some embodiments, the methods comprise culturing cells comprising a polynucleotide or polynucleotides encoding a fEPO polypeptide, an orthogonal RNA synthetase and an orthogonal tRNA under conditions to permit expression of the fEPO polypeptide; and purifying the fEPO polypeptide from the cells and/or culture medium.

The present invention also provides methods of increasing therapeutic half-life, serum half-life or circulation time of fEPO. In some embodiments, the methods comprise substituting a non-naturally encoded amino acid for any one or more amino acids in naturally occurring fEPO and/or linking the fEPO polypeptide to a water soluble polymer.

The present invention also provides methods of treating a patient in need of such treatment with an effective amount of a fEPO molecule of the present invention. In some embodiments, the methods comprise administering to the patient a therapeutically-effective amount of a pharmaceutical composition comprising a fEPO polypeptide comprising a non-naturally-encoded amino acid and a pharmaceutically acceptable carrier. In some embodiments, the non-naturally encoded amino acid is linked to a water soluble polymer.

The present invention also provides fEPO polypeptides comprising a sequence shown in SEQ ID NO: 1, 2, 3, or 4, except that at least one amino acid is substituted by a non-naturally encoded amino acid. In some embodiments, the non-naturally encoded amino acid is linked to a water soluble polymer. In some embodiments, the water soluble polymer comprises a poly(ethylene glycol) moiety. In some embodiments, the non-naturally encoded amino acid is substituted at a position selected from the group consisting of residues including but not limited to 1-6, 21-40, 68-89, 116-136, 162-166 from SEQ ID NO: 2, or SEQ ID NO: 4, or the corresponding amino acid position of SEQ ID NO:1 or SEQ ID NO: 3. In some embodiments, the non-naturally encoded amino acid comprises a carbonyl group, an aminooxy group, a hydrazide group, a hydrazine group, a semicarbazide group, an azide group, or an alkyne group.

The present invention also provides pharmaceutical compositions comprising a pharmaceutically acceptable carrier and a fEPO polypeptide comprising the sequence shown in SEQ ID NO: 1, 2, 3, or 4, wherein at least one amino acid is substituted by a non-naturally encoded amino acid. The present invention also provides pharmaceutical compositions comprising a pharmaceutically acceptable carrier and a fEPO polypeptide comprising the sequence shown in SEQ ID NO: 2 or 4, wherein at least one amino acid is substituted by a non-naturally encoded amino acid. In some embodiments, the non-naturally encoded amino acid comprises a saccharide moiety. In some embodiments, the water soluble polymer is linked to the polypeptide via a saccharide moiety.

BRIEF DESCRIPTION OF THE DRAWINGS

FIG. 1—A diagram of the sequence alignment of human and feline erythropoietin.

FIG. 2—A diagram highlighting the difference between the two sequences deposited in Genbank (Genbank accession No. U00685 and Genbank accession No. L10606), the consensus sequence.

FIG. 8—A chart of some selected sites for incorporation of non-naturally encoded amino acids, the naturally occurring amino acid and the amino acid position from SEQ ID NO: 2 and SEQ ID NO: 4 and the average Cx for those sites.

FIG. 9—A chart of some selected sites for incorporation of non-naturally encoded amino acids, the naturally occurring amino acid and the amino acid position from SEQ ID NO: 2 and SEQ ID NO: 4 and the average Cx for those sites.

FIG. 10a—The optical density at 450 nm graphed against the concentration of formulation buffer.

FIG. 10b—The optical density at 450 nm graphed against the concentration of endotoxin.

FIG. 17—A chart measuring the assay robustness, providing data on the cell passage number, EC50, OD's and dynamic ranges.

FIG. 25—A schematic drawing of the Lucy F vector and the situs of the tRNAs, gene of interest transcriptional element, and the tRNA synthetase.

FIG. 26—A schematic drawing of the Irwin vector and the situs of the tRNAs, gene of interest transcriptional element, and the tRNA synthetase.

FIG. 27—A schematic drawing of the suppression expression construct Nat L BB-Opti FEPO in Lucy F for feline erythropoietin.

FIG. 29—A schematic drawing depicting a suppression expression construct according to the invention encoding a generic antibody with light and heavy chain genes FIG. 30—A bar graph showing the suppression levels of fEPO variants in the presence of pAF measured by ELISA (OD-50).

FIG. 34—A comparison between the cEPO (SEQ ID NO: 31) and fEPO (SEQ ID NO: 4) amino acid sequences showing the 94% homology between the two.

FIG. 35—A comparison between the eEPO (SEQ ID NO: 33) and fEPO (SEQ ID NO: 4) amino acid sequences showing the 94% homology between the two.

DEFINITIONS

Figure 3:
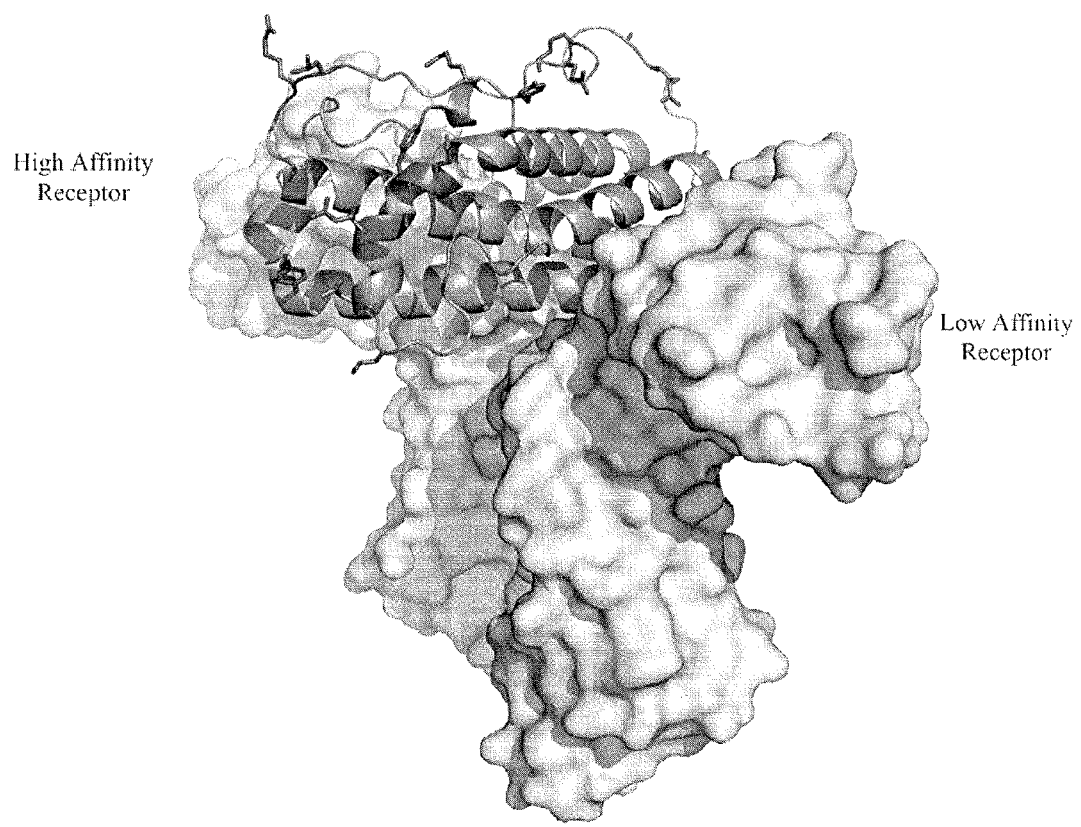
FIG. 3—A diagram of the general structure for the four helical bundle protein erythropoietin (EPO) is shown with high and low affinity receptors.
Figure 4:
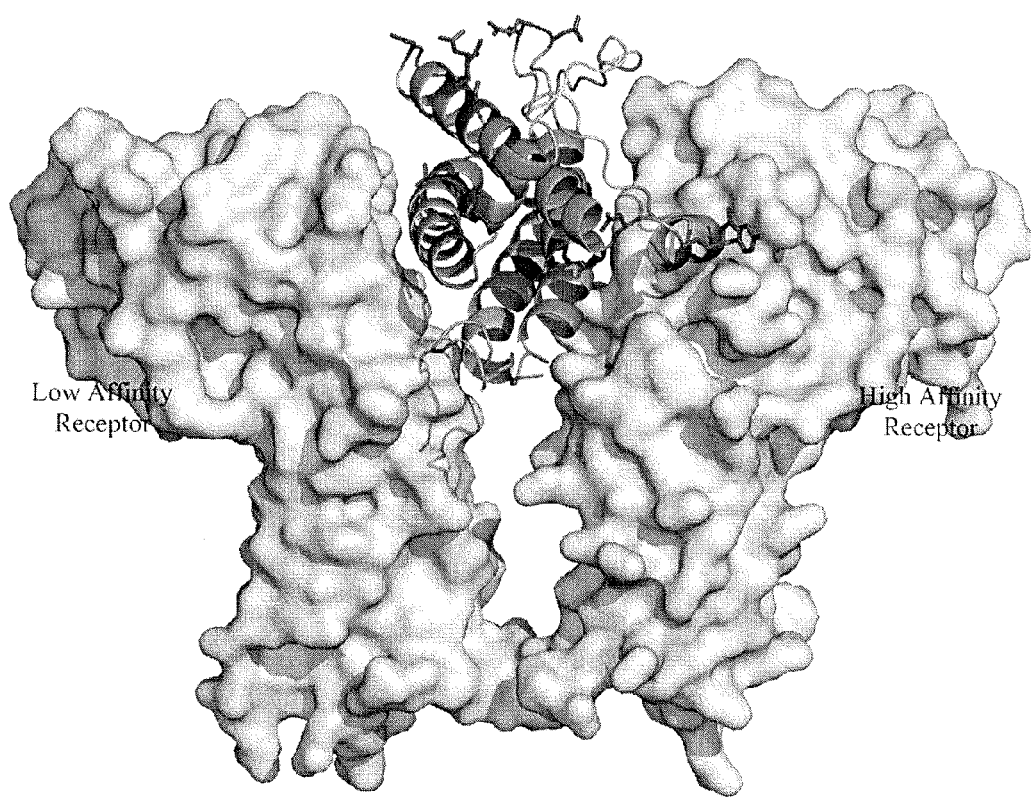
FIG. 4—A diagram of an alternate view of the general structure for the four helical bundle protein erythropoietin (EPO) is shown with high and low affinity receptors.
Figure 5:
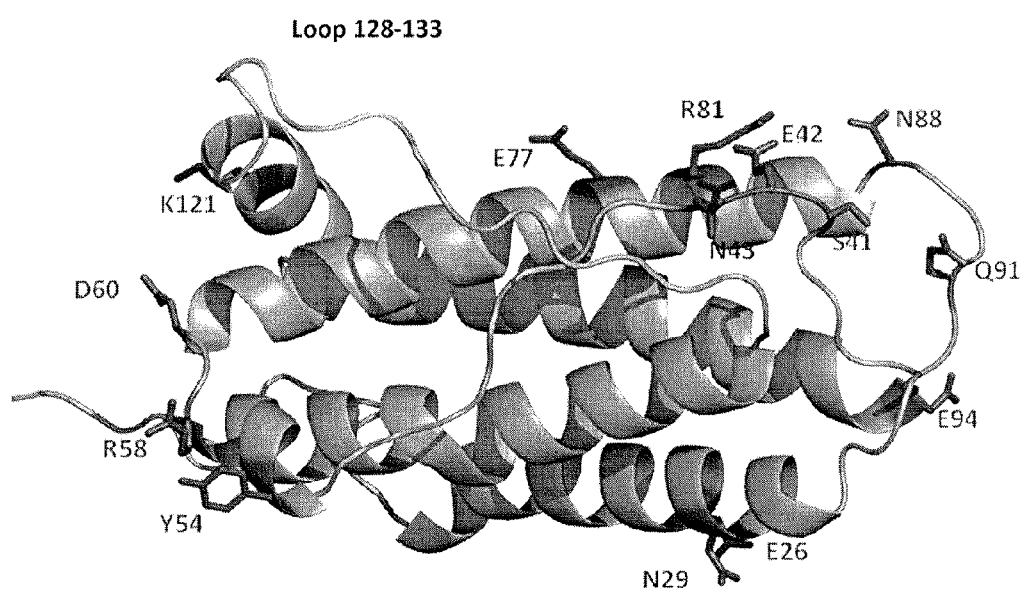
FIG. 5—A diagram showing some selected sites for incorporation of non-naturally encoded amino acids.
Figure 6:
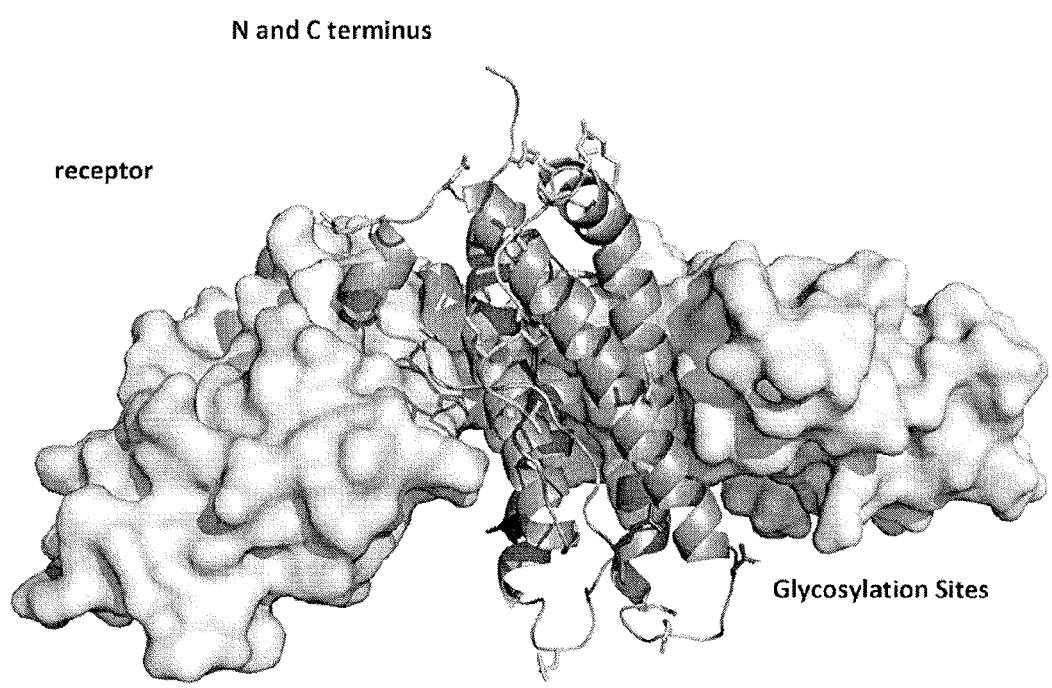
FIG. 6—A diagram showing a top view of some selected sites for incorporation of non-naturally encoded amino acids.
Figure 7:
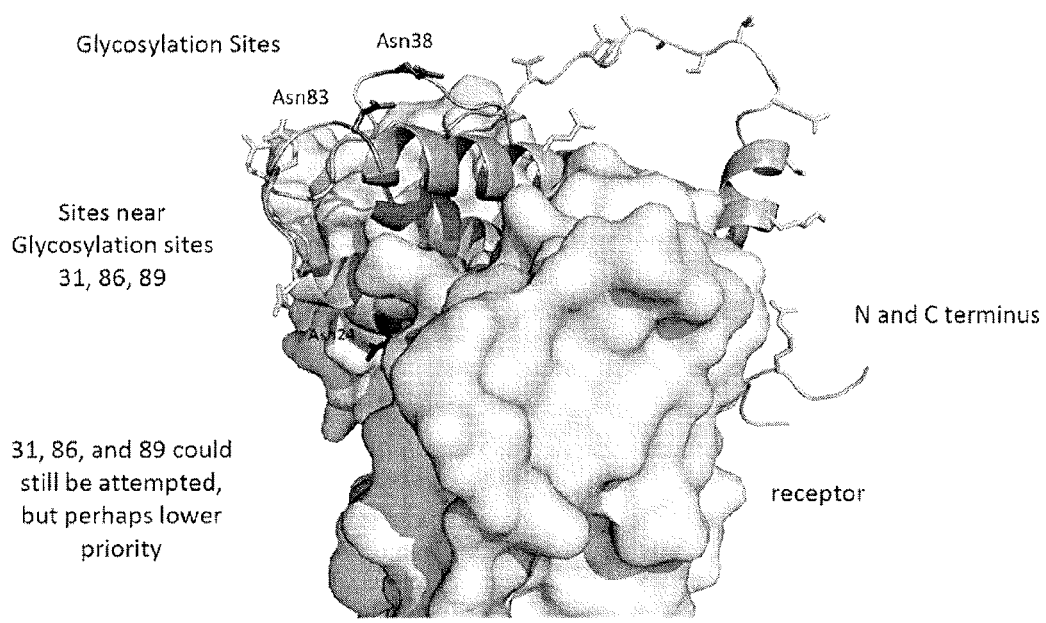
FIG. 7—A diagram showing a side view of some selected sites for incorporation of non-naturally encoded amino acids, and highlighting which of those sites are close to glycosylation sites.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "fEPO" is a reference to one or more such proteins and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

The term "substantially purified" refers to fEPO that may be substantially or essentially free of components that normally accompany or interact with the protein as found in its naturally occurring environment, i.e. a native cell, or host cell in the case of recombinantly produced fEPO. fEPO that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the fEPO or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the fEPO or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" fEPO as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells or *E. coli*, and cell contents. Thus, the term may encompass medium in which the host cell has been grown, e.g., medium into which the fEPO has been secreted, including medium either before or after a proliferation step. The term also may encompass buffers or reagents that contain host cell lysates, such as in the case where fEPO is produced intracellularly and the host cells are lysed or disrupted to release the fEPO.

As used herein, "IRES" or an internal ribosome entry site, is known to those skilled in the art. IRES is a region of a nucleic acid molecule e.g., an mRNA molecule, that allows internal ribosome entry/binding sufficient to initiate translation in an assay for cap-independent translation, such as the bicistronic reporter assay described in U.S. Pat. No. 6,715,821. The presence of an IRES within an mRNA molecule allows cap-independent translation of a linked protein-encoding sequence that otherwise would not be translated. IRES's were first identified in picornaviruses, and are considered the paradigm for cap-independent translation. The 5' UTRS of all picornaviruses are long and mediate translational initiation by directly recruiting and binding ribosomes, thereby circumventing the initial cap-binding step.

IRES elements are frequently found in viral mRNAS, and are rarely found in non-viral mRNAs. To date, the non-viral mRNAS shown to contain functional IRES elements in their respective 5' UTRS include those encoding immunoglobulin heavy chain binding protein (BIP) (Macejak, D. J. et al., Nature 353:90-94 (1991)); *Drosophila* Antennapedia (Oh, S. K. et al., Genes Dev. 6:1643-53 (1992)); and Ultrabithoran (Ye, X. et al., Mol. Cell. Biol. 17:1714-21 (1997)); fibroblast growth factor 2 (Vagner et al., Mol. Cell. Biol. 15:35-47 (1915); initiation factor (Gan et al., J. Biol. Chem. 273: 5006-12 (1992)); protein-oncogene c-myc (Nambru et al., J. Biol. Chem. 272:32061-6 (1995)); Stonely M. Oncogene 16:423-8 (1998)); Vascular endothelial growth factor (VEGF) (Stein J. et al., Mol. Cell. Biol. 18:3112-9 (1998)). Cellular IRES elements have no obvious sequence or structural similarity to IRES sequences or to each other and therefore are identified using translational assays. Another known IRES is the XIAP IRES disclosed in U.S. Pat. No. 6,171,821, incorporated by reference in its entirety herein.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. It is readily apparent to those of ordinary skill in the art that a wide variety of reducing agents are suitable for use in the methods of the present invention.

"Oxidizing agent," as used herein with respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. TWEEN (ethoxylated sorbitan esters) or Triton detergents), Sarkosyl, mild non-ionic detergents (e.g., digitonin), mild cationic detergents such as N->2,3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

As used herein, "erythropoietin" or "EPO" shall include those polypeptides and proteins that have at least one biological activity of feline erythropoietin (fEPO), as well as erythropoietin analogs, erythropoietin isoforms (such as those described in U.S. Pat. No. 5,856,298 which is incorporated by reference herein), erythropoietin mimetics (such as those described in U.S. Pat. No. 6,310,078 which is incorporated by reference herein), erythropoietin fragments, hybrid erythropoietin proteins, fusion proteins oligomers and multimers, homologues, glycosylation pattern variants, and muteins, regardless of the biological activity of same, and further regardless of the method of synthesis or manufacture thereof including, but not limited to, recombinant (whether produced from cDNA or genomic DNA), synthetic, transgenic, and gene activated methods. Specific examples of erythropoietin include, but are not limited to, epoetin alfa (such as those described in U.S. Pat. Nos. 4,667,016; 4,703,008; 5,441,868; 5,547,933; 5,618,698; 5,621,080; 5,756,349; and 5,955,422 which are incorporated by reference herein), darbepoetin alfa (such as described in European patent application EP640619), DYNEPO™ (epoetin delta), human erythropoietin analog (such as the human serum albumin fusion proteins described in international patent application WO9966054 and U.S. Pat. Nos. 6,548,653; and 5,888,772, which are incorporated by reference herein), erythropoietin mutants (such as those described in international patent application WO9938890, and U.S. Pat. Nos. 6,489,293; 5,888,772; 5,614,184; and 5,457,089 which are incorporated by reference herein), erythropoietin omega (which may be produced from an Apa I restriction fragment of the human erythropoietin gene described in U.S. Pat. Nos. 5,688,679; 6,099,830; 6,316,254; and 6,682,910, which are incorporated by reference herein), altered glycosylated human erythropoietin (such as those described in international patent application WO9911781 and EP1064951), and PEG conjugated erythropoietin analogs (such as those described in WO9805363 and U.S. Pat. Nos. 5,643,575; 6,583,272; 6,340,742; and 6,586,398, which are incorporated by reference herein). Specific examples of cell lines modified for expression of endogenous human erythropoietin are described in international patent applications WO9905268 and WO9412650 and U.S. Pat. No. 6,376,218 which are incorporated by reference herein.

The term "feline erythropoietin (fEPO)" or "fEPO polypeptide" refers to erythropoietin or EPO as described above, as well as a polypeptide that retains at least one biological activity of naturally-occurring fEPO. fEPO polypeptides include the pharmaceutically acceptable salts and prodrugs, and prodrugs of the salts, polymorphs, hydrates, solvates, biologically-active fragments, biologically-active variants and stereoisomers of the naturally-occurring feline erythropoietin as well as agonist, mimetic, and antagonist variants of the naturally-occurring human Erythropoietin and polypeptide fusions thereof. Examples of fEPO polypeptides and mimetics include those described in U.S. Pat. Nos. 6,310,078; 5,106,954; 6,703,480; 6,642,353; 5,986,047; and 5,712,370, which are incorporated by reference herein. Fusions comprising additional amino acids at the amino terminus, carboxyl terminus, or both, are encompassed by the term "fEPO polypeptide." Exemplary fusions include, but are not limited to, e.g., methionyl erythropoietin in which a methionine is linked to the N-terminus of fEPO, fusions for the purpose of purification (including but not limited to, to poly-histadine or affinity epitopes), fusions with serum albumin binding peptides and fusions with serum proteins such as serum albumin. The naturally-occurring fEPO nucleic acid and amino acid sequences are known. For the complete naturally-occurring fEPO amino acid sequence as well as the mature naturally-occurring hEPO amino acid sequence, see SEQ ID NO:1 and SEQ ID NO:2, respectively, herein. For the complete consensus fEPO amino acid sequence as well as the mature consensus fEPO amino acid sequence, see SEQ ID NO:3 and SEQ ID NO:4, respectively, herein. In some embodiments, fEPO polypeptides of the invention are substantially identical to SEQ ID NO:1, SEQ ID NO:2, SEQ ID NO:3, or SEQ ID NO:4. Nucleic acid molecules encoding fEPO mutants and mutant fEPO polypeptides are known as well. Examples of fEPO mutants include those disclosed in U.S. Pat. Nos.

6,489,293; 6,153,407; 6,048,971; 5,614,184; and 5,457,089, which are incorporated by reference herein.

Erythropoietin or fEPO has a variety of biological activities including but not limited to binding to its receptor, causing dimerization of its receptor, stimulation of red blood cell production, and stimulating cell proliferation. Examples of some of the biological activities of erythropoietin and hEPO are described in U.S. Pat. Nos. 6,676,947; 6,579,525; 6,531,121; 6,521,245; 6,489,293; 6,368,854; 6,316,254; 6,268,336; 6,239,109; 6,165,283; 5,986,047; 5,830,851; and 5,773,569, which are incorporated by reference herein.

Biologically-active fragments/variants of fEPO include the gene product containing 192 amino acids, of which the first 26 are cleaved during secretion as well as the removal of one or more of the last four amino acids during the formation of the mature form of erythropoietin (SEQ ID NO:1 and SEQ ID NO:2). The term "fEPO polypeptide" also includes the glycosylated forms, with N-linked glycosylation sites at 24, 38, and 83, and O-linked glycosylation site at 126 (Takeuchi et al. (1988) JBC 263: 3657-3663; Saski et al. (1988) Biochemistry 27: 8618-8626). Variants containing single nucleotide changes (i.e. S104N and L105F, P122Q, E13Q, Q58->QQ, G113R) are also considered as biologically active variants of hEPO (Jacobs et al., (1985) Nature 313: 806-810; Funakoshi et al., (1993) Biochem. Biophys. Res. Comm. 195: 717-722). The term "fEPO polypeptide" also includes fEPO heterodimers, homodimers, heteromultimers, or homomultimers of fEPO or any other polypeptide, protein, carbohydrate, polymer, small molecule, ligand, or other active molecule of any type, linked by chemical means or expressed as a fusion protein (Sytkowski et al., (1998) Proc. Natl. Acad. Sci. USA 95(3): 1184-8; and Sytkowski et al. (1999) J. Biol. Chem. 274(35): 24773-8, and U.S. Pat. Nos. 6,187,564; 6,703,480; 5,767,078 which are incorporated by reference herein), as well as polypeptide analogues containing specific deletions, yet maintain biological activity (Boissel et al., (1993) JBC 268: 15983-15993; Wen et al., (1994) JBC 269: 22839-22846; Bittorf et al., (1993) FEBS 336: 133-136; and U.S. Pat. No. 6,153,407 which is incorporated by reference herein).

All references to amino acid positions in fEPO described herein are based on the position in SEQ ID NO: 2, unless otherwise specified (i.e., when it is stated that the comparison is based on SEQ ID NO: 3). Those of skill in the art will appreciate that amino acid positions corresponding to positions in SEQ ID NO: 2 can be readily identified in fEPO fusions, variants, fragments, etc. For example, sequence alignment programs such as BLAST can be used to align and identify a particular position in a protein that corresponds with a position in SEQ ID NO:2. Substitutions, deletions or additions of amino acids described herein in reference to SEQ ID NO: 2 are intended to also refer to substitutions, deletions or additions in corresponding positions in fEPO fusions, variants, fragments, etc. described herein or known in the art and are expressly encompassed by the present invention.

The term "fEPO polypeptide" encompasses fEPO polypeptides comprising one or more amino acid substitutions, additions or deletions. Exemplary substitutions in a wide variety of amino acid positions in naturally-occurring fEPO have been described, including but not limited to substitutions that increase agonist activity, increase solubility of the polypeptide, convert the polypeptide into an antagonist, etc. and are encompassed by the term "fEPO polypeptide."

Feline EPO antagonists include, but are not limited to, those with a substitutions at V11, R14, Y15, D96, K97, S100, R103, S104, T107, L108, and R110 (including but not limited to, V11S, R14Q, Y15I, S100E, R103A, S104I, and L108K, see Elliot et al. 1993) found in the low affinity receptor binding site (site 2). In some embodiments, fEPO antagonists comprise at least one substitution in the regions 10-15 or 100-108 that cause fEPO to act as an antagonist. See, e.g., Elliot et al. 1993 and Cheetham et al. 1998. In some embodiments, the fEPO antagonist comprises a non-naturally encoded amino acid linked to a water soluble polymer that is present in the Site 2 binding region of the hEPO molecule. In some embodiments, the fEPO polypeptide is even further modified by containing the following substitutions: V11S, R14Q, Y15I, S100E, R103A, S104I, and L108K.

In some embodiments, the fEPO polypeptides further comprise an addition, substitution or deletion that modulates biological activity of fEPO. For example, the additions, substitutions or deletions may modulate affinity for the fEPO receptor, modulate (including but not limited to, increases or decreases) receptor dimerization, stabilize receptor dimers, modulate circulating half-life, modulate therapeutic half-life, modulate stability of the polypeptide, modulate dose, modulate release or bio-availability, facilitate purification, or improve or alter a particular route of administration. Similarly, fEPO polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term “fEPO polypeptide” also encompasses fEPO homodimers, heterodimers, homomultimers, and heteromultimers linked directly via non-naturally encoded amino acid side chains, either to the same or different non-naturally encoded amino acid side chains, to naturally-encoded amino acid side chains, or indirectly via a linker. Exemplary linkers including but are not limited to, water soluble polymers such as poly(ethylene glycol) or polydextran or a polypeptide.

A “non-naturally encoded amino acid” refers to an amino acid that is not one of the 20 common amino acids or pyrolysine or selenocysteine. The term “non-naturally encoded amino acid” includes, but is not limited to, amino acids that occur naturally by modification of a naturally encoded amino acid (including but not limited to, the 20 common amino acids or pyrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine.

An “amino terminus modification group” refers to any molecule that can be attached to the amino terminus of a polypeptide. Similarly, a “carboxy terminus modification group” refers to any molecule that can be attached to the carboxy terminus of a polypeptide. Terminus modification groups include but are not limited to various water soluble polymers, peptides or proteins such as serum albumin, or other moieties that increase serum half-life of peptides.

The terms “functional group”, “active moiety”, “activating group”, “leaving group”, “reactive site”, “chemically reactive group” and “chemically reactive moiety” are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages means that the linkages are degradable in water or in aqueous solutions, including for example, blood. Enzymatically unstable or degradable linkages means that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological organism, including but not limited to viruses, bacteria, fungi, plants, animals, and humans. In particular, as used herein, biologically active molecules include but are not limited to any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; 4,569,789; and 4,589,071 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages.

Where substituent groups are specified by their conventional chemical formulas, written from left to right, they equally encompass the chemically identical substituents that would result from writing the structure from right to left, for example, —$CH_2O$— is equivalent to —$OCH_2$—.

The term "substituents" includes but is not limited to "non-interfering substituents". "Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{12}$ aralkyl, $C_1$-$C_{12}$ alkaryl, $C_3$-$C_{12}$ cycloalkyl, $C_3$-$C_{12}$ cycloalkenyl, phenyl, substituted phenyl, toluoyl, xylenyl, biphenyl, $C_2$-$C_{12}$ alkoxyalkyl, $C_2$-$C_{12}$ alkoxyaryl, $C_7$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —NRC(O)—($C_1$-$C_{10}$ alkyl), —C(O)—($C_1$-$C_{10}$ alkyl), $C_2$-$C_{10}$ alkyl thioalkyl, —C(O)O—($C_1$-$C_{10}$ alkyl), —OH, —$SO_2$, =S, —COOH, —$NR_2$, carbonyl, —C(O)—($C_1$-$C_{10}$ alkyl)-CF3, —C(O)—CF3, —C(O)NR2, —($C_1$-$C_{10}$ aryl)-S—($C_6$-$C_{10}$ aryl), —C(O)—($C_1$-$C_{10}$ aryl), —$(CH_2)_m$, —O—(—$(CH_2)_m$, —O—($C_1$-$C_{10}$ alkyl) wherein each m is from 1 to 8, —C(O) $NR_2$, —C(S)$NR_2$, —$SO_2NR_2$, —NRC(O) $NR_2$, —NRC(S) $NR_2$, salts thereof, and the like. Each R as used herein is H, alkyl or substituted alkyl, aryl or substituted aryl, aralkyl, or alkaryl.

The term "halogen" includes fluorine, chlorine, iodine, and bromine.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —$CH_2CH_2$— and —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated and unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

As used herein, the term "water soluble polymer" refers to any polymer that is soluble in aqueous solvents. Linkage of water soluble polymers to fEPO can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding and altered receptor dimerization or multimerization. The water soluble polymer may or may not have its own biological activity. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include but are not limited to polyethylene glycol and serum albumin.

As used herein, the term "polyalkylene glycol" refers to polyethylene glycol, polypropylene glycol, polybutylene glycol, and derivatives thereof. The term "polyalkylene glycol" encompasses both linear and branched polymers and average molecular weights of between 1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, arylalkyl) includes both aryl and heteroaryl rings as defined above. Thus, the term "arylalkyl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy)propyl, and the like).

Each of the above terms (including but not limited to, "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such a radical. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, but are not limited to: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

As used herein, the term "modulated serum half-life" means the positive or negative change in circulating half-life of a modified biologically active molecule relative to its non-modified form. Serum half-life is measured by taking blood samples at various time points after administration of the biologically active molecule, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of a modified biologically active molecule, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, or an increase or decrease in another parameter or mechanism of action of the non-modified molecule.

The term "isolated," when applied to a nucleic acid or protein, denotes that the nucleic acid or protein is substantially free of other cellular components with which it is associated in the natural state. It can be in a homogeneous state. Isolated substances can be in either a dry or semi-dry state, or in solution, including but not limited to an aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it means that the nucleic acid or protein is at least 85% pure, at least 90% pure, at least 95% pure, or at least 99% pure or greater.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

The terms "polypeptide," "peptide" and "protein" are used interchangeably herein to refer to a polymer of amino acid residues. The terms apply to naturally occurring amino acid polymers as well as amino acid polymers in which one or more amino acid residues is a non-naturally encoded amino acid. As used herein, the terms encompass amino acid chains of any length, including full length proteins (i.e., antigens), wherein the amino acid residues are linked by covalent peptide bonds.

Antibodies are proteins, which exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three or four CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, Md. (1991)).

The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are called α, δ, ε, γ and μ, respectively. Of the various human immunoglobulin classes, only human IgG1, IgG2, IgG3 and IgM are known to activate complement.

In vivo, affinity maturation of antibodies is driven by antigen selection of higher affinity antibody variants which are made primarily by somatic hypermutagenesis. A "repertoire shift" also often occurs in which the predominant germline genes of the secondary or tertiary response are seen to differ from those of the primary or secondary response.

The affinity maturation process of the immune system may be replicated by introducing mutations into antibody genes in vitro and using affinity selection to isolate mutants with improved affinity. Such mutant antibodies can be displayed on the surface of filamentous bacteriophage or microorganisms such as yeast, and antibodies can be selected by their affinity for antigen or by their kinetics of dissociation (off-rate) from antigen. Hawkins et al. J. Mol. Biol. 226:889-896 (1992). CDR walking mutagenesis has been employed to affinity mature human antibodies which bind the human envelope glycoprotein gp120 of human immunodeficiency virus type 1 (HIV-1) (Barbas III et al. PNAS (USA) 91: 3809-3813 (1994); and Yang et al. J. Mol. Biol. 254:392-403 (1995)); and an anti-c-erbB-2 single chain Fv fragment (Schier et al. J. Mol. Biol. 263:551567 (1996)). Antibody chain shuffling and CDR mutagenesis were used to affinity mature a high-affinity human antibody directed against the third hypervariable loop of HIV (Thompson et al. J. Mol. Biol. 256:77-88 (1996)). Balint and Larrick Gene 137:109-118 (1993) describe a computer-assisted oligodeoxyribonucleotide-directed scanning mutagenesis whereby all CDRs of a variable region gene are simultaneously and thoroughly searched for improved variants. An αvβ3-specific humanized antibody was affinity matured using an initial limited mutagenesis strategy in which every position of all six CDRs was mutated followed by the expression and screening of a combinatorial library including the highest affinity mutants (Wu et al. PNAS (USA) 95: 6037-6-42 (1998)). Phage displayed antibodies are reviewed in Chiswell and McCafferty TIBTECH 10:80-84 (1992); and Rader and Barbas III Current Opinion in Biotech. 8:503-508 (1997). In each case where mutant antibodies with improved affinity compared to a parent antibody are reported in the above references, the mutant antibody has amino acid substitutions in a CDR.

By "affinity maturation" herein is meant the process of enhancing the affinity of an antibody for its antigen. Methods for affinity maturation include but are not limited to computational screening methods and experimental methods.

By "antibody" herein is meant a protein consisting of one or more polypeptides substantially encoded by all or part of the antibody genes. The immunoglobulin genes include, but are not limited to, the kappa, lambda, alpha, gamma (IgG1, IgG2, IgG3, and IgG4), delta, epsilon and mu constant region genes, as well as the myriad immunoglobulin variable region genes. Antibody herein is meant to include full-length antibodies and antibody fragments, and include antibodies that exist naturally in any organism or are engineered (e.g. are variants).

By "antibody fragment" is meant any form of an antibody other than the full-length form. Antibody fragments herein include antibodies that are smaller components that exist within full-length antibodies, and antibodies that have been engineered. Antibody fragments include but are not limited to Fv, Fc, Fab, and (Fab')$_2$, single chain Fv (scFv), diabodies, triabodies, tetrabodies, bifunctional hybrid antibodies, CDR1, CDR2, CDR3, combinations of CDR's, variable regions, framework regions, constant regions, and the like (Maynard & Georgiou, 2000, Annu. Rev. Biomed. Eng. 2:339-76; Hudson, 1998, Curr. Opin. Biotechnol. 9:395-402).

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins: Structures and Molecular Properties* (W H Freeman & Co.; 2nd edition (December 1993))

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, optionally about 65%, about 70%, about 75%, about 80%, about 85%, about 90%, or about 95% identity over a specified region), when compared and aligned for maximum correspondence over a comparison window, or designated region as measured using one of the following sequence comparison algorithms or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence or a polynucleotide or polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

"Eukaryotic cell" and "eukaryotic cells" include by way of example mammalian cells such as CHO, myeloma, BHK, immune cells, insect cells, avian cells, amphibian cells, e.g., frog oocytes, fungal and yeast cells. Yeast include by way of example *Saccharomyces, Schizosaccharomyces, Hansenula, Candida, Torulopsis, Yarrowia, Pichia,* et al. Particularly preferred yeast for expression include methylotrophic yeast strains, e.g., *Pichia pastoris, Hansenula, polymorpha, Pichia guillermordii, Pichia methanolica, Pichia inositovera,* et al. (See e.g., U.S. Pat. Nos. 4,812,405, 4,818,700, 4,929,555, 5,736,383, 5,955,349, 5,888,768, and 6,258,559, each of which is hereby incorporated by reference for all purposes). These and other patents further describe promoters, terminators, enhancers, signals sequences, and other regulatory sequences useful for facilitating heterologus gene expression in yeast, e.g., protein genes as in the present invention.

As used herein, the term "transformation" shall be used in a broad sense to refer to any introduction of DNA into a recipient host cell that changes the genotype and consequently results in a change in the recipient cell.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus,* etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix,* etc.) phylogenetic domain.

The term "subject" as used herein, refers to an animal, preferably a mammal, most preferably a human, who is the object of treatment, observation or experiment.

DETAILED DESCRIPTION

One of skill in the art will be able to develop and use the same methods given below, for the composition of feline erythropoietin and related methods, for compositions and methods related to canine erythropoietin (cEPO) (SEQ ID NO: 31 mature amino acid sequence, SEQ ID NO: 30 full-length amino acid sequence) and equine erythropoietin (eEPO) (SEQ ID NO: 33 mature amino acid sequence, SEQ ID NO: 32 full-length amino acid sequence), for cEPO and eEPO with an unnatural, non-natural, and/or non-naturally encoded amino acid incorporated into the cEPO and eEPO polypeptides. These polypeptides may also be used as disclosed herein, for treatment of felines or other animals in need thereof, or they may be used in the treatment of canines or equines. FIGS. 34 and 35 provide comparisons between each of the 166 amino acid sequences, for cEPO and eEPO, to fEPO (166 amino acids) which is discussed in greater detail herein, but the disclosure also provides support for the substitution, addition, or deletion of a non-naturally encoded amino acid to SEQ ID NO.s 31 and 33, cEPO and eEPO respectively.

I. Introduction

Feline EPO molecules comprising at least one unnatural amino acid are provided in the invention. In certain embodiments of the invention, EPO with at least one unnatural amino acid includes at least one post-translational modification. In one embodiment, the at least one post-translational modification comprises attachment of a molecule (including but not limited to, a dye, a polymer, including but not limited to a derivative of polyethylene glycol, a photocrosslinker, a cytotoxic compound, an affinity label, a derivative of biotin, a resin, a second protein or polypeptide, an antibody or antibody fragment, a metal chelator, a cofactor, a fatty acid, a carbohydrate, a polynucleotide (including but not limited to, DNA, RNA), etc.) comprising a second reactive group to the at least one unnatural amino acid comprising a first reactive group utilizing chemistry methodology that is known to one of ordinary skill in the art to be suitable for the particular reactive groups. For example, the first reactive group is an alkynyl moiety (including but not limited to, in the unnatural amino acid p-propargyloxyphenylalanine, where the propargyl group is also sometimes refer to as an acetylene moiety) and the second reactive group is an azido moiety, and [3+2] cycloaddition chemistry methodologies are utilized. In another example, the first reactive group is the azido moiety (including but not limited to, in the unnatural amino acid p-azido-L-phenylalanine) and the second reactive group is the alkynyl moiety. In certain embodiments of the modified fEPO of the present invention, at least one unnatural amino acid (including but not limited to, unnatural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell.

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, acetylation, acylation, lipid-modification, palmitoylation, palmitate addition, phosphorylation, glycolipid-linkage modification, and the like. In one embodiment, the post-translational modification comprises attachment of an oligosaccharide to an asparagine by a GlcNAc-asparagine linkage (including but not limited to, where the oligosaccharide comprises (GlcNAc-Man)$_2$-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence, an epitope tag, a FLAG tag, a polyhistidine tag, a GST fusion, and/or the like.

The protein or polypeptide of interest can contain at least one, at least two, at least three, at least four, at least five, at least six, at least seven, at least eight, at least nine, or ten or more non-natural amino acids. The unnatural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein is substituted with an unnatural amino acid.

The present invention provides methods and compositions based on members of the GH supergene family, in particular fEPO, comprising at least one non-naturally encoded amino acid. Introduction of at least one non-naturally encoded amino acid into a GH supergene family member such as fEPO can allow for the application of conjugation chemistries that involve specific chemical reactions, including, but not limited to, with one or more non-naturally encoded amino acids while not reacting with the commonly occurring 20 amino acids. In some embodiments, the GH supergene family member such as fEPO comprising the non-naturally encoded amino acid is linked to a water soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the naturally encoded amino acid. Known chemistry methodologies of a wide variety are suitable for use in the present invention to incorporate a water soluble polymer into the protein. Such methodologies include but are not limited to a Huisgen [3+2] cycloaddition reaction (see, e.g., Padwa, A. in *Comprehensive Organic Synthesis* Vol. 4, (1991) Ed. Trost, B. M., Pergamon, Oxford, p. 1069-1109; and, Huisgen, R. in 1,3-*Dipolar Cycloaddition Chemistry*, (1984) Ed. Padwa, A., Wiley, New York, p. 1-176) with, including but not limited to, acetylene or azide derivatives, respectively.

Because the Huisgen [3+2] cycloaddition method involves a cycloaddition rather than a nucleophilic substitution reaction, proteins can be modified with extremely high selectivity. The reaction can be carried out at room temperature in aqueous conditions with excellent regioselectivity (1,4>1,5) by the addition of catalytic amounts of Cu(I) salts to the reaction mixture. See, e.g., Tornoe, et al., (2002) *Org. Chem.* 67:3057-3064; and, Rostovtsev, et al., (2002) *Angew. Chem. Int. Ed.* 41:2596-2599; and WO 03/101972. A molecule that can be added to a protein of the invention through a [3+2] cycloaddition includes virtually any molecule with a suitable functional group or substituent including but not limited to an azido or acetylene derivative. These molecules can be added to an unnatural amino acid with an acetylene group, including but not limited to, p-propargyloxyphenylalanine, or azido group, including but not limited to p-azido-phenylalanine, respectively.

The five-membered ring that results from the Huisgen[3+2] cycloaddition is not generally reversible in reducing environments and is stable against hydrolysis for extended periods in aqueous environments. Consequently, the physical and chemical characteristics of a wide variety of substances can be modified under demanding aqueous conditions with the active PEG derivatives of the present invention. Even more important, because the azide and acetylene moieties are specific for one another (and do not, for example, react with any of the 20 common, genetically-encoded amino acids), proteins can be modified in one or more specific sites with extremely high selectivity.

The invention also provides water soluble and hydrolytically stable derivatives of PEG derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon.

More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

The present invention provides conjugates of substances having a wide variety of functional groups, substituents or moieties, with other substances including but not limited to water soluble polymers such as PEG, proteins, drugs, small molecules, biomaterials, or any other desirable compound or substance. The present invention also includes conjugates of substances having azide or acetylene moieties with PEG polymer derivatives having the corresponding acetylene or azide moieties. For example, a PEG polymer containing an azide moiety can be coupled to a biologically active molecule at a position in the protein that contains a non-genetically encoded amino acid bearing an acetylene functionality. The linkage by which the PEG and the biologically active molecule are coupled includes but is not limited to the Huisgen [3+2] cyclo addition product.

It is well established in the art that PEG can be used to modify the surfaces of biomaterials (see, e.g., U.S. Pat. No. 6,610,281; Mehvar, R., J. Pharmaceut. Sci., 3(1):125-136 (2000) which are incorporated by reference herein). The invention also includes biomaterials comprising a surface having one or more reactive azide or acetylene sites and one or more of the azide- or acetylene-containing polymers of the invention coupled to the surface via the Huisgen [3+2] cycloaddition linkage. Biomaterials and other substances can also be coupled to the azide- or acetylene-activated polymer derivatives through a linkage other than the azide or acetylene linkage, such as through a linkage comprising a carboxylic acid, amine, alcohol or thiol moiety, to leave the azide or acetylene moiety available for subsequent reactions.

The invention includes a method of synthesizing the azide- and acetylene containing polymers of the invention. In the case of the azide-containing PEG derivative, the azide can be bonded directly to a carbon atom of the polymer. Alternatively, the azide-containing PEG derivative can be prepared by attaching a linking agent that has the azide moiety at one terminus to a conventional activated polymer so that the resulting polymer has the azide moiety at its terminus. In the case of the acetylene-containing PEG derivative, the acetylene can be bonded directly to a carbon atom of the polymer. Alternatively, the acetylene-containing PEG derivative can be prepared by attaching a linking agent that has the acetylene moiety at one terminus to a conventional activated polymer so that the resulting polymer has the acetylene moiety at its terminus.

More specifically, in the case of the azide-containing PEG derivative, a water soluble polymer having at least one active hydroxyl moiety undergoes a reaction to produce a substituted polymer having a more reactive moiety, such as a mesylate, tresylate, tosylate or halogen leaving group, thereon. The preparation and use of PEG derivatives containing sulfonyl acid halides, halogen atoms and other leaving groups are well known to the skilled artisan. The resulting substituted polymer then undergoes a reaction to substitute for the more reactive moiety an azide moiety at the terminus of the polymer. Alternatively, a water soluble polymer having at least one active nucleophilic or electrophilic moiety undergoes a reaction with a linking agent that has an azide at one terminus so that a covalent bond is formed between the PEG polymer and the linking agent and the azide moiety is positioned at the terminus of the polymer. Nucleophilic and electrophilic moieties, including amines, thiols, hydrazides, hydrazines, alcohols, carboxylates, aldehydes, ketones, thioesters and the like, are well known to the skilled artisan.

More specifically, in the case of the acetylene-containing PEG derivative, a water soluble polymer having at least one active hydroxyl moiety undergoes a reaction to displace a halogen or other activated leaving group from a precursor that contains an acetylene moiety. Alternatively, a water soluble polymer having at least one active nucleophilic or electrophilic moiety undergoes a reaction with a linking agent that has an acetylene at one terminus so that a covalent bond is formed between the PEG polymer and the linking agent and the acetylene moiety is positioned at the terminus of the polymer. The use of halogen moieties, activated leaving group, nucleophilic and electrophilic moieties in the context of organic synthesis and the presparation and use of PEG derivatives is well established to practitioners in the art.

The invention also provides a method for the selective modification of proteins to add other substances to the modified protein, including but not limited to water soluble polymers such as PEG and PEG derivatives containing an azide or acetylene moiety. The azide- and acetylene-containing PEG derivatives can be used to modify the properties of surfaces and molecules where biocompatibility, stability, solubility and lack of immunogenicity are important, while at the same time providing a more selective means of attaching the PEG derivatives to proteins than was previously known in the art.

II. Growth Hormone Supergene Family

The following proteins include those encoded by genes of the growth hormone (GH) supergene family (Bazan, F., *Immunology Today* 11: 350-354 (1991); Bazan, J. F. *Science* 257: 410-411 (1992); Mott, H. R. and Campbell, I. D., *Current Opinion in Structural Biology* 5: 114-121 (1995); Silvennoinen, O. and Ihle, J. N., SIGNALLING BY THE HEMATOPOIETIC CYTOKINE RECEPTORS (1996)): growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor, leukemia inhibitory factor, alpha interferon, beta interferon, gamma interferon, omega interferon, tau interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). It is anticipated that additional members of this gene family will be identified in the future through gene cloning and sequencing. Members of the GH supergene family have similar secondary and tertiary structures, despite the fact that they generally have limited amino acid or DNA sequence identity. The shared structural features allow new members of the gene family to be readily identified. Given the extent of structural homology among the members of the GH supergene family, non-naturally encoded amino acids may be incorporated into any members of the GH supergene family using the present invention.

Structures of a number of cytokines, including G-CSF (Hill, C. P., *Proc. Natl. Acad. Sci. USA* 90:5167-5171 (1993)), GM-CSF (Diederichs, K., et al. *Science* 154: 1779-1782 (1991); Walter et al., *J. Mol. Biol.* 224:1075-1085 (1992)), IL-2 (Bazan, J. F. *Science* 257: 410-411 (1992); McKay, D. B. *Science* 257: 412 (1992)), IL-4 (Redfield et al., *Biochemistry* 30: 11029-11035 (1991); Powers et al., *Science* 256:1673-1677 (1992)), and IL-5 (Milburn et al., *Nature* 363: 172-176 (1993)) have been determined by X-ray diffraction and NMR studies and show striking conservation with the GH structure, despite a lack of significant primary sequence homology. EPO is considered to be a member of this family based upon modeling and mutagenesis studies (Boissel et al., *J. Biol. Chem.* 268: 15983-15993 (1993); Wen et al., J. Biol. Chem. 269: 22839-22846 (1994)). A large number of additional cytokines and growth factors including ciliary neurotrophic factor (CNTF), leukemia inhibitory factor (LIF), thrombopoietin (TPO), oncostatin M, macrophage colony stimulating factor (M-CSF), IL-3, IL-6, IL-7, IL-9, IL-12, IL-13, IL-15, and alpha, beta, omega, tau and gamma interferon belong to this family (reviewed in Mott and Campbell, *Current Opinion in Structural Biology* 5: 114-121 (1995); Silvennoinen and Ihle (1996) SIGNALLING BY THE HEMATOPOIETIC CYTOKINE RECEPTORS). All of the above cytokines and growth factors are now considered to comprise one large gene family.

In addition to sharing similar secondary and tertiary structures, members of this family share the property that they must oligomerize cell surface receptors to activate intracellular signaling pathways. Some GH family members, including but not limited to; GH and EPO, bind a single type of receptor and cause it to form homodimers. Other family members, including but not limited to, IL-2, IL4. and IL-6, bind more than one type of receptor and cause the receptors to form heterodimers or higher order aggregates (Davis et al., (1993) *Science* 260: 1805-1808; Paonessa et al., 1995) EMBO J. 14: 1942-1951; Mott and Campbell, *Current Opinion in Structural Biology* 5: 114-121 (1995)). Mutagenesis studies have shown that, like GH, these other cytokines and growth factors contain multiple receptor binding sites, typically two, and bind their cognate receptors sequentially (Mott and Campbell, *Current Opinion in Structural Biology* 5: 114-121 (1995); Matthews et al., (1996) *Proc. Natl. Acad. Sci. USA* 93: 9471-9476). Like GH, the primary receptor binding sites for these other family members occur primarily in the four alpha helices and the A-B loop. The specific amino acids in the helical bundles that participate in receptor binding differ amongst the family members. Most of the cell surface receptors that interact with members of the GH supergene family are structurally related and comprise a second large multi-gene family. See, e.g. U.S. Pat. No. 6,608,183.

A general conclusion reached from mutational studies of various members of the GH supergene family is that the loops joining the alpha helices generally tend to not be involved in receptor binding. In particular the short B-C loop appears to be non-essential for receptor binding in most, if not all, family members. For this reason, the B-C loop may be substituted with non-naturally encoded amino acids as described herein in members of the GH supergene family. The A-B loop, the C-D loop (and D-E loop of interferon/IL-10-like members of the GH superfamily) may also be substituted with a non-naturally-occurring amino acid. Amino acids proximal to helix A and distal to the final helix also tend not to be involved in receptor binding and also may be sites for introducing non-naturally-occurring amino acids. In some embodiments, a non-naturally encoded amino acid is substituted at any position within a loop region, including but not limited to, the first 1, 2, 3, 4, 5, 6, 7, or more amino acids of the A-B, B-C, C-D or D-E loop. In some embodiments, a non-naturally encoded amino acid is substituted within the last 1, 2, 3, 4, 5, 6, 7, or more amino acids of the A-B, B-C, C-D or D-E loop.

Certain members of the GH family, including but not limited to, EPO, IL-2, IL-3, IL-4, IL-6, G-CSF, GM-CSF, TPO, IL-10, IL-12 p35, IL-13, IL-15 and beta-interferon contain N-linked and O-linked sugars. The glycosylation sites in the proteins occur almost exclusively in the loop regions and not in the alpha helical bundles. Because the loop regions generally are not involved in receptor binding and because they are sites for the covalent attachment of sugar groups, they may be useful sites for introducing non-naturally-occurring amino acid substitutions into the proteins. Amino acids that comprise the N- and O-linked glycosylation sites in the proteins may be sites for non-naturally-occurring amino acid substitutions because these amino acids are surface-exposed. Therefore, the natural protein can tolerate bulky sugar groups attached to the proteins at these sites and the glycosylation sites tend to be located away from the receptor binding sites.

Additional members of the GH gene family are likely to be discovered in the future. New members of the GH supergene family can be identified through computer-aided secondary and tertiary structure analyses of the predicted protein sequences. Members of the GH supergene family typically possess four or five amphipathic helices joined by non-helical amino acids (the loop regions). The proteins may contain a hydrophobic signal sequence at their N-terminus to promote secretion from the cell. Such later discovered members of the GH supergen family also are included within this invention.

Reference to fEPO polypeptides in this application is intended to use fEPO as an example of a member of the GH supergene family. Thus, it is understood that the modifications and chemistries described herein with reference to fEPO can be equally applied to any other members of the GH supergene family, including those specifically listed herein.

III. Expression System Producing Single or Multiple Gene Products of Interest from a Single Expression Construct and Used with the Present Invention Described herein are novel expression systems for producing single or multiple gene products of interest from a single expression construct or from multiple expression constructs. In one embodiment the present invention includes a eukaryotic suppression expression system in which suppressed protein genes of interest are transcribed from a single vector encoding all elements necessary for suppression to include an artificial amino acid. In particular, the expression system contains a vector capable of expressing proteins in eukaryotic host cells such that the said protein(s) contains an artificial amino acid. The expression system contains a vector capable of expressing proteins in eukaryotic host cells such that the said protein(s) contains a non-natural amino acid or unnatural amino acid. The expression system contains a vector capable of expressing proteins in eukaryotic host cells such that the said protein(s) contains a non-naturally encoded amino acid such as but not limited to p-acetylphenylalanine (pAF). The expression vectors may comprise the following elements operably linked: single or multiple copies of a suppression tRNA sequence, including promoters and transcription terminators operable in a eukaryotic cell; a promoter linked to a DNA sequence encoding any gene of interest to be expressed (suppressed); and a promoter linked to a mammalian functional tRNA synthetase coding region. An embodiment of the present invention are mammalian cells containing the suppression expression vector, and a method of producing functional suppressed proteins in mammalian cells transfected with the suppression expression vector.

This invention also pertains to the suppression expression of functional proteins at adequate levels of expression via an expression system in a eukaryotic host cell. In one embodiment, the invention relates to the suppression expression of functional proteins in eukaryotic cells, preferably mammalian cells, fungal or yeast cells and still more preferably (Chinese Hamster Ovary) CHO cells, using a suppression expression system.

More specifically, one embodiment of the present invention relates to the suppression expression of functional proteins in eukaryotic cells, for example mammalian cells, fungal or yeast cells using a suppression expression system wherein all suppression elements are contained on a single vector. One embodiment of the present invention relates to the suppression expression of functional proteins in (Chinese Hamster Ovary) CHO cells (ATCC banked cells, as well as known variants and cells and/or cell lines which those of skill in the art would know can be used in place of CHO cells), using a suppression expression system wherein all suppression elements are contained on a single vector. In one aspect of this embodiment of the invention, the suppression expression of functional proteins in mammalian cells comprises using a suppression expression system comprising tRNA, tRNA synthetase, and protein of interest transcriptional/translationals elements.

Another embodiment of the invention provides the option of including single or multiple tRNA elements in independent transcriptional orientation to effectively modulate intracellular expression levels. In another embodiment, the invention provides the option of including a single transcriptional unit which encodes a single protein of interest into which the artificial amino acid is to be introduced. Another embodiment of the invention provides the option of including a multiple transcriptional units which encode multiple proteins of interest or subunits of therein (such as antibody light and heavy chains) into which the artificial amino acid is to be introduced into either on or both proteins.

Another embodiment of the invention is a eukaryotic cell line, such as a CHO cell line, that secretes the suppressed protein, wherein expression of said protein is via the suppression expression system described herein. In some embodiments, the eukaryotic cell is a CHO cell or a yeast cell, e.g., Pichia. Another embodiment of the invention is a culture of mammalian or yeast cells comprising a suppression expression system capable of producing functional suppressed proteins. Vectors containing suppression expression sequences according to the invention may be introduced into the mammalian or yeast cells. During cell culturing, desired exogenous DNA sequences may be introduced to target mammalian or yeast cells, such that exogenous DNA is inserted into the genome of the mammalian or yeast cells randomly or via homologous recombination. Depending upon the sequences employed, functional suppressed proteins may be recovered from the biomass of the cell culture or from the cell culture medium.

Yet another embodiment of the present invention is a method of producing functional suppressed proteins comprising culturing eukaryotic cells, preferably mammalian or yeast cells containing a suppression expression system that expresses antibody light and heavy chain sequences, and recovering functional antibodies from the cell culture. The functional antibodies may be produced in batch fed cell cultures at levels suitable for therapeutic use under conditions optimized for maximal commercial output. For example, CHO cells grown in batch fed cultures in which glucose levels are continuously controlled can produce recombinant protein for at least 12 days or more. See, for example, U.S. Pat. No. 6,180,401 for a discussion relating to the output of recombinant protein by cells grown in batch fed cultures.

A variety of different types of proteins may be expressed according to the instant invention. Types of proteins include single polypeptides or multiple assembled polypeptides such as but no limited to antibodies. For the purposes of this invention, numerous suppression expression vector systems may be employed. For example, a suppression expression vector may contain DNA elements which are derived from bacteria, such as, but not limited to: E. coli, Bacillus, Salmonella; animal viruses such as bovine papillomavirus virus, polyoma virus, adenovirus, vaccinia virus, baculovirus, retroviruses (RSV, MMTV or MOMLV) or SV40 virus. Additionally, cells which have integrated the suppression expression construct DNA into their chromosomes may be selected by introducing one or more markers which allow selection of transfected host cells. The marker may provide for any means known to those skilled in the art for selection, including but not limited to, prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements that may be used in optimizing synthesis of mRNA may include splice signals, as well as transcriptional promoters, enhancers, and termination signals.

More generally, once the vector or DNA sequence encoding the protein subunit has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, PEI, and infection with intact virus. See, Ridgway, A. A. G. "Mammalian Expression Vectors" Chapter 24.2, pp. 470-472 Vectors, Rodriguez and Denhardt, Eds. (Butterworths, Boston, Mass. 1988). Most preferably, for stably integrated vectors, plasmid introduction into the host is via electroporation. The transformed cells are grown under conditions appropriate to the production of the protein and assayed for protein synthesis. Exemplary assay techniques for identifying and quantifying gene products of interest include enzyme-linked immunosorbent assay (ELISA), radioimmunoassay (RIA), or fluorescence-activated cell sorter analysis (FACS), immunohistochemistry and the like.

In one embodiment of the present invention, the host cell line used for protein expression is of mammalian origin. Those skilled in the art can readily determine host cells or cell lines which would be suited for expression of a desired gene product. Exemplary host cell lines include, but are not limited to, DG44 and DUXB11 (Chinese Hamster Ovary lines, DHFR minus), CHO-K1 derivatives, CHO-S, HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). CHO cells are particularly preferred. Host cells or cell lines are typically available from commercial services, the American Tissue Culture Collection or from published literature.

In vitro production allows scale-up to give large amounts of the desired polypeptide produced using the suppression expression system. Techniques for eukaryotic, e.g., mammalian and yeast cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. For isolation and recovery of the antibodies, the immunoglobulins in the culture supernatants may first be concentrated, e.g. by precipitation with ammonium sulphate, dialysis against hygroscopic material such as PEG, filtration through selective membranes, or the like. If necessary and/or desired, the concentrated solutions of multivalent antibodies are purified by the customary chromatography methods, for example gel filtration, ion-exchange chromatography, chromatography over DEAE-cellulose or (immuno-) affinity chromatography.

In one embodiment of the present invention, the eukaryotic cells used for expression are mammalian or yeast cells.

In another embodiment of the present invention, the eukaryotic cells used for expression are CHO cells. In an additional embodiment of the present invention, the eukaryotic cells used for expression are other cells that can be efficiently cultured for high level protein production. As noted above, the obtaining or cloning of protein genes for incorporation into suppression expression systems according to the invention is within the purview of one of ordinary skill in the art. As noted, such protein genes may encode mature genes, full-length proteins, or the genes may be modified, e.g., by chimerization, humanization, domain deletion or site-specific mutagenesis. Proteins produced by the system of the present invention include full-length proteins, mature proteins, cleaved proteins, uncleaved proteins, proteins disclosed herein, antibodies, antibody fragments including, but not limited to, Fv, Fc, Fab, and (Fab')$_2$, single chain Fv (scFv), diabodies, triabodies, tetrabodies, bifunctional hybrid antibodies, CDR1, CDR2, CDR3, combinations of CDR's, variable regions, framework regions, constant regions, and the like.

In an embodiment of the present invention, the expression system produces proteins in eukaryotic cells, (non-limiting example; mammalian cells such as Chinese hamster ovary (CHO) cells, baby hamster kidney (BHK) cells, fibroblast cell lines and myeloma cells). In one embodiment, CHO cells are employed as hosts for a suppression expression system comprising a cistron comprising the following sequences: tRNA sequence gene, a eukaryotic promoter sequence that is functional in the particular eukaryotic cell used for expression such as CMV, SV40 early or actin promoter sequences, preferably CMV; a DNA sequence encoding a protein of interest, preferably at its 5' end, a eukaryotic secretory leader sequence; and flanked by a 5' start and a 3' stop codon, and a poly A sequence at its 3' terminus.

In general, proteins suppressed and expressed according to the present invention may be used in any one of a number of conjugated (i.e. an immunoconjugate) or unconjugated forms. In particular, the proteins of the present invention may be conjugated to cytotoxins such as radioisotopes, therapeutic agents, cytostatic agents, biological toxins or prodrugs. In particularly preferred embodiments, the proteins produced according to the expression system of the present invention may be modified, such as by conjugation to radioisotopes or bioactive peptides. Examples of radioisotopes useful according to the invention include $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re, using anyone of a number of well known chelators or direct labeling. In one embodiment, conjugated and unconjugated proteins may be used together in the same therapeutic regimen, e.g., as used in the currently approved therapeutic regimen employing Zevalin for the treatment of certain non-Hodgkin's lymphomas.

In other embodiments, the proteins of the invention may be included in compositions that comprise modified proteins coupled to drugs, prodrugs or biological response modifiers such as methotrexate, adriamycine, and lymphokines such as interferon. Still other embodiments of the present invention comprise the use of modified proteins conjugated to specific biotoxins such as ricin or diptheria toxin. In yet other embodiments the modified proteins may be complexed with other immunologically active ligands (e.g. antibodies or fragments thereof) wherein the resulting molecule binds to a neoplastic cell and optionally an effector cell such as a T cell. In yet other embodiments the modified proteins may be complexed with other immunologically active ligands (e.g. antibodies or fragments thereof) wherein the resulting molecule binds to a neoplastic cell and an effector cell such as a T cell. The selection of which conjugated and/or unconjugated modified protein to use will depend upon the type and stage of cancer, use of adjunct treatment (e.g., chemotherapy or external radiation) and patient condition. It will be appreciated that one skilled in the art could readily make such a selection in view of the teachings herein.

The invention is further illustrated by non-limiting Examples 2, 3, and 4.

IV. General Recombinant Nucleic Acid Methods for Use with the Invention

In numerous embodiments of the present invention, nucleic acids encoding a fEPO of interest will be isolated, cloned and often altered using recombinant methods. Such embodiments are used, including but not limited to, for protein expression or during the generation of variants, derivatives, expression cassettes, or other sequences derived from a fEPO polypeptide. In some embodiments, the sequences encoding the polypeptides of the invention are operably linked to a heterologous promoter. Isolation of hEPO is described in, e.g., U.S. Pat. Nos. 5,441,868; 5,547,933; 5,618,698; 5,621,080; and 6,544,748, and production of EPO in human cells is described in WO 93/09222, each specification herein incorporated by reference, and these techniques may be applied by one of skill in the art to the isolation and production of fEPO.

A nucleotide sequence encoding a fEPO polypeptide comprising a non-naturally encoded amino acid may be synthesized on the basis of the amino acid sequence of the parent polypeptide, including but not limited to, having the amino acid sequence shown in SEQ ID NO: 2 (or SEQ ID NO: 4, or alternate known sequences or SNPs, if desired), and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Natl. Acad. Sci.* 88: 189-193 (1991); U.S. Pat. No. 6,521,427 which are incorporated by reference herein.

This invention utilizes routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

General texts which describe molecular biological techniques include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, including but not limited to, the generation of genes that include selector codons for production of proteins that include unnatural amino acids, orthogonal tRNAs, orthogonal synthetases, and pairs thereof.

Various types of mutagenesis are used in the invention for a variety of purposes, including but not limited to, to produce libraries of tRNAs, to produce libraries of synthetases, to produce selector codons, to insert selector codons that encode unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the present invention. In one embodiment, mutagenesis can be guided by known information of the naturally occurring molecule or altered or mutated naturally occurring molecule, including but not limited to, sequence, sequence comparisons, physical properties, crystal structure or the like.

The texts and examples found herein describe these procedures. Additional information is found in the following publications and references cited within: Ling et al., *Approaches to DNA mutagenesis: an overview, Anal Biochem.* 254(2): 157-178 (1997); Dale et al., *Oligonucleotide-directed random mutagenesis using the phosphorothioate method, Methods Mol. Biol.* 57:369-374 (1996); Smith, *In vitro mutagenesis, Ann. Rev. Genet.* 19:423-462(1985); Botstein & Shortie, *Strategies and applications of in vitro mutagenesis, Science* 229:1193-1201(1985); Carter, *Site-directed mutagenesis, Biochem. J.* 237:1-7 (1986); Kunkel, *The efficiency of oligonucleotide directed mutagenesis,* in *Nucleic Acids & Molecular Biology* (Eckstein, F. and Lilley, D. M. J. eds., Springer Verlag, Berlin)) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Bass et al., *Mutant Trp repressors with new DNA-binding specificities, Science* 242:240-245 (1988); *Methods in Enzymol.* 100: 468-500 (1983); *Methods in Enzymol.* 154: 329-350 (1987); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); Zoller & Smith, *Oligonucleotide-directed mutagenesis: a simple method using two oligonucleotide primers and a single-stranded DNA template, Methods in Enzymol.* 154:329-350 (1987); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8787 (1985); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Sayers et al., *Y-T Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide,* (1988) *Nucl. Acids Res.* 16: 803-814; Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Improved enzymatic in vitro reactions in the gapped duplex DNA approach to oligonucleotide-directed construction of mutations, Nucl. Acids Res.* 16: 7207 (1988); Fritz et al., *Oligonucleotide-directed construction of mutations: a gapped duplex DNA procedure without enzymatic reactions in vitro, Nucl. Acids Res.* 16: 6987-6999 (1988); Kramer et al., *Point Mismatch Repair, Cell* 38:879-887 (1984); Carter et al., *Improved oligonucleotide site-directed mutagenesis using M13 vectors, Nucl. Acids Res.* 13: 4431-4443 (1985); Carter, *Improved oligonucleotide-directed mutagenesis using M13 vectors, Methods in Enzymol.* 154: 382-403 (1987); Eghtedarzadeh & Henikoff, *Use of oligonucleotides to generate large deletions, Nucl. Acids Res.* 14: 5115 (1986); Wells et al., *Importance of hydrogen-bond formation in stabilizing the transition state of subtilisin, Phil. Trans. R. Soc. Lond.* A 317: 415-423 (1986); Nambiar et al., *Total synthesis and cloning of a gene coding for the ribonuclease S protein, Science* 223: 1299-1301 (1984); Sakamar and Khorana, *Total synthesis and expression of a gene for the a-subunit of bovine rod outer segment guanine nucleotide-binding protein (transducin), Nucl. Acids Res.* 14: 6361-6372 (1988); Wells et al., *Cassette mutagenesis: an efficient method for generation of multiple mutations at defined sites, Gene* 34:315-323 (1985); Grundström et al., *Oligonucleotide-directed mutagenesis by microscale 'shot-gun' gene synthesis, Nucl. Acids Res.* 13: 3305-3316 (1985); Mandecki, *Oligonucleotide-directed double-strand break repair in plasmids of Escherichia coli: a method for site-specific mutagenesis, Proc. Natl. Acad. Sci. USA,* 83:7177-7181 (1986); Arnold, *Protein engineering for unusual environments, Current Opinion in Biotechnology* 4:450-455 (1993); Sieber, et al., Nature Biotechnology, 19:456-460 (2001). W. P. C. Stemmer, *Nature* 370, 389-91 (1994); and, I. A. Lorimer, I. Pastan, *Nucleic Acids Res.* 23, 3067-8 (1995). Additional details on many of the above methods can be found in *Methods in Enzymology* Volume 154, which also describes useful controls for trouble-shooting problems with various mutagenesis methods.

The invention also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824

(1985), infection by viral vectors, high velocity ballistic penetration by small particles with the nucleic acid either within the matrix of small beads or particles, or on the surface (Klein et al., *Nature* 327, 70-73 (1987)).

The engineered host cells can be cultured in conventional nutrient media modified as appropriate for such activities as, for example, screening steps, activating promoters or selecting transformants. These cells can optionally be cultured into transgenic organisms. Other useful references, including but not limited to for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., Easy-Prep™, FlexiPrep™, both from Pharmacia Biotech; Strata-Clean™, from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. mcrc-.com), The Great American Gene Company (Ramona, Calif. available on the World Wide Web at genco.com), Express-Gen Inc. (Chicago, Ill. available on the World Wide Web at expressgen.com), Operon Technologies Inc. (Alameda, Calif.) and many others.

Selector Codons

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), or an opal codon (UGA), an unnatural codon, a four or more base codon, a rare codon, or the like. It is readily apparent to those of ordinary skill in the art that there is a wide range in the number of selector codons that can be introduced into a desired gene, including but not limited to, one or more, two or more, more than three, 4, 5, 6, 7, 8, 9, 10 or more in a single polynucleotide encoding at least a portion of fEPO.

In one embodiment, the methods involve the use of a selector codon that is a stop codon for the incorporation of unnatural amino acids in vivo in a eukaryotic cell. For example, an O-tRNA is produced that recognizes the stop codon, including but not limited to, UAG, and is aminoacylated by an O-RS with a desired unnatural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), 5',3' *Exonuclease in phosphorothioate-based oligonucleotide-directed mutagenesis. Nucleic Acids Res*, 791-802. When the O-RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Selector codons also comprise extended codons, including but not limited to, four or more base codons, such as, four, five, six or more base codons. Examples of four base codons include, including but not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple unnatural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple unnatural amino acids can be encoded in the same cell using a four or more base codon. See, Anderson et al., (2002) *Exploring the Limits of Codon and Anticodon Size, Chemistry and Biology*, 9:237-244; Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry*, 32:7939; and Hohsaka et al., (1999) *J. Am. Chem. Soc.*, 121:34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.*, 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) *J. Mol. Biol.*, 298:195. In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein*, *Nature Biotechnology*, 20:177-182. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.*, 111:8322; and Piccirilli et al., (1990) *Nature*, 343:33; Kool, (2000) *Curr. Opin. Chem. Biol.*, 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) *Curr. Opin. Chem. Biol.*, 4:602; and Guckian and Kool, (1998) *Angew. Chem. Int. Ed. Engl.*, 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.*, 121:11586; and Ogawa et al., (2000) *J. Am. Chem. Soc.*, 122:3274. A 3MN:3MN self-pair can be synthesized by KF with efficiency and selectivity sufficient for biological function. See, e.g., Ogawa et al., (2000) *J. Am. Chem. Soc.*, 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also been developed, which forms a stable pair upon binding Cu(II). See, Meggers et al., (2000) *J. Am. Chem. Soc.*, 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, for example, one or more selector codon for the incorporation of an unnatural amino acid. For example, a nucleic acid for a protein of interest is mutagenized to include one or more selector codon, providing for the incorporation of the one or more unnatural amino acids. The invention includes any such variant, including but not limited to, mutant, versions of any protein, for example, including at least one unnatural amino acid. Similarly, the invention also includes corresponding nucleic acids, i.e., any nucleic acid with one or more selector codon that encodes one or more unnatural amino acid.

Nucleic acid molecules encoding a protein of interest such as fEPO may be readily mutated to introduce a cysteine at any desired position of the polypeptide. Cysteine is widely used to introduce reactive molecules, water soluble polymers, proteins, or a wide variety of other molecules, onto a protein of interest. Methods suitable for the incorporation of cysteine into a desired position of the fEPO polypeptide are well known in the art, such as those described in U.S. Pat. No. 6,608,183, which is incorporated by reference herein, and standard mutagenesis techniques.

V. Non-Naturally Encoded Amino Acids

A very wide variety of non-naturally encoded amino acids are suitable for use in the present invention. Any number of non-naturally encoded amino acids can be introduced into fEPO. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, a fEPO polypeptide that includes a non-naturally encoded amino acid containing an azido functional group can be reacted with a polymer (including but not limited to, poly (ethylene glycol) or, alternatively, a second polypeptide containing an alkyne moiety to form a stable conjugate resulting for the selective reaction of the azide and the alkyne functional groups to form a Huisgen [3+2] cycloaddition product.

The generic structure of an alpha-amino acid is illustrated as follows:

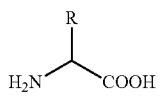

A non-naturally encoded amino acid is typically any structure having the above-listed formula wherein the R group is any substituent other than one used in the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido, hydroxyl-, hydrazine, cyano-, halo-, hydrazide, alkenyl, alkynl, ether, thiol, seleno-, sulfonyl, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable crosslinker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, ketocontaining amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydroxylamine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). See, also, U.S. Patent Application Publications 2003/0082575 and 2003/0108885, incorporated by reference herein.

In addition to unnatural amino acids that contain novel side chains, unnatural amino acids that may be suitable for use in the present invention also optionally comprise modified backbone structures, including but not limited to, as illustrated by the structures of Formula II and III:

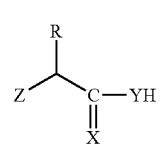

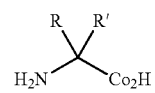

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3,4,6,7,8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, a p-propargyloxy-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) *Incorporation of azides into recombinant proteins for chemoselective modification by the Staudinger ligation*, PNAS 99:19-24, for additional methionine analogs.

In one embodiment, compositions of fEPO that include an unnatural amino acid (such as p-(propargyloxy)-phenylalanine) are provided. Various compositions comprising p-(propargyloxy)-phenylalanine and, including but not limited to, proteins and/or cells, are also provided. In one aspect, a composition that includes the p-(propargyloxy)-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

The chemical moieties via unnatural amino acids that can be incorporated into proteins offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing x-ray structure data. The site-specific introduction of heavy atoms using unnatural amino acids also provides selectivity and flexibility in choosing positions for heavy atoms. Photoreactive unnatural amino acids (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a [3+2] cycloaddition reaction.

Chemical Synthesis of Unnatural Amino Acids

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates*. *J. Chem. Soc.*, 3315-3319; Friedman, O. M. & Chatterrji, R. (1959) *Synthesis of Derivatives of Glutamine as Model Substrates for Anti-Tumor Agents*. *J. Am. Chem. Soc.* 81, 3750-3752; Craig, J. C. et al. (1988) *Absolute Configuration of the Enantiomers of 7-Chloro-4[[4-(diethylamino)-1-methylbutyl]amino]quinoline (Chloroquine)*. *J. Org. Chem.* 53, 1167-1170; Azoulay, M., Vilmont, M. & Frappier, F. (1991) *Glutamine analogues as Potential Antimalarials*, *Eur. J. Med. Chem.* 26, 201-5; Koskinen, A. M. P. & Rapoport, H. (1989) *Synthesis of 4-Substituted Prolines as Conformationally Constrained Amino Acid Analogues*. *J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization*. *J. Org. Chem.* 1989:1859-1866; Barton et al., (1987) *Synthesis of Novel a-Amino-Acids and Derivatives Using Radical Chemistry: Synthesis of L-and D-a-Amino-Adipic Acids, L-a-aminopimelic Acid and Appropriate Unsaturated Derivatives*. *Tetrahedron Lett.* 43:4297-4308; and, Subasinghe et al., (1992) *Quisqualic acid analogues: synthesis of beta-heterocyclic 2-aminopropanoic acid derivatives and their activity at a novel quisqualate-sensitized site*. *J. Med.*

Chem. 35:4602-7. See also, patent application entitled "Protein Arrays," 60/435,821, filed on Dec. 22, 2002.

A. Carbonyl Reactive Groups

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

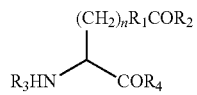

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

The synthesis of p-acetyl-(+/−)-phenylalanine and m-acetyl-(+/−)-phenylalanine is described in Zhang, Z., et al., Biochemistry 42: 6735-6746 (2003), incorporated by reference. Other carbonyl-containing amino acids can be similarly prepared by one skilled in the art.

In some embodiments, a polypeptide comprising a non-naturally encoded amino acid is chemically modified to generate a reactive carbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et. al., Bioconjug. Chem. 3: 262-268 (1992); Geoghegan, K. & Stroh, J., Bioconjug. Chem. 3:138-146 (1992); Gaertner et al., J. Biol. Chem. 269:7224-7230 (1994). However, methods known in the art are restricted to the amino acid at the N-terminus of the peptide or protein.

In the present invention, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685.

The carbonyl functionality can be reacted selectively with a hydrazine-hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl group allows for selective modification in the presence of the other amino acid side chains. See, e.g., Cornish, V. W., et al., J. Am. Chem. Soc. 118:8150-8151 (1996); Geoghegan, K. F. & Stroh, J. G., Bioconjug. Chem. 3:138-146 (1992); Mahal, L. K., et al., Science 276:1125-1128 (1997).

B. Hydrazine, Hydrazide or Semicarbazide Reactive Groups

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

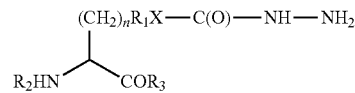

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the alphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one skilled in the art. See, e.g., U.S. Pat. No. 6,281,211.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., J. Am. Chem. Soc. 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

C. Aminooxy-Containing Amino Acids

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semi-carbazides, the enhanced nucleophilicity of the aminooxy group permits it to react efficiently and selectively with a variety of molecules that contain aldehydes or other functional groups with similar chemical reactivity. See, e.g., Shao, J. and Tam, J., J. Am. Chem. Soc. 117:3893-3899 (1995); H. Hang and C. Bertozzi, Acc. Chem. Res. 34:

727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

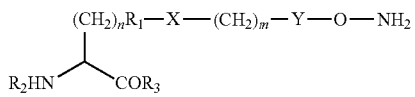

wherein n is 0-10; R1 is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, *J. Org. Chem.* 68: 8853-8858 (2003). Certain aminooxy-containing amino acids, such as L-2-amino-4-(aminooxy)butyric acid), have been isolated from natural sources (Rosenthal, G. et al., *Life Sci.* 60: 1635-1641 (1997). Other aminooxy-containing amino acids can be prepared by one skilled in the art.

D. Azide and Alkyne Reactive Groups

The unique reactivity of azide and alkyne functional groups makes them extremely useful for the selective modification of polypeptides and other biological molecules. Organic azides, particularly alphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., *Science* 301:964-7 (2003); Wang, Q., et al., *J. Am. Chem. Soc.* 125, 3192-3193 (2003); Chin, J. W., et al., *J. Am. Chem. Soc.* 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing fEPO can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., *J. Am. Chem. Soc.* 125, 3192-3193 (2003); Tornoe, C. W., et al., *J. Org. Chem.* 67:3057-3064 (2002); Rostovtsev, et al., *Angew. Chem. Int. Ed.* 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the fEPO polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, *Science* 287, 2007-2010 (2000). The azide-containing amino acid can be either an alkyl azide (including but not limited to, 2-amino-6-azido-1-hexanoic acid) or an aryl azide (p-azido-phenylalanine).

Exemplary water soluble polymers containing an aryl ester and a phosphine moiety can be represented as follows:

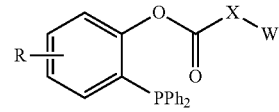

wherein X can be O, N, S or not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —$S(O)_2R'$, —$S(O)_2NR'R"$, —CN and —$NO_2$. R', R", R''' and R'''' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —$C(O)CH_3$, —$C(O)CF_3$, —$C(O)CH_2OCH_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

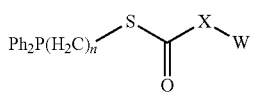

wherein n is 1-10; X can be O, N, S or not present, Ph is phenyl, and W is a water soluble polymer.

Exemplary alkyne-containing amino acids can be represented as follows:

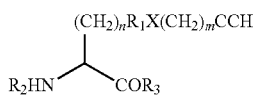

wherein n is 0-10; R1 is an alkyl, aryl, substituted alkyl, or substituted aryl or not present; X is O, N, S or not present; m is 0-10, $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the acetylene moiety is positioned in the para position relative to the alkyl side chain. In some embodiments, n is 1, $R_1$ is phenyl, X is O, m is 1 and the propargyloxy group is positioned in the para position relative to the alkyl side chain (i.e., O-propargyl-tyrosine). In some embodiments, n is 1, $R_1$ and X are not present and m is 0 (i.e., proparylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., *J. Am. Chem. Soc.* 125: 11782-11783 (2003), and 4-alkynyl-L-phenylalanine can be synthesized as described in Kayser, B., et al., *Tetrahedron* 53(7): 2475-2484 (1997). Other alkyne-containing amino acids can be prepared by one skilled in the art.

Exemplary azide-containing amino acids can be represented as follows:

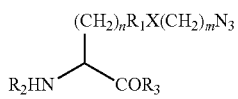

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the azide moiety is positioned para to the alkyl side chain. In some embodiments, n is 0-4 and $R_1$ and X are not present, and m=0. In some embodiments, n is 1, $R_1$ is phenyl, X is O, m is 2 and the β-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of skill in the art, including but not limited to, via displacement of a suitable leaving group (including but not limited to, halide, mesylate, tosylate) or via opening of a suitably protected lactone. See, e.g., *Advanced Organic Chemistry* by March (Third Edition, 1985, Wiley and Sons, New York).

E. Aminothiol Reactive Groups

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, *J. Am. Chem. Soc.* 1995, 117 (14) 3893-3899. In some embodiments, beta-substituted aminothiol amino acids can be incorporated into fEPO polypeptides and then reacted with water soluble polymers comprising an aldehyde functionality. In some embodiments, a water soluble polymer, drug conjugate or other payload can be coupled to a fEPO polypeptide comprising a beta-substituted aminothiol amino acid via formation of the thiazolidine.

Cellular Uptake of Unnatural Amino Acids

Unnatural amino acid uptake by a eukaryotic cell is one issue that is typically considered when designing and selecting unnatural amino acids, including but not limited to, for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which unnatural amino acids, if any, are taken up by cells. See, e.g., the toxicity assays in, e.g., the application entitled "Protein Arrays," 60/435,821, filed on Dec. 22, 2002; and Liu, D. R. & Schultz, P. G. (1999) *Progress toward the evolution of an organism with an expanded genetic code.* *PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, including but not limited to, in a eukaryotic cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, including but not limited to, as developed by Maxygen, Inc. (available on the world wide web at www.maxygen.com), is optionally used to develop novel enzymes and pathways. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.*, 91:10747-10751. Similarly DesignPath™, developed by Genencor (available on the world wide web at genencor.com) is optionally used for metabolic pathway engineering, including but not limited to, to engineer a pathway to create O-methyl-L-trosine in a cell. This technology reconstructs existing pathways in host organisms using a combination of new genes, including but not limited to, identified through functional genomics, and molecular evolution and design. Diversa Corporation (available on the world wide web at diversa.com) also provides technology for rapidly screening libraries of genes and gene pathways, including but not limited to, to create new pathways.

Typically, the unnatural amino acid produced with an engineered biosynthetic pathway of the invention is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Polypeptides with Unnatural Amino Acids

The incorporation of an unnatural amino acid can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), etc. Proteins that include an unnatural amino acid can have enhanced or even entirely new catalytic or biophysical properties. For example, the following properties are optionally modified by inclusion of an unnatural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or noncovalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of Protein Structure and Function, Current Opinion in Chemical Biology*, 4:645-652.

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Proteins or polypeptides of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein.

By producing proteins or polypeptides of interest with at least one unnatural amino acid in eukaryotic cells, proteins or polypeptides will typically include eukaryotic posttranslational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like. In one aspect, the post-translational modification includes attachment of an oligosaccharide (including but not limited to, (GlcNAc-Man)$_2$-Man-GlcNAc-GlcNAc)) to an asparagine by a GlcNAc-asparagine linkage. See also, Table 1, which lists some examples of N-linked oligosaccharides of eukaryotic proteins (additional residues can also be present, which are not shown). In another aspect, the post-translational modification includes attachment of an oligosaccharide (including but not limited to, Gal-GalNAc, Gal-GlcNAc, etc.) to a serine or threonine by a GalNAc-serine or GalNAc-threonine linkage, or a GlcNAc-serine or a GlcNAc-threonine linkage.

TABLE 1

EXAMPLES OF OLIGOSACCHARIDES THROUGH GlcNAc-LINKAGE

| Type | Base Structure |
|---|---|
| High-mannose | Manα1-6<br>            ↘<br>              Manα1-6<br>Manα1-3↗         ↘<br>                      Manβ1-4GlcNAcβ1-4GlcNAcβ1-Asn<br>              Manα1-3↗ |
| Hybrid | Manα1-6↘<br>                  Manβ1-4GlcNAcβ1-4GlcNAcβ1-Asn<br>GlcNAcβ1-2-Manα1-3↗ |
| Complex | GlcNAcβ1-2-Manα1-6↘<br>                          Manβ1-4GlcNAcβ1-4GlcNAcβ1-Asn<br>GlcNAcβ1-2-Manα1-3↗ |
| Xylose | Manα1-6↘<br>              Manβ1-4GlcNAcβ1-4GlcNAcβ1-Asn<br>Xylβ1-2↗ |

In yet another aspect, the post-translation modification includes proteolytic processing of precursors (including but not limited to, calcitonin precursor, calcitonin gene-related peptide precursor, preproparathyroid hormone, preproinsulin, proinsulin, prepro-opiomelanocortin, pro-opiomelanocortin and the like), assembly into a multisubunit protein or macromolecular assembly, translation to another site in the cell (including but not limited to, to organelles, such as the endoplasmic reticulum, the golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) *Am. Chem. Soc.,* 118:8150-8151; Mahal, et al., (1997) *Science,* 276:1125-1128; Wang, et al., (2001) *Science* 292:498-500; Chin, et al., (2002) *Am. Chem. Soc.* 124:9026-9027; Chin, et al., (2002) *Proc. Natl. Acad. Sci.,* 99:11020-11024; Wang, et al., (2003) *Proc. Natl. Acad. Sci.,* 100:56-61; Zhang, et al., (2003) *Biochemistry,* 42:6735-6746; and, Chin, et al., (2003) *Science,* in press. This allows the selective labeling of virtually any protein with a host of reagents including fluorophores, crosslinking agents, saccharide derivatives and cytotoxic molecules. See also, patent application Ser. No. 10/686,944, entitled "Glycoprotein synthesis" filed Jan. 16, 2003, which is incorporated by reference herein. Post-translational modifications, including but not limited to, through an azido amino acid, can also made through the Staudinger ligation (including but not limited to, with triarylphosphine reagents). See, e.g., Kiick et al., (2002) *Incorporation of azides into recombinant proteins for chemoselective modification by the Staudinger ligtation, PNAS* 99:19-24.

This invention provides another highly efficient method for the selective modification of proteins, which involves the genetic incorporation of unnatural amino acids, including but not limited to, containing an azide or alkynyl moiety into proteins in response to a selector codon. These amino acid side chains can then be modified by, including but not limited to, a Huisgen[3+2] cycloaddition reaction (see, e.g., Padwa, A. in *Comprehensive Organic Synthesis,* Vol. 4, (1991) Ed. Trost, B. M., Pergamon, Oxford, p. 1069-1109; and, Huisgen, R. in 1,3-*Dipolar Cycloaddition Chemistry,* (1984) Ed. Padwa, A., Wiley, New York, p. 1-176) with, including but not limited to, alkynyl or azide derivatives, respectively. Because this method involves a cycloaddition rather than a nucleophilic substitution, proteins can be modified with extremely high selectivity. This reaction can be carried out at room temperature in aqueous conditions with excellent regioselectivity (1,4>1,5) by the addition of catalytic amounts of Cu(I) salts to the reaction mixture. See, e.g., Tornoe, et al., (2002) *Org. Chem.* 67:3057-3064; and, Rostovtsev, et al., (2002) *Angew. Chem. Int. Ed.* 41:2596-2599. Another method that can be used is the ligand exchange on a bisarsenic compound with a tetracysteine motif, see, e.g., Griffin, et al., (1998) *Science* 281:269-272.

A molecule that can be added to a protein of the invention through a [3+2] cycloaddition includes virtually any molecule with an azido or alkynyl derivative. Molecules include, but are not limited to, dyes, fluorophores, crosslinking agents, saccharide derivatives, polymers (including but not limited to, derivatives of polyethylene glycol), photocrosslinkers, cytotoxic compounds, affinity labels, derivatives of biotin, resins, beads, a second protein or polypeptide (or more), polynucleotide(s) (including but not limited to, DNA, RNA, etc.), metal chelators, cofactors, fatty acids, carbohydrates, and the like. These molecules can be added to an unnatural amino acid with an alkynyl group, including but not limited to, p-propargyloxyphenylalanine, or azido group, including but not limited to, p-azido-phenylalanine, respectively.

VI. In Vivo Generation of fEPO Comprising Non-Genetically-Encoded Amino Acids

The fEPO polypeptides of the invention can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Patent Application Publications 2003/0082575 (Ser. No. 10/126,927) and 2003/0108885 (Ser. No. 10/126,931), which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O-RS). Typically, the O-RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides, and are generally suitable for ise in the present invention. For example, keto-specific O-tRNA/aminoacyl-tRNA synthetases are described in Wang, L., et al., *Proc. Natl. Acad. Sci. USA* 100:56-61 (2003) and Zhang, Z. et al., *Biochem.* 42(22):6735-6746 (2003). Exemplary O-RS, or portions thereof, are encoded by polynucleotide sequences and include amino acid sequences disclosed in U.S. Patent Application Publications 2003/0082575 (Ser. No. 10/126, 927) and 2003/0108885 (Ser. No. 10/126,931), which are incorporated by reference herein. Corresponding O-tRNA molecules for use with the O-RSs are also described in U.S. Patent Application Publications 2003/0082575 (Ser. No. 10/126,927) and 2003/0108885 (Ser. No. 10/126,931), which are incorporated by reference herein.

An example of an azide-specific O-tRNA/aminoacyl-tRNA synthetase system is described in Chin, J. W., et al., *J. Am. Chem. Soc.* 124:9026-9027 (2002). Exemplary O-RS sequences for p-azido-L-Phe include, but are not limited to, nucleotide sequences SEQ ID NOs: 14-16 and 29-32 and amino acid sequences SEQ ID NOs: 46-48 and 61-64 as disclosed in U.S. Patent Application Publication 2003/0108885 (Ser. No. 10/126,931), which is incorporated by reference herein. Exemplary O-tRNA sequences suitable for use in the present invention include, but are not limited to, nucleotide sequences SEQ ID NOs: 1-3 as disclosed in U.S. Patent Application Publication 2003/0082575 (Ser. No. 10/126,927) which is incorporated by reference herein. Other examples of O-tRNA/aminoacyl-tRNA synthetase pairs specific to particular non-naturally encoded amino acids are described in U.S. Patent Application Publication 2003/0082575 (Ser. No. 10/126,927) which is incorporated by reference herein. 0-RS and O-tRNA that incorporate both keto- and azide-containing amino acids in *S. cerevisiae* are described in Chin, J. W., et al., *Science* 301:964-967 (2003).

Use of O-tRNA/aminoacyl-tRNA synthetases involves selection of a specific codon which encodes the non-naturally encoded amino acid. While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the fEPO polynucleotide coding sequence using mutagenesis methods known in the art (including but not limited to, site-specific mutagenesis, cassette mutagenesis, restriction selection mutagenesis, etc.).

Methods for generating components of the protein biosynthetic machinery, such as O-RSs, O-tRNAs, and orthogonal O-tRNA/O-RS pairs that can be used to incorporate a non-naturally encoded amino acid are described in Wang, L., et al., *Science* 292: 498-500 (2001); Chin, J. W., et al., *J. Am. Chem. Soc.* 124:9026-9027 (2002); Zhang, Z. et al., *Biochemistry* 42: 6735-6746 (2003). Methods and compositions for the in vivo incorporation of non-naturally encoded amino acids are described in U.S. Patent Application Publication 2003/0082575 (Ser. No. 10/126,927) which is incorporated by reference herein. Methods for selecting an orthogonal tRNA-tRNA synthetase pair for use in in vivo translation system of an organism are also described in U.S. Patent Application Publications 2003/0082575 (Ser. No. 10/126, 927) and 2003/0108885 (Ser. No. 10/126,931), which are incorporated by reference herein.

Methods for producing at least one recombinant orthogonal aminoacyl-tRNA synthetase (O-RS) comprise: (a) generating a library of (optionally mutant) RSs derived from at least one aminoacyl-tRNA synthetase (RS) from a first organism, including but not limited to, a prokaryotic organism, such as *Methanococcus jannaschii, Methanobacterium thermoautotrophicum, Halobacterium, Escherichia coli, A. fulgidus, P. furiosus, P. horikoshii, A. pernix, T. thermophilus*, or the like, or a eukaryotic organism; (b) selecting (and/or screening) the library of RSs (optionally mutant RSs) for members that aminoacylate an orthogonal tRNA (O-tRNA) in the presence of a non-naturally encoded amino acid and a natural amino acid, thereby providing a pool of active (optionally mutant) RSs; and/or, (c) selecting (optionally through negative selection) the pool for active RSs (including but not limited to, mutant RSs) that preferentially aminoacylate the O-tRNA in the absence of the non-naturally encoded amino acid, thereby providing the at least one recombinant O-RS; wherein the at least one recombinant O-RS preferentially aminoacylates the O-tRNA with the non-naturally encoded amino acid.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, including but not limited to, alanine.

Libraries of mutant RSs can be generated using various techniques known in the art, including but not limited to rational design based on protein three dimensional RS structure, or mutagenesis of RS nucleotides in a random or rational design technique. For example, the mutant RSs can be generated by site-specific mutations, random mutations, diversity generating recombination mutations, chimeric constructs, rational design and by other methods described herein or known in the art.

In one embodiment, selecting (and/or screening) the library of RSs (optionally mutant RSs) for members that are active, including but not limited to, that aminoacylate an orthogonal tRNA (O-tRNA) in the presence of a non-naturally encoded amino acid and a natural amino acid, includes: introducing a positive selection or screening marker, including but not limited to, an antibiotic resistance gene, or the like, and the library of (optionally mutant) RSs into a plurality of cells, wherein the positive selection and/or screening marker comprises at least one selector codon, including but not limited to, an amber, ochre, or opal codon; growing the plurality of cells in the presence of a selection agent; identifying cells that survive (or show a specific response) in the presence of the selection and/or screening agent by suppressing the at least one selector codon in the positive selection or screening marker, thereby providing a subset of positively selected cells that contains the pool of active (optionally mutant) RSs. Optionally, the selection and/or screening agent concentration can be varied.

In one aspect, the positive selection marker is a chloramphenicol acetyltransferase (CAT) gene and the selector codon is an amber stop codon in the CAT gene. Optionally, the positive selection marker is a β-lactamase gene and the selector codon is an amber stop codon in the β-lactamase gene. In another aspect the positive screening marker comprises a fluorescent or luminescent screening marker or an affinity based screening marker (including but not limited to, a cell surface marker).

In one embodiment, negatively selecting or screening the pool for active RSs (optionally mutants) that preferentially aminoacylate the O-tRNA in the absence of the non-naturally encoded amino acid includes: introducing a negative selection or screening marker with the pool of active (optionally mutant) RSs from the positive selection or screening into a plurality of cells of a second organism, wherein the negative selection or screening marker comprises at least one selector codon (including but not limited to, an antibiotic resistance gene including but not limited to, a chloramphenicol acetyltransferase (CAT) gene); and, identifying cells that survive or show a specific screening response in a first medium supplemented with the non-naturally encoded amino acid and a screening or selection agent, but fail to survive or to show the specific response in a second medium not supplemented with the non-naturally encoded amino acid and the selection or screening agent, thereby providing surviving cells or screened cells with the at least one recombinant O-RS. For example, a CAT identification protocol optionally acts as a positive selection and/or a negative screening in determination of appropriate O-RS recombinants. For instance, a pool of clones is optionally replicated on growth plates containing CAT (which comprises at least one selector codon) either with or without one or more non-naturally encoded amino acid. Colonies growing exclusively on the plates containing non-naturally encoded amino acids are thus regarded as containing recombinant O-RS. In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungus, a yeast, an archaebacterium, a *eubacterium*, a plant, an insect, a protist, etc. In other embodiments, the screening marker comprises a fluorescent or luminescent screening marker or an affinity based screening marker.

In another embodiment, screening or selecting (including but not limited to, negatively selecting) the pool for active (optionally mutant) RSs includes: isolating the pool of active mutant RSs from the positive selection step (b); introducing a negative selection or screening marker, wherein the negative selection or screening marker comprises at least one selector codon (including but not limited to, a toxic marker gene, including but not limited to, a ribonuclease barnase gene, comprising at least one selector codon), and the pool of active (optionally mutant) RSs into a plurality of cells of a second organism; and identifying cells that survive or show a specific screening response in a first medium not supplemented with the non-naturally encoded amino acid, but fail to survive or show a specific screening response in a second medium supplemented with the non-naturally encoded amino acid, thereby providing surviving or screened cells with the at least one recombinant O-RS, wherein the at least one recombinant O-RS is specific for the non-naturally encoded amino acid. In one aspect, the at least one selector codon comprises about two or more selector codons. Such embodiments optionally can include wherein the at least one selector codon comprises two or more selector codons, and wherein the first and second organism are different (including but not limited to, each organism is optionally, including but not limited to, a prokaryote, a eukaryote, a mammal, an *Escherichia coli*, a fungi, a yeast, an archaebacteria, a eubacteria, a plant, an insect, a protist, etc.). Also, some aspects include wherein the negative selection marker comprises a ribonuclease barnase gene (which comprises at least one selector codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O-RS) can further comprise: (d) isolating the at least one recombinant O-RS; (e) generating a second set of O-RS (optionally mutated) derived from the at least one recombinant O-RS; and, (f) repeating steps (b) and (c) until a mutated O-RS is obtained that comprises an ability to preferentially aminoacylate the O-tRNA. Optionally, steps (d)-(f) are repeated, including but not limited to, at least about two times. In one aspect, the second set of mutated O-RS derived from at least one recombinant O-RS can be generated by mutagenesis, including but not limited to, random mutagenesis, site-specific mutagenesis, recombination or a combination thereof.

The stringency of the selection/screening steps, including but not limited to, the positive selection/screening step (b), the negative selection/screening step (c) or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the reporter is detected by luminescence. Optionally, the reporter is displayed on a cell surface, on a phage display or the like and selected based upon affinity or catalytic activity involving the non-naturally encoded amino acid or an analogue. In one embodiment, the mutated synthetase is displayed on a cell surface, on a phage display or the like.

Methods for producing a recombinant orthogonal tRNA (O-tRNA) include: (a) generating a library of mutant tRNAs derived from at least one tRNA, including but not limited to, a suppressor tRNA, from a first organism; (b) selecting (including but not limited to, negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS (O-RS), thereby providing at least one recombinant O-tRNA; wherein the at least one recombinant O-tRNA recognizes a selector codon and is not efficiency recognized by the RS from the second organism and is preferentially aminoacylated by the O-RS. In some embodiments the at least one tRNA is a suppressor tRNA and/or comprises a unique three base codon of natural and/or unnatural bases, or is a nonsense codon, a rare codon, an unnatural codon, a codon comprising at least 4 bases, an amber codon, an ochre codon, or an opal stop codon. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, including but not limited to, prokaryotes (including but not limited to, *Methanococcus jannaschii, Methanobacteium thermoautotrophicum, Escherichia coli, Halobacterium*, etc.), eukaryotes, mammals, fungi, yeasts, archaebacteria, eubacteria, plants, insects, protists, etc. Additionally, the recombinant tRNA is optionally aminoacylated by a non-naturally encoded amino acid, wherein the non-naturally encoded amino acid is biosynthesized in vivo either naturally or through genetic manipulation. The non-naturally encoded amino acid is optionally added to a growth medium for at least the first or second organism.

In one aspect, selecting (including but not limited to, negatively selecting) or screening the library for (optionally mutant) tRNAs that are aminoacylated by an aminoacyl-tRNA synthetase (step (b)) includes: introducing a toxic marker gene, wherein the toxic marker gene comprises at least one of the selector codons (or a gene that leads to the production of a toxic or static agent or a gene essential to the organism wherein such marker gene comprises at least one selector codon) and the library of (optionally mutant) tRNAs into a plurality of cells from the second organism; and, selecting surviving cells, wherein the surviving cells contain the pool of (optionally mutant) tRNAs comprising at least one orthogonal tRNA or nonfunctional tRNA. For example, surviving cells can be selected by using a comparison ratio cell density assay.

In another aspect, the toxic marker gene can include two or more selector codons. In another embodiment of the methods, the toxic marker gene is a ribonuclease barnase gene, where the ribonuclease barnase gene comprises at least one amber codon. Optionally, the ribonuclease barnase gene can include two or more amber codons.

In one embodiment, selecting or screening the pool of (optionally mutant) tRNAs for members that are aminoacylated by an introduced orthogonal RS (O-RS) can include: introducing a positive selection or screening marker gene, wherein the positive marker gene comprises a drug resistance gene (including but not limited to, β-lactamase gene, comprising at least one of the selector codons, such as at least one amber stop codon) or a gene essential to the organism, or a gene that leads to detoxification of a toxic agent, along with the O-RS, and the pool of (optionally mutant) tRNAs into a plurality of cells from the second organism; and, identifying surviving or screened cells grown in the presence of a selection or screening agent, including but not limited to, an antibiotic, thereby providing a pool of cells possessing the at least one recombinant tRNA, where the at least recombinant tRNA is aminoacylated by the O-RS and inserts an amino acid into a translation product encoded by the positive marker gene, in response to the at least one selector codons. In another embodiment, the concentration of the selection and/or screening agent is varied.

Methods for generating specific O-tRNA/O-RS pairs are provided. Methods include: (a) generating a library of mutant tRNAs derived from at least one tRNA from a first organism; (b) negatively selecting or screening the library for (optionally mutan) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS (O-RS), thereby providing at least one recombinant O-tRNA. The at least one recombinant O-tRNA recognizes a selector codon and is not efficiency recognized by the RS from the second organism and is preferentially aminoacylated by the O-RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of a non-naturally encoded amino acid and a natural amino acid, thereby providing a pool of active (optionally mutant) RSs; and, (f) negatively selecting or screening the pool for active (optionally mutant) RSs that preferentially aminoacylate the at least one recombinant O-tRNA in the absence of the non-naturally encoded amino acid, thereby providing the at least one specific O-tRNA/O-RS pair, wherein the at least one specific O-tRNA/O-RS pair comprises at least one recombinant O-RS that is specific for the non-naturally encoded amino acid and the at least one recombinant O-tRNA. Specific O-tRNA/O-RS pairs produced by the methods are included. For example, the specific O-tRNA/O-RS pair can include, including but not limited to, a mutRNATyr-mutTyrRS pair, such as a mutRNATyr-SS12TyrRS pair, a mutRNALeu-mutLeuRS pair, a mutRNAThr-mutThrRS pair, a mutRNAGlu-mutGluRS pair, or the like. Additionally, such methods include wherein the first and third organism are the same (including but not limited to, *Methanococcus jannaschii*).

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from a second organism; and, selecting for surviving cells in the first set that fail to survive in the duplicate cell set or screening for cells showing a specific screening response that fail to give such response in the duplicate cell set, wherein the first set and the duplicate cell set are grown in the presence of a selection or screening agent, wherein the surviving or screened cells comprise the orthogonal tRNA-tRNA synthetase pair for use in the in the in vivo translation system of the second organism. In one embodiment, comparing and selecting or screening includes an in vivo complementation assay. The concentration of the selection or screening agent can be varied.

The organisms of the present invention comprise a variety of organism and a variety of combinations. For example, the first and the second organisms of the methods of the present invention can be the same or different. In one embodiment, the organisms are optionally a prokaryotic organism, including but not limited to, *Methanococcus jannaschii, Methanobacterium thermoautotrophicum, Halobacterium, Escherichia coli, A. fulgidus, P. furiosus, P. horikoshii, A. pernix, T. thermophilus*, or the like. Alternatively, the organisms optionally comprise a eukaryotic organism, including but not limited to, plants (including but not limited to, complex plants such as monocots, or dicots), algae, protists, fungi (including but not limited to, yeast, etc), animals (including but not limited to, mammals, insects, arthropods, etc.), or the like. In another embodiment, the second organism is a prokaryotic organism, including but not limited to, *Methanococcus jannaschii, Methanobacterium thermoautotrophicum, Halobacterium, Escherichia coli, A. fulgidus, Halobacterium, P. furiosus, P. horikoshii, A. pernix, T. thermophilus*, or the like. Alternatively, the second organism can be a eukaryotic organism, including but not limited to, a yeast, a animal cell, a plant cell, a fungus, a mammalian cell, or the like. In various embodiments the first and second organisms are different.

VII. Location of Non-Naturally-Occurring Amino Acids in fEPO

The present invention contemplates incorporation of one or more non-naturally-occurring amino acids into fEPO. One or more non-naturally-occurring amino acids may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids) and/or inserting the non-naturally-occurring amino acid in a location that is not required for activity.

Regions of fEPO can be illustrated as follows, wherein the amino acid positions in fEPO are indicated in the middle row:

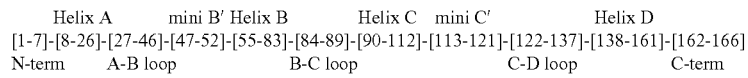

```
   Helix A      mini B' Helix B       Helix C     mini C'         Helix D
[1-7]-[8-26]-[27-46]-[47-52]-[55-83]-[84-89]-[90-112]-[113-121]-[122-137]-[138-161]-[162-166]
  N-term       A-B loop            B-C loop              C-D loop           C-term
```

A variety of biochemical and structural approaches can be employed to select the desired sites for substitution with a non-naturally encoded amino acid within the fEPO polypeptide. It is readily apparent to those of ordinary skill in the art that any position of the polypeptide chain is suitable for selection to incorporate a non-naturally encoded amino acid, and selection may be based on rational design or by random selection for any or no particular desired purpose. Selection of desired sites may be for producing an fEPO molecule having any desired property or activity, including but not limited to agonists, super-agonists, inverse agonists, antagonists, receptor binding modulators, receptor activity modulators, dimer or multimer formation, no change to activity or property compared to the native molecule, or manipulating any physical or chemical property of the polypeptide such as solubility, aggregation, or stability. For example, locations in the polypeptide required for biological activity of fEPO can be identified using alanine scanning or homolog scanning methods known in the art. See, e.g., Bittorf, T. et al. *FEBS*, 336:133-136 (1993) (identifying critical residues for EPO activity), Wen, D., et al. *JBC*, 269:22839-22846 (1994) (alanine scanning mutagenesis employed to identify functionally important domains of hEPO), and Elliot, S. et al. *Blood*, 89:493-502 (1997) (identifying key electrostatic interactions between hEPO and human EPO receptor). Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-naturally encoded amino acid, again depending on the desired activity sought for the polypeptide. Another alternative would be to simply make serial substitutions in each position on the polypeptide chain with a non-naturally encoded amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

The structure and activity of naturally-occurring mutants of fEPO that contain deletions can also be examined to determine regions of the protein that are likely to be tolerant of substitution with a non-naturally encoded amino acid. See, e.g., Bittorf et al., *FEBS*, 336:133 (1993); Wen et al, *JBC*, 269:22839 (1994). Once residues that are likely to be intolerant to substitution with non-naturally encoded amino acids have been eliminated, the impact of proposed substitutions at each of the remaining positions can be examined from the three-dimensional structure of fEPO and its binding proteins. See Syed et al., *Nature*, 395: 511 (1998) and Cheetham et al., *Nature Structural* Biology, 5:861 (1998); x-ray crystallographic and NMR structures of hEPO are available in the Protein Data Bank (PDB, www.rcsb.org with PDB ID's: 1CN4, 1EER, and 1BUY), a centralized database containing three-dimensional structural data of large molecules of proteins and nucleic acids. Thus, by using the known information regarding hEPO, those of skill in the art can readily identify amino acid positions in fEPO (see FIG. 1) that can be substituted with non-naturally encoded amino acids.

In some embodiments, the EPO polypeptides of the invention comprise one or more non-naturally occurring amino acid positioned in a region of the protein that does not disrupt the helices or beta sheet secondary structure of EPO. In some embodiments, the one or more non-naturally encoded amino acid are incorporated or substituted in one or more of the following regions corresponding to secondary structures in EPO as follows: 1-7 (N-terminus), 8-26 (A helix), 27-38 (region between A helix and B helix), 39-41 (Beta sheet 1), 42-46 (region between Beta sheet 1 and mini helix B'), 47-52 (mini B' helix), 53-54 (region between mini B' helix and B helix), 55-83 (B helix), 84-89 (region between B helix and C helix), 90-113 (C helix), 114-121 (mini C' helix), 122-132 (region between mini C' helix and Beta sheet 2), 133-135 (Beta sheet 2), 136-137 (region between Beta sheet 2 and D helix), 138-161 (D helix), 162-166 (C-terminus). In some embodiments, the one or more non-naturally encoded amino acids are incorporated in one of the following positions in EPO: 1, 2, 3, 4, 5, 6, 8, 9, 17, 21, 24, 25, 26, 27, 28, 30, 31, 32, 34, 35, 36, 37, 38, 39, 40, 43, 45, 47, 50, 51, 52, 53, 54, 55, 56, 57, 58, 68, 72, 76, 77, 78, 79, 80, 82, 83, 84, 85, 86, 87, 88, 89, 90, 91, 92, 107, 110, 111, 113, 114, 115, 116, 117, 118, 119, 120, 121, 122, 123, 124, 125, 126, 127, 128, 129, 130, 131, 132, 133, 134, 136, 154, 157, 158, 159, 160, 162, 163, 164, 165 and 166. In some embodiments, the EPO polypeptides of the invention comprise one or more non-naturally occurring amino acids at one or more of the following positions: 21, 24, 27, 28, 30, 31, 36, 37, 38, 55, 72, 83, 85, 86, 87, 89, 113, 116, 119, 120, 121, 123, 124, 125, 126, 127, 128, 129, 130, and 162. In some embodiments, the non-naturally occurring amino acid at these or other positions are linked to a water soluble molecule, including but not limited to positions 21, 24, 38, 83, 85, 86, 89, 116, 119, 121, 124, 125, 126, 127, and 128.

Exemplary sites of incorporation of a non-naturally encoded amino acid include, but are not limited to, those that are excluded from Site I and Site II, may be fully or partially solvent exposed, have minimal or no hydrogen-bonding interactions with nearby residues, may be minimally exposed to nearby reactive residues, and may be in regions that are highly flexible (including but not limited to, C-D loop) or structurally rigid (including but not limited to, B helix) as predicted by the three-dimensional crystal structure of hEPO with its receptor.

A wide variety of non-naturally encoded amino acids can be substituted for, or incorporated into, a given position in fEPO. In general, a particular non-naturally encoded amino acid is selected for incorporation based on an examination of the three dimensional crystal structure of fEPO with its receptor, a preference for conservative substitutions (i.e., aryl-based non-naturally encoded amino acids, such as p-acetylphenylalanine or O-propargyltyrosine substituting for Phe, Tyr or Trp), and the specific conjugation chemistry that one desires to introduce into the fEPO polypeptide (including but not limited to, the introduction of 4-azidophenylalanine if one wants to effect a Huisgen [3+2] cycloaddition with a water soluble polymer bearing an alkyne moiety or a amide bond formation with a water soluble polymer that bears an aryl ester that, in turn, incorporates a phosphine moiety).

In one embodiment, the method further includes incorporating into the protein the unnatural amino acid, where the unnatural amino acid comprises a first reactive group; and contacting the protein with a molecule (including but not limited to, a dye, a polymer, including but not limited to, a derivative of polyethylene glycol, a photocrosslinker, a cytotoxic compound, an affinity label, a derivative of biotin, a resin, a second protein or polypeptide, a metal chelator, a cofactor, a fatty acid, a carbohydrate, a polynucleotide (including but not limited to, DNA, RNA, etc.), etc.) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (including but not limited to, in unnatural amino acid p-propargyloxyphenylalanine) and the second reactive group is the azido moiety. In another example, the first reactive group is the azido moiety (including but not limited to, in the unnatural amino acid p-azido-L-phenylalanine) and the second reactive group is the alkynyl moiety.

A subset of exemplary sites for incorporation of a non-naturally encoded amino acid include, but are not limited to, 1, 2, 4, 17, 21, 24, 27, 28, 30, 31, 32, 34, 36, 37, 38, 40, 50, 53, 55, 58, 65, 68, 72, 76, 80, 82, 83, 85, 86, 87, 89, 113, 115, 116, 119, 120, 121, 122, 123, 124, 125, 126, 127, 128, 129, 130, 131, 132, 134, 136, and 162. An examination of the crystal structure of hEPO and its interactions with the hEPO receptor indicates as well as the molecular modeling provided along with the presently filed application of fEPO indicate that the side chains of these amino acid residues are fully or partially accessible to solvent and the side chain of a non-naturally encoded amino acid may point away from the protein surface and out into the solvent.

Exemplary positions for incorporation of a non-naturally encoded amino acid into fEPO include 21, 24, 28, 30, 31, 36, 37, 38, 55, 72, 83, 85, 86, 87, 89, 113, 116, 119, 120, 121, 123, 124, 125, 126, 127, 128, 129, 130, and 162. An examination of the crystal structure of hEPO and its interactions with the hEPO receptor indicates that the side chains of these amino acid residues are fully exposed to the solvent and the side chain of the native residue points out into the solvent.

In some cases, the non-naturally encoded amino acid substitution(s) or incorporation(s) will be combined with other additions, substitutions, or deletions within the fEPO polypeptide to affect other biological traits of fEPO. In some cases, the other additions, substitutions or deletions may increase the stability (including but not limited to, resistance to proteolytic degradation) of the fEPO polypeptide or increase affinity of the fEPO polypeptide for an erythropoietin receptor. In some cases, the other additions, substitutions or deletions may increase the solubility (including but not limited to, when expressed in *E. coli* or other host cells) of the fEPO polypeptide. In some embodiments sites are selected for substitution with a naturally encoded or non-naturally encoded amino acid in addition to another site for incorporation of a non-naturally encoded amino acid for the purpose of increasing fEPO solubility following expression in *E. coli* recombinant host cells. Examples of such sites in fEPO for amino acid substitution to increase solubility are N36, Q86, G113 and/or Q115, which may be substituted with Lys, Arg, Glu, or any other charged naturally encoded or non-naturally encoded amino acid. In some embodiments, the fEPO polypeptides comprise another addition, substitution, or deletion that modulates affinity for the fEPO receptor, modulates (including but not limited to, increases or decreases) receptor dimerization, stabilizes receptor dimers, modulates circulating half-life, modulates release or bioavailability, facilitates purification, or improves or alters a particular route of administration. Similarly, fEPO polypeptides can comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

For instance, in addition to introducing one or more non-naturally encoded amino acids as set forth herein, one or more of the following substitutions are introduced: S9A, F48S, Y49S, A50S, Q59A, A73G, G101A, T106A, L108A, T132A, R139A, K140A, R143A, S146A, N147A, R150A, and K154A to increase the affinity of the fEPO variant for its receptor (Wen et al., (1994) JBC 269:22839-22846).

In some embodiments, the substitution of a non-naturally encoded amino acid generates a fEPO antagonist. A subset of exemplary sites for incorporation of a non-naturally encoded amino acid include: 10, 11, 14, 15, 96, 97, 100, 103, 104, 107, 110. (Elliot et al. (1997) Blood 89: 493-502; and Cheetham et al. (1998) Nature Structural Biology 5: 861-

866). In other embodiments, the exemplary sites of incorporation of a non-naturally encoded amino acid include residues within the amino terminal region of helix A and a portion of helix C. In another embodiment, substitution of L108 with a non-naturally encoded amino acid such as p-azido-L-phenylalanine or O-propargyl-L-tyrosine. In other embodiments, the above-listed substitutions are combined with additional substitutions that cause the fEPO polypeptide to be a fEPO antagonist. For instance, a non-naturally encoded amino acid is substituted at one of the positions identified herein and a simultaneous substitution is introduced at L108 (including but not limited to, L108K, L108R, L108H, L108D, or L108E).

In some cases, 1, 2, 3, 4, 5, 6, 7, 8, 9, 10, or more amino acids are substituted with a non-naturally-encoded amino acid. In some cases, the fEPO polypeptide further includes 1, 2, 3, 4, 5, 6, 7, 8, 9, 10, or more substitutions of a non-naturally encoded amino acid for a naturally-occurring amino acid. For example, in some embodiments, at least two residues in the following regions of fEPO are substituted with a non-naturally encoded amino acid: 1-7 (N-terminus), 8-26 (A helix), 27-38 (region between A helix and B helix), 39-41 (Beta sheet 1), 42-46 (region between Beta sheet 1 and mini helix B'), 47-52 (mini B' helix), 53-54 (region between mini B' helix and B helix), 55-83 (B helix), 84-89 (region between B helix and C helix), 90-113 (C helix), 114-121 (mini C' helix), 122-132 (region between mini C' helix and Beta sheet 2), 133-135 (Beta sheet 2), 136-137 (region between Beta sheet 2 and D helix), 138-161 (D helix), 162-166 (C-terminus). In some cases, the two or more non-naturally encoded residues are linked to one or more lower molecular weight linear or branched PEGs (approximately~5-20 kDa in mass), thereby enhancing binding affinity and comparable serum half-life relative to the species attached to a single, higher molecular weight PEG.

In some embodiments, up to two of the following residues are substituted with a non-naturally-encoded amino acid at position: 1, 2, 4, 17, 21, 24, 27, 28, 30, 31, 32, 34, 36, 37, 38, 40, 50, 53, 55, 58, 65, 68, 72, 76, 80, 82, 83, 85, 86, 87, 89, 113, 115, 116, 119, 120, 121, 122, 123, 124, 125, 126, 127, 128, 129, 130, 131, 132, 134, 136, and 162. Thus, in some cases, any of the following pairs of substitutions are made: N24X* and G113X*; N38X* and Q115X*; N36X* and S85X*; N36X* and A125X*; N36X* and A128X*; Q86X* and S126X* wherein X* represents a non-naturally encoded amino acid. Preferred sites for incorporation of two or more non-naturally encoded amino acids include combinations of the following residues: 21, 24, 28, 30, 31, 36, 37, 38, 55, 72, 83, 85, 86, 87, 89, 113, 116, 119, 120, 121, 123, 124, 125, 126, 127, 128, 129, 130, and 162. Particularly preferred sites for incorporation of two or more non-naturally encoded amino acids include combinations of the following residues: 21, 24, 38, 83, 86, 89, 116, 119, 124, 125, 126, 127, 128, 129, 130 and 162.

VIII. Expression in Non-Eukaryotes and Eukaryotes

To obtain high level expression of a cloned fEPO polynucleotide, one typically subclones polynucleotides encoding a fEPO polypeptide of the invention into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al.

Bacterial expression systems for expressing fEPO polypeptides of the invention are available in, including but not limited to, *E. coli, Bacillus* sp., and *Salmonella* (Palva et al., Gene 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In cases where orthogonal tRNAs and amino acyl tRNA synthetases (described above) are used to express the fEPO polypeptides of the invention, host cells for expression are selected based on their ability to use the orthogonal components. Exemplary host cells include Gram-positive bacteria (including but not limited to *B. brevis* or *B. subtilis, Pseudomonas* or *Streptomyces*) and Gram-negative bacteria (*E. coli*), as well as yeast and other eukaryotic cells. Cells comprising O-tRNA/O-RS pairs can be used as described herein.

A eukaryotic host cell or non-eukaryotic host cell of the present invention provides the ability to synthesize proteins that comprise unnatural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L). The production of large quantities (including but not limited to, greater that that typically possible with other methods, including but not limited to, in vitro translation) of a protein in a eukaryotic cell including at least one unnatural amino acid is a feature of the invention.

A eukaryotic host cell or non-eukaryotic hose cell of the present invention provides the ability to biosynthesize proteins that comprise unnatural amino acids in large useful quantities. For example, proteins comprising an unnatural amino acid can be produced at a concentration of, including but not limited to, at least 10 µg/liter, at least 50 µg/liter, at least 75 µg/liter, at least 100 µg/liter, at least 200 µg/liter, at least 250 µg/liter, or at least 500 µg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

Expression Systems, Culture, and Isolation fEPO may be expressed in any number of suitable expression systems including, for example, yeast, insect cells, mammalian cells, and bacteria. A description of exemplary expression systems is provided below.

Yeast As used herein, the term "yeast" includes any of the various yeasts capable of expressing a gene encoding fEPO.

Such yeasts include, but are not limited to, ascosporogenous yeasts (Endomycetales), basidiosporogenous yeasts and yeasts belonging to the Fungi imperfecti (Blastomycetes) group. The ascosporogenous yeasts are divided into two families, Spermophthoraceae and Saccharomycetaceae. The latter is comprised of four subfamilies, Schizosaccharomycoideae (e.g., genus *Schizosaccharomyces*), Nadsonioideae, Lipomycoideae and Saccharomycoideae (e.g., genera *Pichia, Kluyveromyces* and *Saccharomyces*). The basidiosporogenous yeasts include the genera *Leucosporidium, Rhodosporidium, Sporidiobolus, Filobasidium, and Filobasidiella*. Yeasts belonging to the Fungi Imperfecti (Blastomycetes) group are divided into two families, Sporobolomycetaceae (e.g., genera *Sporobolomyces* and *Bullera*) and Cryptococcaceae (e.g., genus *Candida*).

Of particular interest for use with the present invention are species within the genera *Pichia, Kluyveromyces, Saccharomyces, Schizosaccharomyces, Hansenula, Torulopsis*, and *Candida*, including, but not limited to, *P. pastoris, P. guillerimondii, S. cerevisiae, S. carlsbergensis, S. diastaticus, S. douglasii, S. kluyveri, S. norbensis, S. oviformis, K. lactis, K. fragilis, C. albicans, C. maltosa*, and *H. polymorpha*.

The selection of suitable yeast for expression of fEPO is within the skill of one of ordinary skill in the art. In selecting yeast hosts for expression, suitable hosts may include those shown to have, for example, good secretion capacity, low proteolytic activity, and overall robustness. Yeast are generally available from a variety of sources including, but not limited to, the Yeast Genetic Stock Center, Department of Biophysics and Medical Physics, University of California (Berkeley, Calif.), and the American Type Culture Collection ("ATCC") (Manassas, Va.).

The term "yeast host" or "yeast host cell" includes yeast that can be, or has been, used as a recipient for recombinant vectors or other transfer DNA. The term includes the progeny of the original yeast host cell that has received the recombinant vectors or other transfer DNA. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a fEPO, are included in the progeny intended by this definition.

Expression and transformation vectors, including extrachromosomal replicons or integrating vectors, have been developed for transformation into many yeast hosts. For example, expression vectors have been developed for *S. cerevisiae* (Sikorski et al., GENETICS (1998) 112:19; Ito et al., J. BACIERIOL. (1983) 153:163; Hinnen et al., PROC. NATL. ACAD. SCI. USA (1978) 75:1929); *C. albicans* (Kurtz et al., MOL. CELL. BIOL. (1986) 6:142); *C. maltosa* (Kunze et al., J. BASIC MICROBIOL. (1985) 25:141); *H. polymorpha* (Gleeson et al., J. GEN. MICROBIOL. (1986) 132:3459; Roggenkamp et al., MOL. GEN. GENET. (1986) 202:302); *K. fragilis* (Das et al., J. BACIERIOL. (1984) 158:1165); *K. lactis* (De Louvencourt et al., J. BACIERIOL. (1983) 154:737; Van den Berg et al., BIO/TECHNOLOGY (1990) 8:135); *P. guillerimondii* (Kunze et al., J. BASIC MICROBIOL. (1985) 25:141); *P. pastoris* (U.S. Pat. Nos. 5,324,639; 4,929,555; and 4,837,148; Cregg et al., MOL. CELL. BIOL. (1985) 5:3376); *Schizosaccharomyces pombe* (Beach and Nurse, NATURE (1981) 300:706); and *Y. lipolytica* (Davidow et al., CURR. GENET. (1985) 10:380 (1985); Gaillardin et al., CURR. GENET. (1985) 10:49); *A. nidulans* (Ballance et al., BIOCHEM. BIOPHYS. RES. COMMUN. (1983) 112:284-89; Tilburn et al., GENE (1983) 26:205-221; and Yelton et al., PROC. NATL. ACAD. SCI. USA (1984) 81:1470-74); *A. niger* (Kelly and Hynes, EMBO J. (1985) 4:475479); *T. reesia* (EP 0 244 234); and filamentous fungi such as, e.g., *Neurospora, Penicillium, Tolypocladium* (WO 91/00357).

Control sequences for yeast vectors are well known to those of ordinary skill in the art and include, but are not limited to, promoter regions from genes such as alcohol dehydrogenase (ADH) (EP 0 284 044); enolase; glucokinase; glucose-6-phosphate isomerase; glyceraldehydes-3-phosphate-dehydrogenase (GAP or GAPDH); hexokinase; phosphofructokinase; 3-phosphoglycerate mutase; and pyruvate kinase (PyK) (EP 0 329 203). The yeast PHO5 gene, encoding acid phosphatase, also may provide useful promoter sequences (Myanohara et al., PROC. NATL. ACAD. SCI. USA (1983) 80:1). Other suitable promoter sequences for use with yeast hosts may include the promoters for 3-phosphoglycerate kinase (Hitzeman et al., J. BIOL. CHEM. (1980) 255:2073); and other glycolytic enzymes, such as pyruvate decarboxylase, triosephosphate isomerase, and phosphoglucose isomerase (Holland et al., BIOCHEMISTRY (1978) 17:4900; Hess et al., J. ADV. ENZYME REG. (1968) 7:149). Inducible yeast promoters having the additional advantage of transcription controlled by growth conditions may include the promoter regions for alcohol dehydrogenase 2; isocytochrome C; acid phosphatase; metallothionein; glyceraldehyde-3-phosphate dehydrogenase; degradative enzymes associated with nitrogen metabolism; and enzymes responsible for maltose and galactose utilization. Suitable vectors and promoters for use in yeast expression are further described in EP 0 073 657.

Yeast enhancers also may be used with yeast promoters. In addition, synthetic promoters may also function as yeast promoters. For example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197. Other examples of hybrid promoters include promoters that consist of the regulatory sequences of the ADH2, GAL4, GAL10, or PHO5 genes, combined with the transcriptional activation region of a glycolytic enzyme gene such as GAP or PyK. See EP 0 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. BIOL. CHEM. (1981) 256:1385). In addition, the origin of replication from the 2μ plasmid origin is suitable for yeast. A suitable selection gene for use in yeast is the trp1 gene present in the yeast plasmid. See Tschemper et al., GENE (1980) 10:157; Kingsman et al., GENE (1979) 7:141. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

Methods of introducing exogenous DNA into yeast hosts are well known to those of ordinary skill in the art, and typically include, but are not limited to, either the transformation of spheroplasts or of intact yeast host cells treated with alkali cations. For example, transformation of yeast can be carried out according to the method described in Hsiao et al., PROC. NATL. ACAD. SCI. USA (1979) 76:3829 and Van Solingen et al., J. BACT. (1977) 130:946. However, other methods for introducing DNA into cells such as by nuclear injection, electroporation, or protoplast fusion may also be used as described generally in SAMBROOK ET AL., MOLECULAR CLONING: A LAB. MANUAL (2001). Yeast host cells may then be cultured using standard techniques known to those of ordinary skill in the art.

Other methods for expressing heterologous proteins in yeast host cells are well known to those of ordinary skill in the art. See generally U.S. Patent Application No. 20020055169, U.S. Pat. Nos. 6,361,969; 6,312,923; 6,183,985; 6,083,723; 6,017,731; 5,674,706; 5,629,203; 5,602,034; and 5,089,398; U.S. Reexamined Pat. Nos. RE37,343 and RE35,749; PCT Published Patent Applications WO 99/078621; WO 98/37208; and WO 98/26080; European Patent Applications EP 0 946 736; EP 0 732 403; EP 0 480 480; EP 0 460 071; EP 0 340 986; EP 0 329 203; EP 0 324 274; and EP 0 164 556. See also Gellissen et al., ANTONIE VAN LEEUWENHOEK (1992) 62(1-2):79-93; Romanos et al., YEAST (1992) 8(6):423-488; Goeddel, METHODS IN ENZYMOLOGY (1990) 185:3-7.

The yeast host strains may be grown in fermentors during the amplification stage using standard feed batch fermentation methods well known to those of ordinary skill in the art. The fermentation methods may be adapted to account for differences in a particular yeast host's carbon utilization pathway or mode of expression control. For example, fermentation of a *Saccharomyces* yeast host may require a single glucose feed, complex nitrogen source (e.g., casein hydrolysates), and multiple vitamin supplementation. In contrast, the methylotrophic yeast *P. pastoris* may require glycerol, methanol, and trace mineral feeds, but only simple ammonium (nitrogen) salts for optimal growth and expression. See, e.g., U.S. Pat. No. 5,324,639; Elliott et al., J. PROTEIN CHEM. (1990) 9:95; and Fieschko et al., BIOTECH. BIOENG. (1987) 29:1113.

Such fermentation methods, however, may have certain common features independent of the yeast host strain employed. For example, a growth limiting nutrient, typically carbon, may be added to the fermentor during the amplification phase to allow maximal growth. In addition, fermentation methods generally employ a fermentation medium designed to contain adequate amounts of carbon, nitrogen, basal salts, phosphorus, and other minor nutrients (vitamins, trace minerals and salts, etc.). Examples of fermentation media suitable for use with *Pichia* are described in U.S. Pat. Nos. 5,324,639 and 5,231,178.

Baculovirus-Infected Insect Cells The term "insect host" or "insect host cell" refers to a insect that can be, or has been, used as a recipient for recombinant vectors or other transfer DNA. The term includes the progeny of the original insect host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a fEPO polypeptide, are included in the progeny intended by this definition.

The selection of suitable insect cells for expression of fEPO is well known to those of ordinary skill in the art. Several insect species are well described in the art and are commercially available including *Aedes aegypti, Bombyx mori, Drosophila melanogaster, Spodoptera frugiperda*, and *Trichoplusia ni*. In selecting insect hosts for expression, suitable hosts may include those shown to have, inter alia, good secretion capacity, low proteolytic activity, and overall robustness. Insect are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.).

Generally, the components of a baculovirus-infected insect expression system include a transfer vector, usually a bacterial plasmid, which contains both a fragment of the baculovirus genome, and a convenient restriction site for insertion of the heterologous gene to be expressed; a wild type baculovirus with a sequences homologous to the baculovirus-specific fragment in the transfer vector (this allows for the homologous recombination of the heterologous gene in to the baculovirus genome); and appropriate insect host cells and growth media. The materials, methods and techniques used in constructing vectors, transfecting cells, picking plaques, growing cells in culture, and the like are known in the art and manuals are available describing these techniques.

After inserting the heterologous gene into the transfer vector, the vector and the wild type viral genome are transfected into an insect host cell where the vector and viral genome recombine. The packaged recombinant virus is expressed and recombinant plaques are identified and purified. Materials and methods for baculovirus/insect cell expression systems are commercially available in kit form from, for example, Invitrogen Corp. (Carlsbad, Calif.). These techniques are generally known to those skilled in the art and fully described in SUMMERS AND SMITH, TEXAS AGRICULTURAL EXPERIMENT STATION BULLETIN NO. 1555 (1987), herein incorporated by reference. See also, RICHARDSON, 39 METHODS IN MOLECULAR BIOLOGY: BACULOVIRUS EXPRESSION PROTOCOLS (1995); AUSUBEL ET AL., CURRENT PROTOCOLS IN MOLECULAR BIOLOGY 16.9-16.11 (1994); KING AND POSSEE, THE BACULOVIRUS SYSTEM: A LABORATORY GUIDE (1992); and O'REILLY ET AL., BACULOVIRUS EXPRESSION VECTORS: A LABORATORY MANUAL (1992).

Indeed, the production of various heterologous proteins using baculovirus/insect cell expression systems is well known in the art. See, e.g., U.S. Pat. Nos. 6,368,825; 6,342,216; 6,338,846; 6,261,805; 6,245,528, 6,225,060; 6,183,987; 6,168,932; 6,126,944; 6,096,304; 6,013,433; 5,965,393; 5,939,285; 5,891,676; 5,871,986; 5,861,279; 5,858,368; 5,843,733; 5,762,939; 5,753,220; 5,605,827; 5,583,023; 5,571,709; 5,516,657; 5,290,686; WO 02/06305; WO 01/90390; WO 01/27301; WO 01/05956; WO 00/55345; WO 00/20032 WO 99/51721; WO 99/45130; WO 99/31257; WO 99/10515; WO 99/09193; WO 97/26332; WO 96/29400; WO 96/25496; WO 96/06161; WO 95/20672; WO 93/03173; WO 92/16619; WO 92/03628; WO 92/01801; WO 90/14428; WO 90/10078; WO 90/02566; WO 90/02186; WO 90/01556; WO 89/01038; WO 89/01037; WO 88/07082.

Vectors that are useful in baculovirus/insect cell expression systems are known in the art and include, for example, insect expression and transfer vectors derived from the baculovirus Autographacalifornica nuclear polyhedrosis virus (AcNPV), which is a helper-independent, viral expression vector. Viral expression vectors derived from this system usually use the strong viral polyhedrin gene promoter to drive expression of heterologous genes. See generally, Reilly ET AL., BACULOVIRUS EXPRESSION VECTORS: A LABORATORY MANUAL (1992).

Prior to inserting the foreign gene into the baculovirus genome, the above-described components, comprising a promoter, leader (if desired), coding sequence of interest, and transcription termination sequence, are typically assembled into an intermediate transplacement construct (transfer vector). Intermediate transplacement constructs are often maintained in a replicon, such as an extra chromosomal element (e.g., plasmids) capable of stable maintenance in a host, such as bacteria. The replicon will have a replication system, thus allowing it to be maintained in a suitable host for cloning and amplification. More specifically, the plasmid may contain the polyhedrin polyadenylation signal (Miller et al., ANN. REV. MICROBIOL. (1988) 42:177) and a prokaryotic ampicillin-resistance (amp) gene and origin of replication for selection and propagation in *E. coli*.

One commonly used transfer vector for introducing foreign genes into AcNPV is pAc373. Many other vectors, known to those of skill in the art, have also been designed including, for example, pVL985, which alters the polyhedrin start codon from ATG to ATT, and which introduces a BamHI cloning site 32 base pairs downstream from the ATT. See Luckow and Summers, 17 VIROLOGY 31 (1989). Other commercially available vectors include, for example, PBlue-Bac4.5/V5-His; pBlueBacHis2; pMelBac; pBlueBac4.5 (Invitrogen Corp., Carlsbad, Calif.).

After insertion of the heterologous gene, the transfer vector and wild type baculoviral genome are co-transfected into an insect cell host. Methods for introducing heterologous DNA into the desired site in the baculovirus virus are known in the art. See SUMMERS AND SMITH, TEXAS AGRICULTURAL EXPERIMENT STATION BULLETIN NO. 1555 (1987); Smith et al., MOL. CELL. BIOL. (1983) 3:2156; Luckow and Summers, VIROLOGY (1989) 17:31. For example, the insertion can be into a gene such as the polyhedrin gene, by homologous double crossover recombination; insertion can also be into a restriction enzyme site engineered into the desired baculovirus gene. See Miller et al., BIOESSAYS (1989) 4:91.

Transfection may be accomplished by electroporation. See TROTTER AND WOOD, 39 METHODS IN MOLECULAR BIOLOGY (1995); Mann and King, J. GEN. VIROL. (1989) 70:3501. Alternatively, liposomes may be used to transfect the insect cells with the recombinant expression vector and the baculovirus. See, e.g., Liebman et al., BIOTECHNIQUES (1999) 26(1):36; Graves et al., BIOCHEMISTRY (1998) 37:6050; Nomura et al., J. BIOL. CHEM. (1998) 273(22):13570; Schmidt et al., PROTEIN EXPRESSION AND PURIFICATION (1998) 12:323; Siffert et al., NATURE GENETICS (1998) 18:45; TILKINS ET AL., CELL BIOLOGY: A LABORATORY HANDBOOK 145-154 (1998); Cai et al., PROTEIN EXPRESSION AND PURIFICATION (1997) 10:263; Dolphin et al., NATURE GENETICS (1997) 17:491; Kost et al., GENE (1997) 190:139; Jakobsson et al., J. BIOL. CHEM. (1996) 271:22203; Rowles et al., J. BIOL. CHEM. (1996) 271(37):22376; Reversey et al., J. BIOL. CHEM. (1996) 271(39):23607-10; Stanley et al., J. BIOL. CHEM. (1995) 270: 4121; Sisk et al., J. VIROL. (1994) 68(2):766; and Peng et al., BIOTECHNIQUES (1993) 14.2:274. Commercially available liposomes include, for example, Cellfectin® and Lipofectin® (Invitrogen, Corp., Carlsbad, Calif.). In addition, calcium phosphate transfection may be used. See TROTTER AND WOOD, 39 METHODS IN MOLECULAR BIOLOGY (1995); Kitts, NAR (1990) 18(19):5667; and Mann and King, J. GEN. VIROL. (1989) 70:3501.

Baculovirus expression vectors usually contain a baculovirus promoter. A baculovirus promoter is any DNA sequence capable of binding a baculovirus RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Moreover, expression may be either regulated or constitutive.

Structural genes, abundantly transcribed at late times in the infection cycle, provide particularly useful promoter sequences. Examples include sequences derived from the gene encoding the viral polyhedron protein (FRIESEN ET AL., *The Regulation of Baculovirus Gene Expression* in THE MOLECULAR BIOLOGY OF BACULOVIRUSES (1986); EP 0 127 839 and 0 155 476) and the gene encoding the p10 protein (Vlak et al., J. GEN. VIROL. (1988) 69:765.

The newly formed baculovirus expression vector is packaged into an infectious recombinant baculovirus and subsequently grown plaques may be purified by techniques known to those skilled in the art. See Miller et al., BIOESSAYS (1989) 4:91; SUMMERS AND SMITH, TEXAS AGRICULTURAL EXPERIMENT STATION BULLETIN NO. 1555 (1987).

Recombinant baculovirus expression vectors have been developed for infection into several insect cells. For example, recombinant baculoviruses have been developed for, inter alia, *Aedes aegypti* (ATCC No. CCL-125), *Bombyx mori* (ATCC No. CRL-8910), *Drosophila melanogaster* (ATCC No. 1963), *Spodoptera frugiperda*, and *Trichoplusia ni*. See WO 89/046,699; Wright, NATURE (1986) 321:718; Carbonell et al., J. VIROL. (1985) 56:153; Smith et al., MOL. CELL. BIOL. (1983) 3:2156. See generally, Fraser et al., IN VITRO CELL. DEV. BIOL. (1989) 25:225. More specifically, the cell lines used for baculovirus expression vector systems commonly include, but are not limited to, Sf9 (*Spodoptera frugiperda*) (ATCC No. CRL-1711), Sf21 (*Spodoptera frugiperda*) (Invitrogen Corp., Cat. No. 11497-013 (Carlsbad, Calif.)), Tri-368 (*Trichopulsia ni*), and High-Five™ BTI-TN-5B1-4 (*Trichopulsia ni*).

Cells and culture media are commercially available for both direct and fusion expression of heterologous polypeptides in a baculovirus/expression, and cell culture technology is generally known to those skilled in the art.

*E. Coli* Bacterial expression techniques are well known in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers are present, which provide for different characteristics.

A bacterial promoter is any DNA sequence capable of binding bacterial RNA polymerase and initiating the downstream (3") transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in Escherichia coli (E. coli) [Raibaud et al., ANNU. REV. GENET. (1984) 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., NATURE (1977) 198:1056], and maltose. Additional examples include promoter sequences derived from biosynthetic enzymes such as tryptophan (trp) [Goeddel et al., NUC. ACIDS RES. (1980) 8:4057; Yelverton et al., NUCL. ACIDS RES. (1981) 9:731; U.S. Pat. No. 4,738,921; EPO Pub. Nos. 036 776 and 121 775]. The β-galactosidase (bla) promoter system [Weissmann (1981) "The cloning of interferon and other mistakes." In Interferon 3 (Ed. I. Gresser)], bacteriophage lambda PL [Shimatake et al., NATURE (1981) 292:128] and T5 [U.S. Pat. No. 4,689,406] promoter systems also provide useful promoter sequences. Preferred methods of the present invention utilize strong promoters, such as the T7 promoter to induce fEPO at high levels. Examples of such vectors are well known in the art and include the pET29 series from Novagen, and the pPOP vectors described in WO99/05297. Such expression systems produce high levels of fEPO in the host without compromising host cell viability or growth parameters.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al., GENE (1983) 25:167; de Boer et al., PROC. NATL. ACAD. SCI. (1983) 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophase T7 RNA polymerase/promoter system is an example of a coupled promoter system [Studier et al., J. MOL. BIOL. (1986) 189:113; Tabor et al., Proc Natl. Acad. Sci. (1985) 82:1074]. In addition, a hybrid promoter can also be comprised of a bacteriophage promoter and an E. coli operator region (EPO Pub. No. 267 851).

In addition to a functioning promoter sequence, an efficient ribosome binding site is also useful for the expression of foreign genes in prokaryotes. In E. coli, the ribosome binding site is called the Shine-Dalgarno (SD) sequence and includes an initiation codon (ATG) and a sequence 3-9 nucleotides in length located 3-11 nucleotides upstream of the initiation codon [Shine et al., NATURE (1975) 254:34]. The SD sequence is thought to promote binding of mRNA to the ribosome by the pairing of bases between the SD sequence and the 3' and of E. coli 16S rRNA [Steitz et al. "Genetic signals and nucleotide sequences in messenger RNA", In Biological Regulation and Development: Gene Expression (Ed. R. F. Goldberger, 1979)]. To express eukaryotic genes and prokaryotic genes with weak ribosome-binding site [Sambrook et al. "Expression of cloned genes in Escherichia coli", Molecular Cloning: A Laboratory Manual, 1989].

The term "bacterial host" or "bacterial host cell" refers to a bacterial that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a fEPO, are included in the progeny intended by this definition.

The selection of suitable host bacteria for expression of fEPO is well known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. In one embodiment of the methods of the present invention, the E. coli host is a strain of BL21. In another embodiment of the methods of the present invention, the E. coli host is a protease minus strain including, but not limited to, OMP- and LON-.

Once a recombinant host cell strain has been established (i.e., the expression construct has been introduced into the host cell and host cells with the proper expression construct are isolated), the recombinant host cell strain is cultured under conditions appropriate for production of fEPO. As will be apparent to one of skill in the art, the method of culture of the recombinant host cell strain will be dependent on the nature of the expression construct utilized and the identity of the host cell. Recombinant host strains are normally cultured using methods that are well known to the art. Recombinant host cells are typically cultured in liquid medium containing assimilatable sources of carbon, nitrogen, and inorganic salts and, optionally, containing vitamins, amino acids, growth factors, and other proteinaceous culture supplements well known to the art. Liquid media for culture of host cells may optionally contain antibiotics or antifungals to prevent the growth of undesirable microorganisms and/or compounds including, but not limited to, antibiotics to select for host cells containing the expression vector.

Recombinant host cells may be cultured in batch or continuous formats, with either cell harvesting (in the case where fEPO accumulates intracellularly) or harvesting of culture supernatant in either batch or continuous formats. For production in prokaryotic host cells, batch culture and cell harvest are preferred.

The fEPO of the invention are normally purified after expression in recombinant systems. fEPO may be purified from host cells by a variety of methods known to the art. Normally, fEPO produced in bacterial host cells is poorly soluble or insoluble (in the form of inclusion bodies). In one embodiment of the present invention, amino acid substitutions may readily be made in the fEPO polypeptide that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods well known to those of ordinary skill in the art. Host cell disruption or homogenization may be performed using well known techniques including, but not limited to, enzymatic cell disruption, sonication, dounce homogenization, or high pressure release disruption. In one embodiment of the method of the present invention, the high pressure release technique is used to disrupt the *E. coli* host cells to release the inclusion bodies of fEPO. It has been found that yields of insoluble fEPO in the form of inclusion bodies may be increased by utilizing only one passage of the *E. coli* host cells through the homogenizer. When handling inclusion bodies of fEPO, it is advantageous to minimize the homogenization time on repetitions in order to maximize the yield of inclusion bodies without loss due to factors such as solubilization, mechanical shearing or proteolysis.

Insoluble or precipitated fEPO may then be solubilized using any of a number of suitable solubilization agents known to the art. Preferably, fEPO is solubilized with urea or guanidine hydrochloride. The volume of the solubilized fEPO-BP should be minimized so that large batches may be produced using conveniently manageable batch sizes. This factor may be significant in a large-scale commercial setting where the recombinant host may be grown in batches that are thousands of liters in volume. In addition, when manufacturing fEPO in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the fEPO inclusion bodies in place of the harsher denaturing agent guanidine hydrochloride. The use of urea significantly reduces the risk of damage to stainless steel equipment utilized in the manufacturing and purification process of fEPO while efficiently solubilizing the fEPO inclusion bodies.

When fEPO is produced as a fusion protein, the fusion sequence is preferably removed. Removal of a fusion sequence may be accomplished by enzymatic or chemical cleavage, preferably by enzymatic cleavage. Enzymatic removal of fusion sequences may be accomplished using methods well known to those in the art. The choice of enzyme for removal of the fusion sequence will be determined by the identity of the fusion, and the reaction conditions will be specified by the choice of enzyme as will be apparent to one skilled in the art. The cleaved fEPO is preferably purified from the cleaved fusion sequence by well known methods. Such methods will be determined by the identity and properties of the fusion sequence and the fEPO, as will be apparent to one skilled in the art. Methods for purification may include, but are not limited to, size-exclusion chromatography, hydrophobic interaction chromatography, ion-exchange chromatography or dialysis or any combination thereof.

fEPO is also preferably purified to remove DNA from the protein solution. DNA may be removed by any suitable method known to the art, such as precipitation or ion exchange chromatography, but is preferably removed by precipitation with a nucleic acid precipitating agent, such as, but not limited to, protamine sulfate. fEPO may be separated from the precipitated DNA using standard well known methods including, but not limited to, centrifugation or filtration. Removal of host nucleic acid molecules is an important factor in a setting where the fEPO is to be used to treat humans and the methods of the present invention reduce host cell DNA to pharmaceutically acceptable levels.

Methods for small-scale or large-scale fermentation can also be used in protein expression, including but not limited to, fermentors, shake flasks, fluidized bed bioreactors, hollow fiber bioreactors, roller bottle culture systems, and stirred tank bioreactor systems. Each of these methods can be performed in a batch, fed-batch, or continuous mode process.

Feline EPO polypeptides of the invention can generally be recovered using methods standard in the art. For example, culture medium or cell lysate can be centrifuged or filtered to remove cellular debris. The supernatant may be concentrated or diluted to a desired volume or diafiltered into a suitable buffer to condition the preparation for further purification. Further purification of the fEPO of the present invention include separating deamidated and clipped forms of the fEPO variant from the intact form.

Any of the following exemplary procedures can be employed for purification of a fEPO polypeptides of the invention: affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), SDS-PAGE, or extraction.

Proteins of the present invention, including but not limited to, proteins comprising unnatural amino acids, antibodies to proteins comprising unnatural amino acids, binding partners for proteins comprising unnatural amino acids, etc., can be purified, either partially or substantially to homogeneity, according to standard procedures known to and used by those of skill in the art. Accordingly, polypeptides of the invention can be recovered and purified by any of a number of methods well known in the art, including but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins comprising unnatural amino acids) are used as purification reagents, including but not limited to, for affinity-based purification of proteins comprising one or more unnatural amino acid(s). Once purified, partially or to homogeneity, as desired, the polypeptides are optionally used for a wide variety of utilities, including but not limited to, as assay components, therapeutics, prophylaxis, diagnostics, research reagents, and/or as immunogens for antibody production.

In addition to other references noted herein, a variety of purification/protein folding methods are well known in the art, including, but not limited to, those set forth in R. Scopes, *Protein Purification*, Springer-Verlag, N.Y. (1982); Deutscher, *Methods in Enzymology* Vol. 182: *Guide to Protein Purification*, Academic Press, Inc. N.Y. (1990); Sandana (1997) *Bioseparation of Proteins*, Academic Press, Inc.; Bollag et al. (1996) *Protein Methods*, 2nd Edition Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3rd Edition Springer Verlag, NY; Janson and Ryden (1998) *Protein Purification: Principles, High Resolution Methods and Applications*, Second Edition Wiley-VCH, NY; and Walker (1998) *Protein Protocols on CD-ROM* Humana Press, NJ; and the references cited therein.

One advantage of producing a protein or polypeptide of interest with an unnatural amino acid in a eukaryotic host cell or non-eukaryotic host cell is that typically the proteins or polypeptides will be folded in their native conformations. However, in certain embodiments of the invention, those of skill in the art will recognize that, after synthesis, expression and/or purification, proteins can possess a conformation different from the desired conformations of the relevant polypeptides. In one aspect of the invention, the expressed protein is optionally denatured and then renatured. This is accomplished utilizing methods known in the art, including but not limited to, by adding a chaperonin to the protein or polypeptide of interest, by solubilizing the proteins in a chaotropic agent such as guanidine HCl, utilizing protein disulfide isomerase, etc.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art (see, the references above, and Debinski, et al. (1993) *J. Biol. Chem.*, 268: 14065-14070; Kreitman and Pastan (1993) *Bioconjug. Chem.*, 4: 581-585; and Buchner, et al., (1992) *Anal. Biochem.*, 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of fEPO, the fEPO thus produced may be misfolded and thus lacks or has reduced biological activity. The bioactivity of the protein may be restored by "refolding". In general, misfolded fEPO is refolded by solubilizing (where the fEPO is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. fEPO may be refolded using standard methods known in the art, such as those described in U.S. Pat. Nos. 4,511,502, 4,511,503, and 4,512,922. The fEPO may also be cofolded with other proteins to form heterodimers or heteromultimers. After refolding or cofolding, the fEPO is preferably further purified.

General Purification Methods Any one of a variety of isolation steps may be performed on the cell lysate comprising fEPO or on any fEPO mixtures resulting from any isolation steps including, but not limited to, affinity chromatography, ion exchange chromatography, hydrophobic interaction chromatography, gel filtration chromatography, high performance liquid chromatography ("HPLC"), reversed phase-HPLC ("RP-HPLC"), expanded bed adsorption, or any combination and/or repetition thereof and in any appropriate order.

Equipment and other necessary materials used in performing the techniques described herein are commercially available. Pumps, fraction collectors, monitors, recorders, and entire systems are available from, for example, Applied Biosystems (Foster City, Calif.), Bio-Rad Laboratories, Inc. (Hercules, Calif.), and Amersham Biosciences, Inc. (Piscataway, N.J.). Chromatographic materials including, but not limited to, exchange matrix materials, media, and buffers are also available from such companies.

Equilibration, and other steps in the column chromatography processes described herein such as washing and elution, may be more rapidly accomplished using specialized equipment such as a pump. Commercially available pumps include, but are not limited to, HILOAD® Pump P-50, Peristaltic Pump P-1, Pump P-901, and Pump P-903 (Amersham Biosciences, Piscataway, N.J.).

Examples of fraction collectors include RediFrac Fraction Collector, FRAC-100 and FRAC-200 Fraction Collectors, and SUPERFRAC® Fraction Collector (Amersham Biosciences, Piscataway, N.J.). Mixers are also available to form pH and linear concentration gradients. Commercially available mixers include Gradient Mixer GM-1 and In-Line Mixers (Amersham Biosciences, Piscataway, N.J.).

The chromatographic process may be monitored using any commercially available monitor. Such monitors may be used to gather information like UV, pH, and conductivity. Examples of detectors include Monitor UV-1, UVICORD® S II, Monitor UV-M II, Monitor UV-900, Monitor UPC-900, Monitor pH/C-900, and Conductivity Monitor (Amersham Biosciences, Piscataway, N.J.). Indeed, entire systems are commercially available including the various AKTA® systems from Amersham Biosciences (Piscataway, N.J.).

In one embodiment of the present invention, for example, the fEPO may be reduced and denatured by first denaturing the resultant purified fEPO in urea, followed by dilution into TRIS buffer containing a reducing agent (such as DTT) at a suitable pH. In another embodiment, the fEPO is denatured in urea in a concentration range of between about 2 M to about 9 M, followed by dilution in TRIS buffer at a pH in the range of about 5.0 to about 8.0. The refolding mixture of this embodiment may then be incubated. In one embodiment, the refolding mixture is incubated at room temperature for four to twenty-four hours. The reduced and denatured fEPO mixture may then be further isolated or purified. As stated herein, the pH of the first fEPO mixture may be adjusted prior to performing any subsequent isolation steps. In addition, the first fEPO mixture or any subsequent mixture thereof may be concentrated using techniques known in the art. Moreover, the elution buffer comprising the first fEPO mixture or any subsequent mixture thereof may be exchanged for a buffer suitable for the next isolation step using techniques well known to those of ordinary skill in the art.

Ion Exchange Chromatography In one embodiment, and as an optional, additional step, ion exchange chromatography may be performed on the first fEPO mixture. See generally ION EXCHANGE CHROMATOGRAPHY: PRINCIPLES AND METHODS (Cat. No. 18-1114-21, Amersham Biosciences (Piscataway, N.J.)). Commercially available ion exchange columns include HITRAP®, HIPREP®, and HILOAD® Columns (Amersham Biosciences, Piscataway, N.J.). Such columns utilize strong anion exchangers such as Q SEPHAROSE® Fast Flow, Q SEPHAROSE® High Performance, and Q SEPHAROSE® XL; strong cation exchangers such as SP SEPHAROSE® High Performance, SP SEPHAROSE® Fast Flow, and SP SEPHAROSE® XL; weak anion exchangers such as DEAE SEPHAROSE® Fast Flow; and weak cation exchangers such as CM SEPHAROSE® Fast Flow (Amersham Biosciences, Piscataway, N.J.). Cation exchange column chromatography may be performed on the fEPO at any stage of the purification process to isolate substantially purified fEPO. The cation exchange chromatography step may be performed using any suitable cation exchange matrix. Useful cation exchange matrices include, but are not limited to, fibrous, porous, non-porous, microgranular, beaded, or cross-linked cation exchange matrix materials. Such cation exchange matrix materials include, but are not limited to, cellulose, agarose, dextran, polyacrylate, polyvinyl, polystyrene, silica, polyether, or composites of any of the foregoing. Following adsorption of the fEPO to the cation exchanger matrix, substantially purified fEPO may be eluted by contacting the matrix with a buffer having a sufficiently high pH or ionic strength to displace the fEPO from the matrix. Suitable buffers for use in high pH elution of substantially purified fEPO include, but are not limited to, citrate, phosphate, formate, acetate, HEPES, and MES buffers ranging in concentration from at least about 5 mM to at least about 100 mM.

Reverse-Phase Chromatography RP-HPLC may be performed to purify proteins following suitable protocols that are known to those of ordinary skill in the art. See, e.g., Pearson et al., ANAL BIOCHEM. (1982) 124:217-230 (1982); Rivier et al., J. CHROM. (1983) 268:112-119; Kunitani et al., J. CHROM. (1986) 359:391-402. RP-HPLC may be performed on the fEPO to isolate substantially purified fEPO. In this regard, silica derivatized resins with alkyl functionalities with a wide variety of lengths, including, but not limited to, at least about $C_3$ to at least about $C_{30}$, at least about $C_3$ to at least about $C_{20}$, or at least about $C_3$ to at least about $C_{18}$, resins may be used. Alternatively, a polymeric resin may be used. For example, TosoHaas Amberchrome CG1000sd resin may be used, which is a styrene polymer resin. Cyano or polymeric resins with a wide variety of alkyl chain lengths may also be used. Furthermore, the RP-HPLC column may be washed with a solvent such as ethanol. A suitable elution buffer containing an ion pairing agent and an organic modifier such as methanol, isopropanol, tetrahydrofuran, acetonitrile or ethanol, may be used to elute the fEPO from the RP-HPLC column. The most commonly used ion pairing agents include, but are not limited to, acetic acid, formic acid, perchloric acid, phosphoric acid, trifluoroacetic acid, heptafluorobutyric acid, triethylamine, tetramethylammonium, tetrabutylammonium, triethylammonium acetate. Elution may be performed using one or more gradients or isocratic conditions, with gradient conditions preferred to reduce the separation time and to decrease peak width. Another method involves the use of two gradients with different solvent concentration ranges. Examples of suitable elution buffers for use herein may include, but are not limited to, ammonium acetate and acetonitrile solutions.

Hydrophobic Interaction Chromatography Purification Techniques Hydrophobic interaction chromatography (HIC) may be performed on the fEPO. See generally HYDROPHOBIC INTERACTION CHROMATOGRAPHY HANDBOOK: PRINCIPLES AND METHODS (Cat. No. 18-1020-90, Amersham Biosciences (Piscataway, N.J.) which is incorporated by reference herein. Suitable HIC matrices may include, but are not limited to, alkyl- or aryl-substituted matrices, such as butyl-, hexyl-, octyl- or phenyl-substituted matrices including agarose, cross-linked agarose, sepharose, cellulose, silica, dextran, polystyrene, poly(methacrylate) matrices, and mixed mode resins, including but not limited to, a polyethyleneamine resin or a butyl- or phenyl-substituted poly(methacrylate) matrix. Commercially available sources for hydrophobic interaction column chromatography include, but are not limited to, HITRAP®, HIPREP®, and HILOAD® columns (Amersham Biosciences, Piscataway, N.J.). Briefly, prior to loading, the HIC column may be equilibrated using standard buffers known to those of ordinary skill in the art, such as an acetic acid/sodium chloride solution or HEPES containing ammonium sulfate. After loading the fEPO, the column may then washed using standard buffers and conditions to remove unwanted materials but retaining the fEPO on the HIC column. fEPO may be eluted with about 3 to about 10 column volumes of a standard buffer, such as a HEPES buffer containing EDTA and lower ammonium sulfate concentration than the equilibrating buffer, or an acetic acid/sodium chloride buffer, among others. A decreasing linear salt gradient using, for example, a gradient of potassium phosphate, may also be used to elute the fEPO molecules. The eluant may then be concentrated, for example, by filtration such as diafiltration or ultrafiltration. Diafiltration may be utilized to remove the salt used to elute fEPO.

Other Purification Techniques Yet another isolation step using, for example, gel filtration (GEL FILTRATION: PRINCIPLES AND METHODS (Cat. No. 18-1022-18, Amersham Biosciences, Piscataway, N.J.) which is incorporated by reference herein, HPLC, expanded bed adsorption, ultrafiltration, diafiltration, lyophilization, and the like, may be performed on the first fEPO mixture or any subsequent mixture thereof, to remove any excess salts and to replace the buffer with a suitable buffer for the next isolation step or even formulation of the final drug product. The yield of fEPO, including substantially purified fEPO, may be monitored at each step described herein using techniques known to those of ordinary skill in the art. Such techniques may also used to assess the yield of substantially purified fEPO following the last isolation step. For example, the yield of fEPO may be monitored using any of several reverse phase high pressure liquid chromatography columns, having a variety of alkyl chain lengths such as cyano RP-HPLC, $C_{18}$RP-HPLC; as well as cation exchange HPLC and gel filtration HPLC.

Purity may be determined using standard techniques, such as SDS-PAGE, or by measuring fEPO using Western blot and ELISA assays. For example, polyclonal antibodies may be generated against proteins isolated from a negative control yeast fermentation and the cation exchange recovery. The antibodies may also be used to probe for the presence of contaminating host cell proteins.

Additional purification procedures include those described in U.S. Pat. No. 4,612,367 and includes, but is not limited to, (1) applying a mixture comprising a fEPO polypeptide to a reverse phase macroporous acrylate ester copolymer resin support at a pH of from about 7 to about 9; and (2) eluting the fEPO polypeptide from said support with an aqueous eluant having a pH of from about 7 to about 9 and containing from about 20% to about 80% by volume of an organic diluent selected from the group consisting of acetone, acetonitrile, and a combination of acetone and acetonitrile.

A typical process for the purification of EPO protein is disclosed in WO 96/35718, to Burg published Nov. 14, 1996, and is described below. Blue Sepharose (Pharmacia) consists of Sepharose beads to the surface of which the Cibacron blue dye is covalently bound. Since EPO binds more strongly to Blue Sepharose than most non-proteinaceous contaminants, some proteinaceous impurities and PVA, EPO can be enriched in this step. The elution of the Blue Sepharose column is performed by increasing the salt concentration as well as the pH. The column is filled with 80-100 l of Blue Sepharose, regenerated with NaOH and equilibrated with equilibration buffer (sodium/calcium chloride and sodium acetate). The acidified and filtered fermenter supernatant is loaded. After completion of the loading, the column is washed first with a buffer similar to the equilibration buffer containing a higher sodium chloride concentration and consecutively with a TRIS-base buffer. The product is eluted with a TRIS-base buffer and collected in a single fraction in accordance with the master elution profile.

Butyl Toyopearl 650 C (Toso Haas) is a polystyrene based matrix to which aliphatic butyl-residues are covalently coupled. Since EPO binds more strongly to this gel than most of the impurities and PVA, it has to be eluted with a buffer containing isopropanol. The column is packed with 30-40 l of Butyl Toyopearl 650 C, regenerated with NaOH, washed with a TRIS-base buffer and equilibrated with a TRIS-base buffer containing isopropanol. The Blue Sepharose eluate is adjusted to the concentration of isopropanol in the column equilibration buffer and loaded onto the column. Then the column is washed with equilibration buffer with increased isopropanol concentration. The product is eluted with elution buffer (TRIS-base buffer with high isopropanol content) and collected in a single fraction in accordance with the master elution profile.

Hydroxyapatite Ultrogel (Biosepra) consists of hydroxyapatite which is incorporated in an agarose matrix to improve the mechanical properties. EPO has a low affinity to hydroxyapatite and can therefore be eluted at lower phosphate concentrations than protein impurities. The column is filled with 30-40 l of Hydroxyapatite Ultrogel and regenerated with a potassium phosphate/calcium chloride buffer and NaOH followed by a TRIS-base buffer. Then it is equilibrated with a TRIS-base buffer containing a low amount of isopropanol and sodium chloride. The EPO containing eluate of the Butyl Toyopearl chromatography is loaded onto the column. Subsequently the column is washed with equilibration buffer and a TRIS-base buffer without isopropanol and sodium chloride. The product is eluted with a TRIS-base buffer containing a low concentration of potassium phosphate and collected in a single fraction in accordance with the master elution profile.

RP-HPLC material Vydac C4 (Vydac) consists of silica gel particles, the surfaces of which carry C4-alkyl chains. The separation of EPO from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silicagel). The Hydroxyapatite Ultrogel eluate is acidified by adding trifluoro-acetic acid and loaded onto the Vydac C4 column. For washing and elution an acetonitrile gradient in diluted trifluoroacetic acid is used. Fractions are collected and immediately neutralized with phosphate buffer. The EPO fractions which are within the IPC limits are pooled.

DEAE Sepharose (Pharmacia) material consists of diethylaminoethyl (DEAE)-groups which are covalently bound to the surface of Sepharose beads. The binding of EPO to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and EPO is eluted with a buffer with increased ionic strength. The column is packed with DEAE Sepharose fast flow. The column volume is adjusted to assure an EPO load in the range of 3-10 mg EPO/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, EPO is eluted from the column with elution buffer (sodium chloride, sodium/potassium phosphate) and collected in a single fraction in accordance with the master elution profile. The eluate of the DEAE Sepharose column is adjusted to the specified conductivity. The resulting drug substance is sterile filtered into Teflon bottles and stored at −70° C.

A wide variety of methods and procedures can be used to assess the yield and purity of a fEPO protein one or more non-naturally encoded amino acids, including but not limited to, the Bradford assay, SDS-PAGE, silver stained SDS-PAGE, coomassie stained SDS-PAGE, mass spectrometry (including but not limited to, MALDI-TOF) and other methods for characterizing proteins known to one skilled in the art.

IX. Expression in Alternate Systems

Several strategies have been employed to introduce unnatural amino acids into proteins in non-recombinant host cells, mutagenized host cells, or in cell-free systems. These systems are also suitable for use in making the fEPO polypeptides of the present invention. Derivatization of amino acids with reactive side-chains such as Lys, Cys and Tyr resulted in the conversion of lysine to $N^2$-acetyl-lysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem.*, 69:923 (2000). A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl.*, 1995, 34:621 (1995); C. J. Noren, S. J. Anthony-Cahill, M. C. Griffith, P. G. Schultz, *A general method for site-specific incorporation of unnatural amino acids into proteins, Science* 244 182-188 (1989); and, J. D. Bain, C. G. Glabe, T. A. Dix, A. R. Chamberlin, E. S. Diala, *Biosynthetic* site-specific incorporation of a non-natural amino acid into a polypeptide, *J. Am. Chem. Soc.* 111 8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.,* 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.,* 284:29 (2000); trifluoromethionine has been used to replace methionine in bacteriophage T4 lysozyme to study its interaction with chitooligosaccharide ligands by $^{19}$F NMR, see, e.g., H. Duewel, E. Daub, V. Robinson and J. F. Honek, *Biochemistry,* 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.,* 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.,* 9:1665 (1990); J. O. Boles, K. Lewinski, M. Kunkle, J. D. Odom, B. Dunlap, L. Lebioda and M. Hatada, *Nat. Struct. Biol.,* 1:283 (1994); N. Budisa, B. Steipe, P. Demange, C. Eckerskorn, J. Kellermann and R. Huber, *Eur. J. Biochem.,* 230:788 (1995); and, N. Budisa, W. Karnbrock, S. Steinbacher, A. Humm, L. Prade, T. Neuefeind, L. Moroder and R. Huber, *J. Mol. Biol.,* 270:616 (1997). Methionine analogs with alkene or alkyne functionalities have also been incorporated efficiently, allowing for additional modification of proteins by chemical means. See, e.g., J. C. M. vanHest and D. A. Tirrell, *FEBS Lett.,* 428:68 (1998); J. C. M. van Hest, K. L. Kiick and D. A. Tirrell, *J. Am. Chem. Soc.,* 122:1282 (2000); and, K. L. Kiick and D. A. Tirrell, *Tetrahedron,* 56:9487 (2000); U.S. Pat. No. 6,586,207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of Ala$^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry,* 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.,* 364:272 (1995); and, N. Sharma, R. Furter, P. Kast and D. A. Tirrell, *FEBS Lett.,* 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S. Nishimura, *J. Biol. Chem.,* 275:40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science,* 292:501 (2001). ValRS can misaminoacylate tRNAVal with Cys, Thr, or aminobutyrate (Abu); these noncognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —CH3 in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. J. C., Barrett, L. Brenner, S. Watts-Tobin, R. *General nature of the genetic code for proteins. Nature,* 1227-1232 (1961); Hofmann, K., Bohn, H. *Studies on polypeptides. XXXVI. The effect of pyrazole-imidazole replacements on the S-protein activating potency of an S-peptide fragment, J. Am Chem,* 5914-5919 (1966); Kaiser, E. T. *Synthetic approaches to biologically active peptides and proteins including enyzmes, Acc Chem Res,* 47-54 (1989); Nakatsuka, T., Sasaki, T., Kaiser, E. T. *Peptide segment coupling catalyzed by the semisynthetic enzyme thiosubtilisin, J Am Chem Soc,* 3808-3810 (1987); Schnolzer, M., Kent, S B H. *Constructing proteins by dovetailing unprotected synthetic peptides: backbone-engineered HIV protease, Science,* 221-225 (1992); Chaiken, I. M. *Semisynthetic peptides and proteins, CRC Crit Rev Biochem,* 255-301 (1981); Offord, R. E. *Protein engineering by chemical means? Protein Eng.,* 151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science,* 243 (1994).

Chemical modification has been used to introduce a variety of unnatural side chains, including cofactors, spin labels and oligonucleotides into proteins in vitro. See, e.g., Corey, D. R., Schultz, P. G. *Generation of a hybrid sequence-specific single-stranded deoxyribonuclease, Science,* 1401-1403 (1987); Kaiser, E. T., Lawrence D. S., Rokita, S. E. *The chemical modification of enzymatic specificity, Rev Biochem,* 565-595 (1985); Kaiser, E. T., Lawrence, D. S. *Chemical mutation of enyzme active sites*, *Science*, 505-511 (1984); Neet, K. E., Nanci A, Koshland, D. E. *Properties of thiol-subtilisin*, *J Biol. Chem*, 6392-6401 (1968); Polgar, L. B., M. L. *A new enzyme containing a synthetically formed active site. Thiol-subtilisin*. *J. Am Chem Soc*, 3153-3154 (1966); and, Pollack, S. J., Nakayama, G. Schultz, P. G. *Introduction of nucleophiles and spectroscopic probes into antibody combining sites*, *Science*, 1038-1040 (1988).

Alternatively, biosynthetic methods that employ chemically modified aminoacyl-tRNAs have been used to incorporate several biophysical probes into proteins synthesized in vitro. See the following publications and references cited within: Brunner, *J. New Photolabeling and crosslinking methods, Annu. Rev Biochem*, 483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci*, 8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins, Science,* 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am Chem Soc,* 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz.,* 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. 5', 3' *Exonuclease in phosphorothioate-based olignoucleotide-directed mutagensis, Nucleic Acids Res*, 791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6): 425-432; and, Ellman, J. A., Mendel, D., Schultz, P. G. *Site-specific incorporation of novel backbone structures into proteins, Science,* 197-200 (1992).

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, *Science*, 268:439 (1995); and, D. A. Dougherty, *Curr. Opin. Chem. Biol.*, 4:645 (2000). A Xenopus oocyte was coinjected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, *J. Biol. Chem.,* 271: 19991 (1996); the incorporation of biotinylated amino acids to identify surface-exposed residues in ion channels, see, e.g., J. P. Gallivan, H. A. Lester and D. A. Dougherty, *Chem. Biol.,* 4:739 (1997); the use of caged tyrosine analogs to monitor conformational changes in an ion channel in real time, see, e.g., J. C. Miller, S. K. Silverman, P. M. England, D. A. Dougherty and H. A. Lester, *Neuron,* 20:619 (1998); and, the use of alpha hydroxy amino acids to change ion channel backbones for probing their gating mechanisms. See, e.g., P. M. England, Y. Zhang, D. A. Dougherty and H. A. Lester, *Cell,* 96:89 (1999); and, T. Lu, A. Y. Ting, J. Mainland, L. Y. Jan, P. G. Schultz and J. Yang, *Nat. Neurosci.,* 4:239 (2001).

The ability to incorporate unnatural amino acids directly into proteins in vivo offers the advantages of high yields of mutant proteins, technical ease, the potential to study the mutant proteins in cells or possibly in living organisms and the use of these mutant proteins in therapeutic treatments. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties. However, the process is difficult, because the complex nature of tRNA-synthetase interactions that are required to achieve a high degree of fidelity in protein translation.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.,* 7:419 (1998).

It may also be possible to obtain expression of a fEPO polynucleotide of the present invention using a cell-free (in-vitro) translational system. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D.-M. and J. R. Swartz, *Biotechnology and Bioengineering,* 74:309-316 (2001); Kim, D.-M. and J. R. Swartz, *Biotechnology Letters,* 22, 1537-1542, (2000); Kim, D.-M., and J. R. Swartz, *Biotechnology Progress,* 16, 385-390, (2000); Kim, D.-M., and J. R. Swartz, *Biotechnology and Bioengineering,* 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of fEPO polypeptides comprising a non-naturally encoded amino acid include the mRNA-peptide fusion technique. See, e.g., R. Roberts and J. Szostak, *Proc. Natl Acad. Sci.* (*USA*) 94 12297-12302 (1997); A. Frankel, et al., *Chemistry & Biology* 10, 1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of fEPO polypeptides comprising one or more non-naturally encoded amino acids to identify polypeptides having desired properties. More recently, in vitro ribosome translations with purified components have been reported that permit the synthesis of peptides substituted with non-naturally encoded amino acids. See, e.g., A. Forster et al., *Proc. Natl Acad. Sci.* (*USA*) 100 6353 (2003).

X. Macromolecular Polymers Coupled to fEPO

A wide variety of macromolecular polymers and other molecules can be linked to fEPO polypeptides of the present invention to modulate biological properties of fEPO, and/or provide new biological properties to the fEPO molecule. These macromolecular polymers can be linked to fEPO via a naturally encoded amino acid, via a non-naturally encoded amino acid, or any functional substituent of a natural or non-natural amino acid, or any substituent or functional group added to a natural or non-natural amino acid.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated fEPO preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tri-, tetra-, etc.) and combine said conjugates with the mono-polymer:protein conjugate prepared using the methods of the present invention, and have a mixture with a predetermined proportion of mono-polymer:protein conjugates.

The polymer selected may be water soluble so that the protein to which it is attached does not precipitate in an aqueous environment, such as a physiological environment. The polymer may be branched or unbranched. Preferably, for therapeutic use of the end-product preparation, the polymer will be pharmaceutically acceptable.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

As used herein, and when contemplating PEG:fEPO conjugates, the term "therapeutically effective amount" refers to an amount which gives an increase in hematocrit that provides benefit to a patient. The amount will vary from one individual to another and will depend upon a number of factors, including the overall physical condition of the patient and the underlying cause of anemia. For example, a therapeutically effective amount of fEPO for a patient suffering from chronic renal failure is 50 to 150 units/kg three times per week. The amount of fEPO used for therapy gives an acceptable rate of hematocrit increase and maintains the hematocrit at a beneficial level (usually at least about 30% and typically in a range of 30% to 36%). A therapeutically effective amount of the present compositions may be readily ascertained by one skilled in the art using publicly available materials and procedures.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to fEPO by the formula:

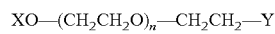

$$XO-(CH_2CH_2O)_n-CH_2CH_2-Y$$

where n is 2 to 10,000 and X is H or a terminal modification, including but not limited to, a $C_{1-4}$ alkyl.

In some cases, a PEG used in the invention terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a fEPO polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the fEPO polypeptide to form a Huisgen[3+2] cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the fEPO polypeptide via a non-naturally encoded amino acid and used to react preferentially with a ketone or aldehyde group present in the water soluble polymer.

Any molecular mass for a PEG can be used as practically desired, including but not limited to, from about 1,000 Daltons (Da) to 100,000 Da or more as desired (including but not limited to, sometimes 1-50 kDa or 10-40 kDa). Branched chain PEGs, including but not limited to, PEG's with each chain having a MW ranging from 10-40 kDa (including but not limited to, 5-20 kDa) can also be used. A wide range of PEG molecules are described in, including but not limited to, the Shearwater Polymers, Inc. catalog, Nektar Theraoeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydroxylamine or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the fEPO variant with a PEG derivative contains a chemical functionality that is reactive with the chemical functionality present on the side chain of the non-naturally encoded amino acid.

The invention provides in some embodiments azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly(ethylene)glycol and other related polymers, including poly(dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly (ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula — $CH_2CH_2O$—$(CH_2CH_2O)_n$—$CH_2CH_2$—, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(-PEG-OH)_m$ in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(—$YCHZ_2)_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

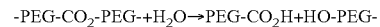

It is understood by those skilled in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol)

("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure:

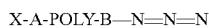
X-A-POLY-B—N=N=N wherein:
N=N=N is an azide moiety;
B is a linking moiety, which may be present or absent;
POLY is a water-soluble non-antigenic polymer;
A is a linking moiety, which may be present or absent and which may be the same as B or different; and
X is a second functional group.

Examples of a linking moiety for A and B include, but are not limited to, a multiply-functionalized alkyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen or sulfur atoms. Other examples of suitable linking groups include those linking groups described in U.S. Pat. Nos. 5,932,462 and 5,643,575; and U.S. Pat. Appl. Publication 2003/0143596, each of which is incorporated by reference herein in its entirety. Those of ordinary skill in the art will recognize that the foregoing list for linking moieties is by no means exhaustive and is merely illustrative, and that all linking moieties having the qualities described above are contemplated to be suitable for use in the present invention.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those skilled in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the present invention.

Specific examples of terminal functional groups in the literature include, but are not limited to, N-succinimidyl carbonate (see e.g., U.S. Pat. Nos. 5,281,698; 5,468,478), amine (see, e.g., Buckmann et al. Makromol. Chem. 182: 1379 (1981), Zaplipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zaplipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Macrolol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314(1993)), acrylol (see, e.g., Sawhney et al., Macromolecules, 26:581 (1993)), vinylsulfone (see, e.g., U.S. Pat. No. 5,900,461). All of the above references are incorporated herein by reference.

In certain embodiments of the present invention, the polymer derivatives of the invention comprise a polymer backbone having the structure:

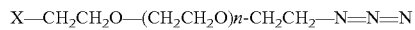
X—CH$_2$CH$_2$O—(CH$_2$CH$_2$O)n-CH$_2$CH$_2$—N=N=N wherein:
X is a functional group as described above; and
n is about 20 to about 4000.
In another embodiment, the polymer derivatives of the invention comprise a polymer backbone having the structure:

X—CH$_2$CH$_2$O—(CH$_2$CH$_2$O)n-CH$_2$CH$_2$—O
—(CH$_2$)$_m$—W—N=N=N wherein:

W is an aliphatic or aromatic linker moiety comprising between 1-10 carbon atoms;

n is about 20 to about 4000; and

X is a functional group as described above.

The azide-containing PEG derivatives of the invention can be prepared by a variety of methods known in the art and/or disclosed herein. In one method, shown below, a water soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing PEG polymer.

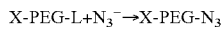

X-PEG-L+N$_3^-$→X-PEG-N$_3$

As shown, a suitable polymer backbone for use in the present invention has the formula X-PEG-L, wherein PEG is poly(ethylene glycol) and X is a functional group which does not react with azide groups and L is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone. Examples of suitable leaving groups include, but are not limited to, chloride, bromide, iodide, mesylate, tresylate, and tosylate.

In another method for preparation of the azide-containing polymer derivatives of the present invention, a linking agent bearing an azide functionality is contacted with a water soluble polymer backbone having an average molecular weight from about 800 Da to about 100,000 Da, wherein the linking agent bears a chemical functionality that will react selectively with a chemical functionality on the PEG polymer, to form an azide-containing polymer derivative product wherein the azide is separated from the polymer backbone by a linking group.

An exemplary reaction scheme is shown below:

X-PEG-M+N-linker-N=N=N→PG-X-PEG-linker-N=N=N wherein:

PEG is poly(ethylene glycol) and X is a capping group such as alkoxy or a functional group as described above; and M is a functional group that is not reactive with the azide functionality but that will react efficiently and selectively with the N functional group.

Examples of suitable functional groups include, but are not limited to, M being a carboxylic acid, carbonate or active ester if N is an amine; M being a ketone if N is a hydrazide or aminooxy moiety; M being a leaving group if N is a nucleophile.

Purification of the crude product may be accomplished by known methods including, but are not limited to, precipitation of the product followed by chromatography, if necessary.

A more specific example is shown below in the case of PEG diamine, in which one of the amines is protected by a protecting group moiety such as tert-butyl-Boc and the resulting mono-protected PEG diamine is reacted with a linking moiety that bears the azide functionality:

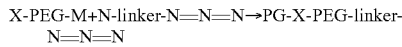

BocHN-PEG-NH$_2$+HO$_2$C—(CH$_2$)$_3$—N=N=N

In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-PEG-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido PEG would allow the attachment of a molecule having an activated electrophilic group, such as an aldehyde, ketone, activated ester, activated carbonate and so forth, to one terminus of the PEG and a molecule having an acetylene group to the other terminus of the PEG.

In another embodiment of the invention, the polymer derivative has the structure:

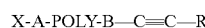

X-A-POLY-B—C≡C—R wherein:

R can be either H or an alkyl, alkene, alkyoxy, or aryl or substituted aryl group;

B is a linking moiety, which may be present or absent;

POLY is a water-soluble non-antigenic polymer;

A is a linking moiety, which may be present or absent and which may be the same as B or different; and X is a second functional group.

Examples of a linking moiety for A and B include, but are not limited to, a multiply-functionalized alkyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen or sulfur atoms. Other examples of suitable linking groups include those linking groups described in U.S. Pat. Nos. 5,932,462 and 5,643,575 and U.S. Pat. Appl. 2003/0143596, each of which is incorporated by reference herein in its entirety. Those of ordinary skill in the art will recognize that the foregoing list for linking moieties is by no means exhaustive and is intended to be merely illustrative, and that a wide variety of linking moieties having the qualities described above are contemplated to be useful in the present invention.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates,

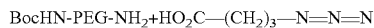

tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

In another embodiment of the present invention, the polymer derivatives comprise a polymer backbone having the structure:

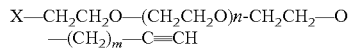

wherein:
X is a functional group as described above;
n is about 20 to about 4000; and
m is between 1 and 10.
Specific examples of each of the heterobifunctional PEG polymers are shown below.

The acetylene-containing PEG derivatives of the invention can be prepared using methods known to those skilled in the art and/or disclosed herein. In one method, a water soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired acetylene-containing polymer.

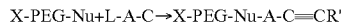

As shown, a preferred polymer backbone for use in the reaction has the formula X-PEG-Nu, wherein PEG is poly (ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment of the present invention, A is an aliphatic linker of between 1-10 carbon atoms or a substituted aryl ring of between 6-14 carbon atoms. X is a functional group which does not react with azide groups and L is a suitable leaving group In another method for preparation of the acetylene-containing polymer derivatives of the invention, a PEG polymer having an average molecular weight from about 800 Da to about 100,000 Da, bearing either a protected functional group or a capping agent at one terminus and a suitable leaving group at the other terminus is contacted by an acetylene anion.

An exemplary reaction scheme is shown below:

wherein:
PEG is poly(ethylene glycol) and X is a capping group such as alkoxy or a functional group as described above; and
R' is either H, an alkyl, alkoxy, aryl or aryloxy group or a substituted alkyl, alkoxyl, aryl or aryloxy group.

In the example above, the leaving group L should be sufficiently reactive to undergo SN2-type displacement when contacted with a sufficient concentration of the acetylene anion. The reaction conditions required to accomplish SN2 displacement of leaving groups by acetylene anions are well known in the art.

Purification of the crude product can usually be accomplished by methods known in the art including, but are not limited to, precipitation of the product followed by chromatography, if necessary.

Water soluble polymers can be linked to the fEPO polypeptides of the invention. The water soluble polymers may be linked via a non-naturally encoded amino acid incorporated in the fEPO polypeptide or any functional group or substituent of a non-naturally encoded or naturally encoded amino acid, or any functional group or substituent added to a non-naturally encoded or naturally encoded amino acid. Alternatively, the water soluble polymers are linked to a fEPO polypeptide incorporating a non-naturally encoded amino acid via a naturally-occurring amino acid (including but not limited to, cysteine, lysine or the amine group of the N-terminal residue). In some cases, the fEPO polypeptides of the invention comprise 1, 2, 3, 4, 5, 6, 7, 8, 9, 10, wherein one or more non-naturally-encoded amino acid(s) linked to water soluble polymer(s) (including but not limited to, PEG and/or oligosaccharides). In some cases, the fEPO polypeptides of the invention further comprise 1, 2, 3, 4, 5, 6, 7, 8, 9, 10, or more naturally-encoded amino acid(s) linked to water soluble polymers. In some cases, the fEPO polypeptides of the invention comprise one or more non-naturally encoded amino acid(s) linked to water soluble polymers and one or more naturally-occurring amino acids linked to water soluble polymers. In some embodiments, the water soluble polymers used in the present invention enhance the serum half-life of the fEPO polypeptide relative to the unconjugated form.

The number of water soluble polymers linked to a fEPO polypeptide (i.e., the extent of PEGylation or glycosylation) of the present invention can be adjusted to provide an altered (including but not limited to, increased or decreased) pharmacologic, pharmacokinetic or pharmacodynamic characteristic such as in vivo half-life. In some embodiments, the half-life of fEPO is increased at least about 10, 20, 30, 40, 50, 60, 70, 80, 90 percent, two fold, five-fold, 10-fold, 50-fold, or at least about 100-fold over an unmodified polypeptide.

PEG Derivatives Containing a Strong Nucleophilic Group (i.e., Hydrazide, Hydrazine, Hydroxylamine or Semicarbazide)

In one embodiment of the present invention, a fEPO polypeptide comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure:

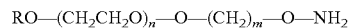

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivative will have the structure:

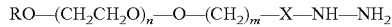

where R is a simple alkyl (methyl, ethyl, propyl, etc.), m is 2-10 and n is 100-1,000 and X is optionally a carbonyl group (C=O) that can be present or absent.

In some embodiments, the semicarbazide-containing PEG derivative will have the structure:

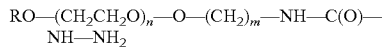

where R is a simple alkyl (methyl, ethyl, propyl, etc.), m is 2-10 and n is 100-1,000.

In another embodiment of the invention, a fEPO polypeptide comprising a carbonyl-containing amino acid is modified with a PEG derivative that contains a terminal hydroxylamine, hydrazide or semicarbazide moiety that is linked to the PEG backbone by means of an amide linkage.

In some embodiments, the hydroxylamine-terminal PEG derivatives have the structure:

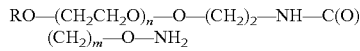

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure:

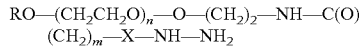

where R is a simple alkyl (methyl, ethyl, propyl, etc.), m is 2-10, n is 100-1,000 and X is optionally a carbonyl group (C=O) that can be present or absent.

In some embodiments, the semicarbazide-containing PEG derivatives have the structure:

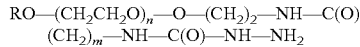

where R is a simple alkyl (methyl, ethyl, propyl, etc.), m is 2-10 and n is 100-1,000.

In another embodiment of the invention, a fEPO polypeptide comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa and, more preferably, from 5-20 kDa.

In another embodiment of the invention, a fEPO polypeptide comprising a non-naturally encoded amino acid is modified with a PEG derivatives having a branched structure. For instance, in some embodiments, the hydrazine- or hydrazide-terminal PEG derivative will have the following structure:

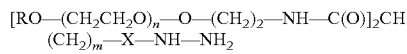

where R is a simple alkyl (methyl, ethyl, propyl, etc.), m is 2-10 and n is 100-1,000, and X is optionally a carbonyl group (C=O) that can be present or absent.

In some embodiments, the PEG derivatives containing a semicarbazide group will have the structure:

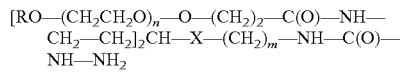

where R is a simple alkyl (methyl, ethyl, propyl, etc.), X is optionally NH, O, S, C(O) or not present, m is 2-10 and n is 100-1,000.

In some embodiments, the PEG derivatives containing a hydoxylamine group will have the structure:

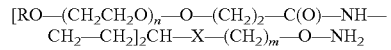

where R is a simple alkyl (methyl, ethyl, propyl, etc.), X is optionally NH, O, S, C(O) or not present, m is 2-10 and n is 100-1,000.

The degree and sites at which the water soluble polymer(s) are linked to fEPO can modulate the binding of fEPO to the fEPO receptor at Site 1. In some embodiments, the linkages are arranged such that the fEPO polypeptide binds the fEPO receptor at Site 1 with a $K_d$ of about 400 nM or lower, with a $K_d$ of 150 nM or lower, and in some cases with a $K_d$ of 100 nM or lower, as measured by an equilib pH is continuously monitored and adjusted if necessary. The reaction is typically allowed to continue for between about 1-48 hours.

The reaction products are subsequently subjected to hydrophobic interaction chromatography to separate the PEGylated fEPO variants from free mPEG(5000)-O—CH$_2$—C≡CH and any high-molecular weight complexes of the pegylated fEPO polypeptide which may form when unblocked PEG is activated at both ends of the molecule, thereby crosslinking fEPO variant molecules. The conditions during hydrophobic interaction chromatography are such that free mPEG(5000)-O—CH$_2$—C≡CH flows through the column, while any crosslinked PEGylated fEPO variant complexes elute after the desired forms, which contain one fEPO variant molecule conjugated to one or more PEG groups. Suitable conditions vary depending on the relative sizes of the cross-linked complexes versus the desired conjugates and are readily determined by those skilled in the art. The eluent containing the desired conjugates is concentrated by ultrafiltration and desalted by diafiltration.

If necessary, the PEGylated fEPO obtained from the hydrophobic chromatography can be purified further by one or more procedures known to those skilled in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (PROTEIN PURIFICATION METHODS, A PRACTICAL APPROACH (Harris & Angal, Eds.) IRL Press 1989, 293-306). The purity of the fEPO-PEG conjugate can be assessed by proteolytic degradation (including but not limited to, trypsin cleavage) followed by mass spectrometry analysis. Pepinsky B., et. al., *J. Pharmcol. & Exp. Ther*. 297(3):1059-66 (2001).

A water soluble polymer linked to an amino acid of a fEPO polypeptide of the invention can be further derivatized or substituted without limitation.

Azide-Containing PEG Derivatives

In another embodiment of the invention, a fEPO polypeptide is modified with a PEG derivative that contains an azide moiety that will react with an alkyne moiety present on the side chain of the non-naturally encoded amino acid. In general, the PEG derivatives will have an average molecular weight ranging from 1-100 kDa and, in some embodiments, from 10-40 kDa.

In some embodiments, the azide-terminal PEG derivative will have the structure:

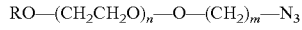

where R is a simple alkyl (methyl, ethyl, propyl, etc.), m is 2-10 and n is 100-1,000 (i.e., average molecular weight is between 5-40 kDa).

In another embodiment, the azide-terminal PEG derivative will have the structure:

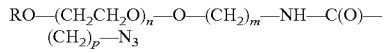

where R is a simple alkyl (methyl, ethyl, propyl, etc.), m is 2-10, p is 2-10 and n is 100-1,000 (i.e., average molecular weight is between 5-40 kDa).

In another embodiment of the invention, a fEPO polypeptide comprising a alkyne-containing amino acid is modified with a branched PEG derivative that contains a terminal azide moiety, with each chain of the branched PEG having a MW ranging from 10-40 kDa and, more preferably, from 5-20 kDa. For instance, in some embodiments, the azide-terminal PEG derivative will have the following structure:

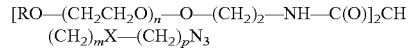

where R is a simple alkyl (methyl, ethyl, propyl, etc.), m is 2-10, p is 2-10, and n is 100-1,000, and X is optionally an O, N, S or carbonyl group (C=O), in each case that can be present or absent.

Alkene-Containing PEG Derivatives

In another embodiment of the invention, a fEPO polypeptide is modified with a PEG derivative that contains an alkyne moiety that will react with an azide moiety present on the side chain of the non-naturally encoded amino acid.

In some embodiments, the alkyne-terminal PEG derivative will have the following structure:

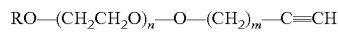

where R is a simple alkyl (methyl, ethyl, propyl, etc.), m is 2-10 and n is 100-1,000 (i.e., average molecular weight is between 5-40 kDa).

In another embodiment of the invention, a fEPO polypeptide comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure:

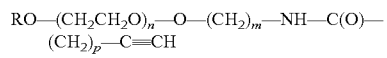

where R is a simple alkyl (methyl, ethyl, propyl, etc.), m is 2-10, p is 2-10 and n is 100-1,000.

In another embodiment of the invention, a fEPO polypeptide comprising an azide-containing amino acid is modified with a branched PEG derivative that contains a terminal alkyne moiety, with each chain of the branched PEG having a MW ranging from 10-40 kDa and, more preferably, from 5-20 kDa. For instance, in some embodiments, the alkyne-terminal PEG derivative will have the following structure:

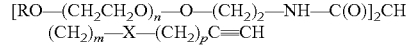

where R is a simple alkyl (methyl, ethyl, propyl, etc.), m is 2-10, p is 2-10, and n is 100-1,000, and X is optionally an O, N, S or carbonyl group (C=O), or not present.

Phosphine-Containing PEG Derivatives

In another embodiment of the invention, a fEPO polypeptide is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives will have an average molecular weight ranging from 1-100 kDa and, in some embodiments, from 10-40 kDa.

In some embodiments, the PEG derivative will have the structure:

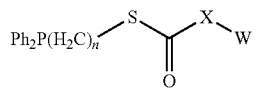

wherein n is 1-10; X can be O, N, S or not present, Ph is phenyl, and W is a water soluble polymer.

In some embodiments, the PEG derivative will have the structure:

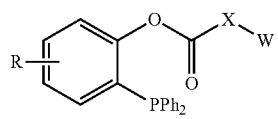

wherein X can be O, N, S or not present, Ph is phenyl, W is a water soluble polymer and R can be H, alkyl, aryl, substituted alkyl and substituted aryl groups. Exemplary R groups include but are not limited to —CH₂, —C(CH₃)₃, —OR', —NR'R", —SR', -halogen, —C(O)R', —CONR'R", —S(O)₂R', —S(O)₂NR'R", —CN and —NO₂. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF₃ and —CH₂CF₃) and acyl (including but not limited to, —C(O)CH₃, —C(O)CF₃, —C(O)CH₂OCH₃, and the like).

Other PEG Derivatives and General PEGylation Techniques

Other exemplary PEG molecules that may be linked to fEPO polypeptides, as well as PEGylation methods include those described in, e.g., U.S. Patent Publication Nos. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/0056171; 2001/0044526; 2001/0027217; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,612,460; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

Enhancing Affinity for Serum Albumin

Various molecules can also be fused to the fEPO polypeptides of the invention to modulate the half-life of fEPO in serum. In some embodiments, molecules are linked or fused to fEPO polypeptides of the invention to enhance affinity for endogenous serum albumin in an animal.

For example, in some cases, a recombinant fusion of a fEPO polypeptide and an albumin binding sequence is made. Exemplary albumin binding sequences include, but are not limited to, the albumin binding domain from streptococcal protein G (see. e.g., Makrides et al., *J. Pharmacol. Exp. Ther*. 277:534-542 (1996) and Sjolander et al., *J, Immunol. Methods* 201:115-123 (1997)), or albumin-binding peptides such as those described in, e.g., Dennis, et al., *J. Biol. Chem.* 277:35035-35043 (2002).

In other embodiments, the fEPO polypeptides of the present invention are acylated with fatty acids. In some cases, the fatty acids promote binding to serum albumin. See, e.g., Kurtzhals, et al., *Biochem. J*. 312:725-731 (1995).

In other embodiments, the fEPO polypeptides of the invention are fused directly with serum albumin (including but not limited to, human serum albumin). See, e.g., U.S. Pat. No. 6,548,653 which is incorporated by reference herein.

Those of skill in the art will recognize that a wide variety of other molecules can also be linked to fEPO in the present invention to modulate binding to serum albumin or other serum components.

XI. Glycosylation of fEPO

The invention includes fEPO polypeptides incorporating one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to fEPO polypeptides either in vivo or in vitro. In some embodiments of the invention, a fEPO polypeptide comprising a carbonyl-containing non-naturally encoded amino acid is modified with a saccharide derivatized with an amino oxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the fEPO polypeptide. See, e.g., H. Liu, et al. *J. Am. Chem. Soc*. 125: 1702-1703 (2003).

In some embodiments of the invention, a fEPO polypeptide comprising a carbonyl-containing non-naturally encoded amino acid is modified directly with a glycan with defined structure prepared as an aminooxy derivative. One skilled in the art will recognize that other functionalities, including azide, alkyne, hydrazide, hydrazine, and semicarbazide, can be used to link the saccharide to the non-naturally encoded amino acid.

In some embodiments of the invention, a fEPO polypeptide comprising an azide or alkynyl-containing non-naturally encoded amino acid can then be modified by, including but not limited to, a Huisgen[3+2] cycloaddition reaction with, including but not limited to, alkynyl or azide derivatives, respectively. This method allows for proteins to be modified with extremely high selectivity.

XII. GH Supergene Family Member Dimers and Multimers

The present invention also provides for GH supergene family member combinations (including but not limited to fEPO) homodimers, heterodimers, homomultimers, or heteromultimers (i.e., trimers, tetramers, etc.) where a GH supergene family member polypeptide such as fEPO containing one or more non-naturally encoded amino acids is bound to another GH supergene family member or variant thereof or any other polypeptide that is a non-GH supergene family member or variant thereof, either directly to the polypeptide backbone or via a linker. Due to its increased molecular weight compared to monomers, the GH supergene family member, such as fEPO, dimer or multimer conjugates may exhibit new or desirable properties, including but not limited to different pharmacological, pharmacokinetic, pharmacodynamic, modulated therapeutic half-life, or modulated plasma half-life relative to the monomeric GH supergene family member. In some embodiments, the GH supergene family member, such as fEPO, dimers of the invention will modulate the dimerization of the GH supergene family member receptor. In other embodiments, the GH supergene family member dimers or multimers of the present invention will act as a GH supergene family member receptor antagonist, agonist, or modulator.

In some embodiments, one or more of the fEPO molecules present in a fEPO containing dimer or multimer comprises a non-naturally encoded amino acid linked to a water soluble polymer that is present within the Site II binding region. As such, each of the fEPO molecules of the dimer or multimer are accessible for binding to the fEPO receptor via the Site I interface but are unavailable for binding to a second fEPO receptor via the Site II interface. Thus, the fEPO dimer or multimer can engage the Site I binding sites of each of two distinct fEPO receptors but, as the fEPO molecules have a water soluble polymer attached to a non-genetically encoded amino acid present in the Site II region, the fEPO receptors cannot engage the Site II region of the fEPO ligand and the dimer or multimer acts as a fEPO antagonist. In some embodiments, one or more of the fEPO molecules present in a fEPO containing dimer or multimer comprises a non-naturally encoded amino acid linked to a water soluble polymer that is present within the Site I binding region, allowing binding to the Site II region. Alternatively, in some embodiments one or more of the fEPO molecules present in a fEPO containing dimer or multimer comprises a non-naturally encoded amino acid linked to a water soluble polymer that is present at a site that is not within the Site I or Site II binding region, such that both are available for binding. In some embodiments a combination of fEPO molecules is used having Site I, Site II, or both available for binding. A combination of fEPO molecules wherein at least one has Site I available for binding, and at least one has Site II available for binding may provide molecules having a desired activity or property. In addition, a combination of fEPO molecules having both Site I and Site II available for binding may produce a super-agonist fEPO molecule.

In some embodiments, the GH supergene family member polypeptides are linked directly, including but not limited to, via an Asn-Lys amide linkage or Cys-Cys disulfide linkage. In some embodiments, the linked GH supergene family member polypeptides, and/or the linked non-GH supergene family member, will comprise different non-naturally encoded amino acids to facilitate dimerization, including but not limited to, an alkyne in one non-naturally encoded amino acid of a first fEPO polypeptide and an azide in a second non-naturally encoded amino acid of a second GH supergene family member polypeptide will be conjugated via a Huisgen [3+2] cycloaddition. Alternatively, a first GH supergene family member, and/or the linked non-GH supergene family member, polypeptide comprising a ketone-containing non-naturally encoded amino acid can be conjugated to a second GH supergene family member polypeptide comprising a hydroxylamine-containing non-naturally encoded amino acid and the polypeptides are reacted via formation of the corresponding oxime.

Alternatively, the two GH supergene family member polypeptides, and/or the linked non-GH supergene family member, are linked via a linker. Any hetero- or homo-bifunctional linker can be used to link the two GH supergene family member, and/or the linked non-GH supergene family member, polypeptides, which can have the same or different primary sequence. In some cases, the linker used to tether the GH supergene family member, and/or the linked non-GH supergene family member, polypeptides together can be a bifunctional PEG reagent.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

In some embodiments, the invention provides multimers comprising one or more GH supergene family member, such as fEPO, formed by reactions with water soluble activated polymers that have the structure:

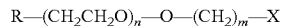

wherein n is from about 5 to 3,000, m is 2-10, X can be an azide, an alkyne, a hydrazine, a hydrazide, an aminooxy group, a hydroxylamine, a acetyl, or carbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

XIII. Measurement of fEPO Activity and Affinity of fEPO for the fEPO Receptor

The fEPO receptor can be prepared as described in U.S. Pat. Nos. 5,387,808; 5,292,654; 5,278,065, which are incorporated by reference herein. fEPO polypeptide activity can be determined using standard in vitro or in vivo assays. For example, cell lines that proliferate in the presence of fEPO (including but not limited to, UT-7 cells, TF-1 cells, FDCP-1/mEPOR, or spleen cells) can be used to monitor fEPO receptor binding. See, e.g., Wrighton et al., (1997) Nature Biotechnology 15:1261-1265; U.S. Pat. Nos. 5,773,569; and 5,830,851, which are incorporated by reference herein. For a non-PEGylated or PEGylated fEPO polypeptide comprising a non-natural amino acid, the affinity of the hormone for its receptor can be measured by using a BIAcore™ biosensor (Pharmacia). In vivo animal models (e.g. murine, etc.) as well as feline trials for testing fEPO activity are known and include those described in, e.g., U.S. Pat. No. 6,696,056; Cotes et al., (1961) Nature 191:1065-1067; U.S. Patent Application Pub. No. 2003/0198691; and Pharm Europa Spec. Issue Erythropoietin BRP Bio 1997(2), which are incorporated by reference herein. Assays for dimerization capability of fEPO polypeptides comprising one or more non-naturally encoded amino acids can be conducted as described in U.S. Pat. No. 6,221,608 which is incorporated by reference herein.

XIV. Measurement of Potency, Functional in Vivo Half-life, and Pharmacokinetic Parameters The potency and functional in vivo half-life of a fEPO polypeptide comprising a non-naturally encoded amino acid can be determined according to the protocol described in U.S. Pat. Nos. 6,586,398; 5,583,272; and U.S. Patent application Publication No. 2003/0198691A1, which are incorporated by reference herein.

Pharmacokinetic parameters for a fEPO polypeptide comprising a non-naturally encoded amino acid can be evaluated in normal Sprague-Dawley male rats (N=5 animals per treatment group). Animals will receive either a single dose of 25 ug/rat iv or 50 ug/rat sc, and approximately 5-7 blood samples will be taken according to a predefined time course, generally covering about 6 hours for a fEPO polypeptide comprising a non-naturally encoded amino acid not conjugated to a water soluble polymer and about 4 days for a fEPO polypeptide comprising a non-naturally encoded amino acid and conjugated to a water soluble polymer. Pharmacokinetic data for fEPO is well-studied in several species and can be compared directly to the data obtained for fEPO comprising a non-naturally encoded amino acid. See Mordenti J., et al., *Pharm. Res.* 8(11):1351-59 (1991).

The specific activity of fEPO in accordance with this invention can be determined by various assays known in the art. The biological activity of the purified fEPO proteins of this invention are such that administration of the fEPO protein by injection to human patients results in bone marrow cells increasing production of reticulocytes and red blood cells compared to non-injected or control groups of subjects. The biological activity of the fEPO muteins, or fragments thereof, obtained and purified in accordance with this invention can be tested by methods according to Pharm. Europa Spec. Issue Erythropoietin BRP Bio 1997(2). Another biological assay for determining the activity of fEPO is the normocythaemic mouse assay (Pharm. Europa Spec. Issue Erythropoietin BRP Bio 1997(2)).

XV. Administration and Pharmaceutical Compositions

The polypeptides or proteins of the invention (including but not limited to, fEPO, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the polypeptides of the invention.

Therapeutic compositions comprising one or more polypeptide of the invention are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of unnatural herein to natural amino acid homologues (including but not limited to, comparison of an EPO modified to include one or more unnatural amino acids to a natural amino acid EPO), i.e., in a relevant assay.

Administration is by any of the routes normally used for introducing a molecule into ultimate contact with blood or tissue cells. The unnatural amino acid containing polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Polypeptide compositions can be administered by a number of routes including, but not limited to oral, intravenous, intraperitoneal, intramuscular, transdermal, subcutaneous, topical, sublingual, or rectal means. Unnatural amino acid polypeptide compositions can also be administered via liposomes. Such administration routes and appropriate formulations are generally known to those of skill in the art.

The unnatural amino acid polypeptide, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GCSF, GMCSF, IFNs, interleukins, antibodies, and/or any other pharmaceutically delivered protein), along with formulations in current use, provide preferred routes of administration and formulation for the unnatural amino acids of the invention.

The dose administered to a patient, in the context of the present invention, is sufficient to have a beneficial therapeutic response in the patient over time, or, including but not limited to, to inhibit infection by a pathogen, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The vectors of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 of the relevant formulation, and/or observation of any side-effects of the unnatural amino acids at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Feline EPO polypeptides of the invention can be administered directly to a mammalian subject. Administration is by any of the routes normally used for introducing fEPO to a subject. The fEPO polypeptide compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, inracerebral, intraarterial, or intravenous), topical (i.e., both skin and mucosal surfaces, including airway surfaces) and transdermal administration, although the most suitable route in any given case will depend on the nature and severity of the condition being treated. Administration can be either local or systemic. The formulations of compounds can be presented in unit-dose or multi-dose sealed containers, such as ampoules and vials. fEPO polypeptides of the invention can be prepared in a mixture in a unit dosage injectable form (including but not limited to, solution, suspension, or emulsion) with a pharmaceutically acceptable carrier. fEPO polypeptides of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., *Remington's Pharmaceutical Sciences*, 17$^{th}$ ed. 1985)).

Suitable carriers include buffers containing phosphate, borate, HEPES, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates, including glucose, mannose, or dextrins; chelating agents such as EDTA; divalent metal ions such as zinc, cobalt, or copper; sugar alcohols such as mannitol or sorbitol; salt-forming counter ions such as sodium; and/or nonionic surfactants such as TWEEN (ethoxylated sorbitan esters), PLURONICS (block copolymers of poly(propylene) oxide and poly(ethylene) oxide), or PEG.

fEPO polypeptides of the invention, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater. Res.*, 15: 167-277 (1981); Langer, *Chem. Tech.*, 12: 98-105 (1982), ethylene vinyl acetate (Langer et al., supra) or poly-D-(–)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (U. Sidman et al., *Biopolymers*, 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Epstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324.

Liposomally entrapped fEPO polypeptides can be prepared by methods described in, e.g., DE 3,218,121; Epstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Composition and size of liposomes are well known or able to be readily determined empirically by one skilled in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res*. 8:1172-1181 (2002); Nielsen U B, et al., *Biochim. Biophys. Acta* 1591(1-3):109-118 (2002); Mamot C, et al., *Cancer Res*. 63: 3154-3161 (2003).

The dose administered to a patient in the context of the present invention should be sufficient to cause a beneficial response in the subject over time. Generally, the total pharmaceutically effective amount of the fEPO of the present invention administered parenterally per dose is in the range of about 0.01 µg/kg/day to about 100 µg/kg, or about 0.05 mg/kg to about 1 mg/kg, of patient body weight, although this is subject to therapeutic discretion. The frequency of dosing is also subject to therapeutic discretion, and may be more frequent or less frequent than the commercially available EPO products approved for use in humans. Generally, a PEGylated fEPO polypeptide of the invention can be administered by any of the routes of administration described above.

XVI. Therapeutic Uses of fEPO Polypeptides of the Invention

The fEPO polypeptides of the invention are useful for treating a wide range of disorders. Administration of the fEPO products of the present invention results in red blood cell formation in humans. The pharmaceutical compositions containing the fEPO glycoprotein products may be formulated at a strength effective for administration by various means to a human patient experiencing blood disorders, characterized by low or defective red blood cell production, either alone or as part condition or disease. Average quantities of the fEPO glycoprotein product may vary and in particular should be based upon the recommendations and prescription of a qualified physician. The exact amount of fEPO is a matter of preference subject to such factors as the exact type of condition being treated, the condition of the patient being treated, as well as the other ingredients in the composition. The fEPO of the present invention may thus be used to stimulate red blood cell production and correct depressed red cell levels. Most commonly, red cell levels are decreased due to anemia. Among the conditions treatable by the present invention include anemia associated with a decline or loss of kidney function (chronic renal failure), anemia associated with myelosuppressive therapy, such as chemotherapeutic or anti-viral drugs (such as AZT), anemia associated with the progression of non-myeloid cancers, and anemia associated with viral infections (such as HIV). Also treatable are conditions which may lead to anemia in an otherwise healthy individual, such as an anticipated loss of blood during surgery. In general, any condition treatable with fEPO may also be treated with the PEG:fEPO conjugates of the present invention. The invention also provides for administration of a therapeutically effective amount of iron in order to maintain increased erythropoiesis during therapy. The amount to be given may be readily determined by one skilled in the art based upon therapy with fEPO.

XVII. Examples

The following examples are offered to illustrate, but not to limit the claimed invention.

Example 1

This example describes one of the many potential sets of criteria for the selection of preferred sites of incorporation of non-naturally encoded amino acids into fEPO.

This example demonstrates how preferred sites within the fEPO polypeptide were selected for introduction of a non-naturally encoded amino acid. Molecular modeling and known information regarding the secondary structure of fEPO was used to determine preferred positions into which one or more non-naturally encoded amino acids could be introduced. Other fEPO structures and known crystal structure information regarding fEPO was utilized to examine potential variation of primary, secondary, or tertiary structural elements between crystal structure datasets. The coordinates for these structures are available from the Protein Data Bank (PDB) (Bernstein et al. *J. Mol. Biol*. 1997, 112, pp 535) or via The Research Collaboratory for Structural Bioinformatics PDB. The structural model 1CN4 contains the entire mature 18 kDa sequence of fEPO with the exception of residues 124-130, the N-terminal A1, and the C-terminal T163, G164, D165, and R166 residues which were omitted due to disorder in the crystal. Two disulfide bridges are present, formed by C7 and C161 and C29 and C33.

Sequence numbering used in this example is according to the amino acid sequence of mature fEPO (18 kDa variant) shown in SEQ ID NO: 2 and SEQ ID NO: 4.

This example describes one of the many potential sets of criteria for the selection of preferred sites of incorporation of non-naturally encoded amino acids into fEPO. Using the criteria described below, the amino acid positions utilized for site-specific incorporation of non-naturally encoded amino acids (for example, p-acetyl-phenylalanine (pAF)) are positions: 53, 55, 116, 89, 72, 86, 128, 129, 130, 131, 132, 133, 134, 135, 31, 163, 120, 76, 24, 38, 37, 49, 83, 21, 36. Several EPO crystal structures were used to determine preferred positions into which one or more non-naturally encoded amino acids could be introduced: the coordinates for these structures are available from the Protein Data Bank (PDB) via The Research Collaboratory for Structural Bioinformatics at www.rcsb.org (PDB IDs 1CN4, 1EER, and 1BUY). X-ray crystal structure information was used to perform solvent accessibility calculations on the fEPO molecule, utilizing the Cx program (Pintar et al. *Bioinformatics*, 2002, Vol. 18, p 980). The solvent accessibility of all atoms was calculated and an average Cx value for each amino acid residue was determined, and is shown in FIG. 8 and FIG. 9. The following criteria were used to evaluate each position of fEPO for the introduction of a non-naturally encoded amino acid: the residue (a) should not interfere with binding of either fEPObp based on structural analysis of fEPO and structural analysis of fEPO and 1CN4, 1EER, and 1BUY (crystallographic structures of hEPO conjugated with hEP- Opb), b) should not be affected by alanine scanning mutagenesis (Bittorf, T. et al. *FEBS*, 336:133-136 (1993), Wen, D., et al. *JBC*, 269:22839-22846 (1994), and Elliot, S. et al. *Blood*, 89:493-502 (1997), (c) should be surface exposed and exhibit a maximum Cx, demonstrating minimal van der Waals or hydrogen bonding interactions with surrounding residues, (d) should be either deleted or variable in fEPO variants (Bittorf, T. et al. *FEBS*, 336:133-136 (1993), Wen, D., et al. *JBC*, 269:22839-22846 (1994), (e) would result in conservative changes upon substitution with a non-naturally encoded amino acid and (f) could be found in either highly flexible regions (including but not limited to CD loop) or structurally rigid regions (including but not limited to Helix B). In addition, further calculations were performed on the fEPO molecule, utilizing the Cx program (Pintar et al. *Bioinformatics*, 18, pp 980) to evaluate the extent of protrusion for each protein atom. As a result, in some embodiments, the non-naturally encoded encoded amino acid is substituted at, but not limited to, one or more of the following positions of fEPO: before position 1 (i.e., at the N-terminus), 1, 2, 3, 4, 7, 8, 9, 10, 13, 17, 20, 21, 24, 25, 27, 30, 31, 32, 34, 36, 37, 38, 40, 43, 49, 50, 52, 53, 54, 55, 56, 58, 65, 68, 69, 72, 75, 76, 79, 80, 82, 83, 84, 85, 86, 87, 88, 89, 90, 92, 93, 110, 111, 115, 116, 117, 118, 119, 120, 121, 122, 123, 124, 125, 126, 127, 128, 129, 130, 131, 132, 133, 134, 136, 139, 159, 161, 162, 163, 164, 165, 166, 167 (i.e., at the carboxyl terminus of the protein), or combinations thereof.

Some sites for generation of a fEPO antagonist include: 10, 11, 14, 15, 96, 97, 100, 103, 104, 107, 110. These sites were chosen utilizing criteria c-e of the agonist design. The antagonist design may also include site-directed modifications of site 1 residues to increase binding affinity to fEPObp.

FIGS. 3-9 show modeling and selection of positions. FIG. 8 shows that in some embodiments, the non-naturally encoded amino acid is substituted at, but not limited to, one or more of the following positions of fEPO: 53, 55, 116, 89, 72, 86, 128, 129, 130, 131, 132, 133, 134, 135, 31, 163, 120, or combinations thereof. FIG. 9 shows that in some embodiments, the non-naturally encoded amino acid is substituted at, but not limited to, one or more of the following positions of fEPO: 53, 55, 76, 24, 116, 38, 89, 37, 72, 86, 49, 83, 21, 36, 128, 129, 130, 131, 132, 133, or combinations thereof.

Example 2

This example details cloning and expression of a modified fEPO polypeptide in *E. coli.*

This example demonstrates how a fEPO polypeptide including a non-naturally encoded amino acid can be expressed in *E. coli*. Nucleotide sequences encoding fEPO are produced generally as described in Matthews et al., (1996) PNAS 93:9471-76. Fetal liver, adult liver, fetal kidney and adult kidney cDNA libraries are templates for cloning cDNA encoding full length and mature fEPO, with fetal liver giving the best result. Primers used for cloning full length and mature fEPO could be primers known to those skilled in the art including 5'cagttacatatgggagttcacgaatgtcctgcctgg3'SEQ ID NO: 21; and 5'cagttacatatgctccaccaagattaatctgtg3'SEQ ID NO: 22. An example of a 3' primer sequence that could be used for this cloning is 5'ctgcaactcgagtcatctgtcccctgtcctgcag3' SEQ ID NO: 23. The reaction conditions for the cloning can be 94° C. for two minutes, with 30 cycles of 94° C. for 30 seconds, 50° C. for one minute, 72° C. for 2 minutes, and 72° C. for 7 minutes, followed by 4° C. reaction termination. Molecules are identified that encode fEPO, including the full length fEPO, the mature form of fEPO lacking the N-terminal signal sequence, and SNPs. The full length and mature fEPO encoding cDNA can be inserted into expression vectors, such as the pBAD HISc, and pET20b expression vectors following optimization of the sequence for cloning and expression without altering amino acid sequence.

An introduced translation system that comprises an orthogonal tRNA (O-tRNA) and an orthogonal aminoacyl tRNA synthetase (O-RS) is used to express fEPO containing a non-naturally encoded amino acid. The O-RS preferentially aminoacylates the O-tRNA with a non-naturally encoded amino acid. In turn the translation system inserts the non-naturally encoded amino acid into fEPO, in response to an encoded selector codon. The following Table (Table 2) includes sequences of fEPO, both full length and mature, and O-RS and O-tRNA sequences, some of which used in these examples, others which were used with hEPO and may be used or optimized for use with fEPO.

TABLE 2

| SEQ ID # | Sequence | Notes | Protein of tRNA or RS |
|---|---|---|---|
| 1 | MGSCECPALLLLLSLLLLPLGLPVLGAPPRLICDSRVLERYILEAREAENVTM GCAEGCSFSENITVPDTKVNFYTWKRMDVGQQAVEVWQGLALLSEAILRG QALLANSSQPSETLQLHVDKAVSSLRSLTSLLRALGAQKEATSLPEATSAAP LRTFTVDTLCKLFRIYSNFLRGKLTLYTGEACRRGDR | Full-length amino acid sequence of fEPO | Protein |
| 2 | APPRLICDSRVLERYILEAREAENVTMGCAEGCSFSENITVPDTKVNFYTWK RMDVGQQAVEVWQGLALLSEAILRGQALLANSSQPSETLQLHVDKAVSSLR SLTSLLRALGAQKEATSLPEATSAAPLRTFTVDTLCKLFRIYSNFLRGKLTLY TGEACRRGDR | The mature amino acid sequence of fEPO | Protein |
| 3 | MGSCECPALLLLLSLLLLPLGLPVLGAPPRLICDSRVLERYILGAREAENVTM GCAEGCSFSENITVPDTKVNFYTWKRMDVGQQAVEVWQGLALLSEAILRG QALLANSSQPSETLQLHVDKAVSSLRSLTSLLRALGAQKEATSLPEATSAAP LRTFTVDTLCKLFRIYSNFLRGKLTLYTGEACRRGDR | SNP variant (E108G) of the full-length amino acid sequence of fEPO | protein |
| 4 | APPRLICDSRVLERYILGAREAENVTMGCAEGCSFSENITVPDTKVNFYTWK RMDVGQQAVEVWQGLALLSEAILRGQALLANSSQPSETLQLHVDKAVSSLR | SNP variant (E108G) | protein |

| SEQ ID # | Sequence | Notes | Protein of tRNA or RS |
|---|---|---|---|
| | SLTSLLRALGAQKEATSLPEATSAAPLRTFTVDTLCKLFRIYSNFLRGKLTLY TGEACRRGDR | of the mature amino acid sequence of fEPO | |
| 5 | CCCAGGGTAGCCAAGCTCGGCCAACGGCGACGGACTCTAAATCCGTTCT CGTAGGAGTTCGAGGGTTCGAATCCCTTCCC TGGGACCA | HLAD03; an optimized amber supressor tRNA | tRNA |
| 6 | GCGAGGGTAGCCAAGCTCGGCCAACGGCGACGGACTTCCTAATCCGTTC TCGTAGGAGTTCGAGGGTTCGAATCCCTCCCCTCGCACCA | HL325A; an optimized AGGA frameshift supressor tRNA | tRNA |
| 7 | MDEFEMIKRNTSEIISEEELREVLKKDEKSAGIGFEPSGKIHLGHYLQIKKMID LQNAGFDIIILLADLHAYLNQKGELDEIRKIGDYNKKVFEAMGLKAKYVYGS TFQLDKDYTLNVYRLALKTTLKRARRSMELIAREDENPKVAEVIYPIMQVNT YYYLCVDVAVGGMEQRKIHMLARELLPKKVVCIHNPVLTGLDGEGKMSSS KGNFIAVDDSPEEIRAKIKKAYCPAGVVEGNPIMEIAKYFLEYPLTIKRPEKF GGDLTVNSYEELESLFKNKELHPMDLKNAVAEELIKILEPIRKRL | Aminoacyl tRNA synthetase for the incorporation of p-azido-L-phenylalanine p-Az-PheRS(6) | RS |
| 8 | MDEFEMIKRNTSEIISEEELREVLKKDEKSAGIGFEPSGKIHLGHYLQIKKMID LQNAGFDIIILLADLHAYLNQKGELDEIRKIGDYNKKVFEAMGLKAKYVYGS SFQLDKDYTLNVYRLALKTTLKRARRSMELIAREDENPKVAEVIYPIMQVNT SHYLCVDVAVGGMEQRKIHMLARELLPKKVVCIHNPVLTGLDGEGKMSSS KGNFIAVDDSPEEIRAKIKKAYCPAGVVEGNPIMEIAKYFLEYPLTIKRPEKF GGDLTVNSYEELESLFKNKELHPMDLKNAVAEELIKILEPIRKRL | Aminoacyl tRNA synthetase for the incorporation of p-benzoyl-L-phenylalanine p-BpaRS(1) | RS |
| 9 | MDEFEMIKRNTSEIISEEELREVLKKDEKAAIGFEPSGKIHLGHYLQIKKMIDL QNAGFDIIILLADLHAYLNQKGELDEIRKIGDYNKKVFEAMGLKAKYVYGSP FQLDKDYTLNVYRLALKTTLKRARRSMELIAREDENPKVAEVIYPIMQVNAI YLAVDVAVGGMEQRKIHMLARELLPKKVVCIHNPVLTGLDGEGKMSSSKG NFIAVDDSPEEIRAKIKKAYCPAGVVEGNPIMEIAKYFLEYPLTIKRPEKFGG DLTVNSYEELESLFKNKELHPMDLKNAVAEELIKILE PIRKR L | Aminoacyl tRNA synthetase for the incorporation of propargyl-phenylalanine Propargyl-PheRS | RS |
| 10 | MDEFE MIKRN TSEII SEEEL REVLK KDEKS AAIGF EPSGK IHLGH YLQIK KMIDL QNAGF DIIIL LADLH AYLNQ KGELD EIRKI GDYNK KVFEA MGLKA KYVYG SPFQL DKDYT LNVYR LALKT TLKRA RRSME LIARE DENPK VAEVI YPIMQ VNIPY LPVD VAVGG MEQRK IHMLA RELLP KKVVC IHNPV LTGLD GEGKM SSSKG NFIAV DDSPE EIRAK IKKAY CPAGV VEGNP IMEIA KYFLE YPLTI KRPEK FGGDL TVNSY EELES LFKNK ELHPM DLKNA VAEEL IKILE PIRKR L | Aminoacyl tRNA synthetase for the incorporation of propargyl-phenylalanine Propargyl-PheRS | RS |
| 11 | MDEFE MIKRN TSEII SEEEL REVLK KDEKS AAIGF EPSGK IHLGH YLQIK KMIDL QNAGF DIIIL LADLH AYLNQ KGELD EIRKI GDYNK KVFEA MGLKA KYVYG SKFQL DKDYT LNVYR LALKT TLKRA RRSME LIARE DENPK VAEVI YPIMQ VNAIY LAVD VAVGG MEQRK IHMLA RELLP KKVVC IHNPV LTGLD GEGKM SSSKG NFIAV DDSPE EIRAK IKKAY CPAGV VEGNP IMEIA KYFLE YPLTI KRPEK FGGDL TVNSY EELES LFKNK ELHPM DLKNA VAEEL IKILE PIRKR L | Aminoacyl tRNA synthetase for the incorporation of propargyl-phenylalanine Propargyl-PheRS | RS |
| 12 | MDEFEMIKRNTSEIISEEELREVLKKDEKSATIGFEPSGKIHLGHYLQIKKMID LQNAGFDIIILLADLHAYLNQKGELDEIRKIGDYNKKVFEAMGLKAKYVYGS NFQLDKDYTLNVYRLALKTTLKRARRSMELIAREDENPKVAEVIYPIMQVN PLHYQCVDVAVGGMEQRKIHMLARELLPKKVVCIHNPVLTGLDGEGKMSS SKGNFIAVDDSPEEIRAKIKKAYCPAGVVEGNPIMEIAKYFLEYPLTIKRPEKF GGDLTVNSYEELESLFKNKELHPMDLKNAVAEELIKILEPIRKRL | Aminoacyl tRNA synthetase for the incorporation of p-azido-phenylalanine p-Az-PheRS(1) | RS |

TABLE 2-continued

| SEQ ID # | Sequence | Notes | Protein of tRNA or RS |
|---|---|---|---|
| 13 | MDEFEMIKRNTSEIISEEELREVLKKDEKSATIGFEPSGKIHLGHYLQIKKMID LQNAGFDIIILLADLHAYLNQKGELDEIRKIGDYNKKVFEAMGLKAKYVYGS SFQLDKDYTLNVYRLALKTTLKRARRSMELIAREDENPKVAEVIYPIMQVNP LHYQCVDVAVGGMEQRKIHMLARELLPKKVVCIHNPVLTGLDGEGKMSSS KGNFIAVDDSPEEIRAKIKKAYCPAGVVEGNPIMEIAKYFLEYPLTIKRPEKF GGDLTVNSYEELESLFKNKELHPMDLKNAVAEELIKILEPIRKRL | Aminoacyl tRNA synthetase for the incorporation of p-azido-phenylalanine p-Az-PheRS(3) | RS |
| 14 | MDEFEMIKRNTSEIISEEELREVLKKDEKSALIGFEPSGKIHLGHYLQIKKMID LQNAGFDIIILLADLHAYLNQKGELDEIRKIGDYNKKVFEAMGLKAKYVYGS TFQLDKDYTLNVYRLALKTTLKRARRSMELIAREDENPKVAEVIYPIMQVNP VHYQCVDVAVGGMEQRKIHMLARELLPKKVVCIHNPVLTGLDGEGKMSSS KGNFIAVDDSPEEIRAKIKKAYCPAGVVEGNPIMEIAKYFLEYPLTIKRPEKF GGDLTVNSYEELESLFKNKELHPMDLKNAVAEELIKILEPIRKRL | Aminoacyl tRNA synthetase for the incorporation of p-azido-phenylalanine p-Az-PheRS(4) | RS |
| 15 | MDEFEMIKRNTSEIISEEELREVLKKDEKSATIGFEPSGKIHLGHYLQIKKMID LQNAGFDIIILLADLHAYLNQKGELDEIRKIGDYNKKVFEAMGLKAKYVYGS SFQLDKDYTLNVYRLALKTTLKRARRSMELIAREDENPKVAEVIYPIMQVNP SHYQGVDVAVGGMEQRKIHMLARELLPKKVVCIHNPVLTGLDGEGKMSSS KGNFIAVDDSPEEIRAKIKKAYCPAGVVEGNPIMEIAKYFLEYPETIKRPEKF GGDLTVNSYEELESLFKNKELHPMDLKNAVAEELIKILEPIRKRL | Aminoacyl tRNA synthetase for the incorporation of p-azido-phenylalanine p-Az-PheRS(2) | RS |
| 16 | MDEFEMIKRNTSEIISEEELREVLKKDEKSALIGFEPSGKIHLGHYLQIKKMID LQNAGFDIIILLADLHAYLNQKGELDEIRKIGDYNKKVFEAMGLKAKYVYGS EFQLDKDYTLNVYRLALKTTLKRARRSMELIAREDENPKVAEVIYPIMQVN GCHYRGVDVAVGGMEQRKIHMLARELLPKKVVCIHNPVLTGLDGEGKMSS SKGNFIAVDDSPEEIRAKIKKAYCPAGVVEGNPIMEIAKYFLEYPLTIKRPEKF GGDLTVNSYEELESLFKNKELHPMDLKNAVAEELIKILEPIRKRL | Aminoacyl tRNA synthetase for the incorporation of p-azido-phenylalanine (LW1) | RS |
| 17 | MDEFEMIKRNTSEIISEEELREVLKKDEKSALIGFEPSGKIHLGHYLQIKKMID LQNAGFDIIILLADLHAYLNQKGELDEIRKIGDYNKKVFEAMGLKAKYVYGS EFQLDKDYTLNVYRLALKTTLKRARRSMELIAREDENPKVAEVIYPIMQVN GTHYRGVDVAVGGMEQRKIHMLARELLPKKVVCIHNPVLTGLDGEGKMSS SKGNFIAVDDSPEEIRAKIKKAYCPAGVVEGNPIMEIAKYFLEYPLTIKRPEKF GGDLTVNSYEELESLFKNKELHPMDLKNAVAEELIKILEPIRKRL | Aminoacyl tRNA synthetase for the incorporation of p-azido-phenylalanine (LW5) | RS |
| 18 | MDEFEMIKRNTSEIISEEELREVLKKDEKSAAIGFEPSGKIHLGHYLQIKKMID LQNAGFDIIILLADLHAYLNQKGELDEIRKIGDYNKKVFEAMGLKAKYVYGS EFQLDKDYTLNVYRLALKTTLKRARRSMELIAREDENPKVAEVIYPIMQVN GGHYLGVDVIVGGMEQRKIHMLARELLPKKVVCIHNPVLTGLDGEGKMSSS KGNFIAVDDSPEEIRAKIKKAYCPAGVVEGNPIMEIAKYFLEYPLTIKRPEKF GGDLTVNSYEELESLFKNKELHPMDLKNAVAEELIKILEPIRKRL | Aminoacyl tRNA synthetase for the incorporation of p-azido-phenylalanine (LW6) | RS |
| 19 | MDEFEMIKRNTSEIISEEELREVLKKDEKSAAIGFEPSGKIHLGHYLQIKKMID LQNAGFDIIILLADLHAYLNQKGELDEIRKIGDYNKKVFEAMGLKAKYVYGS RFQLDKDYTLNVYRLALKTTLKRARRSMELIAREDENPKVAEVIYPIMQVN VIHYDGVDVAVGGMEQRKIHMLARELLPKKVVCIHNPVLTGLDGEGKMSS SKGNFIAVDDSPEEIRAKIKKAYCPAGVVEGNPIMEIAKYFLEYPLTIKRPEKF GGDLTVNSYEELESLFKNKELHPMDLKNAVAEELIKILEPIRKRL | Aminoacyl tRNA synthetase for the incorporation of p-azido-phenylalanine (AzPheRS-5) | RS |
| 20 | MDEFEMIKRNTSEIISEEELREVLKKDEKSAGIGFEPSGKIHLGHYLQIKKMID LQNAGFDIIILLADLHAYLNQKGELDEIRKIGDYNKKVFEAMGLKAKYVYGS TFQLDKDYTLNVYRLALKTTLKRARRSMELIAREDENPKVAEVIYPIMQVNT YYYLGVDVAVGGMEQRKIHMLARELLPKKVVCIHNPVLTGLDGEGKMSSS KGNFIAVDDSPEEIRAKIKKAYCPAGVVEGNPIMEIAKYFLEYPLTIKRPEKF GGDLTVNSYEELESLFKNKELHPMDLKNAVAEELIKILEPIRKRL | Aminoacyl tRNA synthetase for the incorporation of p-azido-phenylalanine (AzPheRS-6) | RS |

TABLE 2-continued

| SEQ ID # | Sequence | Notes | Protein of tRNA or RS |
|---|---|---|---|
| 21 | cagttacatatgggagttcacgaatgtcctgcctgg | Primer for cloning full length hEPO cDNA | |
| 22 | cagttacatatgctccaccaagattaatctgtg | Primer for cloning mature hEPO cDNA | |
| 23 | ctgcaactcgagtcatctgtccctgtcctgcag | 3' Primer for cloning full length and mature hEPO cDNA | |
| 24 | atgggggtgcacgaatgtcctgcctggctgtggcttctcctgtccctgctgt cgctccctctgggcctccagtcctgggcgcccaccacgcctcatctgtga cagccgagtcctggagaggtacctcttggaggccaaggaggccgagaatatc acgacgggctgtgctgaacactgcagcttgaatgagaatatcactgtcccag acaccaaagttaatttctatgcctggaagaggatggaggtcgggcagcaggc cgtagaagtctggcagggcctggccctgctgtcggaagctgtcctgcggggc caggccctgttggtcaactcttcccagccgtgggagcccctgcagctgcatg tggataaagccgtcagtggccttcgcagcctcaccactctgcttcgggctct gcgagcccagaaggaagccatctcccctccagatgcggcctcagctgctcca ctccgaacaatcactgctgacactttccgcaaactcttccgagtctactcca atttcctccggggaaagctgaagctgtacacaggggaggcctgcaggacagg ggacagatga | Nucleotide sequence of full length hEPO cDNA | |
| 25 | gccccaccacgcctcatctgtgacagccgagtcctggagaggtacctcttgg aggccaaggaggccgagaatatcacgacgggctgtgctgaacactgcagctt gaatgagaatatcactgtcccagacaccaaagttaatttctatgcctggaag aggatggaggtcgggcagcaggccgtagaagtctggcagggcctggccctgc tgtcggaagctgtcctgcggggccaggccctgttggtcaactcttcccagcc gtgggagcccctgcagctgcatgtggataaagccgtcagtggccttcgcagc ctcaccactctgcttcgggctctgcgagcccagaaggaagccatctcccctc cagatgcggcctcagctgctccactccgaacaatcactgctgacactttccg caaactcttccgagtctactccaatttcctccggggaaagctgaagctgtac acaggggaggcctgcaggacaggggacagatga | Nucleotide sequence of mature hEPO cDNA | |
| 26 | gccccaccacgcctcatctgtgacagccgagtcctggagaggtacctcttgg aggccaaggaggccgagaatatcacgacgggctgtgctgaacactgcagctt gaatgagaatatcactgtcccagacaccaaagttaatttctatgcctggaag aggatggaggtcgggcagcaggccgtagaagtctggcagggcctggccctgc tgtcggaagctgtcctgcggggccaggccctgttggtcaactcttcccagcc gtgggagcccctgcagctgcatgtggataaagccgtcagtggccttcgcagc ctcaccactctgcttcgggctctgggagcccagaaggaagccatctcccctc cagatgcggcctcagctgctccactccgaacaatcactgctgacactttccg caaactcttccgagtctactccaatttcctccggggaaagctgaagctgtac acaggggaggcctgcaggacaggggacagatga | Nucleotide sequence of G113R hEPO cDNA | |
| 27 | atgctccaccaagattaatctgtgacagccgagtcctggagaggtacctctt ggaggccaaggaggccgagaatatcacgacgggctgtgctgaacactgcagc ttgaatgagaatatcactgtcccagacaccaaagttaatttctatgcctgga agaggatggaggtcgggcagcaggccgtagaagtctggcagggcctggccct gctgtcggaagctgtcctgcggggccaggccctgttggtcaactcttcccag ccgtgggagcccctgcagctgcatgtggataaagccgtcagtggccttcgca gcctcaccactctgcttcgggctctgcgagcccagaaggaagccatctcccc tccagatgcggcctcagctgctccactccgaacaatcactgctgacactttc cgcaaactcttccgagtctactccaatttcctccggggaaagctgaagctgt acacaggggaggcctgcaggacaggggacagatga | Optimized for expression of mature hEPO cDNA in E. coli | |
| 30 | MCEPAPPKPTQSAWHSFPECPALLLLLSLLLLPLGLPVLGAPPRLIC DSRVLERYILEAREAENVTMGCAQGCSFSENITVPDTKVNFYTWKR MDVGQQALEVWQGLALLSEAILRGQALLANASQPSETPQLHVDKA VSSLRSLTSLLRALGAQKEAMSLPEEASPAPLRTFTVDTLCKLFRIY SNFLRGKLTLYTGEACRRGDR | Full-length amino acid sequence of cEPO | Protein |
| 31 | APPRLICDSRVLERYILEAREAENVTMGCAQGCSFSENITVPDTKVN FYTWKRMDVGQQALEVWQGLALLSEAILRGQALLANASQPSETPQ LHVDKAVSSLRSLTSLLRALGAQKEAMSLPEEASPAPLRTFTVDTL CKLFRIYSNFLRGKLTLYTGEACRRGDR | The mature amino acid sequence of cEPO | Protein |

TABLE 2-continued

| SEQ ID # | Sequence | Notes | Protein of tRNA or RS |
|---|---|---|---|
| 32 | MGVRECPALLLLLSLLLPPLGLPALGAPPRLICDSRVLERYILEAREAENVTM GCAEGCSFGENVTVPDTKVNFYSWKRMEVEQQAVEVWQGLALLSEAILQG QALLANSSQPSETLRLHVDKAVSSLRSLTSLLRALGAQKEAISPPDAASAAPL RTFAVDTLCKLFRIYSNFLRGKLKLYTGEACRRGDR | Full-length amino acid sequence of eEPO | Protein |
| 33 | APPRLICDSRVLERYILEAREAENVTMGCAEGCSFGENVTVPDTKVNFYSWK RMEVEQQAVEVWQGLALLSEAILQGQALLANSSQPSETLRLHVDKAVSSLR SLTSLLRALGAQKEAISPPDAASAAPLRTFAVDTLCKLFRIYSNFLRGKLKLY TGEACRRGDR | The mature amino acid sequence of eEPO | Protein |
| 34 | CCGGCGGTAGTTCAGCAGGGCAGAACGGCGGACTCTAAATCCGCATGGC GCTGGTTCAAATCCGGCCCGCCGGACCA | M. jannaschii mtRNA$_{CUA}^{Tyr}$ | tRNA |

TABLE 3

SEQ ID NO: 28
Nucleotide sequence of the suppression expression construct
Nat L BB-Opti FEPO in Lucy F for feline erythropoietin

```
  1 TCGCGCGTTT CGGTGATGAC GGTGAAAACC TCTGACACAT GCAGCTCCCG GAGACGGTCA
    AGCGCGCAAA GCCACTACTG CCACTTTTGG AGACTGTGTA CGTCGAGGGC CTCTGCCAGT

61 CAGCTTGTCT GTAAGCGGAT GCCGGAGCA GACAAGCCCG TCAGGGCGCG TCAGCGGGTG
    GTCGAACAGA CATTCGCCTA CGGCCCTCGT CTGTTCGGGC AGTCCCGCGC AGTCGCCCAC

121 TTGGCGGGTG TCGGGGCTGG CTTAACTATG CGGCATCAGA GCAGATTGTA CTGAGAGTGC
    AACCGCCCAC AGCCCCGACC GAATTGATAC GCCGTAGTCT CGTCTAACAT GACTCTCACG

181 ACCATATGCC CGTCCGCGTA CCGGCGCGCC GGATGCCAAT CGATGAATTC CGGTGTGAAA
    TGGTATACGG GCAGGCGCAT GGCCGCGCGG CCTACGGTTA GCTACTTAAG GCCACACTTT

241 TACCGCACAG ATGCGTAAGG AGAAAATACC GCATCAGGCG CCATTCGCCA TTCAGGCTGC
    ATGGCGTGTC TACGCATTCC TCTTTTATGG CGTAGTCCGC GGTAAGCGGT AAGTCCGACG

301 GCAACTGTTG GGAAGGGCGA TCGGTGCGGG CCTCTTCGCT ATTACGCCAG CTGGCGAAAG
    CGTTGACAAC CCTTCCCGCT AGCCACGCCC GGAGAAGCGA TAATGCGGTC GACCGCTTTC

361 GGGGATGTGC TGCAAGGCGA TTAAGTTGGG TAACGCCAGG GTTTTCCCAG TCACGACGTT
    CCCCTACACG ACGTTCCGCT AATTCAACCC ATTGCGGTCC CAAAAGGGTC AGTGCTGCAA
                                                                      tRNA
                                                                      ~~~~~~~~~~~~~~~~~~
                                                                      H1
                                                                      ~~~~~~~~~~~~~~~~~~

421 GTAAAACGAC GGCCAGTGAA TTGATGCATC CATCAATTCA TATTTGCATG TCGCTATGTG
    CATTTTGCTG CCGGTCACTT AACTACGTAG GTAGTTAAGT ATAAACGTAC AGCGATACAC
                                            tRNA
    ~~~~~~~~~~~~~~~~~~~~~~~~~~~~~~~~~~~~~~~~~~~~~~~~~~~~~~~~~~~~~~~
                          H1
    ~~~~~~~~~~~~~~~~~~~~~~~~~~~~~~~~~~~~~~~~~~~~~~~~~~~~~~~~~~~~~~~

481 TTCTGGGAAA TCACCATAAA CGTGAAATGT CTTTGGATTT GGGAATCTTA TAAGTTCTGT
    AAGACCCTTT AGTGGTATTT GCACTTTACA GAAACCTAAA CCCTTAGAAT ATTCAAGACA
                                            tRNA
    ~~~~~~~~~~~~~~~~~~~~~~~~~~~~~~~~~~~~~~~~~~~~~~~~~~~~~~~~~~~~~~~
           H1                          Hyb1 tRNA
    ~~~~~~~~~~~~~~~~~    ~~~~~~~~~~~~~~~~~~~~~~~~~~~~~~~~~~~~~~~~~~

541 ATGAGACCAC TCGGATCCGG TGGGGTAGCG AAGTGGCTAA ACGCGGCGGA CTCTAAATCC
    TACTCTGGTG AGCCTAGGCC ACCCCATCGC TTCACCGATT TGCGCCGCCT GAGATTTAGG
                  Hyb1 tRNA
    ~~~~~~~~~~~~~~~~~~~~~~~~~~~~~~~~~~~~~~~~
                          tRNA
    ~~~~~~~~~~~~~~~~~~~~~~~~~~~~~~~~~~~~~~~~~~~~~~~~~~
                                                     Term
                                                     ~~~~~~

601 GCTCCCTTTG GGTTCGGCGG TTCGAATCCG TCCCCCACCA TTTTTTGGAA CCTAGGGAAT
    CGAGGGAAAC CCAAGCCGCC AAGCTTAGGC AGGGGGTGGT AAAAAACCTT GGATCCCTTA
```

TABLE 3-continued

```
 661  TCCGGTGTGA AATACCGCAC AGATGCGTAA GGAGAAAATA CCGCATCAGG CGCCATTCGC
       AGGCCACACT TTATGGCGTG TCTACGCATT CCTCTTTTAT GGCGTAGTCC GCGGTAAGCG

721  CATTCAGGCT GCGCAACTGT TGGGAAGGGC GATCGGTGCG GGCCTCTTCG CTATTACGCC
       GTAAGTCCGA CGCGTTGACA ACCCTTCCCG CTAGCCACGC CCGGAGAAGC GATAATGCGG

781  AGCTGGCGAA AGGGGGATGT GCTGCAAGGC GATTAAGTTG GGTAACGCCA GGGTTTTCCC
       TCGACCGCTT TCCCCCTACA CGACGTTCCG CTAATTCAAC CCATTGCGGT CCCAAAAGGG
                                                                    tRNA
                                                                  ~~~~~~~
                                                                    H1
                                                                  ~~~~~~~

841  AGTCACGACG TTGTAAAACG ACGGCCAGTG AATTGATGCA TCCATCAATT CATATTTGCA
       TCAGTGCTGC AACATTTTGC TGCCGGTCAC TTAACTACGT AGGTAGTTAA GTATAAACGT
                                  tRNA
       ~~~~~~~~~~~~~~~~~~~~~~~~~~~~~~~~~~~~~~~~~~~~~~~~~~~~~~~~~~~~~
                                   H1
       ~~~~~~~~~~~~~~~~~~~~~~~~~~~~~~~~~~~~~~~~~~~~~~~~~~~~~~~~~~~~~

901  TGTCGCTATG TGTTCTGGGA AATCACCATA AACGTGAAAT GTCTTTGGAT TTGGGAATCT
       ACAGCGATAC ACAAGACCCT TTAGTGGTAT TTGCACTTTA CAGAAACCTA AACCCTTAGA
                                  tRNA
       ~~~~~~~~~~~~~~~~~~~~~~~~~~~~~~~~~~~~~~~~~~~  ~~~~~~~~~~~~~~~~~
                   H1                                   Hyb1 tRNA
       ~~~~~~~~~~~~~~~~~~~~~~~~~~~~~~              ~~~~~~~~~~~~~~~~~~

961  TATAAGTTCT GTATGAGACC ACTCGGATCC GGTGGGGTAG CGAAGTGGCT AAACGCGGCG
       ATATTCAAGA CATACTCTGG TGAGCCTAGG CCACCCCATC GCTTCACCGA TTTGCGCCGC
                                                                    Term
                                                                  ~~~~~~
                                  tRNA
       ~~~~~~~~~~~~~~~~~~~~~~~~~~~~~~~~~~~~~~~~~~~~~~~~~~~~~~~~~~~~~
                                Hyb1 tRNA
       ~~~~~~~~~~~~~~~~~~~~~~~~~~~~~~~~~~~~~~~~~~~~~~~~~~~~~~~~

1021  GACTCTAAAT CCGCTCCCTT TGGGTTCGGC GGTTCGAATC CGTCCCCCAC CATTTTTTGG
       CTGAGATTTA GGCGAGGGAA ACCCAAGCCG CCAAGCTTAG GCAGGGGGTG GTAAAAAACC

1081  AAGACGTCGA ATTCCGGTGT GAAATACCGC ACAGATGCGT AAGGAGAAAA TACCGCATCA
       TTCTGCAGCT TAAGGCCACA CTTTATGGCG TGTCTACGCA TTCCTCTTTT ATGGCGTAGT

1141  GGCGCCATTC GCCATTCAGG CTGCGCAACT GTTGGGAAGG GCGATCGGTG CGGGCCTCTT
       CCGCGGTAAG CGGTAAGTCC GACGCGTTGA CAACCCTTCC CGCTAGCCAC GCCCGGAGAA

1201  CGCTATTACG CCAGCTGGCG AAAGGGGGAT GTGCTGCAAG GCGATTAAGT TGGGTAACGC
       GCGATAATGC GGTCGACCGC TTTCCCCCTA CACGACGTTC CGCTAATTCA ACCCATTGCG

1261  CAGGGTTTTC CCAGTCACGA CGTTGTAAAA CGACGGCCAG TGAATTGATG CATCCATCAA
       GTCCCAAAAG GGTCAGTGCT GCAACATTTT GCTGCCGGTC ACTTAACTAC GTAGGTAGTT
                                  tRNA
       ~~~~~~~~~~~~~~~~~~~~~~~~~~~~~~~~~~~~~~~~~~~~~~~~~~~~~~~~~~~~
                                   H1
       ~~~~~~~~~~~~~~~~~~~~~~~~~~~~~~~~~~~~~~~~~~~~~~~~~~~~~~~~~~~~

1321  TTCATATTTG CATGTCGCTA TGTGTTCTGG GAAATCACCA TAAACGTGAA ATGTCTTTGG
       AAGTATAAAC GTACAGCGAT ACACAAGACC CTTTAGTGGT ATTTGCACTT TACAGAAACC
                                  tRNA
       ~~~~~~~~~~~~~~~~~~~~~~~~~~~~~~~~~~~~~~~~~~~~~~~~~~~~~~~~~~~~~
                   H1                                   Hyb1 tRNA
       ~~~~~~~~~~~~~~~~~~~~~~~~~~~~~~~~~~~~~~      ~~~~~~~~~~~~~~~~~~

1381  ATTTGGGAAT CTTATAAGTT CTGTATGAGA CCACTCGGAT CCGGTGGGGT AGCGAAGTGG
       TAAACCCTTA GAATATTCAA GACATACTCT GGTGAGCCTA GGCCACCCCA TCGCTTCACC
                                  tRNA
       ~~~~~~~~~~~~~~~~~~~~~~~~~~~~~~~~~~~~~~~~~~~~~~~~~~~~~~~~~~~~
                                Hyb1 tRNA
       ~~~~~~~~~~~~~~~~~~~~~~~~~~~~~~~~~~~~~~~~~~~~~~~~~~~~~~~~

1441  CTAAACGCGG CGGACTCTAA ATCCGCTCCC TTTGGGTTCG GCGGTTCGAA TCCGTCCCCC
       GATTTGCGCC GCCTGAGATT TAGGCGAGGG AAACCCAAGC CGCCAAGCTT AGGCAGGGGG
       Term
       ~~~~~~~
          tRNA
       ~~~~~~~~~~~
        Hyb1 tRNA
       ~~~~
```

TABLE 3-continued

```
1501 ACCATTTTTT GGAACATATG GAATTCCGGT GTGAAATACC GCACAGATGC GTAAGGAGAA
     TGGTAAAAAA CCTTGTATAC CTTAAGGCCA CACTTTATGG CGTGTCTACG CATTCCTCTT

1561 AATACCGCAT CAGGCGCCAT TCGCCATTCA GGCTGCGCAA CTGTTGGGAA GGGCGATCGG
     TTATGGCGTA GTCCGCGGTA AGCGGTAAGT CCGACGCGTT GACAACCCTT CCCGCTAGCC

1621 TGCGGGCCTC TTCGCTATTA CGCCAGCTGG CGAAAGGGGG ATGTGCTGCA AGGCGATTAA
     ACGCCCGGAG AAGCGATAAT GCGGTCGACC GCTTTCCCCC TACACGACGT TCCGCTAATT

1681 GTTGGGTAAC GCCAGGGTTT TCCCAGTCAC GACGTTGTAA AACGACGGCC AGTGAATTGA
     CAACCCATTG CGGTCCCAAA AGGGTCAGTG CTGCAACATT TGCTGCCGG TCACTTAACT
                                                 tRNA
                    ~~~~~~~~~~~~~~~~~~~~~~~~~~~~~~~~~~~~~~~~~~~~~~
                                          H1
                    ~~~~~~~~~~~~~~~~~~~~~~~~~~~~~~~~~~~~~~~~~~~~~~

1741 TGCATCCATC AATTCATATT TGCATGTCGC TATGTGTTCT GGGAAATCAC CATAAACGTG
     ACGTAGGTAG TTAAGTATAA ACGTACAGCG ATACACAAGA CCCTTTAGTG GTATTTGCAC
                                     tRNA
     ~~~~~~~~~~~~~~~~~~~~~~~~~~~~~~~~~~~~~~~~~~~~~~~~~~~~~~~~~~~
                          H1                              Hyb1 tRNA
     ~~~~~~~~~~~~~~~~~~~~~~~~~~~~~~~~~~~~~~~~~~~~~~~~    ~~~~~~

1801 AAATGTCTTT GGATTTGGGA ATCTTATAAG TTCTGTATGA GACCACTCGG ATCCGTGGG
     TTTACAGAAA CCTAAACCCT TAGAATATTC AAGACATACT CTGGTGAGCC TAGGCCACCC
                                     tRNA
     ~~~~~~~~~~~~~~~~~~~~~~~~~~~~~~~~~~~~~~~~~~~~~~~~~~~~~~~~~~~~~~~
                                Hyb1 tRNA
     ~~~~~~~~~~~~~~~~~~~~~~~~~~~~~~~~~~~~~~~~~~~~~~~~~~~~~~~~~~~~~~~

1861 GTAGCGAAGT GGCTAAACGC GGCGGACTCT AAATCCGCTC CCTTTGGGTT CGGCGGTTCG
     CATCGCTTCA CCGATTTGCG CCGCCTGAGA TTTAGGCGAG GGAAACCCAA GCCGCCAAGC
                                Term
                                ~~~~~~~
             tRNA
     ~~~~~~~~~~~~~~~~~~~~~~~~
         Hyb1 tRNA
     ~~~~~~~~~~~~~~~~~~

1921 AATCCGTCCC CCACCATTTT TTGGAACTTA ATTAAGGCGC GCCGGATGCC AATCGGCCAT
     TTAGGCAGGG GGTGGTAAAA AACCTTGAAT TAATTCCGCG CGGCCTACGG TTAGCCGGTA

1981 CACCATCCAA CGGGAAGGCG ATGAATTCCG GTGTGAAATA CCGCACAGAT GCGTAAGGAG
     GTGGTAGGTT GCCCTTCCGC TACTTAAGGC CACACTTTAT GGCGTGTCTA CGCATTCCTC

2041 AAAATACCGC ATCAGGCGCC ATTCGCCATT CAGGCTGCGC AACTGTTGGG AAGGGCGATC
     TTTTATGGCG TAGTCCGCGG TAAGCGGTAA GTCCGACGCG TTGACAACCC TTCCCGCTAG

2101 GGTGCGGGCC TCTTCGCTAT TACGCCAGCT GGCGAAAGGG GATGTGCTG CAAGGCGATT
     CCACGCCCGG AGAAGCGATA ATGCGGTCGA CCGCTTTCCC CTACACGAC GTTCCGCTAA

2161 AAGTTGGGTA ACGCCAGGGT TTTCCCAGTC ACGACGTTGT AAAACGACGG CCAGTGAATT
     TTCAACCCAT TGCGGTCCCA AAAGGGTCAG TGCTGCAACA TTTTGCTGCC GGTCACTTAA
                                                 tRNA
                    ~~~~~~~~~~~~~~~~~~~~~~~~~~~~~~~~~~~~~~~~~~~~~~
                                          H1
                    ~~~~~~~~~~~~~~~~~~~~~~~~~~~~~~~~~~~~~~~~~~~~~~

2221 GATGCATCCA TCAATTCATA TTTGCATGTC GCTATGTGTT CTGGGAAATC ACCATAAACG
     CTACGTAGGT AGTTAAGTAT AAACGTACAG CGATACACAA GACCCTTTAG TGGTATTTGC
                                      H1
     ~~~~~~~~~~~~~~~~~~~~~~~~~~~~~~~~~~~~~~~~~~~~~~~~~~~~~~~~~~~
                              tRNA
     ~~~~~~~~~~~~~~~~~~~~~~~~~~~~~~~~~~~~~~~~~~~~~~~~~~~~~~~~~~~~
                                                         Hyb1 tRNA
                                                         ~~~~

2281 TGAAATGTCT TTGGATTTGG GAATCTTATA AGTTCTGTAT GAGACCACTC GGATCCGGTG
     ACTTTACAGA AACCTAAACC CTTAGAATAT TCAAGACATA CTCTGGTGAG CCTAGGCCAC
                                     tRNA
     ~~~~~~~~~~~~~~~~~~~~~~~~~~~~~~~~~~~~~~~~~~~~~~~~~~~~~~~~~~~~~~~
                                Hyb1 tRNA
     ~~~~~~~~~~~~~~~~~~~~~~~~~~~~~~~~~~~~~~~~~~~~~~~~~~~~~~~~~~~~~~~

2341 GGGTAGCGAA GTGGCTAAAC GCGGCGGACT CTAAATCCGC TCCCTTTGGG TTCGGCGGTT
     CCCATCGCTT CACCGATTTG CGCCGCCTGA GATTTAGGCG AGGGAAACCC AAGCCGCCAA
             Hyb1 tRNA
     ~~~~~~~~~~~~~~~~~~~
             tRNA
```

TABLE 3-continued

```
                          ~~~~~~~~~~~~~~~~~~~~~~~~~~~
                                     Term
                                   ~~~~~~~

2401  CGAATCCGTC CCCCACCATT TTTTGGAACC TAGGGAATTC CGGTGTGAAA TACCGCACAG
      GCTTAGGCAG GGGGTGGTAA AAAACCTTGG ATCCCTTAAG GCCACACTTT ATGGCGTGTC

2461  ATGCGTAAGG AGAAAATACC GCATCAGGCG CCATTCGCCA TTCAGGCTGC GCAACTGTTG
      TACGCATTCC TCTTTTATGG CGTAGTCCGC GGTAAGCGGT AAGTCCGACG CGTTGACAAC

2521  GGAAGGGCGA TCGGTGCGGG CCTCTTCGCT ATTACGCCAG CTGGCGAAAG GGGGATGTGC
      CCTTCCCGCT AGCCACGCCC GGAGAAGCGA TAATGCGGTC GACCGCTTTC CCCCTACACG

2581  TGCAAGGCGA TTAAGTTGGG TAACGCCAGG GTTTTCCCAG TCACGACGTT GTAAAACGAC
      ACGTTCCGCT AATTCAACCC ATTGCGGTCC CAAAAGGGTC AGTGCTGCAA CATTTGCTG
                                                           tRNA
                                              ~~~~~~~~~~~~~~~~~~~~~~~~~~~~~~
                                                          H1
                                              ~~~~~~~~~~~~~~~~~~~~~~~~~~~~~~

2641  GGCCAGTGAA TTGATGCATC CATCAATTCA TATTTGCATG TCGCTATGTG TTCTGGGAAA
      CCGGTCACTT AACTACGTAG GTAGTTAAGT ATAAACGTAC AGCGATACAC AAGACCCTTT
                                       tRNA
      ~~~~~~~~~~~~~~~~~~~~~~~~~~~~~~~~~~~~~~~~~~~~~~~~~~~~~~~~~~~~~~~~~~
                                        H1
      ~~~~~~~~~~~~~~~~~~~~~~~~~~~~~~~~~~~~~~~~~~~~~~~~~~~~~~~~~~~~~~~~~~

2701  TCACCATAAA CGTGAAATGT CTTTGGATTT GGGAATCTTA TAAGTTCTGT ATGAGACCAC
      AGTGGTATTT GCACTTTACA GAAACCTAAA CCCTTAGAAT ATTCAAGACA TACTCTGGTG
                                       tRNA
      ~~~~~~~~~~~~~~~~~~~~~~~~~~~~~~~~~~~~~~~~~~~~~~~~~~~~~~~~~~~~~~~~~~
      H1                               Hyb1 tRNA
      ~~~         ~~~~~~~~~~~~~~~~~~~~~~~~~~~~~~~~~~~~~~~~~~~~~~~~~~~~~~

2761  TCGGATCCGG TGGGGTAGCG AAGTGGCTAA ACGCGGCGGA CTCTAAATCC GCTCCCTTTG
      AGCCTAGGCC ACCCCATCGC TTCACCGATT TGCGCCGCCT GAGATTTAGG CGAGGGAAAC
                                                       Term
                                                     ~~~~~~
                    tRNA
      ~~~~~~~~~~~~~~~~~~~~~~~~~~~~~~~~~~~~~~~~~
                   Hyb1 tRNA
      ~~~~~~~~~~~~~~~~~~~~~~~~~~~~~~~~~~~~~~~~~

2821  GGTTCGGCGG TTCGAATCCG TCCCCCACCA TTTTTTGGAA GACGTCGAAT TCCGGTGTGA
      CCAAGCCGCC AAGCTTAGGC AGGGGGTGGT AAAAAACCTT CTGCAGCTTA AGGCCACACT

2881  AATACCGCAC AGATGCGTAA GGAGAAAATA CCGCATCAGG CGCCATTCGC CATTCAGGCT
      TTATGGCGTG TCTACGCATT CCTCTTTTAT GGCGTAGTCC GCGGTAAGCG GTAAGTCCGA

2941  GCGCAACTGT TGGGAAGGGC GATCGGTGCG GGCCTCTTCG CTATTACGCC AGCTGGCGAA
      CGCGTTGACA ACCCTTCCCG CTAGCCACGC CGGAGAAGC GATAATGCGG TCGACCGCTT

3001  AGGGGGATGT GCTGCAAGGC GATTAAGTTG GTAACGCCA GGGTTTTCCC AGTCACGACG
      TCCCCCTACA CGACGTTCCG CTAATTCAAC CCATTGCGGT CCCAAAAGGG TCAGTGCTGC
                                                                 tRNA
                                                       ~~~~~~~~~~~~~~~~~~~
                                                                H1
                                                       ~~~~~~~~~~~~~~~~~~~

3061  TTGTAAAACG ACGGCCAGTG AATTGATGCA TCCATCAATT CATATTTGCA TGTCGCTATG
      AACATTTTGC TGCCGGTCAC TTAACTACGT AGGTAGTTAA GTATAAACGT ACAGCGATAC
                                       tRNA
      ~~~~~~~~~~~~~~~~~~~~~~~~~~~~~~~~~~~~~~~~~~~~~~~~~~~~~~~~~~~~~~~
                                        H1
      ~~~~~~~~~~~~~~~~~~~~~~~~~~~~~~~~~~~~~~~~~~~~~~~~~~~~~~~~~~~~~~~

3121  TGTTCTGGGA AATCACCATA AACGTGAAAT GTCTTTGGAT TGGGAATCT TATAAGTTCT
      ACAAGACCCT TTAGTGGTAT TTGCACTTTA CAGAAACCTA AACCCTTAGA ATATTCAAGA
                                         tRNA
      ~~~~~~~~~~~~~~~~~~~~~~~~~~~~~~~~~~~~~~~~~~~~~~~~~~~~~~~~~~~~~~~
               H1                       Hyb1 tRNA
      ~~~~~~~~~~~~~~~~       ~~~~~~~~~~~~~~~~~~~~~~~~~~~~~~~~~~~~~~~~~

3181  GTATGAGACC ACTCGGATCC GGTGGGGTAG CGAAGTGGCT AAACGCGGCG GACTCTAAAT
      CATACTCTGG TGAGCCTAGG CCACCCCATC GCTTCACCGA TTTGCGCCGC CTGAGATTTA
```

TABLE 3-continued

```
                                                        Term
                                                       ~~~~~~
                     tRNA
       ~~~~~~~~~~~~~~~~~~~~~~~~~~~~~~~~~~~~~~~~~~~~~~~~~~~~~~
                     Hyb1 tRNA
       ~~~~~~~~~~~~~~~~~~~~~~~~~~~~~~~~~~~~~~~~~~~~~~~~

3241   CCGCTCCCTT TGGGTTCGGC GGTTCGAATC CGTCCCCCAC CATTTTTTGG AACATATGGA
       GGCGAGGGAA ACCCAAGCCG CCAAGCTTAG GCAGGGGGTG GTAAAAAACC TTGTATACCT

3301   ATTCCGGTGT GAAATACCGC ACAGATGCGT AAGGAGAAAA TACCGCATCA GGCGCCATTC
       TAAGGCCACA CTTTATGGCG TGTCTACGCA TTCCTCTTTT ATGGCGTAGT CCGCGGTAAG

3361   GCCATTCAGG CTGCGCAACT GTTGGGAAGG GCGATCGGTG CGGGCCTCTT CGCTATTACG
       CGGTAAGTCC GACGCGTTGA CAACCCTTCC CGCTAGCCAC GCCCGGAGAA GCGATAATGC

3421   CCAGCTGGCG AAAGGGGGAT GTGCTGCAAG GCGATTAAGT TGGGTAACGC CAGGGTTTTC
       GGTCGACCGC TTTCCCCCTA CACGACGTTC CGCTAATTCA ACCCATTGCG GTCCCAAAAG
                                                                 tRNA
                                                                ~~~~~
                                                                  H1
                                                                ~~~~~

3481   CCAGTCACGA CGTTGTAAAA CGACGGCCAG TGAATTGATG CATCCATCAA TTCATATTTG
       GGTCAGTGCT GCAACATTTT GCTGCCGGTC ACTTAACTAC GTAGGTAGTT AAGTATAAAC
                                  tRNA
       ~~~~~~~~~~~~~~~~~~~~~~~~~~~~~~~~~~~~~~~~~~~~~~~~~~~~~~~~~~~~~~
                                   H1
       ~~~~~~~~~~~~~~~~~~~~~~~~~~~~~~~~~~~~~~~~~~~~~~~~~~~~~~~~~~~~~~

3541   CATGTCGCTA TGTGTTCTGG GAAATCACCA TAAACGTGAA ATGTCTTTGG ATTTGGGAAT
       GTACAGCGAT ACACAAGACC CTTTAGTGGT ATTTGCACTT TACAGAAACC TAAACCCTTA
                                   tRNA
       ~~~~~~~~~~~~~~~~~~~~~~~~~~~~~~~~~~~~~~~~~~~~~~~~~~~~~~~~~~~~~~
                    H1                         Hyb1 tRNA
       ~~~~~~~~~~~~~~~~~~~~~~~~~~~~       ~~~~~~~~~~~~~~~~~~~~~~~~~~~~

3601   CTTATAAGTT CTGTATGAGA CCACTCGGAT CCGGTGGGGT AGCGAAGTGG CTAAACGCGG
       GAATATTCAA GACATACTCT GGTGAGCCTA GGCCACCCCA TCGCTTCACC GATTTGCGCC
                                                                 Term
                                                                ~~~~~~
                     tRNA
       ~~~~~~~~~~~~~~~~~~~~~~~~~~~~~~~~~~~~~~~~~~~~~~~~~~~~~~~~~~~~~~
                     Hyb1 tRNA
       ~~~~~~~~~~~~~~~~~~~~~~~~~~~~~~~~~~~~~~~~~~~~~~~~~~~~~~~~~~~~~~

3661   CGGACTCTAA ATCCGCTCCC TTTGGGTTCG GCGGTTCGAA TCCGTCCCCC ACCATTTTTT
       GCCTGAGATT TAGGCGAGGG AAACCCAAGC CGCCAAGCTT AGGCAGGGGG TGGTAAAAAA
                                                 SVO
           ~~~~~~~~~~~~~~~~~~~~~~~~~~~~~~~~~~~~~~~~~~~~~~~~~~~~~~~~~~~

3721   GGAACTTAAT TAAGTACGGG CCTCCAAAAA AGCCTCCTCA CTACTTCTGG AATAGCTCAG
       CCTTGAATTA ATTCATGCCC GGAGGTTTTT TCGGAGGAGT GATGAAGACC TTATCGAGTC
                                                 SVO
       ~~~~~~~~~~~~~~~~~~~~~~~~~~~~~~~~~~~~~~~~~~~~~~~~~~~~~~~~~~~~~~

3781   AGGCAGAGGC GGCCTCGGCC TCTGCATAAA TAAAAAAAAT TAGTCAGCCA TGGGGCGGAG
       TCCGTCTCCG CCGGAGCCGG AGACGTATTT ATTTTTTTTA ATCAGTCGGT ACCCCGCCTC
                                                 SVO
       ~~~~~~~~~~~~~~~~~~~~~~~~~~~~~~~~~~~~~~~~~~~~~~~~~~~~~~~~~~~~~~

3841   AATGGGCGGA ACTGGGCGGA GTTAGGGGCG GGATGGGCGG AGTTAGGGGC GGGACTATGG
       TTACCCGCCT TGACCCGCCT CAATCCCCGC CCTACCCGCC TCAATCCCCG CCCTGATACC
                                                 SVO
       ~~~~~~~~~~~~~~~~~~~~~~~~~~~~~~~~~~~~~~~~~~~~~~~~~~~~~~~~~~~~~~

3901   TTGCTGACTA ATTGAGATGC ATGCTTTGCA TACTTCTGCC TGCTGGGGAG CCTGGGGACT
       AACGACTGAT TAACTCTACG TACGAAACGT ATGAAGACGG ACGACCCCTC GGACCCCTGA
                        SVO                                          CMV
       ~~~~~~~~~~~~~~~~~~~~~~~~~~~~~~~~~~~~~~~~~~~~~~~~~~~~~~~~~   ~~~

3961   TTCCACACCT GGTTGCTGAC TAATTGAGAT GCATGCTTTG CATACTTCTG CCCGCGGAGT
       AAGGTGTGGA CCAACGACTG ATTAACTCTA CGTACGAAAC GTATGAAGAC GGGCGCCTCA
                                 CMV
       ~~~~~~~~~~~~~~~~~~~~~~~~~~~~~~~~~~~~~~~~~~~~~~~~~~~~~~~~~~~~~~

4021   TATTAATAGT AATCAATTAC GGGGTCATTA GTTCATAGCC CATATATGGA GTTCCGCGTT
       ATAATTATCA TTAGTTAATG CCCCAGTAAT CAAGTATCGG GTATATACCT CAAGGCGCAA
                                 CMV
       ~~~~~~~~~~~~~~~~~~~~~~~~~~~~~~~~~~~~~~~~~~~~~~~~~~~~~~~~~~~~~~
```

TABLE 3-continued

```
4081  ACATAACTTA CGGTAAATGG CCCGCCTGGC TGACCGCCCA ACGACCCCCG CCCATTGACG
      TGTATTGAAT GCCATTTACC GGGCGGACCG ACTGGCGGGT TGCTGGGGGC GGGTAACTGC
                                         CMV
      ~~~~~~~~~~~~~~~~~~~~~~~~~~~~~~~~~~~~~~~~~~~~~~~~~~~~~~~~~~~~

4141  TCAATAATGA CGTATGTTCC CATAGTAACG CCAATAGGGA CTTTCCATTG ACGTCAATGG
      AGTTATTACT GCATACAAGG GTATCATTGC GGTTATCCCT GAAAGGTAAC TGCAGTTACC
                                         CMV
      ~~~~~~~~~~~~~~~~~~~~~~~~~~~~~~~~~~~~~~~~~~~~~~~~~~~~~~~~~~~~

4201  GTGGAGTATT TACGGTAAAC TGCCCACTTG GCAGTACATC AAGTGTATCA TATGCCAAGT
      CACCTCATAA ATGCCATTTG ACGGGTGAAC CGTCATGTAG TTCACATAGT ATACGGTTCA
                                         CMV
      ~~~~~~~~~~~~~~~~~~~~~~~~~~~~~~~~~~~~~~~~~~~~~~~~~~~~~~~~~~~~

4261  ACGCCCCCTA TTGACGTCAA TGACGGTAAA TGGCCCGCCT GGCATTATGC CCAGTACATG
      TGCGGGGGAT AACTGCAGTT ACTGCCATTT ACCGGGCGGA CCGTAATACG GGTCATGTAC
                                         CMV
      ~~~~~~~~~~~~~~~~~~~~~~~~~~~~~~~~~~~~~~~~~~~~~~~~~~~~~~~~~~~~

4321  ACCTTATGGG ACTTTCCTAC TTGGCAGTAC ATCTACGTAT TAGTCATCGC TATTACCATG
      TGGAATACCC TGAAAGGATG AACCGTCATG TAGATGCATA ATCAGTAGCG ATAATGGTAC
                                         CMV
      ~~~~~~~~~~~~~~~~~~~~~~~~~~~~~~~~~~~~~~~~~~~~~~~~~~~~~~~~~~~~

4381  GTGATGCGGT TTTGGCAGTA CATCAATGGG CGTGGATAGC GGTTTGACTC ACGGGGATTT
      CACTACGCCA AAACCGTCAT GTAGTTACCC GCACCTATCG CCAAACTGAG TGCCCCTAAA
                                         CMV
      ~~~~~~~~~~~~~~~~~~~~~~~~~~~~~~~~~~~~~~~~~~~~~~~~~~~~~~~~~~~~

4441  CCAAGCCTCC ACCCCATTGA CGTCAATGGG AGTTTGTTTT GGCACCAAAA TCAACGGGAC
      GGTTCGGAGG TGGGGTAACT GCAGTTACCC TCAAACAAAA CCGTGGTTTT AGTTGCCCTG
                                         CMV
      ~~~~~~~~~~~~~~~~~~~~~~~~~~~~~~~~~~~~~~~~~~~~~~~~~~~~~~~~~~~~

4501  TTTCCAAAAT GTCGTAACAA CTCCGCCCCA TTGACGCAAA TGGGCGGTAG GCGTGTACGG
      AAAGGTTTTA CAGCATTGTT GAGGCGGGGT AACTGCGTTT ACCCGCCATC CGCACATGCC
                                         CMV
      ~~~~~~~~~~~~~~~~~~~~~~~~~~~~~~~~~~~~~~~~~~~~~~~~~~~~~~~~~~~~

4561  TGGGAGGTCT ATATAAGCAG AGCTCTCTGG CTAACTAGAG AACCCACTGC TTACTGGCTT
      ACCCTCCAGA TATATTCGTC TCGAGAGACC GATTGATCTC TTGGGTGACG AATGACCGAA
          CMV                                         Nat L
      ~~~~~~~~~                    ~~~~~~~~~~~~~~~~~~~~~~~~~~~~~~~~~

4621  ATCGAAATTA CTAGTCCACC ATGGGGTCGT GCAATGTCC TGCCCTGCTG CTTCTGCTAT
      TAGCTTTAAT GATCAGGTGG TACCCCAGCA CGCTTACAGG ACGGGACGAC GAAGACGATA
                     Nat L
      ~~~~~~~~~~~~~~~~~~~~~~~~~~~~~~~~~~~~~~~~~~
                                                          BB-Opti FEPO
                                                 ~~~~~~~~~~~~~~~~~~~~

4681  CTTTGCTGCT GCTTCCCCTG GGCCTCCCAG TCCTGGGCGC CCCCCCTCGC CTCATCTGTG
      GAAACGACGA CGAAGGGGAC CCGGAGGGTC AGGACCCGCG GGGGGGAGCG GAGTAGACAC
                              BB-Opti FEPO
      ~~~~~~~~~~~~~~~~~~~~~~~~~~~~~~~~~~~~~~~~~~~~~~~~~~~~~~~~~~~~

4741  ACAGCCGAGT CCTGGAGAGG TACATTCTGG AGGCCAGGGA GGCCGAAAAT GTGACCATGG
      TGTCGGCTCA GGACCTCTCC ATGTAAGACC TCCGGTCCCT CCGGCTTTTA CACTGGTACC
                              BB-Opti FEPO
      ~~~~~~~~~~~~~~~~~~~~~~~~~~~~~~~~~~~~~~~~~~~~~~~~~~~~~~~~~~~~

4801  GCTGCGCTGA AGGCTGCAGC TTCAGTGAGA ATATCACCGT TCCGGACACC AAGGTCAACT
      CGACGCGACT TCCGACGTCG AAGTCACTCT TATAGTGGCA AGGCCTGTGG TTCCAGTTGA
                              BB-Opti FEPO
      ~~~~~~~~~~~~~~~~~~~~~~~~~~~~~~~~~~~~~~~~~~~~~~~~~~~~~~~~~~~~

4861  TCTATACCTG GAAGAGGATG GACGTCGGGC AGCAGGCTGT GGAAGTCTGG CAGGGCCTCG
      AGATATGGAC CTTCTCCTAC CTGCAGCCCG TCGTCCGACA CCTTCAGACC GTCCCGGAGC
                              BB-Opti FEPO
      ~~~~~~~~~~~~~~~~~~~~~~~~~~~~~~~~~~~~~~~~~~~~~~~~~~~~~~~~~~~~

4921  CCCTCCTCAG CGAAGCCATC CTGCGGGGCC AGGCCCTGCT GGCCAACTCC TCCCAGCCCT
      GGGAGGAGTC GCTTCGGTAG GACGCCCCGG TCCGGGACGA CCGGTTGAGG AGGGTCGGGA
                              BB-Opti FEPO
      ~~~~~~~~~~~~~~~~~~~~~~~~~~~~~~~~~~~~~~~~~~~~~~~~~~~~~~~~~~~~
```

TABLE 3-continued

```
4981 CTGAGACCCT GCAGCTGCAT GTCGACAAGG CCGTCAGCAG CCTGCGCAGC CTCACCTCCC
     GACTCTGGGA CGTCGACGTA CAGCTGTTCC GGCAGTCGTC GGACGCGTCG GAGTGGAGGG
                              BB-Opti FEPO
     ~~~~~~~~~~~~~~~~~~~~~~~~~~~~~~~~~~~~~~~~~~~~~~~~~~~~~~~~~~~~~~

5041 TGCTGCGCGC ACTGGGAGCC CAGAAGGAAG CCACCTCCCT TCCCGAGGCA ACCTCTGCCG
     ACGACGCGCG TGACCCTCGG GTCTTCCTTC GGTGGAGGGA AGGGCTCCGT TGGAGACGGC
                              BB-Opti FEPO
     ~~~~~~~~~~~~~~~~~~~~~~~~~~~~~~~~~~~~~~~~~~~~~~~~~~~~~~~~~~~~~~

5101 CCCCCTTAAG AACCTTCACT GTGGACACTT TGTGCAAGCT TTTCCGAATC TACTCCAACT
     GGGGGAATTC TTGGAAGTGA CACCTGTGAA ACACGTTCGA AAAGGCTTAG ATGAGGTTGA
                              BB-Opti FEPO
     ~~~~~~~~~~~~~~~~~~~~~~~~~~~~~~~~~~~~~~~~~~~~~~~~~~~~~~~~~~~~~~

5161 TCCTGCGGGG CAAGCTGACG CTGTACACAG GGGAGGCCTG CCGAAGAGGA GACAGGTGAG
     AGGACGCCCC GTTCGACTGC GACATGTGTC CCCTCCGGAC GGCTTCTCCT CTGTCCACTC
                                   BGH
                ~~~~~~~~~~~~~~~~~~~~~~~~~~~~~~~~~~~~~~~~~~~~~~~~~~~

5221 CGGCCGCATC AGCCTCGACT GTGCCTTCTA GTTGCCAGCC ATCTGTTGTT TGCCCCTCCC
     GCCGGCGTAG TCGGAGCTGA CACGGAAGAT CAACGGTCGG TAGACAACAA ACGGGGAGGG
                                   BGH
     ~~~~~~~~~~~~~~~~~~~~~~~~~~~~~~~~~~~~~~~~~~~~~~~~~~~~~~~~~~~~~~

5281 CCGTGCCTTC CTTGACCCTG GAAGGTGCCA CTCCCACTGT CCTTTCCTAA TAAAATGAGG
     GGCACGGAAG GAACTGGGAC CTTCCACGGT GAGGGTGACA GGAAAGGATT ATTTTACTCC
                                   BGH
     ~~~~~~~~~~~~~~~~~~~~~~~~~~~~~~~~~~~~~~~~~~~~~~~~~~~~~~~~~~~~~~

5341 AAATTGCATC GCATTGTCTG AGTAGGTGTC ATTCTATTCT GGGGGGTGGG GTGGGGCAGG
     TTTAACGTAG CGTAACAGAC TCATCCACAG TAAGATAAGA CCCCCCACCC CACCCCGTCC
                                   BGH
     ~~~~~~~~~~~~~~~~~~~~~~~~~~~~~~~~~~~~~~~~~~~~~~~~~~~~~~~~~~~~~~~

5401 ACAGCAAGGG GGAGGATTGG GAAGACAATA GCAGGCATGC TGGGGATGCG GTGGGCTCTA
     TGTCGTTCCC CCTCCTAACC CTTCTGTTAT CGTCCGTACG ACCCCTACGC CACCCGAGAT
                                                               Beta
                                                        ~~~~~~~~~~~~~~~~~~~~~~~~~~~~~

5461 TGGCTTCTGA GGCGGAAAGA ACCAGTGTAC AGCTTTGCTT CTCAATTTCT TATTTGCATA
     ACCGAAGACT CCGCCTTTCT TGGTCACATG TCGAAACGAA GAGTTAAAGA ATAAACGTAT
                                   Beta
     ~~~~~~~~~~~~~~~~~~~~~~~~~~~~~~~~~~~~~~~~~~~~~~~~~~~~~~~~~~~~~~

5521 ATGAGAAAAA AAGGAAAATT AATTTTAACA CCAATTCAGT AGTTGATTGA GCAAATGCGT
     TACTCTTTTT TTCCTTTTAA TTAAAATTGT GGTTAAGTCA TCAACTAACT CGTTTACGCA
                                   Beta
     ~~~~~~~~~~~~~~~~~~~~~~~~~~~~~~~~~~~~~~~~~~~~~~~~~~~~~~~~~~~~~~

5581 TGCCAAAAAG GATGCTTTAG AGACAGTGTT CTCTGCACAG ATAAGGACAA ACATTATTCA
     ACGGTTTTTC CTACGAAATC TCTGTCACAA GAGACGTGTC TATTCCTGTT TGTAATAAGT
                                   Beta
     ~~~~~~~~~~~~~~~~~~~~~~~~~~~~~~~~~~~~~~~~~~~~~~~~~~~~~~~~~~~~~~

5641 GAGGGAGTAC CCAGAGCTGA GACTCCTAAG CCAGTGAGTG GCACAGCATC CAGGGAGAAA
     CTCCCTCATG GGTCTCGACT CTGAGGATTC GGTCACTCAC CGTGTCGTAG GTCCCTCTTT
                                   Beta
     ~~~~~~~~~~~~~~~~~~~~~~~~~~~~~~~~~~~~~~~~~~~~~~~~~~~~~~~~~~~~~~

5701 TATGCTTGTC ATCACCGAAG CCTGATTCCG TAGAGCCACA CCCTGGTAAG GGCCAATCTG
     ATACGAACAG TAGTGGCTTC GGACTAAGGC ATCTCGGTGT GGGACCATTC CCGGTTAGAC
                                   Beta
     ~~~~~~~~~~~~~~~~~~~~~~~~~~~~~~~~~~~~~~~~~~~~~~~~~~~~~~~~~~~~~~

5761 CTCACACAGG ATAGAGAGGG CAGGAGCCAG GGCAGAGCAT ATAAGGTGAG GTAGGATCAG
     GAGTGTGTCC TATCTCTCCC GTCCTCGGTC CCGTCTCGTA TATTCCACTC CATCCTAGTC
                  Beta
     ~~~~~~~~~~~~~~~~~~~~~~~~~~~~~~~~~~~~~~

5821 TTGCTCCTCA CATTTGCTTC TGACATAGTT GTGTTGGGAG CTTGGATAGC TTGGGGGGGG
     AACGAGGAGT GTAAACGAAG ACTGTATCAA CACAACCCTC GAACCTATCG AACCCCCCCC

5881 GACAGCTCAG GGCTGCGATT TCGCGCCAAC TTGACGGCAA TCCTAGCGTG AAGGCTGGTA
     CTGTCGAGTC CCGACGCTAA AGCGCGGTTG AACTGCCGTT AGGATCGCAC TTCCGACCAT
                                 OptEcAFRS
                  ~~~~~~~~~~~~~~~~~~~~~~~~~~~~~~~~~~~~~~~~~~~~~~~~
```

TABLE 3-continued

```
5941  GGATTTTATC CCTCGAGCCA CCATGGCCTC CAGCAACCTG ATCAAGCAGC TCCAGGAGAG
      CCTAAAATAG GGAGCTCGGT GGTACCGGAG GTCGTTGGAC TAGTTCGTCG AGGTCCTCTC
                          OptEcAFRS
      ~~~~~~~~~~~~~~~~~~~~~~~~~~~~~~~~~~~~~~~~~~~~~~~~~~~~~~~~~~~~~~

6001  GGGCCTCGTG GCTCAGGTCA CCGACGAAGA AGCACTCGCT GAAAGACTGG CCCAGGGACC
      CCCGGAGCAC CGAGTCCAGT GGCTGCTTCT TCGTGAGCGA CTTTCTGACC GGGTCCCTGG
                          OptEcAFRS
      ~~~~~~~~~~~~~~~~~~~~~~~~~~~~~~~~~~~~~~~~~~~~~~~~~~~~~~~~~~~~~~

6061  CATTGCACTG ATCTGCGGGT TCGATCCTAC AGCCGACTCT CTCCACCTGG GTCATCTCGT
      GTAACGTGAC TAGACGCCCA AGCTAGGATG TCGGCTGAGA GAGGTGGACC CAGTAGAGCA
                          OptEcAFRS
      ~~~~~~~~~~~~~~~~~~~~~~~~~~~~~~~~~~~~~~~~~~~~~~~~~~~~~~~~~~~~~~

6121  GCCACTGCTG TGTCTCAAAC GGTTTCAGCA GGCTGGCCAC AAGCCCGTCG CACTGGTGGG
      CGGTGACGAC ACAGAGTTTG CCAAAGTCGT CCGACCGGTG TTCGGGCAGC GTGACCACCC
                          OptEcAFRS
      ~~~~~~~~~~~~~~~~~~~~~~~~~~~~~~~~~~~~~~~~~~~~~~~~~~~~~~~~~~~~~~

6181  AGGTGCTACT GGGCTGATTG GCGATCCTAG TTTCAAAGCC GCAGAGCGCA AGCTCAATAC
      TCCACGATGA CCCGACTAAC CGCTAGGATC AAAGTTTCGG CGTCTCGCGT TCGAGTTATG
                          OptEcAFRS
      ~~~~~~~~~~~~~~~~~~~~~~~~~~~~~~~~~~~~~~~~~~~~~~~~~~~~~~~~~~~~~~

6241  CGAGGAGACA GTGCAGGAAT GGGTCGACAA AATCCGAAAG CAGGTCGCCC CATTTCTGGA
      GCTCCTCTGT CACGTCCTTA CCCAGCTGTT TTAGGCTTTC GTCCAGCGGG GTAAAGACCT
                          OptEcAFRS
      ~~~~~~~~~~~~~~~~~~~~~~~~~~~~~~~~~~~~~~~~~~~~~~~~~~~~~~~~~~~~~~

6301  TTTCGACTGC GGAGAGAACT CAGCTATTGC CGCAAATAAC TACGATTGGT TTGGGAATAT
      AAAGCTGACG CCTCTCTTGA GTCGATAACG GCGTTTATTG ATGCTAACCA AACCCTTATA
                          OptEcAFRS
      ~~~~~~~~~~~~~~~~~~~~~~~~~~~~~~~~~~~~~~~~~~~~~~~~~~~~~~~~~~~~~~

6361  GAACGTCCTC ACTTTCCTGC GTGACATCGG TAAACATTTT TCCGTGAATC AGATGATTAA
      CTTGCAGGAG TGAAAGGACG CACTGTAGCC ATTTGTAAAA AGGCACTTAG TCTACTAATT
                          OptEcAFRS
      ~~~~~~~~~~~~~~~~~~~~~~~~~~~~~~~~~~~~~~~~~~~~~~~~~~~~~~~~~~~~~~

6421  CAAGGAAGCT GTGAAGCAGA GGCTAATAG AGAGGGCCAG GGAATCAGCT TCACCGAATT
      GTTCCTTCGA CACTTCGTCT CCGACTTATC TCTCCCGGTC CCTTAGTCGA AGTGGCTTAA
                          OptEcAFRS
      ~~~~~~~~~~~~~~~~~~~~~~~~~~~~~~~~~~~~~~~~~~~~~~~~~~~~~~~~~~~~~~

6481  TTCTTATAAT CTCCTGCAGG GGTACGGTAT GGCCTGTGCA AACAAACAGT ATGGCGTCGT
      AAGAATATTA GAGGACGTCC CCATGCCATA CCGGACACGT TTGTTTGTCA TACCGCAGCA
                          OptEcAFRS
      ~~~~~~~~~~~~~~~~~~~~~~~~~~~~~~~~~~~~~~~~~~~~~~~~~~~~~~~~~~~~~~

6541  GCTGCAGATT GGAGGCAGTG ATCAGTGGGG GAACATCACA TCAGGTATTG ACCTCACTCG
      CGACGTCTAA CCTCCGTCAC TAGTCACCCC CTTGTAGTGT AGTCCATAAC TGGAGTGAGC
                          OptEcAFRS
      ~~~~~~~~~~~~~~~~~~~~~~~~~~~~~~~~~~~~~~~~~~~~~~~~~~~~~~~~~~~~~~

6601  GCGCCTGCAC CAGAATCAGG TCTTTGGACT CACCGTGCCC CTGATCACAA AGGCTGATGG
      CGCGGACGTG GTCTTAGTCC AGAAACCTGA GTGGCACGGG GACTAGTGTT TCCGACTACC
                          OptEcAFRS
      ~~~~~~~~~~~~~~~~~~~~~~~~~~~~~~~~~~~~~~~~~~~~~~~~~~~~~~~~~~~~~~

6661  CACAAAATTT GGTAAGACCG AGGGTGGAGC CGTGTGGCTG GACCCTAAAA AGACATCCCC
      GTGTTTTAAA CCATTCTGGC TCCCACCTCG GCACACCGAC CTGGGATTTT TCTGTAGGGG
                          OptEcAFRS
      ~~~~~~~~~~~~~~~~~~~~~~~~~~~~~~~~~~~~~~~~~~~~~~~~~~~~~~~~~~~~~~

6721  ATACAAATTC TATCAGTTTT GGATCAACAC TGCAGATGCT GACGTCTACC GATTCCTCAA
      TATGTTTAAG ATAGTCAAAA CCTAGTTGTG ACGTCTACGA CTGCAGATGG CTAAGGAGTT
                          OptEcAFRS
      ~~~~~~~~~~~~~~~~~~~~~~~~~~~~~~~~~~~~~~~~~~~~~~~~~~~~~~~~~~~~~~

6781  GTTTTTCACC TTTATGAGCA TTGAGGAAAT CAATGCCCTG GAGGAAGAGG ATAAGAACTC
      CAAAAAGTGG AAATACTCGT AACTCCTTTA GTTACGGGAC CTCCTTCTCC TATTCTTGAG
                          OptEcAFRS
      ~~~~~~~~~~~~~~~~~~~~~~~~~~~~~~~~~~~~~~~~~~~~~~~~~~~~~~~~~~~~~~

6841  TGGCAAAGCT CCCCGTGCAC AGTATGTGCT CGCCGAACAG GTCACAAGGC TGGTGCATGG
      ACCGTTTCGA GGGGCACGTG TCATACACGA GCGGCTTGTC CAGTGTTCCG ACCACGTACC
                          OptEcAFRS
      ~~~~~~~~~~~~~~~~~~~~~~~~~~~~~~~~~~~~~~~~~~~~~~~~~~~~~~~~~~~~~~
```

TABLE 3-continued

```
6901  GGAGGAAGGT CTGCAGGCTG CCAAGAGAAT TACTGAGTGC CTCTTCAGTG GCTCACTGTC
      CCTCCTTCCA GACGTCCGAC GGTTCTCTTA ATGACTCACG GAGAAGTCAC CGAGTGACAG
                                   OptEcAFRS
      ~~~~~~~~~~~~~~~~~~~~~~~~~~~~~~~~~~~~~~~~~~~~~~~~~~~~~~~~~~~~~~~

6961  CGCACTGAGC GAAGCTGACT TTGAGCAGCT CGCCCAGGAT GGAGTGCCTA TGGTCGAGAT
      GCGTGACTCG CTTCGACTGA AACTCGTCGA GCGGGTCCTA CCTCACGGAT ACCAGCTCTA
                                   OptEcAFRS
      ~~~~~~~~~~~~~~~~~~~~~~~~~~~~~~~~~~~~~~~~~~~~~~~~~~~~~~~~~~~~~~~

7021  GGAAAAAGGC GCAGACCTGA TGCAGGCTCT CGTGGATTCT GAGCTGCAGC CAAGTCGGGG
      CCTTTTTCCG CGTCTGGACT ACGTCCGAGA GCACCTAAGA CTCGACGTCG GTTCAGCCCC
                                   OptEcAFRS
      ~~~~~~~~~~~~~~~~~~~~~~~~~~~~~~~~~~~~~~~~~~~~~~~~~~~~~~~~~~~~~~~

7081  GCAGGCCCGC AAGACCATCG CATCAAATGC TATTACAATC AACGGTGAAA ACAGTCCGA
      CGTCCGGGCG TTCTGGTAGC GTAGTTTACG ATAATGTTAG TTGCCACTTT TTGTCAGGCT
                                   OptEcAFRS
      ~~~~~~~~~~~~~~~~~~~~~~~~~~~~~~~~~~~~~~~~~~~~~~~~~~~~~~~~~~~~~~~

7141  CCCCGAGTAC TTCTTTAAGG AAGAGGATCG ACTGTTCGGA CGTTTTACCC TCCTGAGGAG
      GGGGCTCATG AAGAAATTCC TTCTCCTAGC TGACAAGCCT GCAAAATGGG AGGACTCCTC
                 OptEcAFRS                                   IRES
      ~~~~~~~~~~~~~~~~~~~~~~~~~~~~~~~~~~~~       ~~~~~~~~~~~~~~~~~~~~

7201  AGGCAAAAAG AATTATTGTC TGATTTGCTG GAAGTGATCT AGAGGCCGCG CAGTTAACGC
      TCCGTTTTTC TTAATAACAG ACTAAACGAC CTTCACTAGA TCTCCGGCGC GTCAATTGCG
                                   IRES
      ~~~~~~~~~~~~~~~~~~~~~~~~~~~~~~~~~~~~~~~~~~~~~~~~~~~~~~~~~~~~~~~

7261  CGCCCCTCTC CCTCCCCCCC CCTAACGTTA CTGGCCGAAG CCGCTTGGAA TAAGGCCGGT
      GCGGGGAGAG GGAGGGGGGG GGATTGCAAT GACCGGCTTC GGCGAACCTT ATTCCGGCCA
                                   IRES
      ~~~~~~~~~~~~~~~~~~~~~~~~~~~~~~~~~~~~~~~~~~~~~~~~~~~~~~~~~~~~~~~

7321  GTGCGTTTGT CTATATGTTA TATTCCACCA TATTGCCGTC TATTGGCAAT GTGAGGGCCC
      CACGCAAACA GATATACAAT ATAAGGTGGT ATAACGGCAG ATAACCGTTA CACTCCCGGG
                                   IRES
      ~~~~~~~~~~~~~~~~~~~~~~~~~~~~~~~~~~~~~~~~~~~~~~~~~~~~~~~~~~~~~~~

7381  GGAAACCTGG CCCTGTCTTC TTGACGAGCA TTCCTAGGGG TCTTTCCCCT CTCGCCAAAG
      CCTTTGGACC GGGACAGAAG AACTGCTCGT AAGGATCCCC AGAAAGGGGA GAGCGGTTTC
                                   IRES
      ~~~~~~~~~~~~~~~~~~~~~~~~~~~~~~~~~~~~~~~~~~~~~~~~~~~~~~~~~~~~~~~

7441  GAATGCAAGG TCTGTTGAAT GTCGTGAAGG AAGCAGTTCC TCTGGAAGCT TCTTGAAGAC
      CTTACGTTCC AGACAACTTA CAGCACTTCC TTCGTCAAGG AGACCTTCGA AGAACTTCTG
                                   IRES
      ~~~~~~~~~~~~~~~~~~~~~~~~~~~~~~~~~~~~~~~~~~~~~~~~~~~~~~~~~~~~~~~

7501  AAACAACGTC TGTAGCGACC CTTTGCAGGC AGCGGAACCC CCCACCTGGC GACAGGTGCC
      TTTGTTGCAG ACATCGCTGG GAAACGTCCG TCGCCTTGGG GGGTGGACCG CTGTCCACGG
                                   IRES
      ~~~~~~~~~~~~~~~~~~~~~~~~~~~~~~~~~~~~~~~~~~~~~~~~~~~~~~~~~~~~~~~

7561  TCTGCGGCCA AAAGCCACGT GTATAAAATA CACCTGCAAA GGCGGCACAA CCCCAGTGCG
      AGACGCCGGT TTTCGGTGCA CATATTTTAT GTGGACGTTT CCGCCGTGTT GGGGTCACGC
                                   IRES
      ~~~~~~~~~~~~~~~~~~~~~~~~~~~~~~~~~~~~~~~~~~~~~~~~~~~~~~~~~~~~~~~

7621  ACGTTGTGAG TTGGATAGTT GTGGAAAGAG TCAAATGGCT CTCCTCAAGC GTATTCAACA
      TGCAACACTC AACCTATCAA CACCTTTCTC AGTTTACCGA GAGGAGTTCG CATAAGTTGT
                                   IRES
      ~~~~~~~~~~~~~~~~~~~~~~~~~~~~~~~~~~~~~~~~~~~~~~~~~~~~~~~~~~~~~~~

7681  AGGGGCTGAA GGATGCCCAG AAGGTACCCC ATTGTATGGG ATCTGATCTG GGGCCTCGGT
      TCCCCGACTT CCTACGGGTC TTCCATGGGG TAACATACCC TAGACTAGAC CCCGGAGCCA
                                   IRES
      ~~~~~~~~~~~~~~~~~~~~~~~~~~~~~~~~~~~~~~~~~~~~~~~~~~~~~~~~~~~~~~~

7741  ACACATGCTT TACATGTGTT TAGTCGAGGT TAAAAAAACG TCTAGGCCCC CCGAACCACG
      TGTGTACGAA ATGTACACAA ATCAGCTCCA ATTTTTTTGC AGATCCGGGG GGCTTGGTGC
                    IRES
      ~~~~~~~~~~~~~~~~~~~~~~~~~~~~~~~~~~~~~~~~~

7801  GGGACGTGGT ATTCCTTTGA AAAACACGAT GATAATATGG CCACACCCGT CCGAGATCAC
      CCCTGCACCA TAAGGAAACT TTTTGTGCTA CTATTATACC GGTGTGGGCA GGCTCTAGTG
                                   DHFR
      ~~~~~~~~~~~~~~~~~~~~~~~~~~~~~~~~~~~~~~~~~~~~~~~~~~~~~~~~~~~~~~~
```

TABLE 3-continued

```
7861  CCTCGAGCCA CCATGGTTCG ACCATTGAAC TGCATCGTCG CCGTGTCCCA AAATATGGGG
      GGAGCTCGGT GGTACCAAGC TGGTAACTTG ACGTAGCAGC GGCACAGGGT TTTATACCCC
                                      DHFR
      ~~~~~~~~~~~~~~~~~~~~~~~~~~~~~~~~~~~~~~~~~~~~~~~~~~~~~~~~~~~~~~~~

7921  ATTGGCAAGA ACGGAGACCT ACCCTGGCCT CCGCTCAGGA ACGAGTTCAA GTACTTCCAA
      TAACCGTTCT TGCCTCTGGA TGGGACCGGA GGCGAGTCCT TGCTCAAGTT CATGAAGGTT
                                      DHFR
      ~~~~~~~~~~~~~~~~~~~~~~~~~~~~~~~~~~~~~~~~~~~~~~~~~~~~~~~~~~~~~~~~

7981  AGAATGACCA CAACCTCTTC AGTGGAAGGT AAACAGAATC TGGTGATTAT GGGTAGGAAA
      TCTTACTGGT GTTGGAGAAG TCACCTTCCA TTTGTCTTAG ACCACTAATA CCCATCCTTT
                                      DHFR
      ~~~~~~~~~~~~~~~~~~~~~~~~~~~~~~~~~~~~~~~~~~~~~~~~~~~~~~~~~~~~~~~~

8041  ACCTGGTTCT CCATTCCTGA GAAGAATCGA CCTTTAAAGG ACAGAATTAA TATAGTTCTC
      TGGACCAAGA GGTAAGGACT CTTCTTAGCT GGAAATTTCC TGTCTTAATT ATATCAAGAG
                                      DHFR
      ~~~~~~~~~~~~~~~~~~~~~~~~~~~~~~~~~~~~~~~~~~~~~~~~~~~~~~~~~~~~~~~~

8101  AGTAGAGAAC TCAAAGAACC ACCACGAGGA GCTCATTTTC TTGCCAAAAG TTTGGATGAT
      TCATCTCTTG AGTTTCTTGG TGGTGCTCCT CGAGTAAAAG AACGGTTTTC AAACCTACTA
                                      DHFR
      ~~~~~~~~~~~~~~~~~~~~~~~~~~~~~~~~~~~~~~~~~~~~~~~~~~~~~~~~~~~~~~~~

8161  GCCTTAAGAC TTATTGAACA ACCGGAATTG GCAAGTAAAG TAGACATGGT TTGGATAGTC
      CGGAATTCTG AATAACTTGT TGGCCTTAAC CGTTCATTTC ATCTGTACCA AACCTATCAG
                                      DHFR
      ~~~~~~~~~~~~~~~~~~~~~~~~~~~~~~~~~~~~~~~~~~~~~~~~~~~~~~~~~~~~~~~~

8221  GGAGGCAGTT CTGTTTACCA GGAAGCCATG AATCAACCAG GCCACCTCAG ACTCTTTGTG
      CCTCCGTCAA GACAAATGGT CCTTCGGTAC TTAGTTGGTC CGGTGGAGTC TGAGAAACAC
                                      DHFR
      ~~~~~~~~~~~~~~~~~~~~~~~~~~~~~~~~~~~~~~~~~~~~~~~~~~~~~~~~~~~~~~~~

8281  ACAAGGATCA TGCAGGAATT TGAAAGTGAC ACGTTTTTCC CAGAAATTGA TTTGGGGAAA
      TGTTCCTAGT ACGTCCTTAA ACTTTCACTG TGCAAAAAGG GTCTTTAACT AAACCCCTTT
                                      DHFR
      ~~~~~~~~~~~~~~~~~~~~~~~~~~~~~~~~~~~~~~~~~~~~~~~~~~~~~~~~~~~~~~~~

8341  TATAAACTTC TCCCAGAATA CCCAGGCGTC CTCTCTGAGG TCCAGGAGGA AAAAGGCATC
      ATATTTGAAG AGGGTCTTAT GGGTCCGCAG GAGAGACTCC AGGTCCTCCT TTTTCCGTAG
                   DHFR                                     IRES
      ~~~~~~~~~~~~~~~~~~~~~~~~~~~~~~~~~~~  ~~~~~~~~~~~~~~~~~~~~

8401  AAGTATAAGT TGAAGTCTA CGAGAAGAAA GACTAATCTA GAGGCCGCGC ACTTAACGCC
      TTCATATTCA AACTTCAGAT GCTCTTCTTT CTGATTAGAT CTCCGGCGCG TGAATTGCGG
                                      IRES
      ~~~~~~~~~~~~~~~~~~~~~~~~~~~~~~~~~~~~~~~~~~~~~~~~~~~~~~~~~~~~~~~~

8461  GCCCCTCTCC CTCCCCCCCC CCTAACGTTA CTGGCCGAAG CCGCTTGGAA TAAGGCCGGT
      CGGGGAGAGG GAGGGGGGGG GGATTGCAAT GACCGGCTTC GGCGAACCTT ATTCCGGCCA
                                      IRES
      ~~~~~~~~~~~~~~~~~~~~~~~~~~~~~~~~~~~~~~~~~~~~~~~~~~~~~~~~~~~~~~~~

8521  GTGCGTTTGT CTATATGTTA TTTTCCACCA TATTGCCGTC TTTTGGCAAT GTGAGGGCCC
      CACGCAAACA GATATACAAT AAAAGGTGGT ATAACGGCAG AAAACCGTTA CACTCCCGGG
                                      IRES
      ~~~~~~~~~~~~~~~~~~~~~~~~~~~~~~~~~~~~~~~~~~~~~~~~~~~~~~~~~~~~~~~~

8581  GGAAACCTGG CCCTGTCTTC TTGACGAGCA TTCCTAGGGG TCTTTCCCCT CTCGCCAAAG
      CCTTTGGACC GGGACAGAAG AACTGCTCGT AAGGATCCCC AGAAAGGGGA GAGCGGTTTC
                                      IRES
      ~~~~~~~~~~~~~~~~~~~~~~~~~~~~~~~~~~~~~~~~~~~~~~~~~~~~~~~~~~~~~~~~

8641  GAATGCAAGG TCTGTTGAAT GTCGTGAAGG AAGCAGTTCC TCTGGAAGCT TCTTGAAGAC
      CTTACGTTCC AGACAACTTA CAGCACTTCC TTCGTCAAGG AGACCTTCGA AGAACTTCTG
                                      IRES
      ~~~~~~~~~~~~~~~~~~~~~~~~~~~~~~~~~~~~~~~~~~~~~~~~~~~~~~~~~~~~~~~~

8701  AAACAACGTC TGTAGCGACC CTTTGCAGGC AGCGGAACCC CCCACCTGGC GACAGGTGCC
      TTTGTTGCAG ACATCGCTGG GAAACGTCCG TCGCCTTGGG GGGTGGACCG CTGTCCACGG
                                      IRES
      ~~~~~~~~~~~~~~~~~~~~~~~~~~~~~~~~~~~~~~~~~~~~~~~~~~~~~~~~~~~~~~~~

8761  TCTGCGGCCA AAAGCCACGT GTATAAGATA CACCTGCAAA GGCGGCACAA CCCCAGTGCC
      AGACGCCGGT TTTCGGTGCA CATATTCTAT GTGGACGTTT CCGCCGTGTT GGGGTCACGG
                                      IRES
      ~~~~~~~~~~~~~~~~~~~~~~~~~~~~~~~~~~~~~~~~~~~~~~~~~~~~~~~~~~~~~~~~
```

TABLE 3-continued

```
8821  ACGTTGTGAG TTGGATAGTT GTGGAAAGAG TCAAATGGCT CTCCTCAAGC GTATTCAACA
      TGCAACACTC AACCTATCAA CACCTTTCTC AGTTTACCGA GAGGAGTTCG CATAAGTTGT
                                         IRES
      ~~~~~~~~~~~~~~~~~~~~~~~~~~~~~~~~~~~~~~~~~~~~~~~~~~~~~~~~~~~~~~

8881  AGGGGCTGAA GGATGCCCAG AAGGTACCCC ATTGTATGGG ATCTGATCTG GGGCCTCGGT
      TCCCCGACTT CCTACGGGTC TTCCATGGGG TAACATACCC TAGACTAGAC CCCGGAGCCA
                                         IRES
      ~~~~~~~~~~~~~~~~~~~~~~~~~~~~~~~~~~~~~~~~~~~~~~~~~~~~~~~~~~~~~~

8941  ACACATGCTT TACATGTGTT TAGTCGAGGT TAAAAAAACG TCTAGGCCCC CCGAACCACG
      TGTGTACGAA ATGTACACAA ATCAGCTCCA ATTTTTTTGC AGATCCGGGG GGCTTGGTGC
                       IRES                                        Neo
      ~~~~~~~~~~~~~~~~~~~~~~~~~~~~~~~~~~~~~~~~~~~~~       ~~~~~~~~~

9001  GGGACGTGGT TTTCCTTTGA AAAACACGAT GATAATATGG CCACAAGATC TATGCTTGAA
      CCCTGCACCA AAAGGAAACT TTTTGTGCTA CTATTATACC GGTGTTCTAG ATACGAACTT
                                         Neo
      ~~~~~~~~~~~~~~~~~~~~~~~~~~~~~~~~~~~~~~~~~~~~~~~~~~~~~~~~~~~~~~

9061  CAAGATGGAT TGCACGCAGG TTCTCCGGCC GCTTGGGTGG AGAGGCTATT CGGCTATGAC
      GTTCTACCTA ACGTGCGTCC AAGAGGCCGG CGAACCCACC TCTCCGATAA GCCGATACTG
                                         Neo
      ~~~~~~~~~~~~~~~~~~~~~~~~~~~~~~~~~~~~~~~~~~~~~~~~~~~~~~~~~~~~~~

9121  TGGGCACAAC AGACAATCGG CTGCTCTGAT GCCGCCGTGT TCCGGCTGTC AGCGCAGGGG
      ACCCGTGTTG TCTGTTAGCC GACGAGACTA CGGCGGCACA AGGCCGACAG TCGCGTCCCC
                                         Neo
      ~~~~~~~~~~~~~~~~~~~~~~~~~~~~~~~~~~~~~~~~~~~~~~~~~~~~~~~~~~~~~~

9181  CGCCCGGTTC TTTTTGTCAA GACCGACCTG TCCGGTGCCC TGAATGAACT GCAGGACGAG
      GCGGGCCAAG AAAAACAGTT CTGGCTGGAC AGGCCACGGG ACTTACTTGA CGTCCTGCTC
                                         Neo
      ~~~~~~~~~~~~~~~~~~~~~~~~~~~~~~~~~~~~~~~~~~~~~~~~~~~~~~~~~~~~~~

9241  GCAGCGCGGC TATCGTGGCT GGCCACGACG GCGTTCCTT GCGCAGCTGT GCTCGACGTT
      CGTCGCGCCG ATAGCACCGA CCGGTGCTGC CCGCAAGGAA CGCGTCGACA CGAGCTGCAA
                                         Neo
      ~~~~~~~~~~~~~~~~~~~~~~~~~~~~~~~~~~~~~~~~~~~~~~~~~~~~~~~~~~~~~~

9301  GTCACTGAAG CGGGAAGGGA CTGGCTGCTA TTGGGCGAAG TGCCGGGGCA GGATCTCCTG
      CAGTGACTTC GCCCTTCCCT GACCGACGAT AACCCGCTTC ACGGCCCCGT CCTAGAGGAC
                                         Neo
      ~~~~~~~~~~~~~~~~~~~~~~~~~~~~~~~~~~~~~~~~~~~~~~~~~~~~~~~~~~~~~~

9361  TCATCTCACC TTGCTCCTGC CGAGAAAGTA TCCATCATGG CTGATGCAAT GCGGCGGCTG
      AGTAGAGTGG AACGAGGACG GCTCTTTCAT AGGTAGTACC GACTACGTTA CGCCGCCGAC
                                         Neo
      ~~~~~~~~~~~~~~~~~~~~~~~~~~~~~~~~~~~~~~~~~~~~~~~~~~~~~~~~~~~~~~

9421  CATACGCTTG ATCCGGCTAC CTGCCCATTC GACCACCAAG CGAAACATCG CATCGAGCGA
      GTATGCGAAC TAGGCCGATG GACGGGTAAG CTGGTGGTTC GCTTTGTAGC GTAGCTCGCT
                                         Neo
      ~~~~~~~~~~~~~~~~~~~~~~~~~~~~~~~~~~~~~~~~~~~~~~~~~~~~~~~~~~~~~~

9481  GCACGTACTC GGATGGAAGC CGGTCTTGTC GATCAGGATG ATCTGGACGA AGAGCATCAG
      CGTGCATGAG CCTACCTTCG GCCAGAACAG CTAGTCCTAC TAGACCTGCT TCTCGTAGTC
                                         Neo
      ~~~~~~~~~~~~~~~~~~~~~~~~~~~~~~~~~~~~~~~~~~~~~~~~~~~~~~~~~~~~~~

9541  GGGCTCGCGC CAGCCGAACT GTTCGCCAGG CTCAAGGCGC GCATGCCCGA CGGCGAGGAT
      CCCGAGCGCG GTCGGCTTGA CAAGCGGTCC GAGTTCCGCG CGTACGGGCT GCCGCTCCTA
                                         Neo
      ~~~~~~~~~~~~~~~~~~~~~~~~~~~~~~~~~~~~~~~~~~~~~~~~~~~~~~~~~~~~~~

9601  CTCGTCGTGA CCCATGGCGA TGCCTGCTTG CCGAATATCA TGGTGGAAAA TGGCCGCTTT
      GAGCAGCACT GGGTACCGCT ACGGACGAAC GGCTTATAGT ACCACCTTTT ACCGGCGAAA
                                         Neo
      ~~~~~~~~~~~~~~~~~~~~~~~~~~~~~~~~~~~~~~~~~~~~~~~~~~~~~~~~~~~~~~

9661  TCTGGATTCA TCGACTGTGG CCGGCTGGGT GTGGCGGACC GCTATCAGGA CATAGCGTTG
      AGACCTAAGT AGCTGACACC GGCCGACCCA CACCGCCTGG CGATAGTCCT GTATCGCAAC
                                         Neo
      ~~~~~~~~~~~~~~~~~~~~~~~~~~~~~~~~~~~~~~~~~~~~~~~~~~~~~~~~~~~~~~

9721  GCTACCCGTG ATATTGCTGA AGAGCTTGGC GGCGAATGGG CTGACCGCTT CCTCGTGCTT
      CGATGGGCAC TATAACGACT TCTCGAACCG CCGCTTACCC GACTGGCGAA GGAGCACGAA
                                         Neo
      ~~~~~~~~~~~~~~~~~~~~~~~~~~~~~~~~~~~~~~~~~~~~~~~~~~~~~~~~~~~~~~
```

TABLE 3-continued

```
9781  TACGGTATCG CCGCTCCCGA TTCGCAGCGC ATCGCCTTCT ATCGCCTTCT TGACGAGTTC
      ATGCCATAGC GGCGAGGGCT AAGCGTCGCG TAGCGGAAGA TAGCGGAAGA ACTGCTCAAG
           Neo
           ~~~~~

9841  TTCTGACAAT TGCACGGGCT ACGAGATTTC GATTCCACCG CCGCCTTCTA TGAAAGGTTG
      AAGACTGTTA ACGTGCCCGA TGCTCTAAAG CTAAGGTGGC GGCGGAAGAT ACTTTCCAAC

9901  GGCTTCGGAA TCGTTTTCCG GGACGCCGGC TGGATGATCC TCCAGCGCGG GGATCTCATG
      CCGAAGCCTT AGCAAAAGGC CCTGCGGCCG ACCTACTAGG AGGTCGCGCC CCTAGAGTAC
                                                SV40 PolyA
                                                ~~~~~~~~~~~~~~~~~~~~~~~~~~~~~~~~~~~~~~~~

9961  CTGGAGTTCT TCGCCCACCC CAACTTGTTT ATTGCAGCTT ATAATGGTTA CAAATAAAGC
      GACCTCAAGA AGCGGGTGGG GTTGAACAAA TAACGTCGAA TATTACCAAT GTTTATTTCG
                                 SV40 PolyA
      ~~~~~~~~~~~~~~~~~~~~~~~~~~~~~~~~~~~~~~~~~~~~~~~~~~~~~~~~~~~~~~~~~

10021 AATAGCATCA CAAATTTCAC AAATAAAGCA TTTTTTTCAC TGCATTCTAG TTGTGGTTTG
      TTATCGTAGT GTTTAAAGTG TTTATTTCGT AAAAAAAGTG ACGTAAGATC AACACCAAAC
                SV40 PolyA
      ~~~~~~~~~~~~~~~~~~~~~~~~~~~~~~~~

10081 TCCAAACTCA TCAATGTATC TTATCATGTC GGTTACCCCC GTCCGACATG TGAGCAAAAG
      AGGTTTGAGT AGTTACATAG AATAGTACAG CCAATGGGGG CAGGCTGTAC ACTCGTTTTC
                                                                ~~~~~~~~~~
                                                                  pUC Ori

10141 GCCAGCAAAA GGCCAGGAAC CGTAAAAAGG CCGCGTTGCT GGCGTTTTTC CATAGGCTCC
      CGGTCGTTTT CCGGTCCTTG GCATTTTTCC GGCGCAACGA CCGCAAAAAG GTATCCGAGG
      ~~~~~~~~~~~~~~~~~~~~~~~~~~~~~~~~~~~~~~~~~~~~~~~~~~~~~~~~~~~~~~~~~
                       pUC Ori

10201 GCCCCCCTGA CGAGCATCAC AAAAATCGAC GCTCAAGTCA GAGGTGGCGA AACCCGACAG
      CGGGGGGACT GCTCGTAGTG TTTTTAGCTG CGAGTTCAGT CTCCACCGCT TTGGGCTGTC
      ~~~~~~~~~~~~~~~~~~~~~~~~~~~~~~~~~~~~~~~~~~~~~~~~~~~~~~~~~~~~~~~~~
                                  pUC Ori

10261 GACTATAAAG ATACCAGGCG TTTCCCCCTG GAAGCTCCCT CGTGCGCTCT CCTGTTCCGA
      CTGATATTTC TATGGTCCGC AAAGGGGGAC CTTCGAGGGA GCACGCGAGA GGACAAGGCT
      ~~~~~~~~~~~~~~~~~~~~~~~~~~~~~~~~~~~~~~~~~~~~~~~~~~~~~~~~~~~~~~~~~
                                  pUC Ori

10321 CCCTGCCGCT TACCGGATAC CTGTCCGCCT TTCTCCCTTC GGGAAGCGTG GCGCTTTCTC
      GGGACGGCGA ATGGCCTATG GACAGGCGGA AAGAGGGAAG CCCTTCGCAC CGCGAAAGAG
      ~~~~~~~~~~~~~~~~~~~~~~~~~~~~~~~~~~~~~~~~~~~~~~~~~~~~~~~~~~~~~~~~~
                                  pUC Ori

10381 ATAGCTCACG CTGTAGGTAT CTCAGTTCGG TGTAGGTCGT TCGCTCCAAG CTGGGCTGTG
      TATCGAGTGC GACATCCATA GAGTCAAGCC ACATCCAGCA AGCGAGGTTC GACCCGACAC
      ~~~~~~~~~~~~~~~~~~~~~~~~~~~~~~~~~~~~~~~~~~~~~~~~~~~~~~~~~~~~~~~~~
                                  pUC Ori

10441 TGCACGAACC CCCCGTTCAG CCCGACCGCT GCGCCTTATC CGGTAACTAT CGTCTTGAGT
      ACGTGCTTGG GGGGCAAGTC GGGCTGGCGA CGCGGAATAG GCCATTGATA GCAGAACTCA
      ~~~~~~~~~~~~~~~~~~~~~~~~~~~~~~~~~~~~~~~~~~~~~~~~~~~~~~~~~~~~~~~~~
                                  pUC Ori

10501 CCAACCCGGT AAGACACGAC TTATCGCCAC TGGCAGCAGC CACTGGTAAC AGGATTAGCA
      GGTTGGGCCA TTCTGTGCTG AATAGCGGTG ACCGTCGTCG GTGACCATTG TCCTAATCGT
      ~~~~~~~~~~~~~~~~~~~~~~~~~~~~~~~~~~~~~~~~~~~~~~~~~~~~~~~~~~~~~~~~~
                                  pUC Ori

10561 GAGCGAGGTA TGTAGGCGGT GCTACAGAGT TCTTGAAGTG GTGGCCTAAC TACGGCTACA
      CTCGCTCCAT ACATCCGCCA CGATGTCTCA AGAACTTCAC CACCGGATTG ATGCCGATGT
      ~~~~~~~~~~~~~~~~~~~~~~~~~~~~~~~~~~~~~~~~~~~~~~~~~~~~~~~~~~~~~~~~~
                                  pUC Ori

10621 CTAGAAGAAC AGTATTTGGT ATCTGCGCTC TGCTGAAGCC AGTTACCTTC GGAAAAAGAG
      GATCTTCTTG TCATAAACCA TAGACGCGAG ACGACTTCGG TCAATGGAAG CCTTTTTCTC
      ~~~~~~~~~~~~~~~~~~~~~~~~~~~~~~~~~~~~~~~~~~~~~~~~~~~~~~~~~~~~~~~~~
                                  pUC Ori

10681 TTGGTAGCTC TTGATCCGGC AAACAAACCA CCGCTGGTAG CGGTGGTTTT TTTGTTTGCA
      AACCATCGAG AACTAGGCCG TTTGTTTGGT GGCGACCATC GCCACCAAAA AAACAAACGT
      ~~~~~~~~~~~~~~~~~~~~~~~~~~~~~~~~~~~~~~~~~~~~~~~~~~~~~~~~~~~~~~~~~
                                  pUC Ori
```

TABLE 3-continued

```
10741  AGCAGCAGAT TACGCGCAGA AAAAAAGGAT CTCAAGAAGA TCCTTTGATC TTTTCTACGG
       TCGTCGTCTA ATGCGCGTCT TTTTTTCCTA GAGTTCTTCT AGGAAACTAG AAAAGATGCC
       ~~~~~~~~~~~~~~~~~~~~~~~~~~~~~~~~~~~~~~~~~~~~~~~~~~~~~~~~~~~~
                                 pUC Ori

10801  GGTCTGACGC TCAGTGGAAC GAAAACTCAC GTTAAGGGAT TTTGGTCATG AGATTATCAA
       CCAGACTGCG AGTCACCTTG CTTTTGAGTG CAATTCCCTA AAACCAGTAC TCTAATAGTT
       ~
       .

10861  AAAGGATCTT CACCTAGATC CTTTTAAATT AAAAATGAAG TTTTAAATCA ATCTAAAGTA
       TTTCCTAGAA GTGGATCTAG GAAAATTTAA TTTTTACTTC AAAATTTAGT TAGATTTCAT

10921  TATATGAGTA AACTTGGTCT GACAGTTACC AATGCTTAAT CAGTGAGGCA CCTATCTCAG
       ATATACTCAT TTGAACCAGA CTGTCAATGG TTACGAATTA GTCACTCCGT GGATAGAGTC
                                                  ~~~~~~~~~~~~~~~~~~~~~~~~~~~~~~~~~~~~
                                                                  Amp

10981  CGATCTGTCT ATTTCGTTCA TCCATAGTTG CCTGACTCCC CGTCGTGTAG ATAACTACGA
       GCTAGACAGA TAAAGCAAGT AGGTATCAAC GGACTGAGGG GCAGCACATC TATTGATGCT
       ~~~~~~~~~~~~~~~~~~~~~~~~~~~~~~~~~~~~~~~~~~~~~~~~~~~~~~~~~~~~
                                  Amp

11041  TACGGGAGGG CTTACCATCT GGCCCCAGTG CTGCAATGAT ACCGCGAGAC CCACGCTCAC
       ATGCCCTCCC GAATGGTAGA CCGGGGTCAC GACGTTACTA TGGCGCTCTG GGTGCGAGTG
       ~~~~~~~~~~~~~~~~~~~~~~~~~~~~~~~~~~~~~~~~~~~~~~~~~~~~~~~~~~~~
                                  Amp

11101  CGGCTCCAGA TTTATCAGCA ATAAACCAGC CAGCCGGAAG GGCCGAGCGC AGAAGTGGTC
       GCCGAGGTCT AAATAGTCGT TATTTGGTCG GTCGGCCTTC CCGGCTCGCG TCTTCACCAG
       ~~~~~~~~~~~~~~~~~~~~~~~~~~~~~~~~~~~~~~~~~~~~~~~~~~~~~~~~~~~~
                                  Amp

11161  CTGCAACTTT ATCCGCCTCC ATCCAGTCTA TTAATTGTTG CCGGGAAGCT AGAGTAAGTA
       GACGTTGAAA TAGGCGGAGG TAGGTCAGAT AATTAACAAC GGCCCTTCGA TCTCATTCAT
       ~~~~~~~~~~~~~~~~~~~~~~~~~~~~~~~~~~~~~~~~~~~~~~~~~~~~~~~~~~~~
                                  Amp

11221  GTTCGCCAGT TAATAGTTTG CGCAACGTTG TTGCCATTGC TACAGGCATC GTGGTGTCAC
       CAAGCGGTCA ATTATCAAAC GCGTTGCAAC AACGGTAACG ATGTCCGTAG CACCACAGTG
       ~~~~~~~~~~~~~~~~~~~~~~~~~~~~~~~~~~~~~~~~~~~~~~~~~~~~~~~~~~~~
                                  Amp

11281  GCTCGTCGTT TGGTATGGCT TCATTCAGCT CCGGTTCCCA ACGATCAAGG CGAGTTACAT
       CGAGCAGCAA ACCATACCGA AGTAAGTCGA GGCCAAGGGT TGCTAGTTCC GCTCAATGTA
       ~~~~~~~~~~~~~~~~~~~~~~~~~~~~~~~~~~~~~~~~~~~~~~~~~~~~~~~~~~~~
                                  Amp

11341  GATCCCCCAT GTTGTGCAAA AAAGCGGTTA GCTCCTTCGG TCCTCCGATC GTTGTCAGAA
       CTAGGGGGTA CAACACGTTT TTTCGCCAAT CGAGGAAGCC AGGAGGCTAG CAACAGTCTT
       ~~~~~~~~~~~~~~~~~~~~~~~~~~~~~~~~~~~~~~~~~~~~~~~~~~~~~~~~~~~~
                                  Amp

11401  GTAAGTTGGC CGCAGTGTTA TCACTCATGG TTATGGCAGC ACTGCATAAT TCTCTTACTG
       CATTCAACCG GCGTCACAAT AGTGAGTACC AATACCGTCG TGACGTATTA AGAGAATGAC
       ~~~~~~~~~~~~~~~~~~~~~~~~~~~~~~~~~~~~~~~~~~~~~~~~~~~~~~~~~~~~
                                  Amp

11461  TCATGCCATC CGTAAGATGC TTTTCTGTGA CTGGTGAGTA CTCAACCAAG TCATTCTGAG
       AGTACGGTAG GCATTCTACG AAAAGACACT GACCACTCAT GAGTTGGTTC AGTAAGACTC
       ~~~~~~~~~~~~~~~~~~~~~~~~~~~~~~~~~~~~~~~~~~~~~~~~~~~~~~~~~~~~
                                  Amp

11521  AATAGTGTAT GCGGCGACCG AGTTGCTCTT GCCCGGCGTC AATACGGGAT AATACCGCGC
       TTATCACATA CGCCGCTGGC TCAACGAGAA CGGGCCGCAG TTATGCCCTA TTATGGCGCG
       ~~~~~~~~~~~~~~~~~~~~~~~~~~~~~~~~~~~~~~~~~~~~~~~~~~~~~~~~~~~~
                                  Amp

11581  CACATAGCAG AACTTTAAAA GTGCTCATCA TTGGAAAACG TTCTTCGGGG CGAAAACTCT
       GTGTATCGTC TTGAAATTTT CACGAGTAGT AACCTTTTGC AAGAAGCCCC GCTTTTGAGA
       ~~~~~~~~~~~~~~~~~~~~~~~~~~~~~~~~~~~~~~~~~~~~~~~~~~~~~~~~~~~~
                                  Amp

11641  CAAGGATCTT ACCGCTGTTG AGATCCAGTT CGATGTAACC CACTCGTGCA CCCAACTGAT
       GTTCCTAGAA TGGCGACAAC TCTAGGTCAA GCTACATTGG GTGAGCACGT GGGTTGACTA
       ~~~~~~~~~~~~~~~~~~~~~~~~~~~~~~~~~~~~~~~~~~~~~~~~~~~~~~~~~~~~
                                  Amp
```

TABLE 3-continued

```
11701  CTTCAGCATC TTTTACTTTC ACCAGCGTTT CTGGGTGAGC AAAAACAGGA AGGCAAAATG
       GAAGTCGTAG AAAATGAAAG TGGTCGCAAA GACCCACTCG TTTTTGTCCT TCCGTTTTAC
                                  ~~~~~~~~~~~~~~~~~~~~~~~~~~~~~~~~~~~~~~~
                                                   Amp

11761  CCGCAAAAAA GGGAATAAGG GCGACACGGA AATGTTGAAT ACTCATACTC TTCCTTTTTC
       GGCGTTTTTT CCCTTATTCC CGCTGTGCCT TTACAACTTA TGAGTATGAG AAGGAAAAAG
       ~~~~~~~~~~~~~~~~~~~~~~~~~~~~~~~~~~~~~~~~~~~~~
                           Amp
                                                                ~~~~~~~~~~
                                                                  Amp P

11821  AATATTATTG AAGCATTTAT CAGGGTTATT GTCTCATGAG CGGATACATA TTTGAATGTA
       TTATAATAAC TTCGTAAATA GTCCCAATAA CAGAGTACTC GCCTATGTAT AAACTTACAT
       ~~~~~~~~~~~~~~~~~~~~~~~~~~~~~~~~~~~~~~~~~~~~~~~~~~~~~~~~~~~~~~~~
                                  Amp P

11881  TTTAGAAAAA TAAACAAATA GGGGTTCCGC GCACATTTCC CCGAAAAGTG CCACCTGACG
       AAATCTTTTT ATTTGTTTAT CCCCAAGGCG CGTGTAAAGG GGCTTTTCAC GGTGGACTGC
       ~~~~~~~~~~~~~~~~~~~~~~~~~~~
                Amp P

11941  TCTAAGAAAC CATTATTATC ATGACATTAA CCTATAAAAA TAGGCGTATC ACGAGGCCCT
       AGATTCTTTG GTAATAATAG TACTGTAATT GGATATTTTT ATCCGCATAG TGCTCCGGGA

12001  TTCGTC
       AAGCAG
```

SEQ ID NO: 29
nucleotide sequence of the suppression expression construct
Nat L BB-Opti FEPO in Irwin for feline erythropoietin

```
  1  TCGCGCGTTT CGGTGATGAC GGTGAAAACC TCTGACACAT GCAGCTCCCG GAGACGGTCA
     AGCGCGCAAA GCCACTACTG CCACTTTTGG AGACTGTGTA CGTCGAGGGC CTCTGCCAGT

61  CAGCTTGTCT GTAAGCGGAT GCCGGGAGCA GACAAGCCCG TCAGGGCGCG TCAGCGGGTG
     GTCGAACAGA CATTCGCCTA CGGCCCTCGT CTGTTCGGGC AGTCCCGCGC AGTCGCCCAC

121  TTGGCGGGTG TCGGGGCTGG CTTAACTATG CGGCATCAGA GCAGATTGTA CTGAGAGTGC
     AACCGCCCAC AGCCCCGACC GAATTGATAC GCCGTAGTCT CGTCTAACAT GACTCTCACG

181  ACCATATGCC CGTCCGCGTA CCGGCGCGCC GGATGCCAAT CGATGAATTC CGGTGTGAAA
     TGGTATACGG GCAGGCGCAT GGCCGCGCGG CCTACGGTTA GCTACTTAAG GCCACACTTT

241  TACCGCACAG ATGCGTAAGG AGAAAATACC GCATCAGGCG CCATTCGCCA TTCAGGCTGC
     ATGGCGTGTC TACGCATTCC TCTTTTATGG CGTAGTCCGC GGTAAGCGGT AAGTCCGACG

301  GCAACTGTTG GGAAGGGCGA TCGGTGCGGG CCTCTTCGCT ATTACGCCAG CTGGCGAAAG
     CGTTGACAAC CCTTCCCGCT AGCCACGCCC GGAGAAGCGA TAATGCGGTC GACCGCTTTC

361  GGGGATGTGC TGCAAGGCGA TTAAGTTGGG TAACGCCAGG GTTTTCCCAG TCACGACGTT
     CCCCTACACG ACGTTCCGCT AATTCAACCC ATTGCGGTCC CAAAAGGGTC AGTGCTGCAA
                                                              tRNA
                                                         ~~~~~~~~~~~~~~~~~~~~~
                                                                   H1
                                                         ~~~~~~~~~~~~~~~~~~~~~

421  GTAAAACGAC GGCCAGTGAA TTGATGCATC CATCAATTCA TATTTGCATG TCGCTATGTG
     CATTTTGCTG CCGGTCACTT AACTACGTAG GTAGTTAAGT ATAAACGTAC AGCGATACAC
                                        tRNA
     ~~~~~~~~~~~~~~~~~~~~~~~~~~~~~~~~~~~~~~~~~~~~~~~~~~~~~~~~~~~~~~~~
                                         H1
     ~~~~~~~~~~~~~~~~~~~~~~~~~~~~~~~~~~~~~~~~~~~~~~~~~~~~~~~~~~~~~~~~

481  TTCTGGGAAA TCACCATAAA CGTGAAATGT CTTTGGATTT GGGAATCTTA TAAGTTCTGT
     AAGACCCTTT AGTGGTATTT GCACTTTACA GAAACCTAAA CCCTTAGAAT ATTCAAGACA
     tRNA
     ~~~~~~~~~~~~~~~~~~~~~~~~~~~~~~~~~~~~~~~~~~~~~~~~~~~~~~~~~~~~~~~~
              H1                        Hyb1 tRNA
     ~~~~~~~~~~~~~          ~~~~~~~~~~~~~~~~~~~~~~~~~~~

541  ATGAGACCAC TCGGATCCGG TGGGGTAGCG AAGTGGCTAA ACGCGGCGGA CTCTAAATCC
     TACTCTGGTG AGCCTAGGCC ACCCCATCGC TTCACCGATT TGCGCCGCCT GAGATTTAGG
                 Hyb1 tRNA
     ~~~~~~~~~~~~~~~~~~~~~~~~~~~~~~~~~~~~~
                         tRNA
     ~~~~~~~~~~~~~~~~~~~~~~~~~~~~~~~~~~~~~~~~~~~~~~~~~~
                                                     Term
                                                     ~~~~~~
```

TABLE 3-continued

```
 601  GCTCCCTTTG GGTTCGGCGG TTCGAATCCG TCCCCCACCA TTTTTTGGAA CCTAGGGAAT
      CGAGGGAAAC CCAAGCCGCC AAGCTTAGGC AGGGGGTGGT AAAAAACCTT GGATCCCTTA

661  TCCGGTGTGA ATACCGCAC AGATGCGTAA GGAGAAAATA CCGCATCAGG CGCCATTCGC
      AGGCCACACT TTATGGCGTG TCTACGCATT CCTCTTTTAT GGCGTAGTCC GCGGTAAGCG

721  CATTCAGGCT GCGCAACTGT TGGGAAGGGC GATCGGTGCG GGCCTCTTCG CTATTACGCC
      GTAAGTCCGA CGCGTTGACA ACCCTTCCCG CTAGCCACGC CCGGAGAAGC GATAATGCGG

781  AGCTGGCGAA AGGGGGATGT GCTGCAAGGC GATTAAGTTG GGTAACGCCA GGGTTTTCCC
      TCGACCGCTT TCCCCCTACA CGACGTTCCG CTAATTCAAC CCATTGCGGT CCCAAAAGGG
                                                                     tRNA
                                                                    ~~~~~~~
                                                                      H1
                                                                    ~~~~~~~

841  AGTCACGACG TTGTAAAACG ACGGCCAGTG AATTGATGCA TCCATCAATT CATATTTGCA
      TCAGTGCTGC AACATTTTGC TGCCGGTCAC TTAACTACGT AGGTAGTTAA GTATAAACGT
                                tRNA
      ~~~~~~~~~~~~~~~~~~~~~~~~~~~~~~~~~~~~~~~~~~~~~~~~~~~~~~~~~~~~~~~~~
                                 H1
      ~~~~~~~~~~~~~~~~~~~~~~~~~~~~~~~~~~~~~~~~~~~~~~~~~~~~~~~~~~~~~~~~~

901  TGTCGCTATG TGTTCTGGGA AATCACCATA AACGTGAAAT GTCTTTGGAT TTGGGAATCT
      ACAGCGATAC ACAAGACCCT TTAGTGGTAT TTGCACTTTA CAGAAACCTA AACCCTTAGA
                             tRNA
      ~~~~~~~~~~~~~~~~~~~~~~~~~~~~~          ~~~~~~~~~~~~~~~~~~~~~~~~~~
                  H1                                   Hyb1 tRNA
      ~~~~~~~~~~~~~~~~~~~~~~~~~~~~~          ~~~~~~~~~~~~~~~~~~~~~~~~~~

961  TATAAGTTCT GTATGAGACC ACTCGGATCC GGTGGGGTAG CGAAGTGGCT AAACGCGGCG
      ATATTCAAGA CATACTCTGG TGAGCCTAGG CCACCCCATC GCTTCACCGA TTTGCGCCGC
                                                                     Term
                                                                    ~~~~~~
                          tRNA
      ~~~~~~~~~~~~~~~~~~~~~~~~~~~~~~~~~~~~~~~~~~~~~~~~~~~~~~~~~~~~~~~
                         Hyb1 tRNA
      ~~~~~~~~~~~~~~~~~~~~~~~~~~~~~~~~~~~~~~~~~~~~~~~~~~~~~~~~~~~~~~~

1021  GACTCTAAAT CCGCTCCCTT TGGGTTCGGC GGTTCGAATC CGTCCCCCAC CATTTTTTGG
      CTGAGATTTA GGCGAGGGAA ACCCAAGCCG CCAAGCTTAG GCAGGGGGTG GTAAAAAACC

1081  AAGACGTCGA ATTCCGGTGT GAAATACCGC ACAGATGCGT AAGGAGAAAA TACCGCATCA
      TTCTGCAGCT TAAGGCCACA CTTTATGGCG TGTCTACGCA TTCCTCTTTT ATGGCGTAGT

1141  GGCGCCATTC GCCATTCAGG CTGCGCAACT GTTGGGAAGG GCGATCGGTG CGGGCCTCTT
      CCGCGGTAAG CGGTAAGTCC GACGCGTTGA CAACCCTTCC CGCTAGCCAC GCCCGGAGAA

1201  CGCTATTACG CCAGCTGGCG AAAGGGGGAT GTGCTGCAAG GCGATTAAGT TGGGTAACGC
      GCGATAATGC GGTCGACCGC TTTCCCCCTA CACGACGTTC CGCTAATTCA ACCCATTGCG

1261  CAGGGTTTTC CCAGTCACGA CGTTGTAAAA CGACGGCCAG TGAATTGATG CATCCATCAA
      GTCCCAAAAG GGTCAGTGCT GCAACATTTT GCTGCCGGTC ACTTAACTAC GTAGGTAGTT
                                  tRNA
      ~~~~~~~~~~~~~~~~~~~~~~~~~~~~~~~~~~~~~~~~~~~~~~~~~~~~~~~~~~~~~~~
                                   H1
      ~~~~~~~~~~~~~~~~~~~~~~~~~~~~~~~~~~~~~~~~~~~~~~~~~~~~~~~~~~~~~~~

1321  TTCATATTTG CATGTCGCTA TGTGTTCTGG GAAATCACCA TAAACGTGAA ATGTCTTTGG
      AAGTATAAAC GTACAGCGAT ACACAAGACC CTTTAGTGGT ATTTGCACTT TACAGAAACC
                         tRNA
      ~~~~~~~~~~~~~~~~~~~~~~~~~~~~~~~~~~~~~~          ~~~~~~~~~~~~~~~~~
                          H1                                Hyb1 tRNA
      ~~~~~~~~~~~~~~~~~~~~~~~~~~~~~~~~~~~~~~          ~~~~~~~~~~~~~~~~~

1381  ATTTGGGAAT CTTATAAGTT CTGTATGAGA CCACTCGGAT CCGGTGGGGT AGCGAAGTGG
      TAAACCCTTA GAATATTCAA GACATACTCT GGTGAGCCTA GGCCACCCCA TCGCTTCACC
                                  tRNA
      ~~~~~~~~~~~~~~~~~~~~~~~~~~~~~~~~~~~~~~~~~~~~~~~~~~~~~~~~~~~~~~~
                               Hyb1 tRNA
      ~~~~~~~~~~~~~~~~~~~~~~~~~~~~~~~~~~~~~~~~~~~~~~~~~~~~~~~~~~~~~~~

1441  CTAAACGCGG CGGACTCTAA ATCCGCTCCC TTTGGGTTCG GCGGTTCGAA TCCGTCCCCC
      GATTTGCGCC GCCTGAGATT TAGGCGAGGG AAACCCAAGC CGCCAAGCTT AGGCAGGGGG
```

TABLE 3-continued

```
       Term
       ~~~~~~~
       tRNA
    ~~~~~~~~~~~
     Hyb1 tRNA
     ~~~~

1501 ACCATTTTTT GGAACATATG GAATTCCGGT GTGAAATACC GCACAGATGC GTAAGGAGAA
     TGGTAAAAAA CCTTGTATAC CTTAAGGCCA CACTTTATGG CGTGTCTACG CATTCCTCTT

1561 AATACCGCAT CAGGCGCCAT TCGCCATTCA GGCTGCGCAA CTGTTGGGAA GGGCGATCGG
     TTATGGCGTA GTCCGCGGTA AGCGGTAAGT CCGACGCGTT GACAACCCTT CCCGCTAGCC

1621 TGCGGGCCTC TTCGCTATTA CGCCAGCTGG CGAAAGGGGG ATGTGCTGCA AGGCGATTAA
     ACGCCCGGAG AAGCGATAAT GCGGTCGACC GCTTTCCCCC TACACGACGT TCCGCTAATT

1681 GTTGGGTAAC GCCAGGGTTT TCCCAGTCAC GACGTTGTAA AACGACGCC AGTGAATTGA
     CAACCCATTG CGGTCCCAAA AGGGTCAGTG CTGCAACATT TGCTGCCGG TCACTTAACT
                                                      tRNA
                 ~~~~~~~~~~~~~~~~~~~~~~~~~~~~~~~~~~~~~~~~~~~~~~~~
                                         H1
                 ~~~~~~~~~~~~~~~~~~~~~~~~~~~~~~~~~~~~~~~~~~~~~~~~

1741 TGCATCCATC AATTCATATT TGCATGTCGC TATGTGTTCT GGGAAATCAC CATAAACGTG
     ACGTAGGTAG TTAAGTATAA ACGTACAGCG ATACACAAGA CCCTTTAGTG GTATTTGCAC
                            tRNA
     ~~~~~~~~~~~~~~~~~~~~~~~~~~~~~~~~~~~~~~~~~~~~~~~~~~~~~~~~~~~~~~
                            H1                              Hyb1 tRNA
     ~~~~~~~~~~~~~~~~~~~~~~~~~~~~~~~~~~~~~~~~~~~~~  ~~~~~~

1801 AAATGTCTTT GGATTTGGGA ATCTTATAAG TTCTGTATGA GACCACTCGG ATCCGGTGGG
     TTTACAGAAA CCTAAACCCT TAGAATATTC AAGACATACT CTGGTGAGCC TAGGCCACCC
                                 tRNA
     ~~~~~~~~~~~~~~~~~~~~~~~~~~~~~~~~~~~~~~~~~~~~~~~~~~~~~~~~~~~~~~
                            Hyb1 tRNA
     ~~~~~~~~~~~~~~~~~~~~~~~~~~~~~~~~~~~~~~~~~~~~~~~~~~~~~~~~~~~~~~

1861 GTAGCGAAGT GGCTAAACGC GGCGGACTCT AAATCCGCTC CCTTTGGGTT CGGCGGTTCG
     CATCGCTTCA CCGATTTGCG CCGCCTGAGA TTTAGGCGAG GGAAACCCAA GCCGCCAAGC
                             Term
                            ~~~~~~~
              tRNA
     ~~~~~~~~~~~~~~~~~~~~~~~~
           Hyb1 tRNA                              SVO
     ~~~~~~~~~~~~~~~~~~                ~~~~~~~~~~~~~~~~~~~~~

1921 AATCCGTCCC CCACCATTTT TTGGAACTTA ATTAAGTACG GGCCTCCAAA AAAGCCTCCT
     TTAGGCAGGG GGTGGTAAAA AACCTTGAAT TAATTCATGC CCGGAGGTTT TTTCGGAGGA
                                           SVO
     ~~~~~~~~~~~~~~~~~~~~~~~~~~~~~~~~~~~~~~~~~~~~~~~~~~~~~~~~~~~~~~

1981 CACTACTTCT GGAATAGCTC AGAGGCAGAG GCGGCCTCGG CCTCTGCATA AATAAAAAAA
     GTGATGAAGA CCTTATCGAG TCTCCGTCTC CGCCGGAGCC GGAGACGTAT TTATTTTTTT
                                           SVO
     ~~~~~~~~~~~~~~~~~~~~~~~~~~~~~~~~~~~~~~~~~~~~~~~~~~~~~~~~~~~~~~

2041 ATTAGTCAGC CATGGGGCGG AGAATGGGCG GAACTGGGCG GAGTTAGGGG CGGGATGGGC
     TAATCAGTCG GTACCCCGCC TCTTACCCGC CTTGACCCGC CTCAATCCCC GCCCTACCCG
                                           SVO
     ~~~~~~~~~~~~~~~~~~~~~~~~~~~~~~~~~~~~~~~~~~~~~~~~~~~~~~~~~~~~~~

2101 GGAGTTAGGG GCGGGACTAT GGTTGCTGAC TAATTGAGAT GCATGCTTTG CATACTTCTG
     CCTCAATCCC CGCCCTGATA CCAACGACTG ATTAACTCTA CGTACGAAAC GTATGAAGAC
                                           SVO
     ~~~~~~~~~~~~~~~~~~~~~~~~~~~~~~~~~~~~~~~~~~~~~~~~~~~~~~~~~~~~~~

2161 CCTGCTGGGG AGCCTGGGGA CTTTCCACAC CTGGTTGCTG ACTAATTGAG ATGCATGCTT
     GGACGACCCC TCGGACCCCT GAAAGGTGTG GACCAACGAC TGATTAACTC TACGTACGAA
         SVO                                    CMV
     ~~~~~~~~~~~~~~~~  ~~~~~~~~~~~~~~~~~~~~~~~~~~~~~~~~~~~~~~~~~~~~

2221 TGCATACTTC TGCCCGCGGA GTTATTAATA GTAATCAATT ACGGGGTCAT TAGTTCATAG
     ACGTATGAAG ACGGGCGCCT CAATAATTAT CATTAGTTAA TGCCCCAGTA ATCAAGTATC
                                           CMV
     ~~~~~~~~~~~~~~~~~~~~~~~~~~~~~~~~~~~~~~~~~~~~~~~~~~~~~~~~~~~~~~

2281 CCCATATATG GAGTTCCGCG TTACATAACT TACGGTAAAT GGCCCGCCTG GCTGACCGCC
     GGGTATATAC CTCAAGGCGC AATGTATTGA ATGCCATTTA CCGGGCGGAC CGACTGGCGG
                                           CMV
     ~~~~~~~~~~~~~~~~~~~~~~~~~~~~~~~~~~~~~~~~~~~~~~~~~~~~~~~~~~~~~~
```

TABLE 3-continued

```
2341  CAACGACCCC CGCCCATTGA CGTCAATAAT GACGTATGTT CCCATAGTAA CGCCAATAGG
      GTTGCTGGGG GCGGGTAACT GCAGTTATTA CTGCATACAA GGGTATCATT GCGGTTATCC
                                     CMV
      ~~~~~~~~~~~~~~~~~~~~~~~~~~~~~~~~~~~~~~~~~~~~~~~~~~~~~~~~~~~~~~

2401  GACTTTCCAT TGACGTCAAT GGGTGGAGTA TTTACGGTAA ACTGCCCACT TGGCAGTACA
      CTGAAAGGTA ACTGCAGTTA CCCACCTCAT AAATGCCATT TGACGGGTGA ACCGTCATGT
                                     CMV
      ~~~~~~~~~~~~~~~~~~~~~~~~~~~~~~~~~~~~~~~~~~~~~~~~~~~~~~~~~~~~~~

2461  TCAAGTGTAT CATATGCCAA GTACGCCCCC TATTGACGTC AATGACGGTA ATGGCCCGC
      AGTTCACATA GTATACGGTT CATGCGGGGG ATAACTGCAG TTACTGCCAT TTACCGGGCG
                                     CMV
      ~~~~~~~~~~~~~~~~~~~~~~~~~~~~~~~~~~~~~~~~~~~~~~~~~~~~~~~~~~~~~~

2521  CTGGCATTAT GCCCAGTACA TGACCTTATG GGACTTTCCT ACTTGGCAGT ACATCTACGT
      GACCGTAATA CGGGTCATGT ACTGGAATAC CCTGAAAGGA TGAACCGTCA TGTAGATGCA
                                     CMV
      ~~~~~~~~~~~~~~~~~~~~~~~~~~~~~~~~~~~~~~~~~~~~~~~~~~~~~~~~~~~~~~

2581  ATTAGTCATC GCTATTACCA TGGTGATGCG GTTTTGGCAG TACATCAATG GGCGTGGATA
      TAATCAGTAG CGATAATGGT ACCACTACGC CAAAACCGTC ATGTAGTTAC CCGCACCTAT
                                     CMV
      ~~~~~~~~~~~~~~~~~~~~~~~~~~~~~~~~~~~~~~~~~~~~~~~~~~~~~~~~~~~~~~

2641  GCGGTTTGAC TCACGGGGAT TTCCAAGCCT CCACCCCATT GACGTCAATG GGAGTTTGTT
      CGCCAAACTG AGTGCCCCTA AAGGTTCGGA GGTGGGGTAA CTGCAGTTAC CCTCAAACAA
                                     CMV
      ~~~~~~~~~~~~~~~~~~~~~~~~~~~~~~~~~~~~~~~~~~~~~~~~~~~~~~~~~~~~~~

2701  TTGGCACCAA AATCAACGGG ACTTTCCAAA ATGTCGTAAC AACTCCGCCC CATTGACGCA
      AACCGTGGTT TTAGTTGCCC TGAAAGGTTT TACAGCATTG TTGAGGCGGG GTAACTGCGT
                                     CMV
      ~~~~~~~~~~~~~~~~~~~~~~~~~~~~~~~~~~~~~~~~~~~~~~~~~~~~~~~~~~~~~~

2761  AATGGGCGGT AGGCGTGTAC GGTGGGAGGT CTATATAAGC AGAGCTCTCT GGCTAACTAG
      TTACCCGCCA TCCGCACATG CCACCCTCCA GATATATTCG TCTCGAGAGA CCGATTGATC
                  CMV                                      Nat L
      ~~~~~~~~~~~~~~~~~~~~~~~~~~~~~~~~~~         ~~~~~~~~~~~~~~~~~~~~

2821  AGAACCCACT GCTTACTGGC TTATCGAAAT TACTAGTCCA CCATGGGGTC GTGCGAATGT
      TCTTGGGTGA CGAATGACCG AATAGCTTTA ATGATCAGGT GGTACCCCAG CACGCTTACA
                                     Nat L
      ~~~~~~~~~~~~~~~~~~~~~~~~~~~~~~~~~~~~~~~~~~~~~~~~~~~~~~~~~~~~~~

2881  CCTGCCCTGC TGCTTCTGCT ATCTTTGCTG CTGCTTCCCC TGGGCCTCCC AGTCCTGGGC
      GGACGGGACG ACGAAGACGA TAGAAACGAC GACGAAGGGG ACCCGGAGGG TCAGGACCCG
                                  BB-Opti FEPO
      ~~~~~~~~~~~~~~~~~~~~~~~~~~~~~~~~~~~~~~~~~~~~~~~~~~~~~~~~~~~~~~
      AlaProProArg LeuIleCys AspSerArg ValLeuGluArg TyrIleLeu GluAlaArg 2941  GCCCCCCCTC GCCTCATCTG TGACAGCCGA GTCCTGGAGA GGTACATTCT GGAGGCCAGG
      CGGGGGGGAG CGGAGTAGAC ACTGTCGGCT CAGGACCTCT CCATGTAAGA CCTCCGGTCC
                                  BB-Opti FEPO
      ~~~~~~~~~~~~~~~~~~~~~~~~~~~~~~~~~~~~~~~~~~~~~~~~~~~~~~~~~~~~~~
      GluAlaGluAsn ValThrMet GlyCysAla GluGlyCysSer PheSerGlu AsnIleThr 3001  GAGGCCGAAA ATGTGACCAT GGGCTGCGCT GAAGGCTGCA GCTTCAGTGA AAATATCACC
      CTCCGGCTTT TACACTGGTA CCCGACGCGA CTTCCGACGT CGAAGTCACT TTATAGTGG
                                  BB-Opti FEPO
      ~~~~~~~~~~~~~~~~~~~~~~~~~~~~~~~~~~~~~~~~~~~~~~~~~~~~~~~~~~~~~~
      ValProAspThr LysValAsn PheTyrThr TrpLysArgMet AspValGly GlnGlnAla 3061  GTTCCGGACA CCAAGGTCAA CTTCTATACC TGGAAGAGGA TGGACGTCGG GCAGCAGGCT
      CAAGGCCTGT GGTTCCAGTT GAAGATATGG ACCTTCTCCT ACCTGCAGCC CGTCGTCCGA
                                  BB-Opti FEPO
      ~~~~~~~~~~~~~~~~~~~~~~~~~~~~~~~~~~~~~~~~~~~~~~~~~~~~~~~~~~~~~~
      ValGluValTrp GlnGlyLeu AlaLeuLeu SerGluAlaIle LeuArgGly GlnAlaLeu 3121  GTGGAAGTCT GGCAGGGCCT CGCCCTCCTC AGCGAAGCCA TCCTGCGGGG CCAGGCCCTG
      CACCTTCAGA CCGTCCCGGA GCGGGAGGAG TCGCTTCGGT AGGACGCCCC GGTCCGGGAC
                                  BB-Opti FEPO
      ~~~~~~~~~~~~~~~~~~~~~~~~~~~~~~~~~~~~~~~~~~~~~~~~~~~~~~~~~~~~~~
      LeuAlaAsnSer SerGlnPro SerGluThr LeuGlnLeuHis ValAspLys AlaValSer
```

TABLE 3-continued

```
3181  CTGGCCAACT CCTCCCAGCC CTCTGAGACC CTGCAGCTGC ATGTCGACAA GGCCGTCAGC
      GACCGGTTGA GGAGGGTCGG GAGACTCTGG GACGTCGACG TACAGCTGTT CCGGCAGTCG
                          BB-Opti FEPO
      ~~~~~~~~~~~~~~~~~~~~~~~~~~~~~~~~~~~~~~~~~~~~~~~~~~~~~~~~~~~~~~
      SerLeuArgSer LeuThrSer LeuLeuArg AlaLeuGlyAla GlnLysGlu AlaThrSer 3241  AGCCTGCGCA GCCTCACCTC CCTGCTGCGC GCACTGGGAG CCCAGAAGGA AGCCACCTCC
      TCGGACGCGT CGGAGTGGAG GGACGACGCG CGTGACCCTC GGGTCTTCCT TCGGTGGAGG
                          BB-Opti FEPO
      ~~~~~~~~~~~~~~~~~~~~~~~~~~~~~~~~~~~~~~~~~~~~~~~~~~~~~~~~~~~~~~
      LeuProGluAla ThrSerAla AlaProLeu ArgThrPheThr ValAspThr LeuCysLys 3301  CTTCCCGAGG CAACCTCTGC CGCCCCCTTA AGAACCTTCA CTGTGGACAC TTTGTGCAAG
      GAAGGGCTCC GTTGGAGACG GCGGGGGAAT TCTTGGAAGT GACACCTGTG AAACACGTTC
                          BB-Opti FEPO
      ~~~~~~~~~~~~~~~~~~~~~~~~~~~~~~~~~~~~~~~~~~~~~~~~~~~~~~~~~~~~~~
      LeuPheArgIle TyrSerAsn PheLeuArg GlyLysLeuThr LeuTyrThr GlyGluAla 3361  CTTTTCCGAA TCTACTCCAA CTTCCTGCGG GGCAAGCTGA CGCTGTACAC AGGGGAGGCC
      GAAAAGGCTT AGATGAGGTT GAAGGACGCC CCGTTCGACT GCGACATGTG TCCCCTCCGG
         BB-Opti FEPO                                      BGH
      ~~~~~~~~~~~~~~~~~~~~~~                      ~~~~~~~~~~~~~~~~~~~~
      CysArgArgGly AspArg***

3421  TGCCGAAGAG GAGACAGGTG AGCGGCCGCA TCAGCCTCGA CTGTGCCTTC TAGTTGCCAG
      ACGGCTTCTC CTCTGTCCAC TCGCCGGCGT AGTCGGAGCT GACACGGAAG ATCAACGGTC
                                        BGH
      ~~~~~~~~~~~~~~~~~~~~~~~~~~~~~~~~~~~~~~~~~~~~~~~~~~~~~~~~~~~~~~

3481  CCATCTGTTG TTTGCCCCTC CCCCGTGCCT TCCTTGACCC TGGAAGGTGC CACTCCCACT
      GGTAGACAAC AAACGGGGAG GGGGCACGGA AGGAACTGGG ACCTTCCACG GTGAGGGTGA
                                        BGH
      ~~~~~~~~~~~~~~~~~~~~~~~~~~~~~~~~~~~~~~~~~~~~~~~~~~~~~~~~~~~~~~

3541  GTCCTTTCCT AATAAAATGA GGAAATTGCA TCGCATTGTC TGAGTAGGTG TCATTCTATT
      CAGGAAAGGA TTATTTTACT CCTTTAACGT AGCGTAACAG ACTCATCCAC AGTAAGATAA
                                        BGH
      ~~~~~~~~~~~~~~~~~~~~~~~~~~~~~~~~~~~~~~~~~~~~~~~~~~~~~~~~~~~~~~

3601  CTGGGGGGTG GGGTGGGGCA GGACAGCAAG GGGGAGGATT GGGAAGACAA TAGCAGGCAT
      GACCCCCCAC CCCACCCCGT CCTGTCGTTC CCCCTCCTAA CCCTTCTGTT ATCGTCCGTA
            BGH                                                   Beta
      ~~~~~~~~~~~~~~~~~~~                                     ~~~~~~~~

3661  GCTGGGGATG CGGTGGGCTC TATGGCTTCT GAGGCGGAAA GAACCAGTGT ACAGCTTTGC
      CGACCCCTAC GCCACCCGAG ATACCGAAGA CTCCGCCTTT CTTGGTCACA TGTCGAAACG
                                       Beta
      ~~~~~~~~~~~~~~~~~~~~~~~~~~~~~~~~~~~~~~~~~~~~~~~~~~~~~~~~~~~~~~

3721  TTCTCAATTT CTTATTTGCA TAATGAGAAA AAAAGGAAAA TTAATTTTAA CACCAATTCA
      AAGAGTTAAA GAATAAACGT ATTACTCTTT TTTTCCTTTT AATTAAAATT GTGGTTAAGT
                                       Beta
      ~~~~~~~~~~~~~~~~~~~~~~~~~~~~~~~~~~~~~~~~~~~~~~~~~~~~~~~~~~~~~~

3781  GTAGTTGATT GAGCAAATGC GTTGCCAAAA AGGATGCTTT AGAGACAGTG TTCTCTGCAC
      CATCAACTAA CTCGTTTACG CAACGGTTTT TCCTACGAAA TCTCTGTCAC AAGAGACGTG
                                       Beta
      ~~~~~~~~~~~~~~~~~~~~~~~~~~~~~~~~~~~~~~~~~~~~~~~~~~~~~~~~~~~~~~

3841  AGATAAGGAC AAACATTATT CAGAGGGAGT ACCCAGAGCT GAGACTCCTA AGCCAGTGAG
      TCTATTCCTG TTTGTAATAA GTCTCCCTCA TGGGTCTCGA CTCTGAGGAT TCGGTCACTC
                                       Beta
      ~~~~~~~~~~~~~~~~~~~~~~~~~~~~~~~~~~~~~~~~~~~~~~~~~~~~~~~~~~~~~~

3901  TGGCACAGCA TCCAGGGAGA AATATGCTTG TCATCACCGA AGCCTGATTC CGTAGAGCCA
      ACCGTGTCGT AGGTCCCTCT TTATACGAAC AGTAGTGGCT TCGGACTAAG GCATCTCGGT
                                       Beta
      ~~~~~~~~~~~~~~~~~~~~~~~~~~~~~~~~~~~~~~~~~~~~~~~~~~~~~~~~~~~~~~

3961  CACCCTGGTA AGGGCCAATC TGCTCACACA GGATAGAGAG GGCAGGAGCC AGGGCAGAGC
      GTGGGACCAT TCCCGGTTAG ACGAGTGTGT CCTATCTCTC CCGTCCTCGG TCCCGTCTCG
                                       Beta
      ~~~~~~~~~~~~~~~~~~~~~~~~~~~~~~~~~~~~~~~~~~~~~~~~~~~~~~~~~~~~~~

4021  ATATAAGGTG AGGTAGGATC AGTTGCTCCT CACATTTGCT TCTGACATAG TTGTGTTGGG
      TATATTCCAC TCCATCCTAG TCAACGAGGA GTGTAAACGA AGACTGTATC AACACAACCC
```

TABLE 3-continued

```
4081  AGCTTGGATA GCTTGGGGGG GGGACAGCTC AGGGCTGCGA TTTCGCGCCA ACTTGACGGC
      TCGAACCTAT CGAACCCCCC CCCTGTCGAG TCCCGACGCT AAAGCGCGGT TGAACTGCCG
                                                        OptEcAFRS
                                                        ~~~~~~~~~~~~~~~~~

4141  AATCCTAGCG TGAAGGCTGG TAGGATTTTA TCCCTCGAGC CACCATGGCC TCCAGCAACC
      TTAGGATCGC ACTTCCGACC ATCCTAAAAT AGGGAGCTCG GTGGTACCGG AGGTCGTTGG
                              OptEcAFRS
      ~~~~~~~~~~~~~~~~~~~~~~~~~~~~~~~~~~~~~~~~~~~~~~~~~~~~~~~~~~~~~~

4201  TGATCAAGCA GCTCCAGGAG AGGGGCCTCG TGGCTCAGGT CACCGACGAA GAAGCACTCG
      ACTAGTTCGT CGAGGTCCTC TCCCCGGAGC ACCGAGTCCA GTGGCTGCTT CTTCGTGAGC
                              OptEcAFRS
      ~~~~~~~~~~~~~~~~~~~~~~~~~~~~~~~~~~~~~~~~~~~~~~~~~~~~~~~~~~~~~~

4261  CTGAAAGACT GGCCCAGGGA CCCATTGCAC TGATCTGCGG GTTCGATCCT ACAGCCGACT
      GACTTTCTGA CCGGGTCCCT GGGTAACGTG ACTAGACGCC CAAGCTAGGA TGTCGGCTGA
                              OptEcAFRS
      ~~~~~~~~~~~~~~~~~~~~~~~~~~~~~~~~~~~~~~~~~~~~~~~~~~~~~~~~~~~~~~

4321  CTCTCCACCT GGGTCATCTC GTGCCACTGC TGTGTCTCAA ACGGTTTCAG CAGGCTGGCC
      GAGAGGTGGA CCCAGTAGAG CACGGTGACG ACACAGAGTT TGCCAAAGTC GTCCGACCGG
                              OptEcAFRS
      ~~~~~~~~~~~~~~~~~~~~~~~~~~~~~~~~~~~~~~~~~~~~~~~~~~~~~~~~~~~~~~

4381  ACAAGCCCGT CGCACTGGTG GGAGGTGCTA CTGGGCTGAT TGGCGATCCT AGTTTCAAAG
      TGTTCGGGCA GCGTGACCAC CCTCCACGAT GACCCGACTA ACCGCTAGGA TCAAAGTTTC
                              OptEcAFRS
      ~~~~~~~~~~~~~~~~~~~~~~~~~~~~~~~~~~~~~~~~~~~~~~~~~~~~~~~~~~~~~~

4441  CCGCAGAGCG CAAGCTCAAT ACCGAGGAGA CAGTGCAGGA ATGGGTCGAC AAAATCCGAA
      GGCGTCTCGC GTTCGAGTTA TGGCTCCTCT GTCACGTCCT TACCCAGCTG TTTTAGGCTT
                              OptEcAFRS
      ~~~~~~~~~~~~~~~~~~~~~~~~~~~~~~~~~~~~~~~~~~~~~~~~~~~~~~~~~~~~~~

4501  AGCAGGTCGC CCCATTTCTG GATTTCGACT GCGGAGAGAA CTCAGCTATT GCCGCAAATA
      TCGTCCAGCG GGGTAAAGAC CTAAAGCTGA CGCCTCTCTT GAGTCGATAA CGGCGTTTAT
                              OptEcAFRS
      ~~~~~~~~~~~~~~~~~~~~~~~~~~~~~~~~~~~~~~~~~~~~~~~~~~~~~~~~~~~~~~

4561  ACTACGATTG GTTTGGGAAT ATGAACGTCC TCACTTTCCT GCGTGACATC GGTAAACATT
      TGATGCTAAC CAAACCCTTA TACTTGCAGG AGTGAAAGGA CGCACTGTAG CCATTTGTAA
                              OptEcAFRS
      ~~~~~~~~~~~~~~~~~~~~~~~~~~~~~~~~~~~~~~~~~~~~~~~~~~~~~~~~~~~~~~

4621  TTTCCGTGAA TCAGATGATT AACAAGGAAG CTGTGAAGCA GAGGCTGAAT AGAGAGGGCC
      AAAGGCACTT AGTCTACTAA TTGTTCCTTC GACACTTCGT CTCCGACTTA TCTCTCCCGG
                              OptEcAFRS
      ~~~~~~~~~~~~~~~~~~~~~~~~~~~~~~~~~~~~~~~~~~~~~~~~~~~~~~~~~~~~~~

4681  AGGGAATCAG CTTCACCGAA TTTTCTTATA ATCTCCTGCA GGGGTACGGT ATGGCCTGTG
      TCCCTTAGTC GAAGTGGCTT AAAAGAATAT TAGAGGACGT CCCCATGCCA TACCGGACAC
                              OptEcAFRS
      ~~~~~~~~~~~~~~~~~~~~~~~~~~~~~~~~~~~~~~~~~~~~~~~~~~~~~~~~~~~~~~

4741  CAAACAAACA GTATGGCGTC GTGCTGCAGA TTGGAGGCAG TGATCAGTGG GGGAACATCA
      GTTTGTTTGT CATACCGCAG CACGACGTCT AACCTCCGTC ACTAGTCACC CCCTTGTAGT
                              OptEcAFRS
      ~~~~~~~~~~~~~~~~~~~~~~~~~~~~~~~~~~~~~~~~~~~~~~~~~~~~~~~~~~~~~~

4801  CATCAGGTAT TGACCTCACT CGGCGCCTGC ACCAGAATCA GGTCTTTGGA CTCACCGTGC
      GTAGTCCATA ACTGGAGTGA GCCGCGGACG TGGTCTTAGT CCAGAAACCT GAGTGGCACG
                              OptEcAFRS
      ~~~~~~~~~~~~~~~~~~~~~~~~~~~~~~~~~~~~~~~~~~~~~~~~~~~~~~~~~~~~~~

4861  CCCTGATCAC AAAGGCTGAT GGCACAAAAT TTGGTAAGAC CGAGGGTGGA GCCGTGTGGC
      GGGACTAGTG TTTCCGACTA CCGTGTTTTA AACCATTCTG GCTCCCACCT CGGCACACCG
                              OptEcAFRS
      ~~~~~~~~~~~~~~~~~~~~~~~~~~~~~~~~~~~~~~~~~~~~~~~~~~~~~~~~~~~~~~

4921  TGGACCCTAA AAAGACATCC CCATACAAAT TCTATCAGTT TTGGATCAAC ACTGCAGATG
      ACCTGGGATT TTTCTGTAGG GGTATGTTTA AGATAGTCAA AACCTAGTTG TGACGTCTAC
                              OptEcAFRS
      ~~~~~~~~~~~~~~~~~~~~~~~~~~~~~~~~~~~~~~~~~~~~~~~~~~~~~~~~~~~~~~

4981  CTGACGTCTA CCGATTCCTC AAGTTTTTCA CCTTTATGAG CATTGAGGAA ATCAATGCCC
      GACTGCAGAT GGCTAAGGAG TTCAAAAAGT GGAAATACTC GTAACTCCTT TAGTTACGGG
                              OptEcAFRS
      ~~~~~~~~~~~~~~~~~~~~~~~~~~~~~~~~~~~~~~~~~~~~~~~~~~~~~~~~~~~~~~
```

TABLE 3-continued

```
5041  TGGAGGAAGA GGATAAGAAC TCTGGCAAAG CTCCCCGTGC ACAGTATGTG CTCGCCGAAC
      ACCTCCTTCT CCTATTCTTG AGACCGTTTC GAGGGGCACG TGTCATACAC GAGCGGCTTG
                                    OptEcAFRS

5101  AGGTCACAAG GCTGGTGCAT GGGGAGGAAG GTCTGCAGGC TGCCAAGAGA ATTACTGAGT
      TCCAGTGTTC CGACCACGTA CCCCTCCTTC CAGACGTCCG ACGGTTCTCT TAATGACTCA
                                    OptEcAFRS

5161  GCCTCTTCAG TGGCTCACTG TCCGCACTGA GCGAAGCTGA CTTTGAGCAG CTCGCCCAGG
      CGGAGAAGTC ACCGAGTGAC AGGCGTGACT CGCTTCGACT GAAACTCGTC GAGCGGGTCC
                                    OptEcAFRS

5221  ATGGAGTGCC TATGGTCGAG ATGGAAAAAG GCGCAGACCT GATGCAGGCT CTCGTGGATT
      TACCTCACGG ATACCAGCTC TACCTTTTTC GCGTCTGGA CTACGTCCGA GAGCACCTAA
                                    OptEcAFRS

5281  CTGAGCTGCA GCCAAGTCGG GGGCAGGCCC GCAAGACCAT CGCATCAAAT GCTATTACAA
      GACTCGACGT CGGTTCAGCC CCCGTCCGGG CGTTCTGGTA GCGTAGTTTA CGATAATGTT
                                    OptEcAFRS

5341  TCAACGGTGA AAAACAGTCC GACCCCGAGT ACTTCTTTAA GGAAGAGGAT CGACTGTTCG
      AGTTGCCACT TTTTGTCAGG CTGGGGCTCA TGAAGAAATT CCTTCTCCTA GCTGACAAGC
                                    OptEcAFRS

5401  GACGTTTTAC CCTCCTGAGG AGAGGCAAAA AGAATTATTG TCTGATTTGC TGGAAGTGAT
      CTGCAAAATG GGAGGACTCC TCTCCGTTTT TCTTAATAAC AGACTAAACG ACCTTCACTA
                                      IRES

5461  CTAGAGGCCG CGCAGTTAAC GCCGCCCCTC TCCCTCCCCC CCCCTAACGT TACTGGCCGA
      GATCTCCGGC GCGTCAATTG CGGCGGGGAG AGGGAGGGGG GGGGATTGCA ATGACCGGCT
                                      IRES

5521  AGCCGCTTGG AATAAGGCCG GTGTGCGTTT GTCTATATGT TATATTCCAC CATATTGCCG
      TCGGCGAACC TTATTCCGGC CACACGCAAA CAGATATACA ATATAAGGTG GTATAACGGC
                                      IRES

5581  TCTATTGGCA ATGTGAGGGC CCGGAAACCT GGCCCTGTCT TCTTGACGAG CATTCCTAGG
      AGATAACCGT TACACTCCCG GGCCTTTGGA CCGGGACAGA AGAACTGCTC GTAAGGATCC
                                      IRES

5641  GGTCTTTCCC CTCTCGCCAA AGGAATGCAA GGTCTGTTGA ATGTCGTGAA GGAAGCAGTT
      CCAGAAAGGG GAGAGCGGTT TCCTTACGTT CCAGACAACT TACAGCACTT CCTTCGTCAA
                                      IRES

5701  CCTCTGGAAG CTTCTTGAAG ACAAACAACG TCTGTAGCGA CCCTTTGCAG GCAGCGGAAC
      GGAGACCTTC GAAGAACTTC TGTTTGTTGC AGACATCGCT GGGAAACGTC CGTCGCCTTG
                                      IRES

5761  CCCCCACCTG GCGACAGGTG CCTCTGCGGC CAAAAGCCAC GTGTATAAAA TACACCTGCA
      GGGGGTGGAC CGCTGTCCAC GGAGACGCCG GTTTTCGGTG CACATATTTT ATGTGGACGT
                                      IRES

5821  AAGGCGGCAC AACCCCAGTG CGACGTTGTG AGTTGGATAG TTGTGGAAAG AGTCAAATGG
      TTCCGCCGTG TTGGGGTCAC GCTGCAACAC TCAACCTATC AACACCTTTC TCAGTTTACC
                                      IRES

5881  CTCTCCTCAA GCGTATTCAA CAAGGGGCTG AAGGATGCCC AGAAGGTACC CCATTGTATG
      GAGAGGAGTT CGCATAAGTT GTTCCCCGAC TTCCTACGGG TCTTCCATGG GGTAACATAC
                                      IRES

5941  GGATCTGATC TGGGGCCTCG GTACACATGC TTTACATGTG TTTAGTCGAG GTTAAAAAAA
      CCTAGACTAG ACCCCGGAGC CATGTGTACG AAATGTACAC AAATCAGCTC CAATTTTTTT
                                      IRES
```

TABLE 3-continued

```
6001 CGTCTAGGCC CCCCGAACCA CGGGGACGTG GTATTCCTTT GAAAAACACG ATGATAATAT
     GCAGATCCGG GGGGCTTGGT GCCCCTGCAC CATAAGGAAA CTTTTTGTGC TACTATTATA
      IRES                                        DHFR
     ~~~~~~~                                      ~~~~~~~~~~~~~~~~~~~~

6061 GGCCACACCC GTCCGAGATC ACCCTCGAGC CACCATGGTT CGACCATTGA ACTGCATCGT
     CCGGTGTGGG CAGGCTCTAG TGGGAGCTCG GTGGTACCAA GCTGGTAACT TGACGTAGCA
                                          DHFR
     ~~~~~~~~~~~~~~~~~~~~~~~~~~~~~~~~~~~~~~~~~~~~~~~~~~~~~~~~~~~~~~

6121 CGCCGTGTCC CAAAATATGG GGATTGGCAA GAACGGAGAC CTACCCTGGC CTCCGCTCAG
     GCGGCACAGG GTTTTATACC CCTAACCGTT CTTGCCTCTG GATGGGACCG GAGGCGAGTC
                                          DHFR
     ~~~~~~~~~~~~~~~~~~~~~~~~~~~~~~~~~~~~~~~~~~~~~~~~~~~~~~~~~~~~~~

6181 GAACGAGTTC AAGTACTTCC AAAGAATGAC CACAACCTCT TCAGTGGAAG GTAAACAGAA
     CTTGCTCAAG TTCATGAAGG TTTCTTACTG GTGTTGGAGA AGTCACCTTC CATTTGTCTT
                                          DHFR
     ~~~~~~~~~~~~~~~~~~~~~~~~~~~~~~~~~~~~~~~~~~~~~~~~~~~~~~~~~~~~~~

6241 TCTGGTGATT ATGGGTAGGA AAACCTGGTT CTCCATTCCT GAGAAGAATC GACCTTTAAA
     AGACCACTAA TACCCATCCT TTTGGACCAA GAGGTAAGGA CTCTTCTTAG CTGGAAATTT
                                          DHFR
     ~~~~~~~~~~~~~~~~~~~~~~~~~~~~~~~~~~~~~~~~~~~~~~~~~~~~~~~~~~~~~~

6301 GGACAGAATT AATATAGTTC TCAGTAGAGA ACTCAAAGAA CCACCACGAG GAGCTCATTT
     CCTGTCTTAA TTATATCAAG AGTCATCTCT TGAGTTTCTT GGTGGTGCTC CTCGAGTAAA
                                          DHFR
     ~~~~~~~~~~~~~~~~~~~~~~~~~~~~~~~~~~~~~~~~~~~~~~~~~~~~~~~~~~~~~~

6361 TCTTGCCAAA AGTTTGGATG ATGCCTTAAG ACTTATTGAA CAACCGGAAT TGGCAAGTAA
     AGAACGGTTT TCAAACCTAC TACGGAATTC TGAATAACTT GTTGGCCTTA ACCGTTCATT
                                          DHFR
     ~~~~~~~~~~~~~~~~~~~~~~~~~~~~~~~~~~~~~~~~~~~~~~~~~~~~~~~~~~~~~~

6421 AGTAGACATG GTTTGGATAG TCGGAGGCAG TTCTGTTTAC CAGGAAGCCA TGAATCAACC
     TCATCTGTAC CAAACCTATC AGCCTCCGTC AAGACAAATG GTCCTTCGGT ACTTAGTTGG
                                          DHFR
     ~~~~~~~~~~~~~~~~~~~~~~~~~~~~~~~~~~~~~~~~~~~~~~~~~~~~~~~~~~~~~~

6481 AGGCCACCTC AGACTCTTTG TGACAAGGAT CATGCAGGAA TTTGAAAGTG ACACGTTTTT
     TCCGGTGGAG TCTGAGAAAC ACTGTTCCTA GTACGTCCTT AAACTTTCAC TGTGCAAAAA
                                          DHFR
     ~~~~~~~~~~~~~~~~~~~~~~~~~~~~~~~~~~~~~~~~~~~~~~~~~~~~~~~~~~~~~~

6541 CCCAGAAATT GATTTGGGGA AATATAAACT TCTCCCAGAA TACCCAGGCG TCCTCTCTGA
     GGGTCTTTAA CTAAACCCCT TTATATTTGA AGAGGGTCTT ATGGGTCCGC AGGAGAGACT
                                          DHFR
     ~~~~~~~~~~~~~~~~~~~~~~~~~~~~~~~~~~~~~~~~~~~~~~~~~~~~~~~~~~~~~~

6601 GGTCCAGGAG GAAAAAGGCA TCAAGTATAA GTTTGAAGTC TACGAGAAGA AAGACTAATC
     CCAGGTCCTC CTTTTTCCGT AGTTCATATT CAAACTTCAG ATGCTCTTCT TTCTGATTAG

6661 TAGAGCCAGA TCTCCAATTG CACGGGCTAC GAGATTTCGA TTCCACCGCC GCCTTCTATG
     ATCTCGGTCT AGAGGTTAAC GTGCCCGATG CTCTAAAGCT AAGGTGGCGG CGGAAGATAC

6721 AAAGGTTGGG CTTCGGAATC GTTTTCCGGG ACGCCGGCTG GATGATCCTC CAGCGCGGGG
     TTTCCAACCC GAAGCCTTAG CAAAAGGCCC TGCGGCCGAC CTACTAGGAG GTCGCGCCCC
                                                               SV40 PolyA
                                                              ~~~~~~~~~~~~~~~~~~~~

6781 ATCTCATGCT GGAGTTCTTC GCCCACCCCA ACTTGTTTAT TGCAGCTTAT AATGGTTACA
     TAGAGTACGA CCTCAAGAAG CGGGTGGGGT TGAACAAATA ACGTCGAATA TTACCAATGT
                  SV40 PolyA
     ~~~~~~~~~~~~~~~~~~~~~~~~~~~~~~~~~~~~~~~~~~~~~~~~~~~~~~~~~~~~~~

6841 AATAAAGCAA TAGCATCACA AATTTCACAA ATAAAGCATT TTTTTCACTG CATTCTAGTT
     TTATTTCGTT ATCGTAGTGT TTAAAGTGTT TATTTCGTAA AAAAAGTGAC GTAAGATCAA
                  SV40 PolyA
     ~~~~~~~~~~~~~~~~~~~~~~~~~~~~~~~~~~~~~~~~~

6901 GTGGTTTGTC CAAACTCATC AATGTATCTT ATCATGTCGG TTACCCCCGT CCGACATGTG
     CACCAAACAG GTTTGAGTAG TTACATAGAA TAGTACAGCC AATGGGGGCA GGCTGTACAC
                                                                    pUC Ori
                                                                   ~~~~~~~

6961 AGCAAAAGGC CAGCAAAAGG CCAGGAACCG TAAAAAGGCC GCGTTGCTGG CGTTTTTCCA
     TCGTTTTCCG GTCGTTTTCC GGTCCTTGGC ATTTTTCCGG CGCAACGACC GCAAAAAGGT
     ~~~~~~~~~~~~~~~~~~~~~~~~~~~~~~~~~~~~~~~~~~~~~~~~~~~~~~~~~~~~~~
                               pUC Ori
```

TABLE 3-continued

```
7021  TAGGCTCCGC CCCCCTGACG AGCATCACAA AAATCGACGC TCAAGTCAGA GGTGGCGAAA
      ATCCGAGGCG GGGGGACTGC TCGTAGTGTT TTTAGCTGCG AGTTCAGTCT CCACCGCTTT
      ~~~~~~~~~~~~~~~~~~~~~~~~~~~~~~~~~~~~~~~~~~~~~~~~~~~~~~~~~~~~
                                    pUC Ori

7081  CCCGACAGGA CTATAAAGAT ACCAGGCGTT TCCCCCTGGA AGCTCCCTCG TGCGCTCTCC
      GGGCTGTCCT GATATTTCTA TGGTCCGCAA AGGGGGACCT TCGAGGGAGC ACGCGAGAGG
      ~~~~~~~~~~~~~~~~~~~~~~~~~~~~~~~~~~~~~~~~~~~~~~~~~~~~~~~~~~~~
                                    pUC Ori

7141  TGTTCCGACC CTGCCGCTTA CCGGATACCT GTCCGCCTTT CTCCCTTCGG GAAGCGTGGC
      ACAAGGCTGG GACGGCGAAT GGCCTATGGA CAGGCGGAAA GAGGGAAGCC CTTCGCACCG
      ~~~~~~~~~~~~~~~~~~~~~~~~~~~~~~~~~~~~~~~~~~~~~~~~~~~~~~~~~~~~
                                    pUC Ori

7201  GCTTTCTCAT AGCTCACGCT GTAGGTATCT CAGTTCGGTG TAGGTCGTTC GCTCCAAGCT
      CGAAAGAGTA TCGAGTGCGA CATCCATAGA GTCAAGCCAC ATCCAGCAAG CGAGGTTCGA
      ~~~~~~~~~~~~~~~~~~~~~~~~~~~~~~~~~~~~~~~~~~~~~~~~~~~~~~~~~~~~
                                    pUC Ori

7261  GGGCTGTGTG CACGAACCCC CCGTTCAGCC CGACCGCTGC GCCTTATCCG GTAACTATCG
      CCCGACACAC GTGCTTGGGG GGCAAGTCGG GCTGGCGACG CGGAATAGGC CATTGATAGC
      ~~~~~~~~~~~~~~~~~~~~~~~~~~~~~~~~~~~~~~~~~~~~~~~~~~~~~~~~~~~~
                                    pUC Ori

7321  TCTTGAGTCC AACCCGGTAA GACACGACTT ATCGCCACTG GCAGCAGCCA CTGGTAACAG
      AGAACTCAGG TTGGGCCATT CTGTGCTGAA TAGCGGTGAC CGTCGTCGGT GACCATTGTC
      ~~~~~~~~~~~~~~~~~~~~~~~~~~~~~~~~~~~~~~~~~~~~~~~~~~~~~~~~~~~~
                                    pUC Ori

7381  GATTAGCAGA GCGAGGTATG TAGGCGGTGC TACAGAGTTC TTGAAGTGGT GGCCTAACTA
      CTAATCGTCT CGCTCCATAC ATCCGCCACG ATGTCTCAAG AACTTCACCA CCGGATTGAT
      ~~~~~~~~~~~~~~~~~~~~~~~~~~~~~~~~~~~~~~~~~~~~~~~~~~~~~~~~~~~~
                                    pUC Ori

7441  CGGCTACACT AGAAGAACAG TATTTGGTAT CTGCGCTCTG CTGAAGCCAG TTACCTTCGG
      GCCGATGTGA TCTTCTTGTC ATAAACCATA GACGCGAGAC GACTTCGGTC AATGGAAGCC
      ~~~~~~~~~~~~~~~~~~~~~~~~~~~~~~~~~~~~~~~~~~~~~~~~~~~~~~~~~~~~
                                    pUC Ori

7501  AAAAAGAGTT GGTAGCTCTT GATCCGGCAA ACAAACCACC GCTGGTAGCG GTGGTTTTTT
      TTTTTCTCAA CCATCGAGAA CTAGGCCGTT TGTTTGGTGG CGACCATCGC CACCAAAAAA
      ~~~~~~~~~~~~~~~~~~~~~~~~~~~~~~~~~~~~~~~~~~~~~~~~~~~~~~~~~~~~
                                    pUC Ori

7561  TGTTTGCAAG CAGCAGATTA CGCGCAGAAA AAAAGGATCT CAAGAAGATC CTTTGATCTT
      ACAAACGTTC GTCGTCTAAT GCGCGTCTTT TTTTCCTAGA GTTCTTCTAG GAAACTAGAA
      ~~~~~~~~~~~~~~~~~~~~~~~~~~~~~~~~~~~~~~~~~~~~~~~~~~~~~~~~~~~~
                                    pUC Ori

7621  TTCTACGGGG TCTGACGCTC AGTGGAACGA AAACTCACGT TAAGGGATTT TGGTCATGAG
      AAGATGCCCC AGACTGCGAG TCACCTTGCT TTTGAGTGCA ATTCCCTAAA ACCAGTACTC
      ~~~~~~~~~~
       pUC Ori

7681  ATTATCAAAA AGGATCTTCA CCTAGATCCT TTTAAATTAA AAATGAAGTT TTAAATCAAT
      TAATAGTTTT TCCTAGAAGT GGATCTAGGA AAATTTAATT TTTACTTCAA AATTTAGTTA

7741  CTAAAGTATA TATGAGTAAA CTTGGTCTGA CAGTTACCAA TGCTTAATCA GTGAGGCACC
      GATTTCATAT ATACTCATTT GAACCAGACT GTCAATGGTT ACGAATTAGT CACTCCGTGG
                                                  ~~~~~~~~~~~~~~~~~~~~~~~~~~
                                                              Amp

7801  TATCTCAGCG ATCTGTCTAT TTCGTTCATC CATAGTTGCC TGACTCCCCG TCGTGTAGAT
      ATAGAGTCGC TAGACAGATA AAGCAAGTAG GTATCAACGG ACTGAGGGGC AGCACATCTA
      ~~~~~~~~~~~~~~~~~~~~~~~~~~~~~~~~~~~~~~~~~~~~~~~~~~~~~~~~~~~~
                                      Amp

7861  AACTACGATA CGGGAGGGCT TACCATCTGG CCCCAGTGCT GCAATGATAC CGCGAGACCC
      TTGATGCTAT GCCCTCCCGA ATGGTAGACC GGGGTCACGA CGTTACTATG GCGCTCTGGG
      ~~~~~~~~~~~~~~~~~~~~~~~~~~~~~~~~~~~~~~~~~~~~~~~~~~~~~~~~~~~~
                                      Amp

7921  ACGCTCACCG GCTCCAGATT TATCAGCAAT AAACCAGCCA GCCGGAAGGG CCGAGCGCAG
      TGCGAGTGGC CGAGGTCTAA ATAGTCGTTA TTTGGTCGGT CGGCCTTCCC GGCTCGCGTC
      ~~~~~~~~~~~~~~~~~~~~~~~~~~~~~~~~~~~~~~~~~~~~~~~~~~~~~~~~~~~~
                                      Amp
```

TABLE 3-continued

```
7981 AAGTGGTCCT GCAACTTTAT CCGCCTCCAT CCAGTCTATT AATTGTTGCC GGGAAGCTAG
     TTCACCAGGA CGTTGAAATA GGCGGAGGTA GGTCAGATAA TTAACAACGG CCCTTCGATC
     ~~~~~~~~~~~~~~~~~~~~~~~~~~~~~~~~~~~~~~~~~~~~~~~~~~~~~~~~~~~~~~~~
                                  Amp

8041 AGTAAGTAGT TCGCCAGTTA ATAGTTTGCG CAACGTTGTT GCCATTGCTA CAGGCATCGT
     TCATTCATCA AGCGGTCAAT TATCAAACGC GTTGCAACAA CGGTAACGAT GTCCGTAGCA
     ~~~~~~~~~~~~~~~~~~~~~~~~~~~~~~~~~~~~~~~~~~~~~~~~~~~~~~~~~~~~~~~~
                                  Amp

8101 GGTGTCACGC TCGTCGTTTG GTATGGCTTC ATTCAGCTCC GGTTCCCAAC GATCAAGGCG
     CCACAGTGCG AGCAGCAAAC CATACCGAAG TAAGTCGAGG CCAAGGGTTG CTAGTTCCGC
     ~~~~~~~~~~~~~~~~~~~~~~~~~~~~~~~~~~~~~~~~~~~~~~~~~~~~~~~~~~~~~~~~
                                  Amp

8161 AGTTACATGA TCCCCCATGT TGTGCAAAAA AGCGGTTAGC TCCTTCGGTC CTCCGATCGT
     TCAATGTACT AGGGGGTACA ACACGTTTTT TCGCCAATCG AGGAAGCCAG GAGGCTAGCA
     ~~~~~~~~~~~~~~~~~~~~~~~~~~~~~~~~~~~~~~~~~~~~~~~~~~~~~~~~~~~~~~~~
                                  Amp

8221 TGTCAGAAGT AAGTTGGCCG CAGTGTTATC ACTCATGGTT ATGGCAGCAC TGCATAATTC
     ACAGTCTTCA TTCAACCGGC GTCACAATAG TGAGTACCAA TACCGTCGTG ACGTATTAAG
     ~~~~~~~~~~~~~~~~~~~~~~~~~~~~~~~~~~~~~~~~~~~~~~~~~~~~~~~~~~~~~~~~
                                  Amp

8281 TCTTACTGTC ATGCCATCCG TAAGATGCTT TTCTGTGACT GGTGAGTACT CAACCAAGTC
     AGAATGACAG TACGGTAGGC ATTCTACGAA AAGACACTGA CCACTCATGA GTTGGTTCAG
     ~~~~~~~~~~~~~~~~~~~~~~~~~~~~~~~~~~~~~~~~~~~~~~~~~~~~~~~~~~~~~~~~
                                  Amp

8341 ATTCTGAGAA TAGTGTATGC GGCGACCGAG TTGCTCTTGC CCGGCGTCAA TACGGGATAA
     TAAGACTCTT ATCACATACG CCGCTGGCTC AACGAGAACG GGCCGCAGTT ATGCCCTATT
     ~~~~~~~~~~~~~~~~~~~~~~~~~~~~~~~~~~~~~~~~~~~~~~~~~~~~~~~~~~~~~~~~
                                  Amp

8401 TACCGCGCCA CATAGCAGAA CTTTAAAAGT GCTCATCATT GGAAAACGTT CTTCGGGGCG
     ATGGCGCGGT GTATCGTCTT GAAATTTTCA CGAGTAGTAA CCTTTTGCAA GAAGCCCCGC
     ~~~~~~~~~~~~~~~~~~~~~~~~~~~~~~~~~~~~~~~~~~~~~~~~~~~~~~~~~~~~~~~~
                                  Amp

8461 AAAACTCTCA AGGATCTTAC CGCTGTTGAG ATCCAGTTCG ATGTAACCCA CTCGTGCACC
     TTTTGAGAGT TCCTAGAATG GCGACAACTC TAGGTCAAGC TACATTGGGT GAGCACGTGG
     ~~~~~~~~~~~~~~~~~~~~~~~~~~~~~~~~~~~~~~~~~~~~~~~~~~~~~~~~~~~~~~~~
                                  Amp

8521 CAACTGATCT TCAGCATCTT TTACTTTCAC CAGCGTTTCT GGGTGAGCAA AAACAGGAAG
     GTTGACTAGA AGTCGTAGAA AATGAAAGTG GTCGCAAAGA CCCACTCGTT TTTGTCCTTC
     ~~~~~~~~~~~~~~~~~~~~~~~~~~~~~~~~~~~~~~~~~~~~~~~~~~~~~~~~~~~~~~~~
                                  Amp

8581 GCAAAATGCC GCAAAAAAGG GAATAAGGGC GACACGGAAA TGTTGAATAC TCATACTCTT
     CGTTTTACGG CGTTTTTTCC CTTATTCCCG CTGTGCCTTT ACAACTTATG AGTATGAGAA
     ~~~~~~~~~~~~~~~~~~~~~~~~~~~~~~~~~~~~~~~~~~~~~~~~~~~~~~~~~~
                               Amp

~
                                                           Amp P

8641 CCTTTTTCAA TATTATTGAA GCATTTATCA GGGTTATTGT CTCATGAGCG GATACATATT
     GGAAAAAGTT ATAATAACTT CGTAAATAGT CCCAATAACA GAGTACTCGC CTATGTATAA
     ~~~~~~~~~~~~~~~~~~~~~~~~~~~~~~~~~~~~~~~~~~~~~~~~~~~~~~~~~~~~~~~~
                                 Amp P

8701 TGAATGTATT TAGAAAAATA AACAAATAGG GGTTCCGCGC ACATTTCCCC GAAAAGTGCC
     ACTTACATAA ATCTTTTTAT TTGTTTATCC CCAAGGCGCG TGTAAAGGGG CTTTTCACGG
     ~~~~~~~~~~~~~~~~~~~~~~~~~~~~~~~~~~~
                   Amp P

8761 ACCTGACGTC TAAGAAACCA TTATTATCAT GACATTAACC TATAAAAATA GGCGTATCAC
     TGGACTGCAG ATTCTTTGGT AATAATAGTA CTGTAATTGG ATATTTTTAT CCGCATAGTG

8821 GAGGCCCTTT CGTC
     CTCCGGGAAA GCAG
```

The transformation of *E. coli* with plasmids containing the modified fEPO gene and the orthogonal aminoacyl tRNA synthetase/tRNA pair (specific for the desired non-naturally encoded amino acid) allows the site-specific incorporation of non-naturally encoded amino acid into the fEPO polypeptide. The transformed *E. coli*, grown at 37° C. in media containing between 0.01-100 mM of the particular non-naturally encoded amino acid, expresses modified fEPO with high fidelity and efficiency. The His-tagged fEPO containing a non-naturally encoded amino acid is produced by the *E. coli* host cells as inclusion bodies or aggregates. The aggregates are solubilized and affinity purified under denaturing conditions in 6M guanidine HCl. Refolding is performed by dialysis at 4° C. overnight in 50 mM TRIS-HCl, pH8.0, 40 µM $CuSO_4$, and 2% (w/v) Sarkosyl. The material is then dialyzed against 20 mM TRIS-HCl, pH 8.0, 100 mM NaCl, 2 mM $CaCl_2$, followed by removal of the His-tag. See Boissel et al., (1993) 268:15983-93. Methods for purification of fEPO are well known in the art (Nahri et al., (1991) JBC, Vol 266, pp 23022-23026; Narhi et al., (2001) Protein Engineering, Vol 14, pp 135-140; Darling et al., (2002) Biochemistry Vol 41, pp 14524-14531; Boissel et al., (1993) 268:15983-93; and WO0032772A2) and are confirmed by SDS-PAGE, Western Blot analyses, or electrospray-ionization ion trap mass spectrometry.

Example 3

A suppression expression DNA expression vector was constructed according to the invention, expressing feline erythropoietin protein (fEPO).

A. Expression Vector Construction

The expression construct, depicted in FIG. 25, comprises eight copies of a hybrid tRNA gene encoding an tRNA transcript capable of being charge with p-acetylphenylalanine by it's cognate tRNA synthetase. Each copy of the tRNA gene includes a H1 promoter region, the tRNA sequence and a polymerase III transcription termination signal.

Following the tRNA genes is located a Simian virus SV40 origin of replication (SVO), which facilitates replication of the expression construct (vector) in COS cells following transient transfection.

Thereafter is located an expression cassette for the gene sequences of interest, which in this case is the feline EPO coding region. First in the cassette is the human cytomegalovirus promoter (CMV), which drives expression of the message. The message in this construct encodes the feline erythropoietin (fEPO), which is sequentially preceded by the natural signal peptide (Nat L). The message is followed by the bovine growth hormone polyadenylation signal (BGH).

Thereafter is situated an expression cassette beginning with the mouse beta-globulin major promoter (beta), situated within the cassette so as to drive the expression of sequences encoding the optimized *E. coli* acetylphenylalanine tRNA synthetase (OptEcAFRS), the murine dihydrofolate reductase (DHFR) and the *salmonella* neomycin phosphotransferase gene (Neo) each separated by an internal ribosome entry site (IRES) derived from the Encephalomyocarditis virus geneome. The Neo sequence is followed by the SV40 early polyadenylation signal (SV).

The vector also contains sequences required for replication in bacteria, including the colE1 origin (pUC Ori) of replication and the beta-lactamase gene to confer ampicillin resistance (Amp).

The EMCV is commercially available, cDNA was commercially synthesized to the IRES region within the viral genome. PCR (polymerase chain reaction) amplification of that cDNA was performed in order to amplify the DNA, as well as to add 5' and 3' ends suitable for insertion between the coding domains. The ATG trinucleotide at position 834-836 (Genbank accession number NC-001479) was used as the start codon for the DHFR and Neo sequences.

Because the literature indicates that translation of the open reading frame downstream of the IRES would be less efficient than the upstream open reading frame (translation initiated by 5' CAP), the strategy was taken to place the DHFR and Neo genes following independent IRES elements to selectively impair said dominant selectable markers in an effort to ease clone selection.

Two versions of the suppression expression vector were generated and designated Lucy F (FIG. 25) and Irwin (FIG. 26). Lucy F contains 8 copies of the tRNA genes, a second IRES, and the Neo gene. The Neo gene is included to allow for selection of stable integrated plasmids into the cell genome via treatment with G418. Irwin by contrast contains only 4 copies of the tRNA genes and lacks the second IRES and Neo. Irwin is thereby smaller in size and better suited for transient expression of suppressed proteins for generation of experimental levels of protein production.

B. CHO Cell Expression

Figure 28:
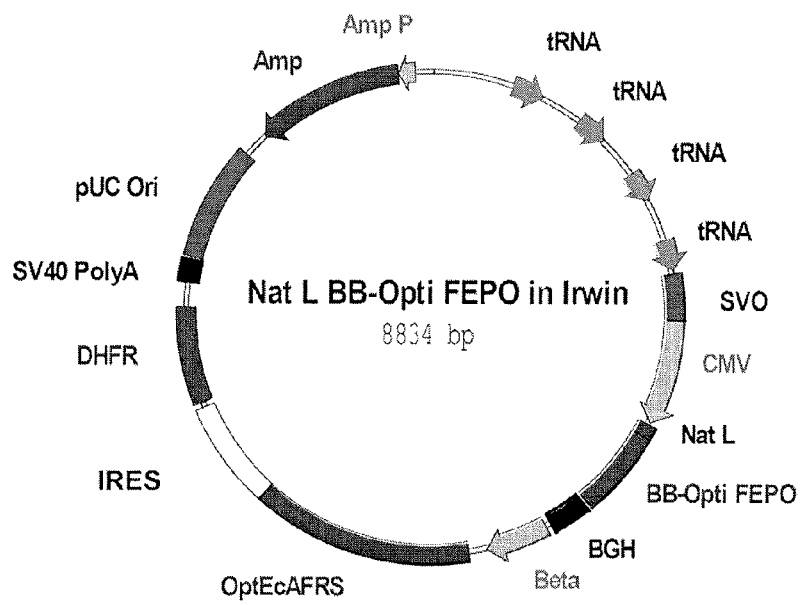
FIG. 28—A schematic drawing of the suppression expression construct Nat L BB-Opti FEPO in Irwin for feline erythropoietin.

The vector "Nat L BB-Opti FEPO in Irwin", a map of which is depicted in FIG. 28, and the sequence of which is set forth in Table 3 containing the suppression elements and encoding the feline EPO protein was transfected into CHO-S cells using a transient transfection protocol. These transfections were performed in parallel with wild type and 22 variants of fEPO such that amber codons were placed within the coding region subject to suppression in a manner so as to retain fEPO bioactivity and glycan structure. The 22 variants of fEPO include those shown in FIG. 30: K52, Q86, E89, E31, E21, E37, R131, K116, F133, L130, R53, Y49, T132, A1, S120, R76, P129, S36, D55, A128, E72, R163. Experimental results indicate the wild type sequence expresses well and that suppression expression of the 22 different variants varied widely, but at least 19 of the 22 demonstrated expression as detectable by ELISA. Accordingly, an embodiment of the inventive suppression expression construct is expected to express gene sequences of interest with amber suppression codons located at a variety of positions.

Transient expression of fEPO may be used to accommodate some technical challenges in producing this protein e.g. having an isoelectric point around pH 4 and the high glycosylation of fEPO (over 40% of the mass) which can affect conjugation efficiency and some site accessibility, therefore alternate chemistries may be used as well as alternate expression systems.

Example 4

Generation of G418 Resistant Cell Lines

The suppression expression construct in this example encodes the modified feline EPO protein with the amber codon positioned at residue 1 replacing the normal alanine residue. This expression construct is referred to as "Nat L BB-Opti FEPO in Lucy F", a map of which is depicted in FIG. 27, and the sequence of which is set forth in Table 3.

Nat L BB-Opti FEPO A1 in Lucy F (containing the amber codon at position A1) was transfected into the CHO-DG44 parent cell line. Transfections were performed using 0.5, 1.0, or 2.0 ug linearized DNA per 4.times.10.sup.6 CHO cells per 96 well plate. Dominant selection of stably transfected cells was accomplished via the expression construct encoded neomycin resistance marker and media (CHO-S-SFM II+HT) containing G418.

Viable wells were identified, expanded to small scale (50 ml) shaker culture and cellular productivity assessed by ELISA assay. A variety of G418 resistant cell isolates were obtained producing easily detectable secreted fEPO. Two in particular, 5B5 and 15B3 were determined to be producing 0.07 and 0.1 mg/L in 3-4 days respectively, or 0.03 picogram/cell/day (pcd). Secreted fEPO was detected by ELISA as using the StemCell EPO ELISA KIT-Immunoassy for Human Erythropoietin, cat #01630.

Example 5
A. Increases in Expression Via Genomic Amplification

The Lucy F suppression expression system contains an expression cassette encoding the murine DHFR gene. As the parent CHO-DG44 cell line used for expression is completely deficient in DHFR enzymatic activity (double deletion), amplification of the integrated target gene (murine DHFR) is possible by growth selection in media containing methotrexate (MTX). During this amplification, the directly linked protein gene (in this example fEPO) is concomitantly amplified. Thus it is possible to isolate cell lines producing elevated amounts of fEPO. Our first round selection of G418 resistant cell lines is performed in 5 nM MTX. Highest level producers (as determined by ELISA) are then identified and characterized.

The fEPO G418 resistant cell lineages 5B5 and 15B3 were subjected to 5 nM MTX amplification. In each case the suppression expression levels are elevated following amplification and are listed below.

TABLE 4

| Cell Line | G418 pg/cell/day | G418 mg/L/3-4 days | 5 nM MTX pg/cell/day | 5 nM MTX mg/L/3-4 days | Fold increase in pg/cell/day |
|---|---|---|---|---|---|
| 5B5 | 0.03 | 0.07 | — | — | |
| 5B5-8C9 | 0.03 | 0.07 | 0.14 | 0.41 | 4.7 |
| 15B3 | 0.03 | 0.10 | — | — | |
| 15B3-7E3 | 0.03 | 0.10 | 0.10 | 0.22 | 3.3 |

As can be seen from the above table, expression levels at 5 nM MTX amplification are elevated roughly 3-5 fold. Subsequent amplifications at increasing concentrations of MTX are expected to yield further increase in productivity.

Example 6

Twenty-two fEPO variants were transiently expressed in Chinese hamster ovary cells (CHOs). The variants of fEPO were constructed into expression vector, which contains tRNA and RS. Wild type of fEPO was constructed into another expression vector, which doesn't contain tRNA and RS. Plasmids (variants and w.t. fEPO) were transfected into CHO cells with or without pAF using transfection method developed by company.

Method of Transient Expression of w.t. fEPO and Variants of fEPO

A solution of polyethyleimine (PEI), a 25 kDa linear from Polysciences, was prepared at 1 mg/ml in distilled water, the pH was adjusted to 7.2 and filter sterilized using a 0.22 µm filter before use.

Figure 30:
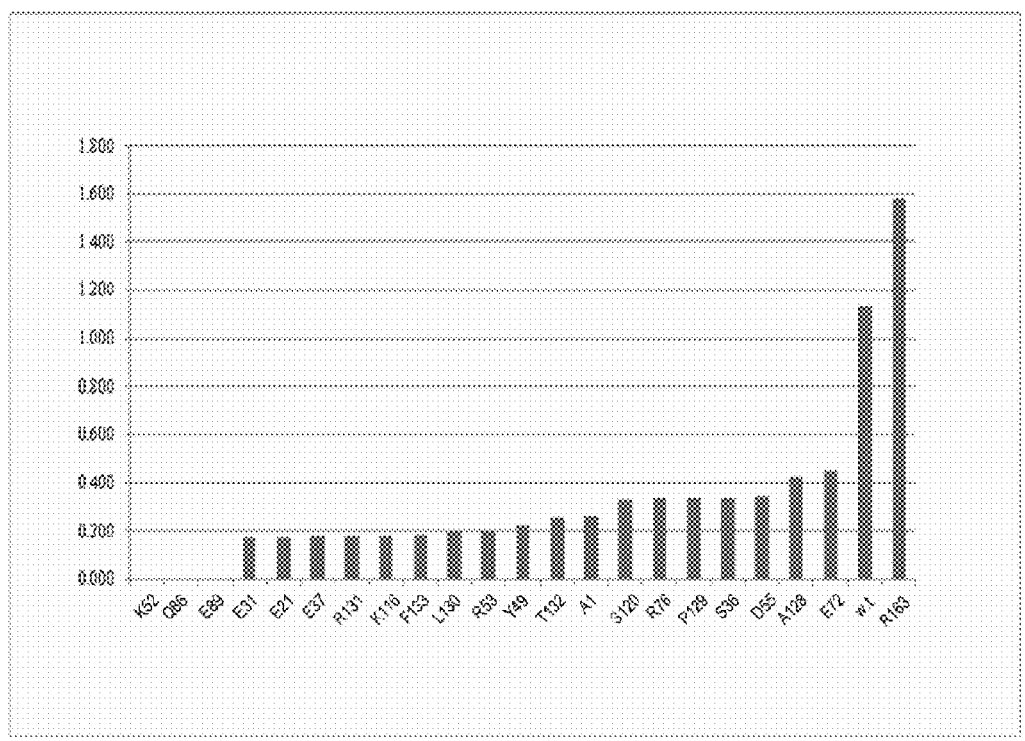

CHO cells (Invitrogen) were maintained in CHO Free-Style media with glutamine supplemented. A 30 mL culture was prepared in 125 ml Erlenmeyer flask from Corning. Cells were seeded at 0.5×6/ml day before transfection. Cell density was adjusted to 1×10$^6$/mL with growth medium before transfection. Para-acetyl-phenylalanine was added in a concentration of 1 mM before transfection. DNA, 37 µg of DNA, was dissolved in RPMI medium and then 74 µL of 1 mg/mL PEI solution was added into RPMI media containing DNA. This was incubated for 15 minutes. Then DNA and PEI mixture were added into 30 ml culture in 125 ml Erlenmeyer flask. The flask was then transferred to 37° C. incubator after which the supernatant was quantified by human ELISA assay 72 hrs after transfection. FIG. 30 shows the suppression levels of fEPO variants in the presence of pAF.

Each variant of fEPO was suppressed at different levels, modulated by the position of pAF. K52, Q86, and E89 were not detected by ELISA assay in the presence of pAF. Without pAF, the variants of fEPO weren't detected by ELISA assay. The supernatants were also assayed by TF-1 assay for function. The results of this experiment are shown in FIG. 30.

Example 7

Figure 11:
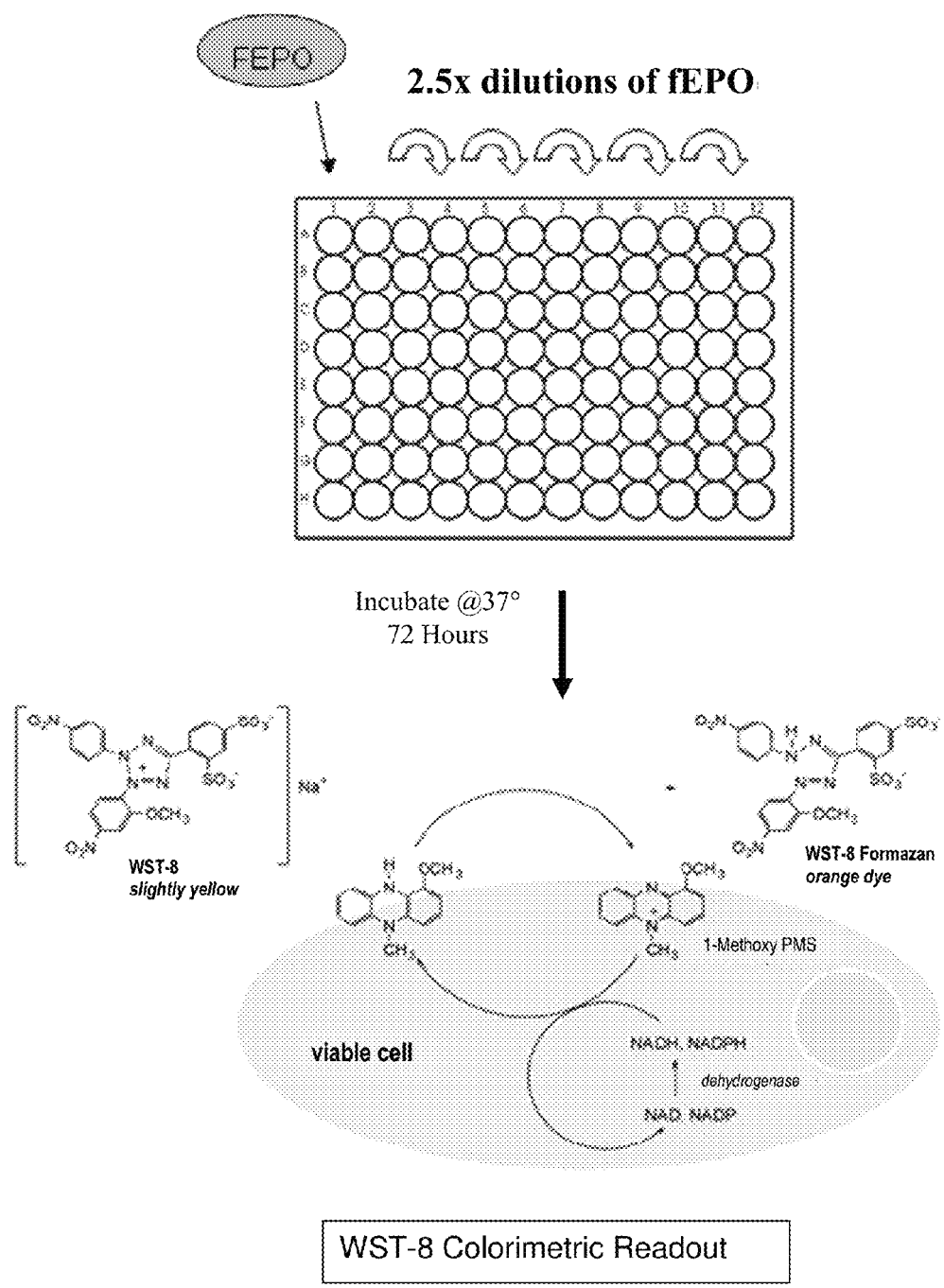
FIG. 11—A diagram of the TF-1 proliferation assay.
Figure 12:
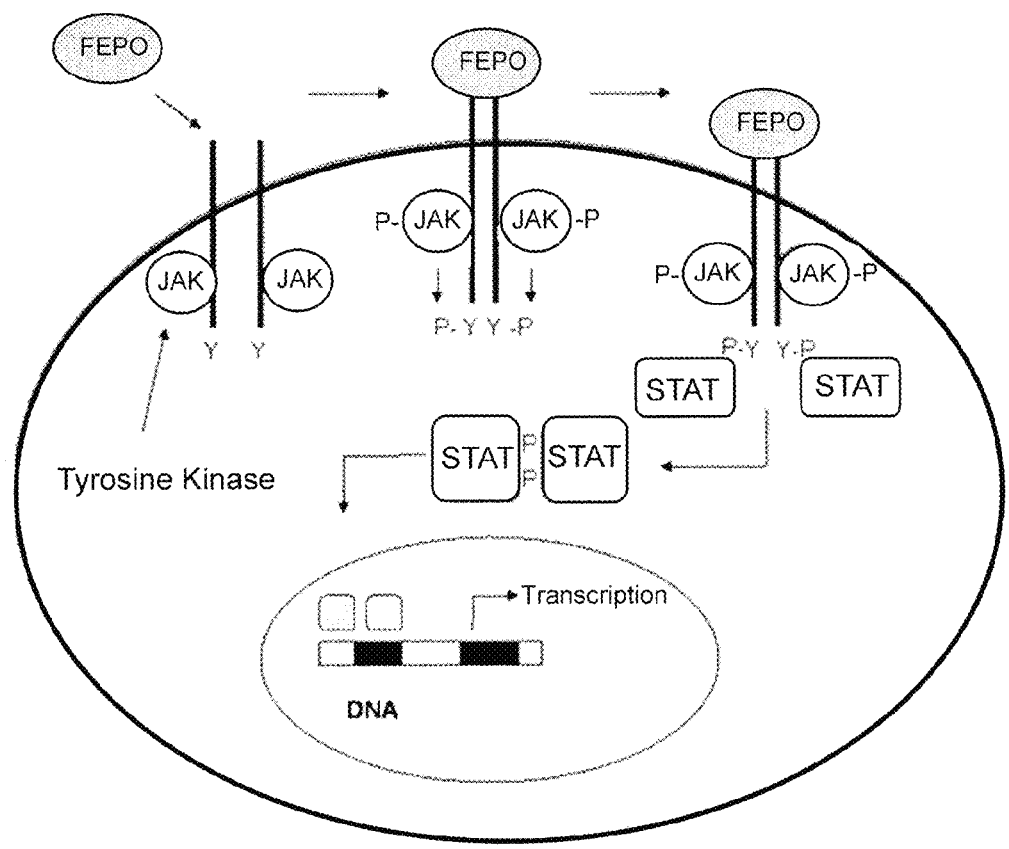
FIG. 12—A diagram of fEPO receptors homodimerizing upon ligand binding.
Figure 13:
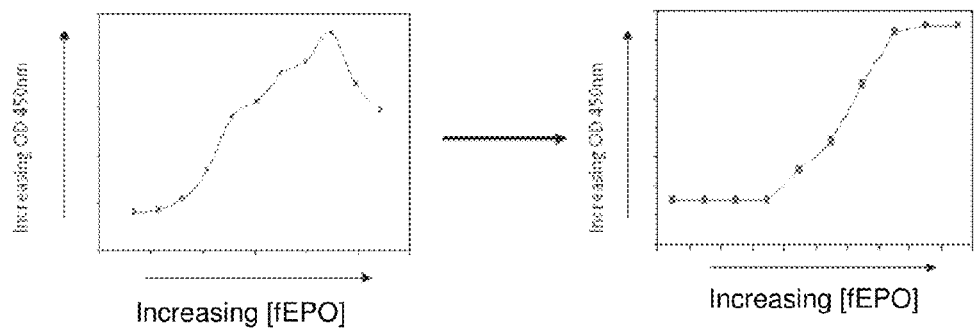
FIG. 13—The OD at 450 nm plotted against increasing concentrations of fEPO showing a bell-shaped dose response curve.
Figure 14:
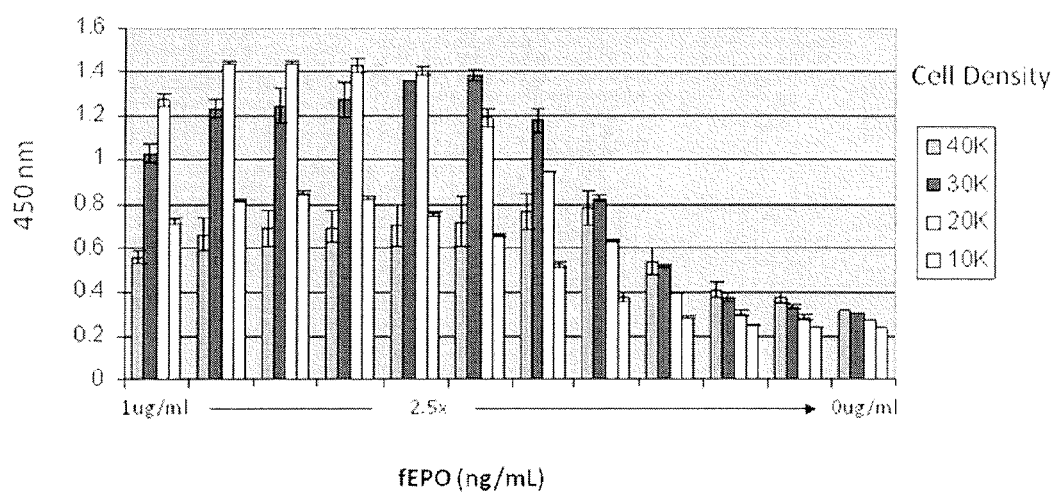
FIG. 14—A displaying different seeding densities of TF-1 cells. This graph shows that, given, for example, the JAK-STAT signal transduction pathway, for optimal activity in response to fEPO the ratio of between fEPO and fEPO receptor is 1:2.
Figure 15:
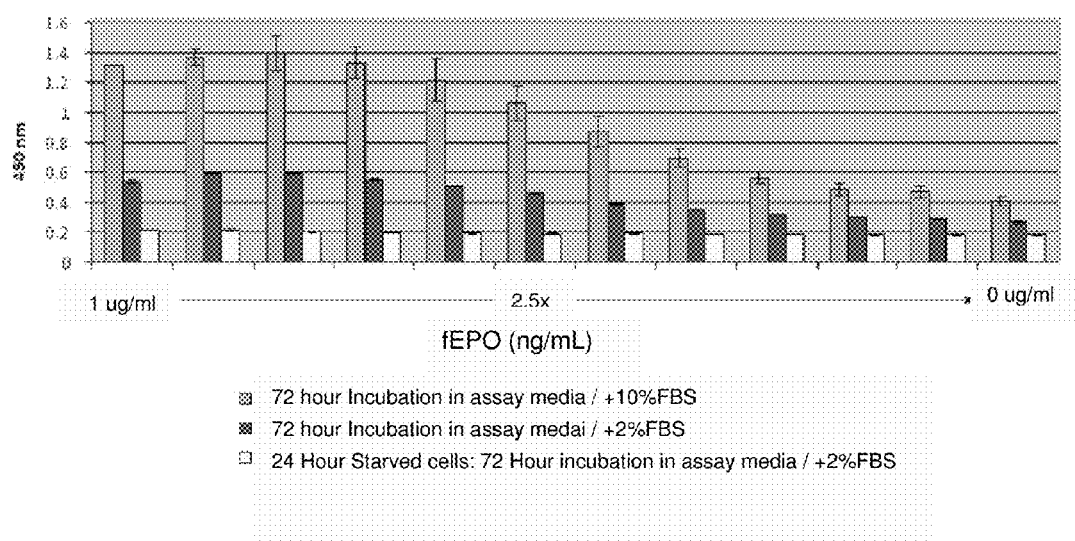
FIG. 15—A graph of experimental results determining whether cell starvation would synchronize cellular division and result in a greater dynamic range—the results showed that this was not particularly advantageous.
Figure 16:
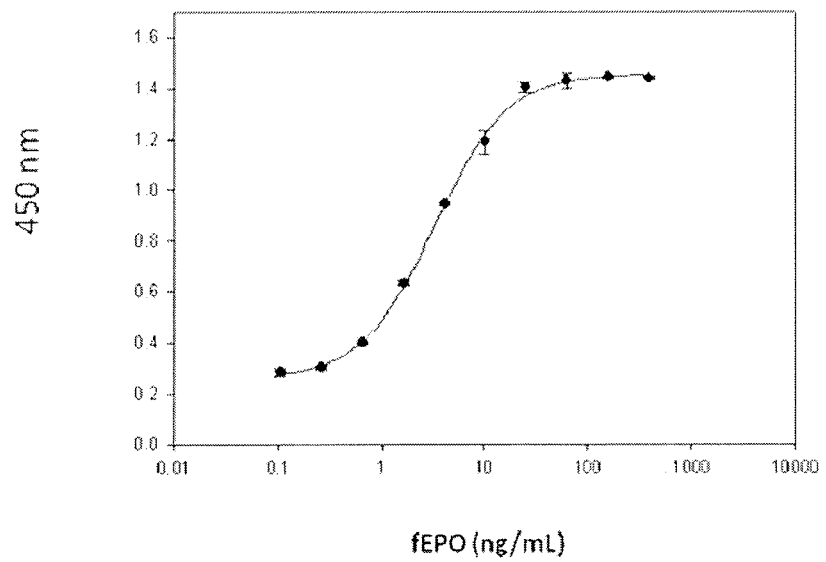
FIG. 16—A graph of conditions used for the TF-1 assay with seeding density of 20,000, an incubation time of 72 hours, fEPO starting concentration of 500 ng/ml and dilution 2.5×.
Figure 18:
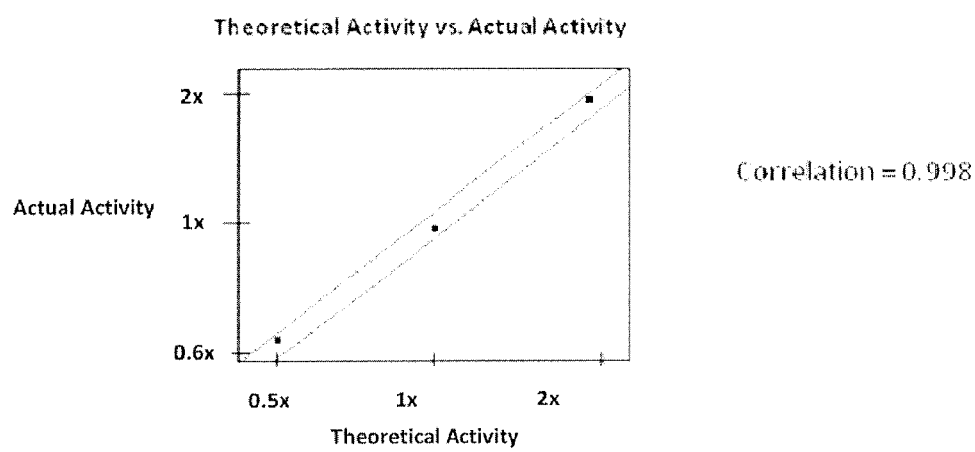
FIG. 18—A chart and graph of the TF-1 assay performance with wild type fEPO and formulation buffer.
Figure 19:
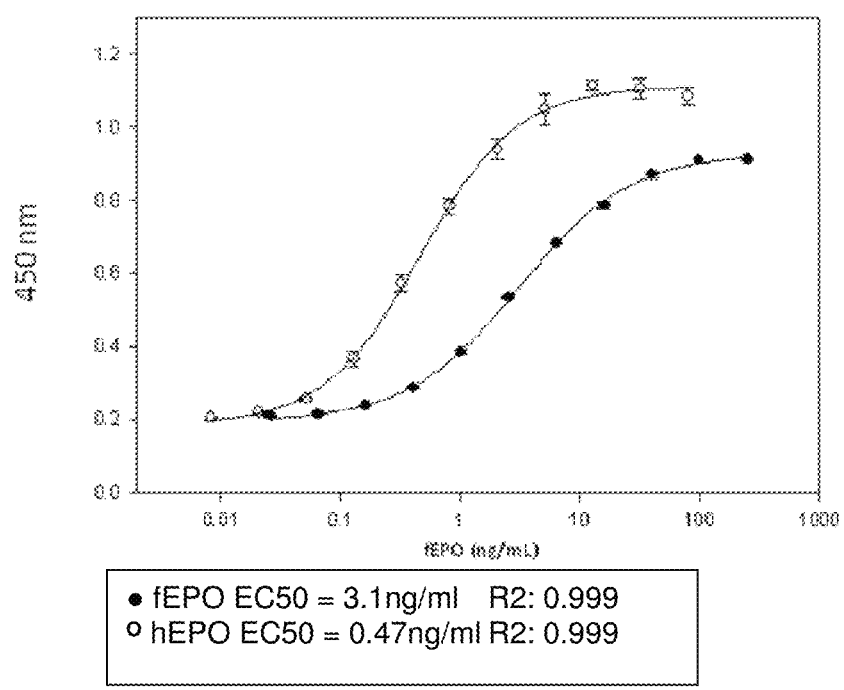
FIG. 19—A graph comparing the assay performance between wild type EPOs for human and feline.
Figure 20:
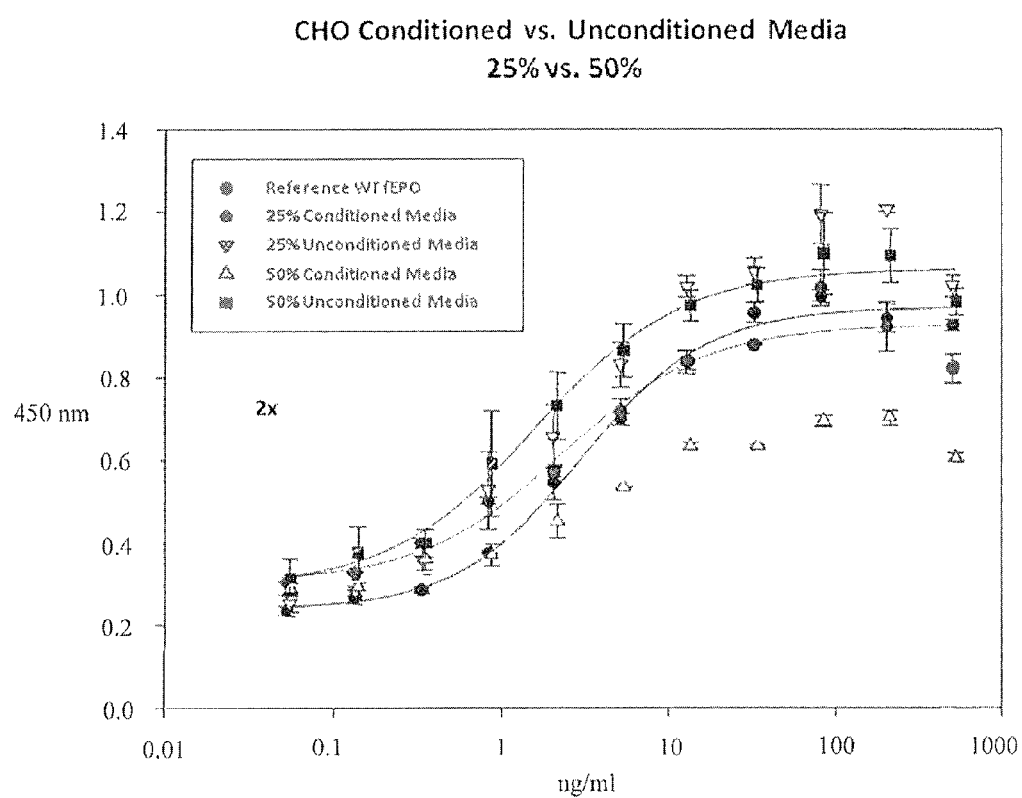
FIG. 20—A graph of measured ODs against varying concentrations of CHO conditioned and unconditioned media with wild type fEPO as control.
Figure 21:
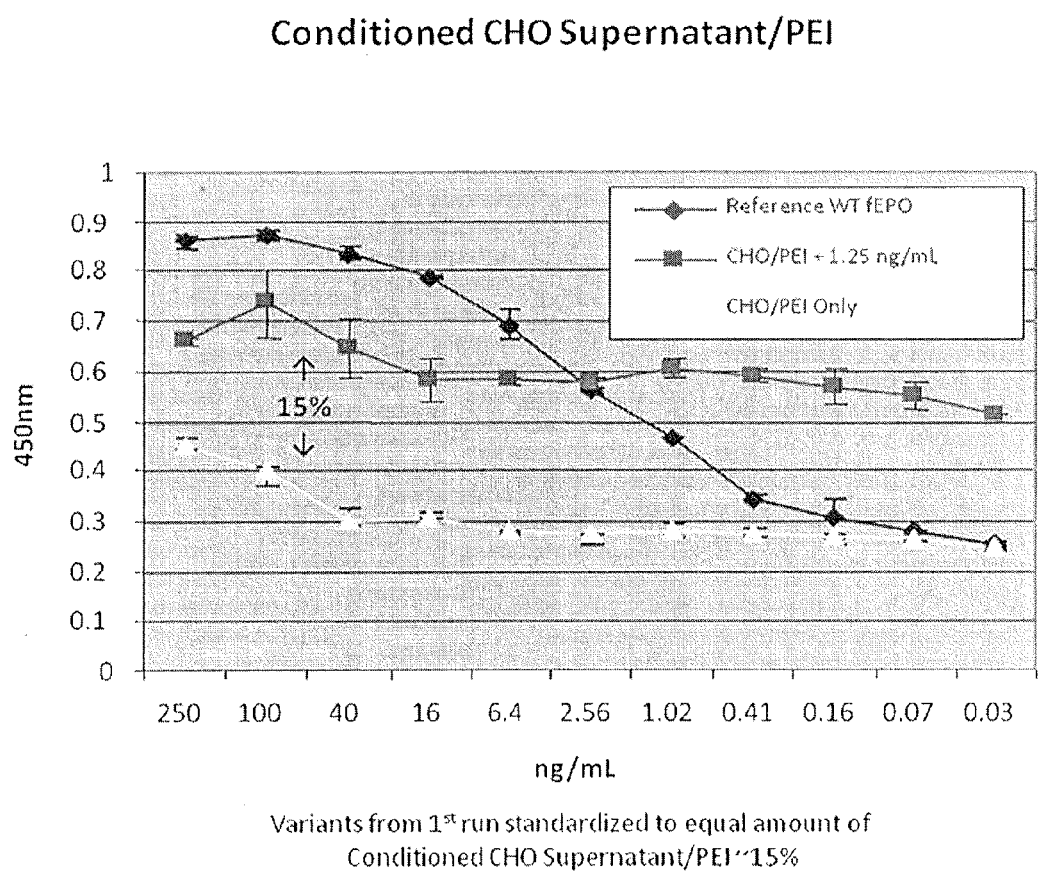
FIG. 21—A graph comparing wild type fEPO, CHO/PEI+ 1.25 ng/mL fEPO and CHO/PEI alone in decreasing concentrations and their measured ODs.
Figure 22:
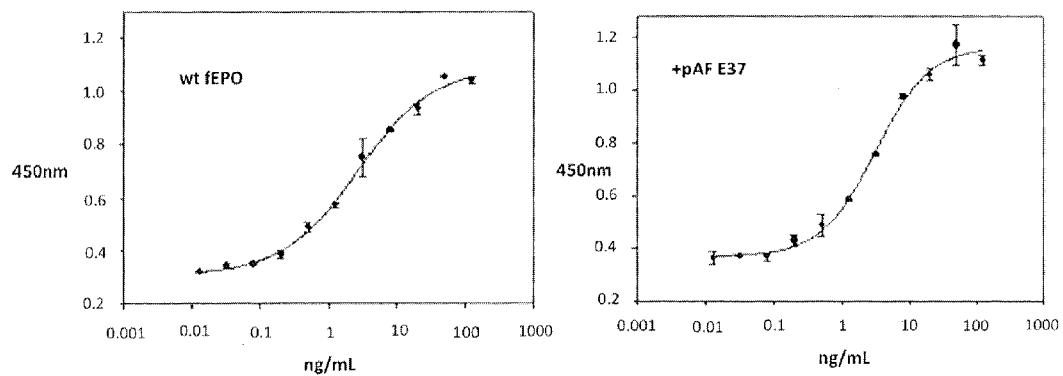
FIG. 22—A chart and graphs of the relative activity of fEPO variants with an incorporated non-natural amino acid, pAF, as compared to wild type fEPO.
Figure 23:
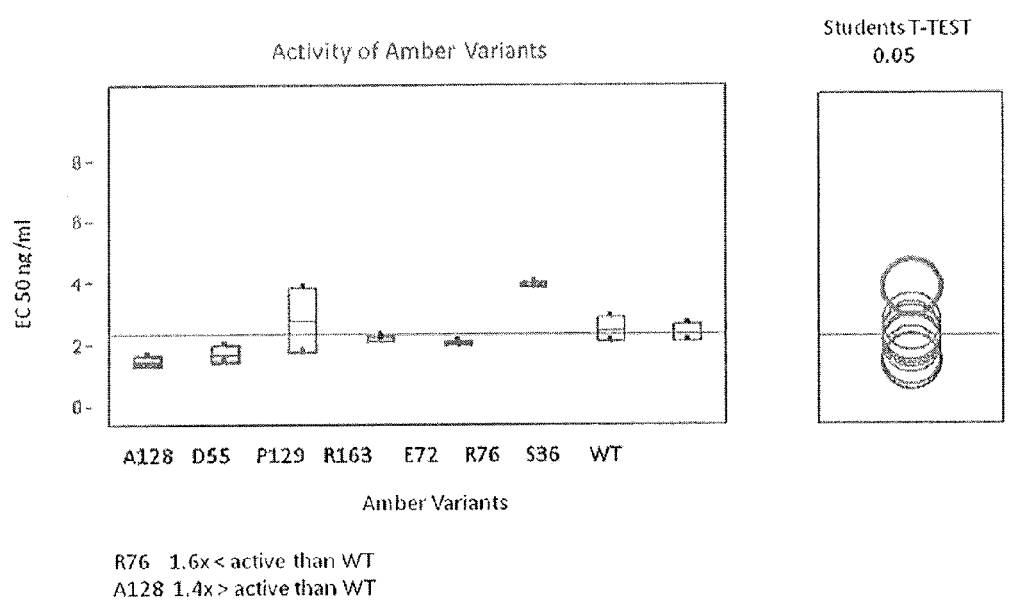
FIG. 23—A bar graph of several fEPO variants with incorporated pAF at specified sites and each of ther ED50 ng/mL measurements.
Figure 24:
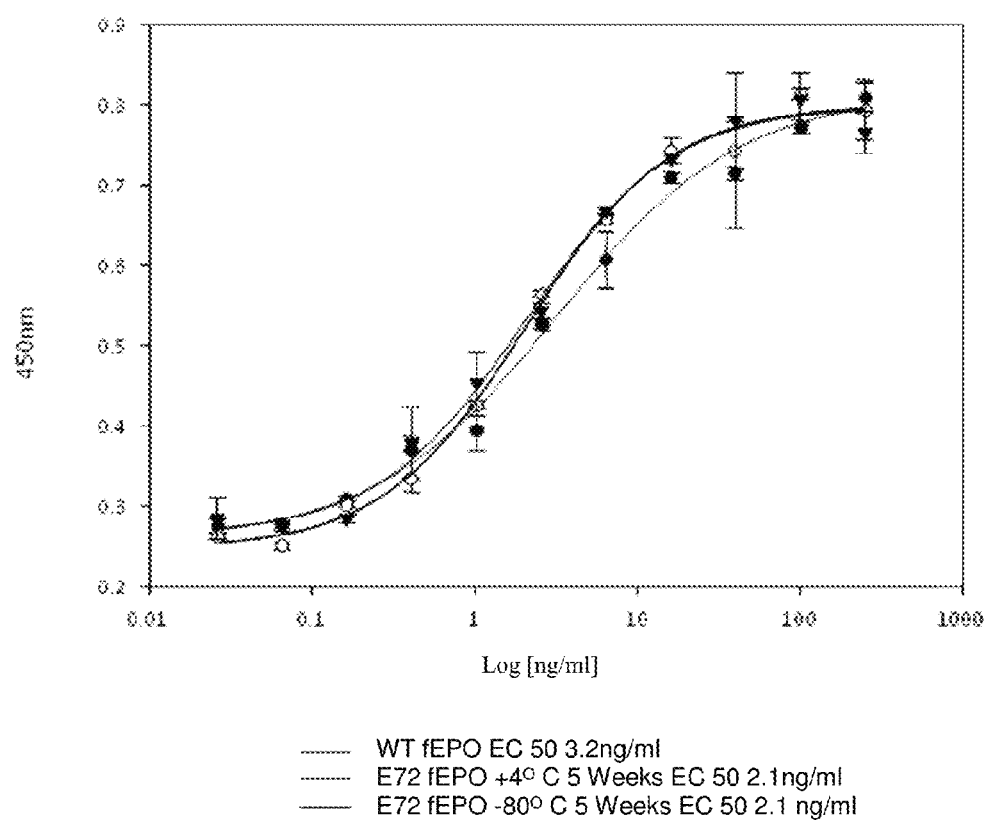
FIG. 24—A graph of E72 fEPO variant stored at four degrees and minus eighty degrees over five weeks, as compared to wild type fEPO, and their ODs.

TF-1 proliferation assay and TF-1 functional fEPO assays are shown in FIGS. 11-24. TF-1 cells were seeded at 150,000 cells/ml in a T-75 flask in growth medium overnight and on the day of the assay, cells were seeded at 20,000 cells/well in 50 ul of assay medium (FIG. 11). TF-1 cells were purchased from ATCC and the cell line was established from the bone marrow cells of a patient with erythroleukemia. The cell line shows growth dependency with IL-1, GMcsf, EPO and fEPO. Activity is measured by proliferation of TF-1 cells in response to fEPO. The extent of proliferation is measured by WST-8. Cleavage of tetrazolium salt wst-8 to formazan by cellular mitochondrial dehydogenase is directly proportional to the number of living cells. The formazan dye produced by viable cells is quantified by measuring the absorbance of the dye solution at 450 nm (FIG. 13, FIG. 16, FIG. 19, FIG. 20, FIG. 21). In FIG. 13, the conditions were TF-1 cells seeded at varying densities of 40,000; 30,000; 20,000; and 10,000 cells per well. Two different incubation times, 48 hours and 72 hours, were used, as well as two different fEPO concentrations (2500 ng/mL and 500 ng/mL), two different dilution schemes (3× and 2.5×), and 24 hour starved cells as well as un-starved cells were used. Results of these experiments and functional assays are described and shown in the figures and figure descriptions.

Example 8

Purification of Wild-Type and Para-Acetylphenylalanine (pAF) Variants of Feline Erythropoietin (fEPO), and Selective Conjugation of Polyethylene Glycol) to pAF Variants Purification of fEPO and pAF variants involves concentration and diafiltration, followed by three column chromatography steps: phenylboronate, anion exchange, and hydrophobic interaction. Prior to PEGylation, the purified material is concentrated and exchanged into PEGylation buffer.

UF/DF: Cell culture supernatant was concentrated and exchanged in X diavolumes of 50 mM HEPES pH 8.5 prior to chromatography loading using a Slice 200 (Sartorius Stedim) system connected to a MasterFlex pump.

Phenylboronate (PB) Chromatography

Phenylboronate resin was performed in negative capture mode using ProSep PB column equilibrated in 50 mM HEPES, pH 8.5. Material was collected in the flow-through wash (50 mM HEPES, pH 8.5). Impurities were removed with step elutions in 50 mM HEPES, 50 mM sorbitol pH 8.5; 50 mM Tris, 6 M urea, pH 8.5; and 100 mM acetic acid.

Material from the PB flow-through was exchanged into 20 mM Tris pH 8.0 by UF/DF into 20 mM Tris pH 8.0 as described above prior to loading onto anion exchange chromatography.

Anion Exchange Chromatography (AEX)

Material was purified using a Q Sepharose High Performance column in an XK 16 column (GE Healthcare, Piscataway, N.J.), flow rate 120 cm/h. Material was loaded onto a column equilibrated in 20 mM Tris pH 8.0 Elution was conducted using a linear AB gradient, where Buffer A=20 MM Tris pH 8.0, Buffer B=20 mM Tris, 500 mM NaCl pH 8.0. Fixed-volume fractions were collected and analyzed by SDS-PAGE and anti-EPO ELISA.

Hydrophobic Interaction Chromatography (HIC)

AEX pool containing fEPO was diluted in 3.5 M ammonium sulfate to obtain a final 1.5 M ammonium sulfate concentration. Material was loaded onto a Phenyl Sepharose High Performance resin, 120 cm/h, equilibrated in 20 mM Tris, 1.5 M ammonium sulfate pH 8.0. Elution was performed over a 20 CV linear AB gradient, where A=20 mM Tris, 1.5 M ammonium sulfate pH 8.0 and B=20 mM Tris, 50% (v/v) ethylene glycol, pH 8.0. Fixed-volume fractions were collected and analyzed by SDS-PAGE and anti-EPO ELISA.

PEGylation of fEPO pAF Variants

Figure 31:
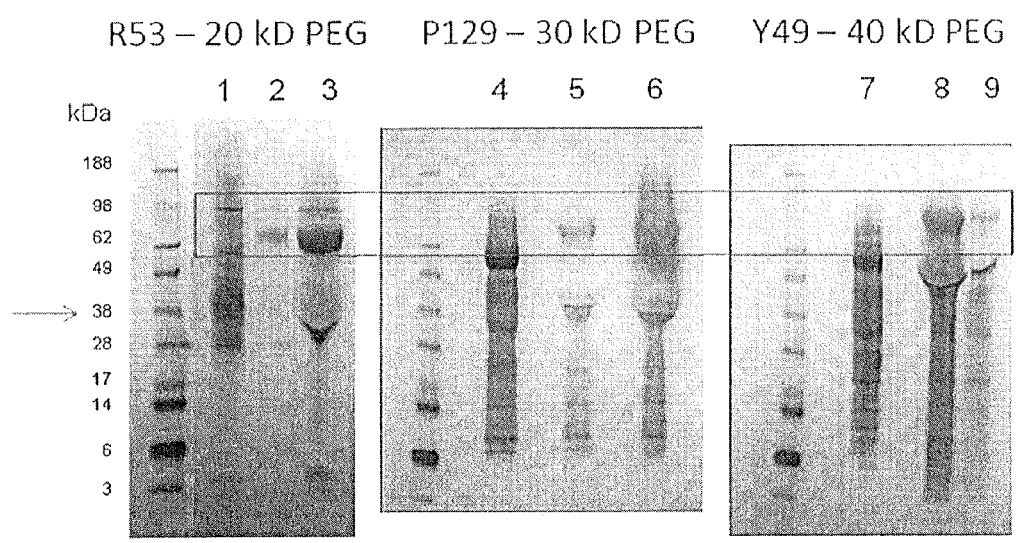
FIG. 31—Shows a comparison of PEGylated fEPO migration by SDS-PAGE. Lanes 1-3: 20 kDa PEG reactions with fEPO R53 pAF variant. Lane 1: R53, 8 µg fEPO load, no PEG. Lane 2: R53 PEGylation, 2 µg fEPO load. Lane 3: R53 PEGylation, 8 µg fEPO load. Lanes 4-6: 30 kDa PEG reactions with fEPO P129 pAF variant. Lane 4: P129, 8 µg fEPO load, no PEG. Lane 5: P129 PEGylation, 2 µg fEPO load. Lane 6: P129 PEGylation, 8 µg fEPO load. Lanes 7-9: 40 kDa PEG reactions with fEPO Y49 pAF variant. Lane 7: Y49, 8 µg fEPO load, no PEG. Lane 9: Y49 PEGylation, 8 µg fEPO load. Lane 9: Y49 PEGylation, 2 µg fEPO load. The horizontal arrow at 38 kDa indicates the location of unPEGylated fEPO migration. The boxed rectangle indicates the region of PEGylated fEPO migration.
Figure 32:
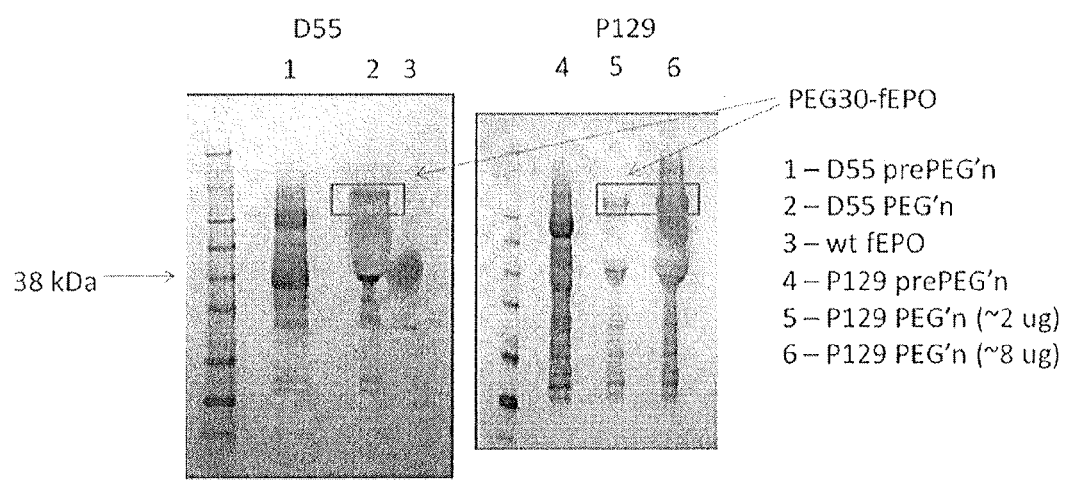
FIG. 32—An SDS-PAGE gel showing the PEGylation reactions (30 kDa) for fEPO D55 and P129 pAF variants, showing these two PEGylated variants. Lane 1: D55, no PEG. Lane 2: D55 PEGylation Lane 3: wild-type fEPO, no incubation. Lane 4: P129, 8 µg fEPO load, no PEG. Lane 5: P129 PEGylation, 2 µg fEPO load. Lane 6: P129 PEGylation, 8 µg fEPO load. The horizontal arrow at 38 kDa indicates the location of unPEGylated fEPO migration. The boxed rectangle indicates the region of PEGylated fEPO migration.
Figure 33:
FIG. 33—An SDS-PAGE gel showing the successful pegylation reaction (30 kDa) for fEPO A1 pAF variant. Lane 1 shows wild-type fEPO, 8 µg load, no incubation and lane 2: shows PEGylated A1.

Relevant fractions were pooled and concentrated to ~5 mg/ml with a VivaSpin column 10 000 MWCO @ 15000×g, 10 min per spin. Sample was exchanged into 20 mM sodium acetate, 1 mM EDTA, pH 4.0. PEGylation was commenced using a 12:1 mol ratio of PEG:protein using 20 kD PEG-oxyamine (Sunbright ME200-CA), and 1% (w/v) acethydrazide adjusted to pH 4.0 with acetic acid. PEGylation was conducted at 28 C for >12 hours and analyzed by SDS-PAGE (FIG. 31, FIG. 32, and FIG. 33). Variant A1 was PEGylated with a 30 kDa PEG, variant Y49 was PEGylated with a 40 kDa PEG, variant R53 was PEGylated with a 20 kDa PEG, variant D55 was PEGylated with a 30 kDa PEG, variant P129 was PEGylated with a 30 kDa PEG.

Example 9

This example details introduction of a carbonyl-containing amino acid and subsequent reaction with an aminooxy-containing PEG.

This example demonstrates a method for the generation of a fEPO polypeptide that incorporates a ketone-containing non-naturally encoded amino acid that is subsequently reacted with an aminooxy-containing PEG of approximately 5,000 MW. Each of the residues 21, 24, 38, 83, 85, 86, 89, 116, 119, 121, 124, 125, 126, 127, and 128 is separately substituted with a non-naturally encoded amino acid having the following structure:

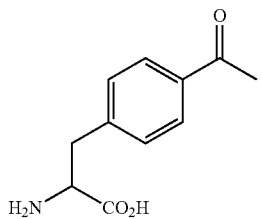

The sequences utilized for site-specific incorporation of p-acetyl-phenylalanine into fEPO are disclosed in Table 2, and sequences (e.g. muttRNA and TyrRS LW1, 5, or 6) described above.

Once modified, the fEPO variant comprising the carbonyl-containing amino acid is reacted with an aminooxy-containing PEG derivative of the form:

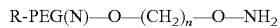
R-PEG(N)—O—(CH$_2$)$_n$—O—NH$_2$ where R is methyl, n is 3 and N is approximately 5,000 MW. The purified fEPO containing p-acetylphenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. J. Am. Chem. Soc. 1959, 81, pp 475). The PEG-fEPO is then diluted into appropriate buffer for immediate purification and analysis.

Example 10

Conjugation with a PEG consisting of a hydroxylamine group linked to the PEG via an amide linkage.

A PEG reagent having the following structure is coupled to a ketone-containing non-naturally encoded amino acid using the procedure described in the above examples:

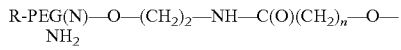
R-PEG(N)—O—(CH$_2$)$_2$—NH—C(O)(CH$_2$)$_n$—O—NH$_2$ where R=methyl, n=4 and N is approximately 20,000 MW. The reaction, purification, and analysis conditions are as described in the above examples.

Example 11

This example details the introduction of two distinct non-naturally encoded amino acids into fEPO This example demonstrates a method for the generation of a fEPO polypeptide that incorporates non-naturally encoded amino acid comprising a ketone functionality at two positions among the following residues: N24X* and G113X*; N38X* and Q115X*; N36X* and S85X*; N36X* and A125X*; N36X* and A128X*; Q86X* and S126X* wherein X* represents a non-naturally encoded amino acid. The fEPO polypeptide is prepared as described in the above examples, except that the suppressor codon is introduced at two distinct sites within the nucleic acid.

Example 12

This example details conjugation of fEPO polypeptide to a hydrazide-containing PEG and subsequent in situ reduction A fEPO polypeptide incorporating a carbonyl-containing amino acid is prepared according to the procedure described in the above examples. Once modified, a hydrazide-containing PEG having the following structure is conjugated to the fEPO polypeptide:

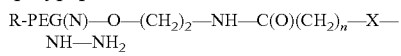
R-PEG(N)—O—(CH$_2$)$_2$—NH—C(O)(CH$_2$)$_n$—X—NH—NH$_2$ where R=methyl, n=2 and N=10,000 MW and X is a carbonyl (C=O) group. The purified fEPO containing p-acetylphenylalanine is dissolved at between 0.1-10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and the corresponding hydrazone is reduced in situ by addition of stock 1M NaCNBH$_3$ (Sigma Chemical, St. Louis, Mo.), dissolved in H$_2$O, to a final concentration of 10-50 mM. Reactions are carried out in the dark at 4° C. to RT for 18-24 hours. Reactions are stopped by addition of 1 M Tris (Sigma Chemical, St. Louis, Mo.) at about pH 7.6 to a final Tris concentration of 50 mM or diluted into appropriate buffer for immediate purification.

Example 13

This example details introduction of an alkyne-containing amino acid into fEPO and derivatization with mPEG-azide.

The following residues, 21, 24, 38, 83, 85, 86, 89, 116, 119, 121, 124, 125, 126, 127, and 128, are each substituted with the following non-naturally encoded amino acid:

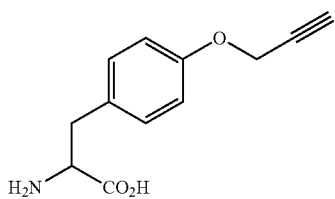 [SMILES: C#CCOc1ccc(CC(N)C(=O)O)cc1]

The sequences utilized for site-specific incorporation of p-propargyl-tyrosine into fEPO are muttRNA, et. al. that are described in the above examples. The fEPO polypeptide containing the propargyl tyrosine is expressed in *E. coli* and purified using the conditions described above.

The purified fEPO containing propargyl-tyrosine dissolved at between 0.1-10 mg/mL in PB buffer (100 mM sodium phosphate, 0.15 M NaCl, pH=8) and a 10 to 1000-fold excess of an azide-containing PEG is added to the reaction mixture. A catalytic amount of $CuSO_4$ and Cu wire are then added to the reaction mixture. After the mixture is incubated (including but not limited to, about 4 hours at room temperature or 37° C., or overnight at 4° C.), $H_2O$ is added and the mixture is filtered through a dialysis membrane. The sample can be analyzed for the addition, including but not limited to, by similar procedures described in the above examples.

In this Example, the PEG will have the following structure:

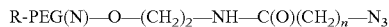

R-PEG(N)—O—(CH$_2$)$_2$—NH—C(O)(CH$_2$)$_n$—N$_3$ where R is methyl, n is 4 and N is 10,000 MW.

Example 14

This example details substitution of a large, hydrophobic amino acid in fEPO with propargyl tyrosine.

A Phe, Trp or Tyr residue present within one the following regions of fEPO: 1-7 (N-terminus), 27-38 (region between A helix and B helix), 39-41 (Beta sheet 1), 42-46 (region between Beta sheet 1 and mini helix B'), 47-52 (mini B' helix), 53-54 (region between mini B' helix and B helix), 84-89 (region between B helix and C helix), 114-121 (mini C' helix), 122-132 (region between mini C' helix and Beta sheet 2), 133-135 (Beta sheet 2), 136-137 (region between Beta sheet 2 and D helix), 162-166 (C-terminus, is substituted with the following non-naturally encoded amino acid as described in the above examples:

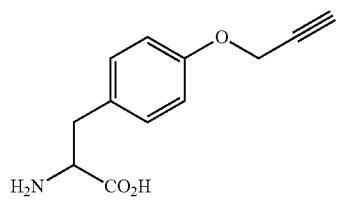

Once modified, a PEG is attached to the fEPO variant comprising the alkyne-containing amino acid. The PEG will have the following structure:

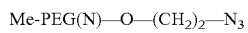

Me-PEG(N)—O—(CH$_2$)$_2$—N$_3$ and coupling procedures would follow those described in the above examples. This will generate a fEPO variant comprising a non-naturally encoded amino acid that is approximately isosteric with one of the naturally-occurring, large hydrophobic amino acids and which is modified with a PEG derivative at a distinct site within the polypeptide.

Example 15

This example details generation of a fEPO homodimer, heterodimer, homomultimer, or heteromultimer separated by one or more PEG linkers.

The alkyne-containing fEPO variant described in the above examples is reacted with a bifunctional PEG derivative of the form:

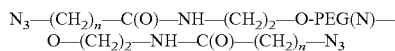

N$_3$—(CH$_2$)$_n$—C(O)—NH—(CH$_2$)$_2$—O-PEG(N)—
O—(CH$_2$)$_2$—NH—C(O)—(CH$_2$)$_n$—N$_3$ where n is 4 and the PEG has an average MW of approximately 5,000, to generate the corresponding fEPO homodimer where the two fEPO molecules are physically separated by PEG. In an analogous manner a fEPO polypeptide may be coupled to one or more other polypeptides to form heterodimers, homomultimers, or heteromultimers. Coupling, purification, and analyses will be performed as described in the above examples.

Example 16

This example details coupling of a saccharide moiety to fEPO.

One residue of the following is substituted with the non-natural encoded amino acid below: 21, 24, 28, 30, 31, 36, 37, 38, 55, 72, 83, 85, 86, 87, 89, 113, 116, 119, 120, 121, 123, 124, 125, 126, 127, 128, 129, 130, and 162 as described in the above examples.

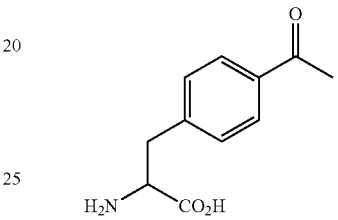

Once modified, the fEPO variant comprising the carbonyl-containing amino acid is reacted with a β-linked aminooxy analogue of N-acetylglucosamine (GlcNAc). The fEPO variant (10 mg/mL) and the aminooxy saccharide (21 mM) are mixed in aqueous 100 mM sodium acetate buffer (pH 5.5) and incubated at 37° C. for 7 to 26 hours. A second saccharide is coupled to the first enzymatically by incubating the saccharide-conjugated fEPO (5 mg/mL) with UDP-galactose (16 mM) and β-1,4-galacytosyltransferase (0.4 units/mL) in 150 mM HEPES buffer (pH 7.4) for 48 hours at ambient temperature (Schanbacher et al. *J. Biol. Chem.* 1970, 245, 5057-5061).

Example 17

This example details generation of a PEGylated fEPO antagonist.

One of the following residues, 21, 24, 28, 30, 31, 36, 37, 38, 55, 72, 83, 85, 86, 87, 89, 113, 116, 119, 120, 121, 123, 124, 125, 126, 127, 128, 129, 130, and 162, is substituted with the following non-naturally encoded amino acid as described in the above examples.

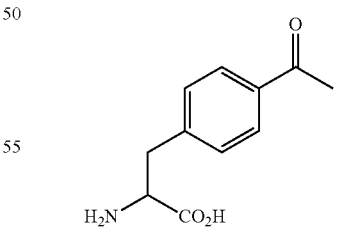

Once modified, the fEPO variant comprising the carbonyl-containing amino acid will be reacted with an aminooxy-containing PEG derivative of the form:

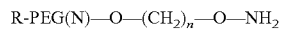

R-PEG(N)—O—(CH$_2$)$_n$—O—NH$_2$ where R is methyl, n is 4 and N is 20,000 MW to generate a fEPO antagonist comprising a non-naturally encoded amino acid that is modified with a PEG derivative at a single site within the polypeptide. Coupling, purification, and analyses is performed as described in the above examples.

Example 18

Generation of a fEPO Homodimer, Heterodimer, Homomultimer, or Heteromultimer in which the fEPO Molecules are Linked Directly A fEPO variant comprising the alkyne-containing amino acid can be directly coupled to another fEPO variant comprising the azido-containing amino acid, each of which comprise non-naturally encoded amino acid substitutions at the sites described in the above examples. This will generate the corresponding fEPO homodimer where the two fEPO variants are physically joined at the site 2 binding interface. In an analogous manner a fEPO polypeptide may be coupled to one or more other polypeptides to form heterodimers, homomultimers, or heteromultimers. Coupling, purification, and analyses is performed as described in the above examples.

Example 19

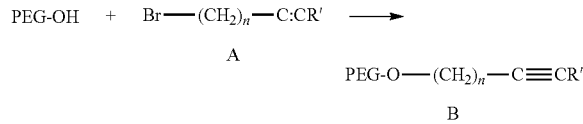

The polyalkylene glycol (P-OH) is reacted with the alkyl halide (A) to form the ether (B). In these compounds, n is an integer from one to nine and R' can be a straight- or branched-chain, saturated or unsaturated C1, to C20 alkyl or heteroalkyl group. R' can also be a C3 to C7 saturated or unsaturated cyclic alkyl or cyclic heteroalkyl, a substituted or unsubstituted aryl or heteroaryl group, or a substituted or unsubstituted alkaryl (the alkyl is a C1 to C20 saturated or unsaturated alkyl) or heteroalkaryl group. Typically, P—OH is polyethylene glycol (PEG) or monomethoxy polyethylene glycol (mPEG) having a molecular weight of 800 to 40,000 Daltons (Da).

Example 20

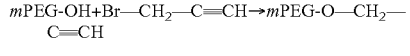

mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). A solution of propargyl bromide, dissolved as an 80% weight solution in xylene (0.56 mL, 5 mmol, 50 equiv., Aldrich), and a catalytic amount of KI were then added to the solution and the resulting mixture was heated to reflux for 2 h. Water (1 mL) was then added and the solvent was removed under vacuum. To the residue was added $CH_2Cl_2$ (25 mL) and the organic layer was separated, dried over anhydrous $Na_2SO_4$, and the volume was reduced to approximately 2 mL. This $CH_2Cl_2$ solution was added to diethyl ether (150 mL) drop-wise. The resulting precipitate was collected, washed with several portions of cold diethyl ether, and dried to afford propargyl-O-PEG.

Example 21

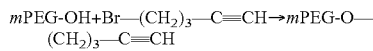

The mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). Fifty equivalents of 5-chloro-1-pentyne (0.53 mL, 5 mmol, Aldrich) and a catalytic amount of KI were then added to the mixture. The resulting mixture was heated to reflux for 16 hours. Water (1 mL) was then added and the solvent was removed under vacuum. To the residue was added $CH_2Cl_2$ (25 mL) and the organic layer was separated, dried over anhydrous $Na_2SO_4$, and the volume was reduced to approximately 2 mL. This $CH_2Cl_2$ solution was added to diethyl ether (150 mL) drop-wise. The resulting precipitate was collected, washed with several portions of cold diethyl ether, and dried to afford the corresponding alkyne.

Example 22

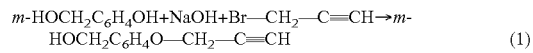 (1)

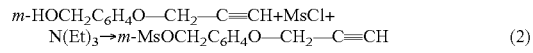 (2)

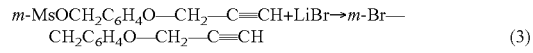 (3)

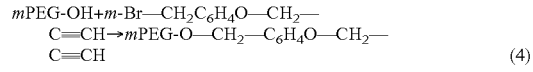 (4)

To a solution of 3-hydroxybenzylalcohol (2.4 g, 20 mmol) in THF (50 mL) and water (2.5 mL) was first added powdered sodium hydroxide (1.5 g, 37.5 mmol) and then a solution of propargyl bromide, dissolved as an 80% weight solution in xylene (3.36 mL, 30 mmol). The reaction mixture was heated at reflux for 6 hours. To the mixture was added 10% citric acid (2.5 mL) and the solvent was removed under vacuum. The residue was extracted with ethyl acetate (3×15 mL) and the combined organic layers were washed with saturated NaCl solution (10 mL), dried over MgSO4 and concentrated to give the 3-propargyloxybenzyl alcohol.

Methanesulfonyl chloride (2.5 g, 15.7 mmol) and triethylamine (2.8 mL, 20 mmol) were added to a solution of compound 3 (2.0 g, 11.0 mmol) in $CH_2Cl_2$ at 0° C. and the reaction was placed in the refrigerator for 16 hours. A usual work-up afforded the mesylate as a pale yellow oil. This oil (2.4 g, 9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous $Na_2SO_4$, and concentrated to give the desired bromide.

mPEG-OH 20 kDa (1.0 g, 0.05 mmol, Sunbio) was dissolved in THF (20 mL) and the solution was cooled in an ice bath. NaH (6 mg, 0.25 mmol) was added with vigorous stirring over a period of several minutes followed by addition of the bromide obtained from above (2.55 g, 11.4 mmol) and a catalytic amount of KI. The cooling bath was removed and the resulting mixture was heated to reflux for 12 hours. Water (1.0) was added to the mixture and the solvent was removed under vacuum. To the residue was added $CH_2Cl_2$ (25 mL) and the organic layer was separated, dried over anhydrous $Na_2SO_4$, and the volume was reduced to approximately 2 mL. Dropwise addition to an ether solution (150 mL) resulted in a white precipitate, which was collected to yield the PEG derivative.

Example 23

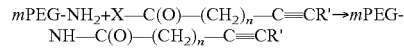

The terminal alkyne-containing poly(ethylene glycol) polymers can also be obtained by coupling a poly(ethylene glycol) polymer containing a terminal functional group to a reactive molecule containing the alkyne functionality as shown above.

Example 24

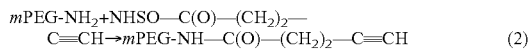

4-pentynoic acid (2.943 g, 3.0 mmol) was dissolved in CH2Cl2 (25 mL). N-hydroxysuccinimide (3.80 g, 3.3 mmol) and DCC (4.66 g, 3.0 mmol) were added and the solution was stirred overnight at room temperature. The resulting crude NHS ester 7 was used in the following reaction without further purification.

mPEG-NH$_2$ with a molecular weight of 5,000 Da (mPEG-NH$_2$, 1 g, Sunbio) was dissolved in THF (50 mL) and the mixture was cooled to 4° C. NHS ester 7 (400 mg, 0.4 mmol) was added portion-wise with vigorous stirring. The mixture was allowed to stir for 3 hours while warming to room temperature. Water (2 mL) was then added and the solvent was removed under vacuum. To the residue was added CH$_2$Cl$_2$ (50 mL) and the organic layer was separated, dried over anhydrous Na$_2$SO$_4$, and the volume was reduced to approximately 2 mL. This CH$_2$Cl$_2$ solution was added to ether (150 mL) drop-wise. The resulting precipitate was collected and dried in vacuo.

Example 25

This example represents the preparation of the methane sulfonyl ester of poly(ethylene glycol), which can also be referred to as the methanesulfonate or mesylate of poly (ethylene glycol). The corresponding tosylate and the halides can be prepared by similar procedures.

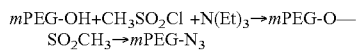

The mPEG-OH (MW=3,400, 25 g, 10 mmol) in 150 mL of toluene was azeotropically distilled for 2 hours under nitrogen and the solution was cooled to room temperature. To the solution was added 40 mL of dry CH$_2$Cl$_2$ and 2.1 mL of dry triethylamine (15 mmol). The solution was cooled in an ice bath and 1.2 mL of distilled methanesulfonyl chloride (15 mmol) was added dropwise. The solution was stirred at room temperature under nitrogen overnight and the reaction was quenched by adding 2 mL of absolute ethanol. The mixture was evaporated under vacuum to remove solvents, primarily those other than toluene, filtered, concentrated again under vacuum, and then precipitated into 100 mL of diethyl ether. The filtrate was washed with several portions of cold diethyl ether and dried in vacuo to afford the mesylate.

The mesylate (20 g, 8 mmol) was dissolved in 75 ml of THF and the solution was cooled to 4° C. To the cooled solution was added sodium azide (1.56 g, 24 mmol). The reaction was heated to reflux under nitrogen for 2 hours. The solvents were then evaporated and the residue diluted with CH$_2$Cl$_2$ (50 mL). The organic fraction was washed with NaCl solution and dried over anhydrous MgSO$_4$. The volume was reduced to 20 ml and the product was precipitated by addition to 150 ml of cold dry ether.

Example 26

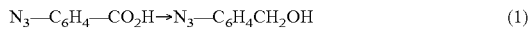

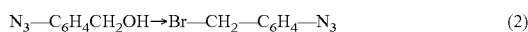

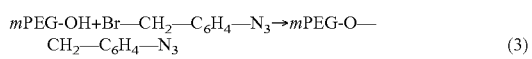

4-azidobenzyl alcohol can be produced using the method described in U.S. Pat. No. 5,998,595. Methanesulfonyl chloride (2.5 g, 15.7 mmol) and triethylamine (2.8 mL, 20 mmol) were added to a solution of 4-azidobenzyl alcohol (1.75 g, 11.0 mmol) in CH$_2$Cl$_2$ at 0° C. and the reaction was placed in the refrigerator for 16 hours. A usual work-up afforded the mesylate as a pale yellow oil. This oil (9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous Na$_2$SO$_4$, and concentrated to give the desired bromide.

mPEG-OH 20 kDa (2.0 g, 0.1 mmol, Sunbio) was treated with NaH (12 mg, 0.5 mmol) in THF (35 mL) and the bromide (3.32 g, 15 mmol) was added to the mixture along with a catalytic amount of KI. The resulting mixture was heated to reflux for 12 hours. Water (1.0) was added to the mixture and the solvent was removed under vacuum. To the residue was added CH$_2$Cl$_2$ (25 mL) and the organic layer was separated, dried over anhydrous Na$_2$SO$_4$, and the volume was reduced to approximately 2 mL. Dropwise addition to an ether solution (150 mL) resulted in a precipitate, which was collected to yield mPEG-O—CH$_2$—C$_6$H$_4$—N$_3$.

Example 27

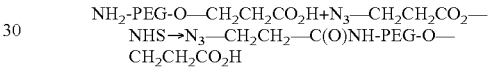

NH$_2$—PEG-O—CH$_2$CH$_2$CO$_2$H (MW 3,400 Da, 2.0 g) was dissolved in a saturated aqueous solution of NaHCO$_3$ (10 mL) and the solution was cooled to 0° C. 3-azido-1-N-hydroxysuccinimdo propionate (5 equiv.) was added with vigorous stirring. After 3 hours, 20 mL of H$_2$O was added and the mixture was stirred for an additional 45 minutes at room temperature. The pH was adjusted to 3 with 0.5 N H$_2$SO$_4$ and NaCl was added to a concentration of approximately 15 wt %. The reaction mixture was extracted with CH$_2$Cl$_2$ (100 mL×3), dried over Na$_2$SO$_4$ and concentrated. After precipitation with cold diethyl ether, the product was collected by filtration and dried under vacuum to yield the omega-carboxy-azide PEG derivative.

Example 28

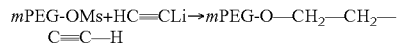

To a solution of lithium acetylide (4 equiv.), prepared as known in the art and cooled to −78° C. in THF, is added dropwise a solution of mPEG-OMs dissolved in THF with vigorous stirring. After 3 hours, the reaction is permitted to warm to room temperature and quenched with the addition of 1 mL of butanol. 20 mL of H$_2$O is then added and the mixture was stirred for an additional 45 minutes at room temperature. The pH was adjusted to 3 with 0.5 N H$_2$SO$_4$ and NaCl was added to a concentration of approximately 15 wt %. The reaction mixture was extracted with CH$_2$Cl$_2$ (100 mL×3), dried over Na$_2$SO$_4$ and concentrated. After precipitation with cold diethyl ether, the product was collected by filtration and dried under vacuum to yield the omega-carboxy-azide PEG derivative.

Example 29

The azide- and acetylene-containing amino acids were incorporated site-selectively into proteins using the methods described in L. Wang, et al., (2001), *Science* 292:498-500, J. W. Chin et al., *Science* 301:964-7 (2003)), J. W. Chin et al., (2002), *Journal of the American Chemical Society* 124: 9026-9027; J. W. Chin, & P. G. Schultz, (2002), *ChemBioChem* 11:1135-1137; J. W. Chin, et al., (2002), *PNAS United States of America* 99:11020-11024: and, L. Wang, & P. G. Schultz, (2002), *Chem. Comm.*, 1-10. Once the amino acids were incorporated, the cycloaddition react was carried out with 0.01 mM protein in phosphate buffer (PB), pH 8, in the presence of 2 mM PEG derivative, 1 mM $CuSO_4$, and ~1 mg Cu-wire for 4 hours at 37° C.

Example 30

In Vitro and In Vivo Activity of PEGylated fEPO Determined by the Normocythaemic Mouse Assay PEG-fEPO, unmodified fEPO and buffer solution are administered to mice. The results will show superior activity and prolonged half life of the PEGylated fEPO of the present invention compared to unmodified fEPO which is indicated by significantly increased amounts of reticulocytes and a shift of reticulocyte count maximum using the same dose per mouse.

The normocythaemic mouse bioassay is known in the art (Pharm. Europa Spec. Issue Erythropoietin BRP Bio 1997 (2)). The samples are diluted with BSA-PBS. Normal healthy mice, 7-15 weeks old, are administered s.c. 0.2 ml of PEGylated fEPO of the present invention. Over a period of 4 days starting 72 hours after the administration, blood is drawn by puncture of the tail vein and diluted such that 1 µl of blood was present in 1 ml of an 0.15 µmol acridine orange staining solution. The staining time is 3 to 10 minutes. The reticulocyte counts are carried out microfluorometrically in a flow cytometer by analysis of the red fluorescence histogram (per 30,000 blood cells analyzed). Each investigated group consists of 5 mice per day, and the mice are bled only once.

Bioassay In addition, fEPO polypeptides of the present invention are evaluated with respect to in vitro biological activity using a fEPO receptor binding assay and a cell proliferation assay in which bioactivity is determined by Ba/F3-fEPOR cell proliferation. The protocol for each assay is described in Wrighton et al. (1997) Nature Biotechnology 15:1261-1265, and in U.S. Pat. Nos. 5,773,569 and 5,830,851. $EC_{50}$ values for the fEPO polypeptides prepared according to this invention are the concentration of compound required to produce 50% of the maximal activity obtained with recombinant erythropoietin.

Example 31

Clinical Trial of the Safety and/or Efficacy of PEGylated fEPO Comprising a Non-Naturally Encoded Amino Acid Objective To compare the safety and pharmacokinetics of subcutaneously administered PEGylated recombinant feline EPO comprising a non-naturally encoded amino acid with the commercially available hEPO product PROCRIT or ARANESP.

Patients Eighteen healthy cats of similar profile (age and weight) are enrolled in this study. The subjects have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to hEPO or fEPO within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design This is a Phase I, single-center, open-label, randomized, two-period crossover study in healthy male volunteers. Eighteen subjects are randomly assigned to one of two treatment sequence groups (nine subjects/group). EPO is administered over two separate dosing periods as a bolus s.c. injection in the upper thigh using equivalent doses of the PEGylated fEPO comprising a non-naturally encoded amino acid and the commercially available product chosen. The dose and frequency of administration of the commercially available product is as instructed in the package label. Additional dosing, dosing frequency, or other parameter as desired, using the commercially available products may be added to the study by including additional groups of subjects. Each dosing period is separated by a time period to be based off of the human trial version (e.g. a 14-day washout period). Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the PEGylated fEPO as well. Multiple formulations of EPO that are approved for use may be used in this study. Epoetin alfa marketed as PROCRIT® and/or darbepoitein marketed as ARANESP® are commercially available EPO products that have also been used therapeutically in animals. The experimental formulation of fEPO is the PEGylated fEPO comprising a non-naturally encoded amino acid.

Blood Sampling Serial blood is drawn by direct vein puncture before and after administration of EPO. Venous blood samples (5 mL) for determination of serum erythropoietin concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods A radioimmunoassay (RIA) kit procedure (Diagnostic Systems Laboratory [DSL], Webster Tex.), is used for the determination of serum erythropoietin concentrations. The commercially available RIA is a double-antibody, competitive method that uses a rabbit polyclonal antiserum to urinary erythropoietin as the primary antibody and an $^{125}$I-labeled urinary erythropoietin as the tracer. Epoetin alfa or darbepoietin is substituted for urinary erythropoietin provided in the DSL kit, in standards and quality control samples. Standard concentrations used in the assay are 7.8, 15.6, 31.3, 50, 62.5, 100, and 125 mIU/mL. Sensitivity, defined as the mean back-fit value for the lowest standard giving acceptable precision, is 8.6 mIU/mL, and the assay range is extended to 2,000 mIU/mL through quality control dilutions.

Safety Determinations Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis Post-dose serum concentration values are corrected for pre-dose baseline erythropoietin concentrations by subtracting from each of the post-dose values the mean baseline erythropoietin concentration determined from averaging the erythropoietin levels from the three samples collected at 30, 20, and 10 minutes before dosing. Pre-dose serum erythropoietin concentrations are not included in the calculation of the mean value if they are below the quantification level of the assay. Pharmacokinetic parameters are determined from serum concentration data corrected for baseline erythropoietin concentrations. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appeared similar.

Pharmacokinetic Results Mean serum erythropoietin concentration-time profiles (uncorrected for baseline erythropoietin levels) in all 18 subjects after receiving a single dose of commercially available hEPO (PROCRIT® or ARANESP®) are compared to the PEGylated fEPO and/or research or commercial fEPOs which are available. The PEGylated fEPO for comparison is one of the present invention, comprising a non-naturally encoded amino acid at each time point measured. All subjects should have pre-dose baseline erythropoietin concentrations within the normal physiologic range. Pharmacokinetic parameters are determined from serum data corrected for pre-dose mean baseline erythropoietin concentrations and the $C_{max}$ and $t_{max}$ are determined. The mean $t_{max}$ for hEPO (PROCRIT®) is significantly shorter than the tmax for the PEGylated hEPO comprising the non-naturally encoded amino acid. Terminal half-life values are significantly shorter for hEPO (PROCRIT®) compared with the terminal half-life for the PEGylated fEPO comprising a non-naturally encoded amino acid.

Although the present study is conducted in healthy subjects, similar absorption characteristics and safety profiles would be anticipated in other patient populations; such as patients with cancer or chronic renal failure, post injury with injury-induced anemia, pediatric renal failure patients, patients in autologous predeposit programs, or patients scheduled for elective surgery.

In conclusion, subcutaneously administered single doses of PEGylated fEPO comprising non-naturally encoded amino acid are safe and well tolerated by healthy subjects. Based on a comparative incidence of adverse events, clinical laboratory values, vital signs, and physical examination results, the safety profiles of research/commercial EPOs, hEPO (PROCRIT®) and PEGylated fEPO comprising non-naturally encoded amino acid are equivalent. The PEGylated fEPO comprising non-naturally encoded amino acid potentially provides large clinical utility to patients and health care providers.

Example 32

In Vivo Activity of PEGylated fEPO Variants

The impact of PEG on the duration of activity of a protein is at least partially dependent on the size and structure (linear vs. branched) of the PEG. The comparative ability of different PEG size variants of fEPO to increase hematocrits (Hct) was evaluated in healthy cats.

Recombinant fEPO variants containing a p-acetylphenylalanine (pAF) substitution at position A1 were expressed in a Chinese hamster ovary cell expression system. The protein was PEGylated with either 20 kD, 30 kD or 40 kD oxyamino PEG at the site of the non-native amino acid substitution. The PEGylated fEPO variants were formulated in a formulation buffer consisting of 20 mM NaPO4, 140 mM NaCl, 0.005% polysorbate-80 at pH 6.2.

Twenty-four cats healthy (12 male/12 female) weighing approximately 3-6 kg were purchased from a Class A vendor and allowed to acclimate to the study facility, their diet and husbandry procedures. Baseline blood samples were collected on Days —14 and Day —7 prior to enrollment in the study. Cats were sedated with acepromazine and isoflurine to reduce the stress of collecting blood samples. Animals which were free of clinical signs of disease and which had Hct values within the normal reference ranges for healthy cats were selected for enrollment in the study.

Cats were assigned to one of four treatment groups using a randomized block design which equalized baseline hematocrits between treatments.

TABLE 5

| Treatment | Dose Regimen | # of Animals |
|---|---|---|
| 1) Formulation Buffer | SIDX1 | 6 (3M/3F) |
| 2) fEPO A1 pAF-20K PEG | 8 μg/kg, SIDX1 | 6 (3M/3F) |
| 3) fEPO A1 pAF-30K PEG | 8 μg/kg, SIDX1 | 6 (3M/3F) |
| 4) fEPO A1 pAF-40K PEG | 8 μg/kg, SIDX1 | 6 (3M/3F) |

Animals were bled on Day 0 prior to treatment and weighed. Animals were treated once with their assigned treatments by subcutaneous injection.

Additional blood samples were collected on Days 3, 7, 10, 14, 17, 21, 24, 28, 31, 35, 38 and 42 post-treatment. Hematocrits were determined for each sample. Daily feed consumption was also measured and animals were observed daily for any health issues.

Figure 36:
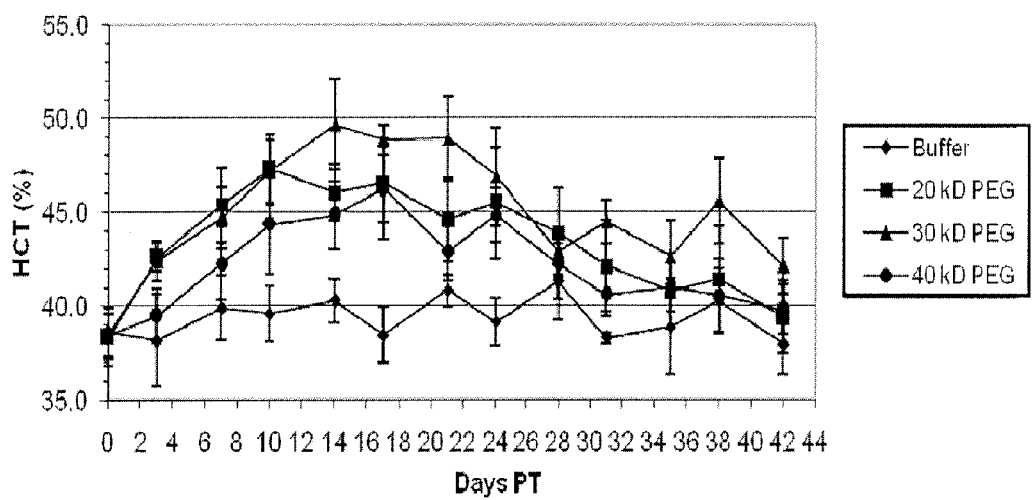
FIG. 36—A graph showing the effects of the various treatments upon hematocrits and red blood cells (RBC) from the experiment run in example 32.

The effects of the various treatments upon hematocrits and RBC are presented in FIG. 36.

Significant increases in Hct values relative to the buffer controls were observed with either the 20 kD or 30 kD PEGylated fEPO variants within 3 days of dosing. Animals treated with the 40 kD PEG variant exhibited significant increases relative to the buffer controls by approximately 10 days post-treatment. Maximum Hct values were observed on Day 10 for animals treated with the 20 kD PEG variant, Day 14 for the 30 kD PEG variant and Day 17 for the 40 kD PEG variant. Hematocrits for animals treated with either the 20 or 30 kD PEG variants were significantly greater than the buffer controls through at least 28 days post-dosing. These results suggest administration of PEG fEPO once per month should be adequate to support the maintenance of increased Hct levels. There were no adverse events observed during the course of the study.

Example 33
Efficacy of PEGylated fEPO Variants in Anemic Cats

The ability of PEGylated fEPO variants to restore normal red blood cell (RBC) numbers in cats with anemia can be evaluated in cats with stage III or stage IV chronic kidney disease (CKD). Cats with this condition exhibit moderate to severe non-regenerative anemia due to the loss of parenchymal renal cells which are the primary source of endogenous fEPO.

To evaluate the ability of PEGylated fEPO to increase red blood cell numbers in cats with CKD and anemia, 12 cats (6 males and 6 females) weighing approximately 3-6 kg with a clinical history of CKD and hematocrits<30% are acclimated to the study facility, their diet and husbandry procedures. Hematocrits and RBC counts from blood samples collected on Days —14 and Day —7 prior to enrollment in the study are used as baseline controls for each animal.

Cats are assigned to one of three treatment groups using a randomized block design which equalizes baseline hematocrits and RBCs between treatments. Each treatment group contains four animals (2 males/2 females). PEGylated fEPO is administered once via subcutaneous injection at doses ranging from 2-8 µg/kg.

Additional blood samples are collected on Days 3, 7, 10, 14, 17, 21, 24, 28 and 31 post-treatment. Hematocrits and RBC counts are determined for each sample. Daily feed consumption is also measured and animals are observed and scored daily for clinical signs of depression and/or lethargy to assess quality of life.

Efficacy is determined by comparing the post-treatment hematocrits and RBC counts with the baseline values obtained prior to administration of the protein. The protein is considered efficacious if the mean daily hematocrit and RBC count values exhibit a statistically significant increase relative to the baseline values or if the mean daily values increase to within the normal reference range values for these parameters at any point during the post-treatment period.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a feline with anemia comprising administering to the feline a therapeutically-effective amount of a feline erythropoietin (fEPO) polypeptide comprising a non-naturally encoded amino acid, wherein the non-naturally encoded amino acid is substituted at a position selected from the group consisting of residues 49, 53, 76, 131, 132, and 133 of SEQ ID NO: 2, wherein the non-naturally encoded amino acid is selected from the group consisting of p-acetylphenylalanine, p-propargyl-tyrosine, m-acetylphenylalanine, O-propargyl-tyrosine, O-methyl-L-tyrosine, 3-methyl-phenylalanine, O-4-allyl-L-tyrosine, 4-propyl-L-tyrosine, L-Dopa, a fluorinated phenylalanine, isopropyl-L-phenylalanine, p-azido-L-phenylalanine, p-acyl-L-phenylalanine, p-benzoyl-L-phenylalanine, phosphonotyrosine, p-iodo-phenylalanine, p-bromophenylalanine, p-amino-L-phenylalanine, and an isopropyl-L-phenylalanine.

2. The method of claim 1, wherein the non-naturally encoded amino acid is selected from the group consisting of p-acetylphenylalanine, p-propargyl-tyrosine, m-acetylphenylalanine, and O-propargyl-tyrosine.

3. The method of claim 1, wherein the poly(ethylene glycol) moiety has a molecular weight of between about 1 kilodalton (kDa) and about 100 kDa.

4. The method of claim 1, wherein the poly(ethylene glycol) moiety has a molecular weight of between about 1 kDa and about 50 kDa.

5. The method of claim 1, wherein the poly(ethylene glycol) moiety has a molecular weight of between about 5 kDa and about 40 kDa.

6. The method of claim 1, wherein said anemia is non-regenerative anemia.

7. The method of claim 1, wherein the non-naturally encoded amino acid is linked to a water soluble polymer comprising a poly(ethylene glycol) moiety.

8. The method of claim 7, wherein the fEPO polypeptide is substituted at a position selected from the group consisting of residues 49 and 53 of SEQ ID NO: 2.

9. The method of claim 8, wherein the poly(ethylene glycol) moiety has a molecular weight of about 20 kDa.

10. The method of claim 8, wherein the poly(ethylene glycol) moiety has a molecular weight of about 30 kDa.

11. The method of claim 8, wherein the poly(ethylene glycol) moiety has a molecular weight of about 40 kDa.

12. The method of claim 8, wherein said anemia is non-regenerative anemia.

* * * * *